US008637244B2

(12) United States Patent
Helgadottir et al.

(10) Patent No.: US 8,637,244 B2
(45) Date of Patent: Jan. 28, 2014

(54) GENETIC MARKERS FOR RISK MANAGEMENT OF ATRIAL FIBRILLATION, ATRIAL FLUTTER, AND STROKE

(75) Inventors: Anna Helgadottir, Reykjavik (IS); Daniel Gudbjartsson, Reykjavik (IS)

(73) Assignee: deCODE Genetics ehf., Reykjavik (IS)

( * ) Notice: Subject to any disclaimer, the term of this patent is extended or adjusted under 35 U.S.C. 154(b) by 996 days.

(21) Appl. No.: 12/302,463

(22) PCT Filed: Dec. 5, 2007

(86) PCT No.: PCT/IS2007/000021
§ 371 (c)(1), (2), (4) Date: Nov. 25, 2008

(87) PCT Pub. No.: WO2008/068780
PCT Pub. Date: Jun. 12, 2008

(65) Prior Publication Data

US 2009/0325163 A1 Dec. 31, 2009

(30) Foreign Application Priority Data

Dec. 5, 2006 (IS) .............................................. 8576
Jun. 29, 2007 (IS) .............................................. 8658

(51) Int. Cl.
*C12Q 1/68* (2006.01)
*G01N 33/48* (2006.01)
*A61B 5/02* (2006.01)
*C07H 21/04* (2006.01)

(52) U.S. Cl.
USPC .......... 435/6.11; 702/19; 600/508; 536/24.31

(58) Field of Classification Search
None
See application file for complete search history.

(56) References Cited

U.S. PATENT DOCUMENTS

| | | | |
|---|---|---|---|
| 4,376,110 | A | 3/1983 | David et al. |
| 4,851,330 | A | 7/1989 | Kohne |
| 5,143,854 | A | 9/1992 | Pirrung et al. |
| 5,223,409 | A | 6/1993 | Ladner et al. |
| 5,288,611 | A | 2/1994 | Kohne |
| 5,288,644 | A | 2/1994 | Beavis et al. |
| 5,384,261 | A | 1/1995 | Winkler et al. |
| 5,424,186 | A | 6/1995 | Fodor et al. |
| 5,837,832 | A | 11/1998 | Chee et al. |
| 5,858,659 | A | 1/1999 | Sapolsky et al. |

FOREIGN PATENT DOCUMENTS

| | | |
|---|---|---|
| WO | WO-90/02809 | 3/1990 |
| WO | WO-90/15070 | 12/1990 |
| WO | WO-91/17271 | 11/1991 |
| WO | WO-92/01047 | 1/1992 |

(Continued)

OTHER PUBLICATIONS

Schott, J.-J. et al. Am. J. Hum. Genet. 57:1114-1122 (1995).*

(Continued)

*Primary Examiner* — Diana Johannsen
(74) *Attorney, Agent, or Firm* — Marshall, Gerstein & Borun LLP

(57) ABSTRACT

The invention relates to procedure and methods of determining a susceptibility to cardiac arrhythmia, including Atrial Fibrillation, Atrial Flutter and Stroke, by assessing the presence or absence of alleles at polymorphic markers found to be associated with Atrial Fibrillation, Atrial Flutter and Stroke. The invention further relates to kits encompassing reagents for assessing such markers, and diagnostic methods, uses and procedures for utilizing such susceptibility markers.

26 Claims, 4 Drawing Sheets

Location: 111,900,000 | 111,950,000 | 112,000,000 | 112,050,000
Illumina SNPs
rs2200733
rs13143308
rs10033464
D4s406
PITX2 CA397714 AF017091 DA725631 DB324364
R² in CEPH CEU HapMap
R² in YRI HapMap
R² in CHB + JPT HapMap

(56) References Cited

FOREIGN PATENT DOCUMENTS

| | | |
|---|---|---|
| WO | WO-92/09690 | 6/1992 |
| WO | WO-92/10092 | 6/1992 |
| WO | WO-92/15679 | 9/1992 |
| WO | WO-92/20791 | 11/1992 |
| WO | WO-93/01288 | 1/1993 |
| WO | WO-93/22456 | 11/1993 |
| WO | WO-2004/028341 | 4/2004 |

OTHER PUBLICATIONS

NCBI dbSNP database, build 123, refSNP entry for ss23943555 (submission of rs2220427), 5 pages, Oct. 2004.*

Lee, K-T. et al. Cardiology 116:151-156 (Jul. 2010).*

NCBI dbSNP database, build 123, refSNP entry for ss23943489 (submission of rs2200733), 3 pages, Oct. 2004.*

NCBI dbSNP database, build 123, refSNP entry for ss23943605 (submission for rs10033464), 2 pages, Oct. 2004.*

Paterson, D.S. et al. Pediatric Research 68(5):409 (2010).*

Brass et al., The genetics of cerebrovascular disease. *Baillieres Clin. Neurol.* 4, 221-45 (1995).

Adams et al. Classification of subtype of acute ischemic stroke. Definitions for use in a multicenter clinical trial. TOAST. Trial of Org 10172 in Acute Stroke Treatment. *Stroke*, 24:35-41 (1993).

Agami, RNAi and related mechanisms and their potential use for therapy. *Curr. Opin. Chem. Biol.* 6(6):829-34 (2002).

Allard et al., PARK7 and nucleoside diphosphate kinase A as plasma markers for the early diagnosis of stroke. *Clin. Chem.* 51:2043-51 (2005).

Alpert et al., Myocardial infarction redefined—a consensus document of The Joint European Society of Cardiology/American College of Cardiology Committee for the redefinition of myocardial infarction. *J. Am. Coll. Cardiol.* 36: 959-69 (2000).

Altschul et al., Gapped BLAST and PSI-BLAST: a new generation of protein database search programs. *Nucl. Acids Res.*, 25(1):3389-402 (1997).

Amarzguioui et al. Approaches for chemically synthesized siRNA and vector-mediated RNAi. *FEBS Lett.* 579(26):5974-81 (2005).

Amundadottir et al., A common variant associated with prostate cancer in European and African populations. *Nat. Genet.* 38: 652-8 (2006).

Arnar et al. Familial aggregation of atrial fibrillation in Iceland. *Eur. Heart J.* 27:708-12 (2006).

Barthelemy et al., Automatic cardiac event recorders reveal paroxysmal atrial fibrillation after unexplained strokes or transient ischemic attacks. *Ann. Noninvasive Electrocardiol.* 8:194-9 (2003).

Baum et al. Methylenetetrahydrofolate reductase gene A222V polymorphism and risk of ischemic stroke. *Clin. Chem. Lab. Med.* 42:1370-6 (2004).

Becker, Biomarkers in atrial fibrillation: investigating biologic plausibility, cause, and effect. *J. Thromb. Thrombolysis*, 19:71-5 (2005).

Benhorin et al., Identification of a new SCN5A mutation, D1840G, associated with the long QT syndrome. Database Human Mutation, Wiley InterScience; SNPs on chromosome 4q25-27 and stroke, http://www.interscience.wiley.com/journal/67501911/abstract?cretry=1&sretry=0, 1998.

Bennett, Efficiency of antisense oligonucleotide drug delivery. *Antisense Nucleic Acid Drug.Dev.* 12(3):215-24 (2002).

Berger et al., The glu298asp polymorphism in the nitric oxide synthase 3 gene is associated with the risk of ischemic stroke in two large independent case-control studies. *Hum. Genet.* 121:169-78 (2007).

Bonita, Epidemiology of stroke. *Lancet*, 339:342-4 (1992).

Bosher et al., RNA interference: genetic wand and genetic watchdog. *Nat. Cell Biol.* 2(2):E31-6(2000).

Brass et al., A study of twins and stroke. Stroke 23, 221-3 (1992).

Brummelkamp et al., A system for stable expression of short interfering RNAs in mammalian cells. *Science*, 296(5567): 550-3 (2002).

Chen et al., Fluorescence polarization in homogeneous nucleic acid analysis. *Genome Res.* 9(5): 492-8 (1999).

Chen et al., KCNQ1 gain-of-function mutation in familial atrial fibrillation. *Science*, 299(5604): 251-4 (2003).

Chen et al., The evolution of gene regulation by transcription factors and microRNAs, *Nat. Rev. Genet.* 8(2): 93-103 (2007).

Chen, Clinical development of antisense oligonucleotides as anticancer therapeutics. *Methods Mol. Med.* 75:621-636 (2003).

Chi et al., Genomewide view of gene silencing by small interfering RNAs. *Proc. Natl. Acad. Sci. USA*, 100(11):6343-6 (2003).

Church et al., Genome sequencing. *Proc. Natl. Acad. Sci. USA*, 81 (7):1991-5 (1988).

Connolly et al., Clopidogrel plus aspirin versus oral anticoagulation for atrial fibrillation in the Atrial fibrillation Clopidogrel Trial with Irbesartan for prevention of Vascular Events (ACTIVE W): a randomised controlled trial. *Lancet*, 367:1903-12 (2006).

Cotton et al., Reactivity of cytosine and thymine in single-base-pair mismatches with hydroxylamine and osmium tetroxide and its application to the study of mutations. *Proc. Natl. Acad. Sci. USA*, 85(12):4397-401 (1985).

Curran et al., A molecular basis for cardiac arrhythmia: Herg mutation cause Longot Syndrome. *Cell*, 80: 795-803 (1995).

Daly et al., High-resolution haplotype structure in the human genome. *Nature Genet.* 29(2):229-32 (2001).

Dawson et al., A first-generation linkage disequilibrium map of human chromosome 22. *Nature*, 418(6897):544-8 (2002).

Devlin et al., Genomic control for association studies. *Biometrics*, 55:997-1004 (1999).

Devlin et al., Genomic control to the extreme. *Nat. Genetics*, 36:1129-30 (2004).

Dias et al., Antisense oligonucleotides: Basic concepts and mechanisms. *Mol. Cancer Ther.* 1(5):347-55 (2002).

Dichgans, Genetics of ischaemic stroke. *Lancet Neurol.* 6:149-61 (2007).

Ellinor et al. Mutations in the long QT gene, KCNQ1, are an uncommon cause of atrial fibrillation. *Heart*, 90:1487-8 (2004).

Ellinor et al., Familial aggregation in lone atrial fibrillation. *Hum. Genet.* 118:179-84 (2005).

Ellinor et al., Locus for atrial fibrillation maps to chromosome 6q14-16. *Circulation*, 107(23): 2880-3 (2003).

Ellinor et al., Potassium channel gene mutations rarely cause atrial fibrillation. *BMC Med. Genet.* 7:70 (2006).

Falk et al., Haplotype relative risks: an easy reliable way to construct a proper control sample for risk calculations. *Ann. Hum. Genet.* 51(Pt 3):227-33 (1987).

Faucourt et al., The pitx2 homeobox protein is required early for endoderm formation and nodal signaling. *Dev. Biol.* 229:287-306 (2001).

Feinberg et al., Prevalence, age distribution, and gender of patients with atrial fibrillation. Analysis and implications. *Arch. Intern. Med.* 155:469-73 (1995).

Ferro, Cardioembolic stroke: an update. *Lancet Neurol.* 2:177-88 (2003).

Fire et al., Potent specific genetic interference by double-stranded RNA in *Caenorhabditis elegans. Nature*, 391(6669):806-11 (1998).

Flavell et al., Analysis of the beta-delta-globin gene loci in normal and Hb Lepore DNA: direct determination of gene linkage and intergene distance. *Cell*, 15(1):25-41 (1978).

Flossmann et al., Systematic review of methods and results of studies of the genetic epidemiology of ischemic stroke. *Stroke*, 35:212-27 (2004).

Fodor et al., Light-directed, spatially addressable parallel chemical synthesis. *Science*, 251(4995):767-73 (1991).

Fox et al. Parental atrial fibrillation as a risk factor for atrial fibrillation in offspring. *JAMA*, 291: 2851-5 (2004).

Franco et al., The role of Pitx2 during cardiac development. Linking left-right signaling and congenital heart atrial fibrillation and /or strokes. *Trends Cardiovasc. Med.* 13:157-63 (2003).

Fuchs et al., Targeting recombinant antibodies to the surgace of *Escherichia coli*: Fusion to a peptidoglycan associated lipoprotein. *Bio/Technology*, 9: 1370-2 (1991).

(56) References Cited

OTHER PUBLICATIONS

Fuster et al., ACC/AHA/ESC Guidelines for the Management of Patients With Atrial Fibrillation: Executive Summary a Report of the American College of Cardiology/American Heart Association Task Force on Practice Guidelines and the European Society of Cardiology Committee for Practice Guidelines and Policy Conferences (Committee to Develop Guidelines for the Management of Patients With Atrial Fibrillation) Developed in Collaboration With the North American Society of Pacing and Electrophysiology. *Circulation*, 104:2118-50 (2001).
Gabriel et al., The structure of haplotype blocks in the human genome. *Science*, 296(5576):2225-9 (2002).
Gage et al., Cost-effectiveness of preference-based antithrombotic therapy for patients with nonvalvular atrial fibrillation. *Stroke*, 29:1083-91 (1998).
Galfre et al., Antibodies to major histocompatibility antigens produced by hybrid cell lines. *Nature*, 266(5602):550-2 (1977).
Geever et al., Direct identification of sickle cell anemia by blot hybridization. *Proc. Natl. Acad. Sci. USA*, 78(8):5081-5 (1981).
Gibbs et al., Detection of single DNA base differences by competitive oligonucleotide priming. *Nucl. Acids Res.* 17:2437-48 (1989).
Go et al., Prevalence of diagnosed atrial fibrillation in adults: National implications for rhythm management and stroke prevention: the Anticoagulation and Risk Factors in Atrial Fibrillation (ATRIA) Study. *JAMA* , 285:2370-5 (2001).
Grant et al. Variant of transcription factor 7-like 2 (TCF7L2) gene confers risk of type 2 diabetes. *Nat. Genet*. 38:320-3 (2006).
Gretarsdottir et al., The gene encoding phosphodiesterase 4D confers risk of ischemic stroke. *Nat. Genet*. 35:131-8 (2003).
Griffiths et al., Human anti-self antibodies with high specificity from phage display libraries. *EMBO J.* 12(2):725-34 (1993).
Gudbjartsson et al., Variants conferring risk of atrial fibrillation on chromosome 4q25. *Nature* 448: 353-7 (2007).
Gunel et al., Mapping a gene causing cerebral cavernous malformation to 7q11.2-q21. *Proc. Natl. Acad. Sci. USA*, 92:6620-4 (1995).
Hart et al., Meta-analysis: antithrombotic therapy to prevent stroke in patients who have nonvalvular atrial fibrillation. *Ann. Intern. Med.* 146:857-67 (2007).
Hassan et al., Genetics and ischaemic stroke. *Brain*, 123(Pt 9):1784-812 (2000).
Hay et al., Bacteriophage cloning and *Escherichia coli* expression of a human IgM Fab. *Hum. Antibodies Hybridomas* 3(2):81-5 (1992).
Hong et al., Short QT syndrome and atrial fibrillation caused by mutation in KCNH2. *J. Cardiovasc. Electrophysiol.* 16, 394-6 (2005).
Hunter, Genetics: A touch of elegance with RNAi. *Curr. Biol.* 9(12):R440-2 (1999).
Huse et al., Generation of a large combinatorial library of the immunoglobulin repertoire in phase lambda. *Science* 246(4935):1275-81 (1989).
International HapMap Consortium, A haplotype map of the human genome. *Nature*, 437(7063):1299-320 (2005).
International Search Report, PCT/IS2007/000021, European Patent Office, dated Jul. 29, 2008.
Jabaudon et al., Usefulness of ambulatory 7-day ECG monitoring for the detection of atrial fibrillation and flutter after acute stroke and transient ischemic attack. *Stroke*, 35: 1647-51 (2004).
Jeffreys et al., Intensely punctate meiotic recombination in the class II region of the major histocompatibility complex. *Nat. Genet.* 29(2):217-22 (2001).
Jerrard-Dunne et al., Evaluating the genetic component of ischemic stroke subtypes: A family history study. *Stroke*, 34:1364-9 (2003).
Jousilahti et al., Parental history of cardiovascular disease and risk of stroke. A prospective follow-up of 14371 middle-aged men and women in Finland. *Stroke*, 28:1361-6 (1997).
Joutel et al., Notch3 mutations in Cadasil, a hereditary adult-onset condition causing stroke and dementia. *Nature*, 383:707-10 (1996).
Karlin et al., Applications and statistics for multiple high-scoring segments in molecular sequences. *Proc. Natl. Acad. Sci. USA*, 90:5873-7 (1993).
Keating et al., Linkage of a cardiac arrhythmia, the long QT syndrome, and the Harvey ras-1 gene. *Science*, 252(5006): 704-6 (1991).
Kim et al., Strategies for silencing human disease using RNA interference. *Nature Rev. Genet*. 8(3):173-204 (2007).
Kim et al., Synthetic dsRNA Dicer substrates enhance RNAi potency and efficacy. *Nat. Biotechnol*. 23(2):222-6 (2005).
Kohler et al., Continuous cultures of fused cells secreting antibody of predefined specificity. *Nature*, 256:495-7 (1975).
Kozbor et al., The production of monoclonal antibodies from human lymphocytes. *Immunol. Today* 4(3): 72-9 (1983).
Kraus et al., Detection and isolation of novel protein-tyrosine kinase genes employing reduced stringency hybridization. *Methods Enzymol*. 200:546-56 (1991).
Kurreck, Antisense technologies. *Eur. J. Biochem*. 270:1628-44 (2003).
Kutyavin et al., A novel endonuclease IV post-PCR genotyping system. *Nucl. Acids Res*. 34: e128 (2006).
Lavery et al., Antisense and RNAi: powerful tools in drug target discovery and validation. *Curr. Opin. Drug Discov. Devel*. 6(4):561-9 (2003).
Lerner, How to make a hybridoma. *Yale J. Biol. Med*. 54(5):387-402 (1981).
Levy et al., Mutation of the Alzheimer's disease amyloid gene in hereditary cerebral hemorrhage, Dutch type. *Science*, 248:1124-6 (1990).
Levy, Epidemiology and classification of atrial fibrillation. *J. Cardiovasc. Electrophysiol*. 8:S78-82 (1998).
Lewontin, The Interaction of Selection and Linkage. I. General Considerations; Heterotic Models. *Genetics*, 49:49-67 (1964).
Lewontin, The interaction of selective and linkage, II, optimum models. *Genetics*, 50:757-82 (1964).
Leys et al., Stroke prevention: management of modifiable vascular risk factors. *J. Neurol*. 249:507-17 (2002).
Lip et al., Antithrombotic treatment in atrial fibrillation. *Heart*, 92:155-61 (2006).
Lip et al., Atrial fibrillation and stroke prevention. *Lancet Neurol*. 6, 981-93 (2007).
Maekawa et al., Genetic polymorphism and haplotypes of the human cardiac sodium channel alpha subunit gene (SCN5A) in Japanese and their association with arrhythmia. *Ann. Hum. Genet*. 69(Pt4):413-28 (2005).
Maniatis et al., The first linkage disequilibrium (LD) maps: Delineation of hot and cold blocks by diplotype analysis. *Proc. Natl. Acad. Sci. USA*, 99:2228-33 (2002).
Mantel et al., Statistical aspects of the analysis of data from retrospective studies of atrial fibrillation and/or stroke. *J. Natl. Cancer Inst*. 22:719-48 (1959).
Markus, Genes for stroke. *J. Neurol. Neurosurg. Psychiatry*, 75:1229-31 (2004).
Marques et al., A structural basis for discriminating between self and nonself double-stranded RNAs in mammalian cells. *Nat. Biotechnol*. 24(5):559-65 (2006).
May et al., Crossover clustering and rapid decay of linkage disequilibrium in the Xp/Yp pseudoautosomal gene SHOX. *Nat. Genet*. 31(3):272-5 (2002).
McManus et al., Gene silencing in mammals by small interfering RNAs. *Nat. Rev. Genet*. 3:737-47 (2002).
Miyasaka et al. Secular trends in incidence of atrial fibrillation in Olmsted County, Minnesota, 1980 to 2000, and implications on the projections for future prevalence. *Circulation*, 114:119-25 (2006).
Mohr et al., The Harvard Cooperative Stroke Registry: a prospective registry. *Neurology*, 28:754-62 (1978).
Mommersteeg et al., Molecular pathway for the localized formation of the sinoatrial node. *Circ. Res*. 100(3): 354-62 (2007).
Monks et al., Genetic inheritance of gene expression in human cell lines. *Am. J. Hum. Genet*. 75:1094-105 (2004).
Motsinger et al., Risk factor interactions and genetic effects associated with post-operative atrial fibrillation. *Pac. Symp. Biocomput*. 584-95 (2006).
Murtagh et al., Cardioembolic stroke. *Curr. Atheroscler. Rep*. 8: 310-6 (2006).
Myers et al., A fine-scale map of recombination rates and hotspots across the human genome. *Science*, 310(5746):321-4 (2005).

(56) References Cited

OTHER PUBLICATIONS

Myers et al., Detection of single base substitutions by ribonuclease cleavage at mismatches in RNA:DNA duplexes. *Science*, 230(4731):1242-6 (1985).
Myers et al., The distribution and causes of meiotic recombination in the human genome. *Biochem. Soc. Trans*. 34(Pt 4):526-30 (2006).
NCBI Database entry for SNP ss3141258, Accession No. rs2200733, dated Jun. 8, 2001.
Nicolae et al., Measuring the relative information in allele-sharing linkage studies. *Biometrics*, 60(2):368-75 (2004).
Nielsen et al., Peptide nucleic acid (PNA). A DNA mimic with a peptide backbone. *Bioconjug. Chem*. 5(1):3-7 (1994).
Nielsen et al., Sequence-selective recognition of DNA by strand displacement with a thymine-substituted polyamide. *Science*, 254:1497-1500 (1991).
Nomenclature and criteria for diagnosis of ischemic heart atrial fibrillation and /or stroke. Report of the Joint International Society and Federation of Cardiology/World Health Organization task force on standardization of clinical nomenclature. *Circulation*, 59:607-9 (1979).
Olesen et al., Association of the 5-HT2A receptor gene polymorphism 102T/C with ischemic stroke. *J. Mol. Neurosci*. 30(3): 678-84 (2006).
Olson et al., Kv1.5 channelopathy due to KCNA5 loss-of-function mutation causes human atrial fibrillation. *Hum. Mol. Genet*. 15:2185-91 (2006).
Orita et al., Detection of polymorphisms of human DNA by gel electrophoresis as single-strand conformation polymorphisms. *Proc. Natl. Acad. Sci. USA*, 86(8):2766-70 (1989).
Palsdottir et al., Mutation in cystatin C gene causes hereditary brain haemorrhage. *Lancet*, 2:603-4 (1988).
Pasdar eta I., Paraoxonase gene polymorphisms and haplotype analysis in a stroke population. *BMC Med. Genet*. 7(1): 28 (2006).
Patil et al., Blocks of limited haplotype diversity revealed by high-resolution scanning of human chromosome 21. *Science*, 294(5547):1719-23 (2001).
Pearson et al., Improved tools for biological sequence comparison. *Proc. Natl. Acad. Sci. USA*, 85:2444-8 (1988).
Phillips et al., Chromosome-wide distribution of haplotype blocks and the role of recombination hot spots. *Nat. Genet*. 33(3):382-7 (2003).
Plasterk et al., The silence of the genes. *Curr. Opin. Genet. Dev*. 10(5):562-7 (2000).
Prystowsky, Management of atrial fibrillation: therapeutic options and clinical decisions. *Am. J. Cardiol*. 85:3D-11D (2000).
Reich et al, Linkage disequilibrium in the human genome. *Nature*, 411:199-204 (2001).
Reynolds, et al., Rational siRNA design for RNA interference. *Nat. Biotechnol*. 22:326-30 (2004).
Risch et al., The future of genetic studies of complex human diseases. *Science*, 273:1516-7 (1996).
Risch et al., The relative power of family-based and case-control designs for linkage disequilibrium studies of complex human diseases I. DNA pooling. *Genome Res*., 8(12):1273-88 (1998).
Rubattu et al., Chromosomal mapping of quantitative trait loci contributing to stroke in a rat model of complex human disease. *Nat. Genet*. 13:429-34 (1996).
Sacco et al., American Heart Association Prevention Conference. IV. Prevention and Rehabilitation of Stroke. Risk factors. *Stroke*, 28:1507-17 (1997).
Sahoo et al., Mutations in the gene encoding KRIT1, a Krev-1/rap1a binding protein, cause cerebral cavernous malformations (CCM1). *Hum. Mol. Genet*. 8:2325-33 (1999).
Saiki et al., Analysis of enzymatically amplified beta-globin and HLA-DQ alpha DNA with allele-specific oligonucleotide probes. *Nature*, 324:163-6 (1986).
Sanger et al., DNA sequencing with chain-terminating inhibitors. *Proc. Natl. Acad. Sci. USA*, 74(12):5463-7 (1977).
Schadt et al., Genetics of gene expression surveyed in maize, mouse and man. *Nature*, 422: 297-302 (2003).
Sheffield et al., Attachment of a 40-base-pair G + C-rich sequence (GC-clamp) to genomic DNA fragments by the polymerase chain reaction results in improved detection of single-base changes. *Proc. Natl. Acad. Sci. USA*, 86(1):232-6 (1989).
Shi, Mammalian RNAi for the masses. *Trends Genet*. 19:9-12 (2003).
Shuey et al., RNAi: gene-silencing in therapeutic intervention. *Drug Discov. Today*, 7(20):1040-6 (2002).
Siolas et al., Synthetic shRNAs as potent RNAi triggers. *Nat. Biotechnol*. 23(2):227-31 (2005).
Smith et al., A high-density admixture map for disease gene discovery in African Americans. *Am. J. Hum. Genet*. 74:1001-13 (2004).
Souto et al., A genomewide exploration suggests a new candidate gene at chromosome 11q23 as the major determinant of plasma homocysteine levels: Results from the GAIT project. *Am. J. Hum. Genet*. 75(6): 925-33 (2005).
Stefansson et al., A common inversion under selection in Europeans. *Nat. Genet*. 37:129-37 (2005).
Stephens et al., Antisense oligonucleotide therapy and cancer. *Curr. Opin. Mol. Ther*. 5(2):118-22 (2003).
Strong et al., Preventing stroke: Saving lives around the world. *Lancet Neurol*. 6: 182-7 (2007).
Stumpf et al., A Y chromosome census of the British Isles *Curr. Biol*. 13:1-8 (2003).
Terwilliger et al., A haplotype-based 'haplotype relative risk' approach to detecting allelic associates. *Hum. Hered*. 42:337-46 (1992).
Thompson, Applications of antisense and siRNAs during preclinical drug development. *Drug Discovery Today*, 7(17):912-7 (2002).
Torellis et al., Advance and Adam: two algorithms for the analysis of global similarity between homologous informational sequences. *Comput. Appl. Biosci*. 10(1):3-5 (1994).
Tournier-Lasserve et al., Cerebral autosomal dominant arteriopathy with subcortical infarcts and leukoencephalopathy maps to chromosome 19q12. *Nat. Genet*. 3:256-9 (1993).
Vickers et al., Efficient reduction of target RNAs by small interfering RNA and RNase H-dependent antisense agents. *J. Biol. Chem*. 278:7108-18 (2003).
Waldo, The interrelationship between atrial fibrillation and atrial flutter. *Prog. Cardiovasc. Dis*. 48:41-56 (2005).
Wall et al., Haplotype blocks and linkage disequilibrium in the human genome. *Nat. Rev. Genet*. 4(8):587-97 (2003).
Walraven et al., Oral anticoagulants vs aspirin in nonvalvular atrial fibrillation: an individual patient meta-analysis. *JAMA*, 288:2441-8 (2002).
Wang et al., Antisense anticancer oligonucleotide therapeutics. *Curr. Cancer Drug Targets* 1(3):177-96 (2001).
Wang et al., Distribution of recombination crossovers and the origin of haplotype blocks: the interplay of population history, recombination, and mutation. *Am. J. Hum. Genet*. 71(5):1227-34 (2002).
Wichmann et al., KORA-gen—resource for population genetics, controls and a broad spectrum of disease phenotypes. *Gesundheitswesen*, 67(Suppl 1): S26-30 (2005).
Wolf et al., Atrial fibrillation as an independent risk factor for stroke: the Framingham Study. *Stroke*, 22:983-8 (1991).
Wolf et al., Preventing stroke in atrial fibrillation. *Am. Fam. Physician*, 56:2242-50 (1997).
Xia et al., Kir2.1 gain-of-function mutation underlies familial atrial fibrillation. *Biochem. Biophys. Res. Commun*. 332: 1012-9 (2005).
Xia et al., siRNA-mediated gene silencing in vitro and in vivo. *Nat. Biotechnol*. 20(10):1006-10 (2002).
Yang et al. Development and validation of stroke risk equation for Hong Kong Chinese patients with type 2 diabetes: the Hong Kong Diabetes Registry. *Diabetes Care*, 30:65-70 (2007).
Yang et al. Identification of a KCNE2 gain-of-function mutation in patients with familial atrial fibrillation. *Am. J. Hum. Genet*. 75:899-905 (2004).
Zhang et al., A dynamic programming algorithm for haplotype block partitioning. *Proc. Natl. Acad. Sci. USA*, 99:7335-9 (2002).
Zhang et al., Polymorphism of SG13S114T/A in the AL0X5AP gene and the risk for stroke in a large Chinese cohort. *Yi. Chuan Xue Bao*, 33(8): 678-84 (2006).
Zini et al. Identification of metabolic pathways of brain angiotensin II and III using specific aminopeptidase inhibitors: predominant role of angiotensin III in the control of vasopressin release. *Proc. Natl. Acad. Sci. USA*, 93:11968-73 (1996).

* cited by examiner

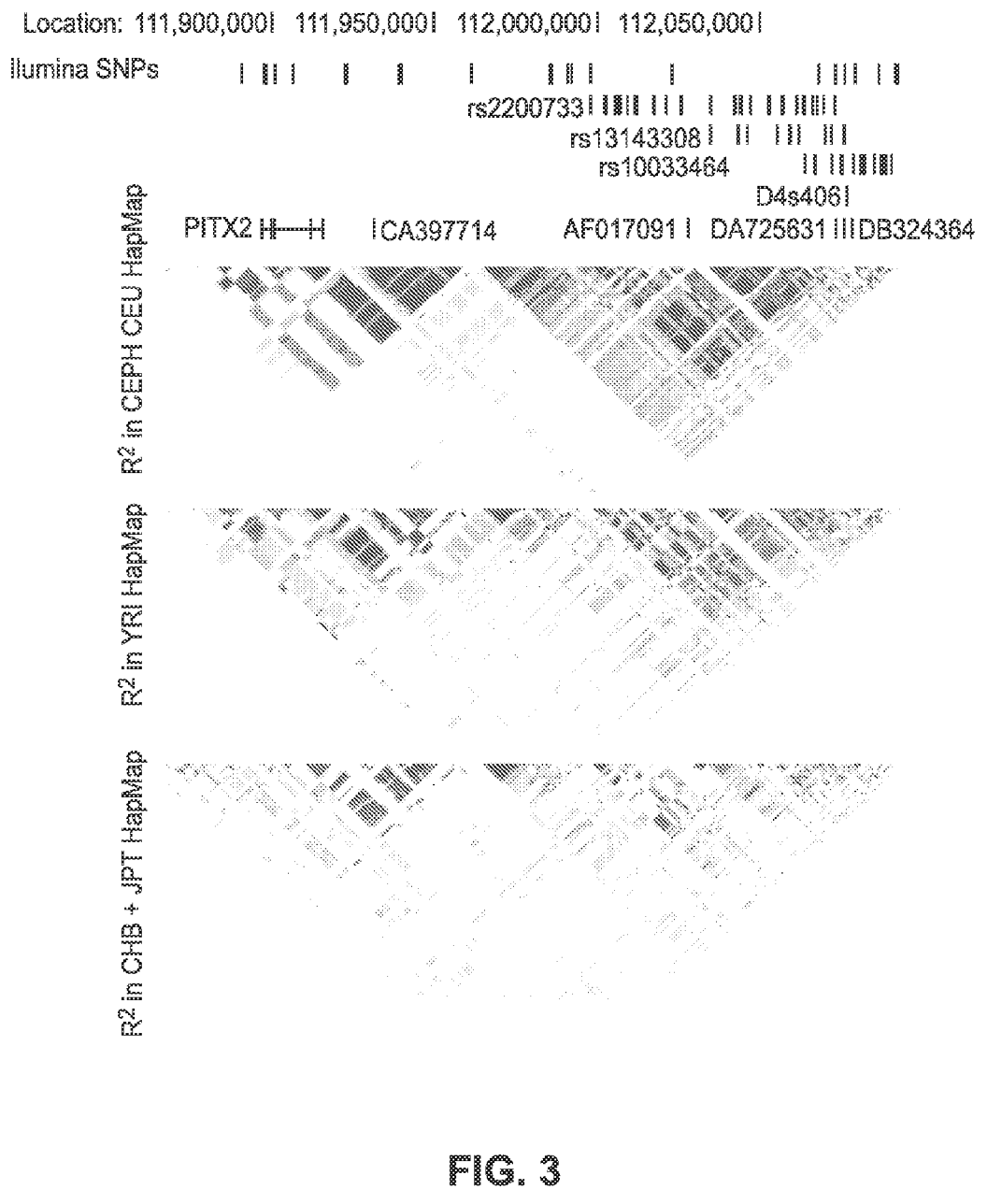

Location: 111,900,000 111,950,000 112,000,000 112,050,000

Illumina SNPs rs2200733 rs13143308 rs10033464

D4s406

PITX2 CA397714 AF017091 DA725631 DB324364

$R^2$ in CEPH CEU HapMap $R^2$ in YRI HapMap $R^2$ in CHB + JPT HapMap

FIG. 3

SEQUENCE LISTING

```
<160> NUMBER OF SEQ ID NOS: 64

<210> SEQ ID NO 1
<211> LENGTH: 201
<212> TYPE: DNA
<213> ORGANISM: Homo sapiens

<400> SEQUENCE: 1

tgtattctta acagtctgtg tataatccta aatgatacac atgggttggc atagtgtgct      60

cagtttgatt ccagggatat ctcaggctta tttaacaatg ytacccttag aacaacatta     120

gcatactaat ctatactact ggccgcgaac cacattcctt ggtatctttt aactggatgg     180

attgagacta ttgccccaga t                                               201


<210> SEQ ID NO 2
<211> LENGTH: 201
<212> TYPE: DNA
<213> ORGANISM: Homo sapiens

<400> SEQUENCE: 2

ggcttttaat acattactgg aagtttaaga aatttaaaaa atattttttc tcttgacaaa      60

ccctgttttt aaaatagatg gaattgctag ggattcggct rgtgttaatt gcatttttct     120

attcctgtgc tatgtgtact aatcaccatc ctatgccccc ttcacctgct ctctaagtcc     180

cctgtagatg aatgcctctg a                                               201


<210> SEQ ID NO 3
<211> LENGTH: 201
<212> TYPE: DNA
<213> ORGANISM: Homo sapiens

<400> SEQUENCE: 3
```

gttaacacaa ttattgattt cctgtctctc attccccagt aatcctcttc agtcttccat 60
atcttagtaa tagtaccatc atcctctagg tccttaatct rtaaatctag tagtctttct 120
ggatttccca gctacttctt ttcagtgtct tgcatggtta ctttttttga tgtattcttt 180
aaacagtggt gttttggctt a 201

<210> SEQ ID NO 4
<211> LENGTH: 201
<212> TYPE: DNA
<213> ORGANISM: Homo sapiens

<400> SEQUENCE: 4
tcagaaatat actaatggag ttctttattg aaagaaaaca tatataagaa tcttcttaat 60
ataagaataa tatctgctcc atcaactgca tctcaaaatt ygtgctagga tttagcaagt 120
tgtacaaaga acacaagcct ttatctcaat aggtctgggt tcttttccca attgtcactg 180
gctgtgtgac atcaagaaaa a 201

<210> SEQ ID NO 5
<211> LENGTH: 201
<212> TYPE: DNA
<213> ORGANISM: Homo sapiens

<400> SEQUENCE: 5
ggaaaatggt gtgcattatt taaagaaggt ccccagaatg ttgtataaaa tttgtccact 60
ggatgaaaat gtatatactt accaacaaag gaggttgtga satatagtct gtccatgttc 120
atgaggaaga ggagaacaaa tattgggaaa aagctagctt cttagacaca agaacaatga 180
cagaggcatt taaaaatgtg t 201

<210> SEQ ID NO 6
<211> LENGTH: 201
<212> TYPE: DNA
<213> ORGANISM: Homo sapiens

<400> SEQUENCE: 6
atgaggaaga ggagaacaaa tattgggaaa aagctagctt cttagacaca agaacaatga 60
cagaggcatt taaaaatgtg tcccagataa ttgagaaaaa maccagcaaa aaaaggaagg 120
ggagtgaacc cgggaggcgg agcttgcagt gagccgagat tgcgccactg cagtccagcc 180
tgggcgacag agcaagactc t 201

<210> SEQ ID NO 7
<211> LENGTH: 200
<212> TYPE: DNA
<213> ORGANISM: Homo sapiens

<400> SEQUENCE: 7
atcttctgat ttgggtagtg gtgcattttc acccaaagct aaattgcaaa gaaagtggac 60
aatgatcaag catagatatt gatcccatat ttcttaacct ytatgaatct attatcttcc 120
aaaaatccat ttaggattta gatagaaagc aggatttcct tttgactcta cagtgtataa 180
aacacagaac atctgagaaa 200

<210> SEQ ID NO 8
<211> LENGTH: 201
<212> TYPE: DNA
<213> ORGANISM: Homo sapiens

<400> SEQUENCE: 8
tgcgtgtgtg tatgcataca agcatgcatg tatgcatgtt atcctgatgc cgcttttgtg 60
ttctttttct gtttttctct cctgcaagac atgtactctg mcagttttct gtattttctg 120
gttgtttctg agatttaaga aaacaagcca tttctgcaga aacccgcaac aaagggtagg 180
ttgatttaca tcagtatttg g 201

<210> SEQ ID NO 9
<211> LENGTH: 201
<212> TYPE: DNA
<213> ORGANISM: Homo sapiens

<400> SEQUENCE: 9
gaagactggg gcagcaccga ctcccacaat ccgttccacc aattcaccct acgacacaaa 60
ctaaacagca agcaaacaaa atcctctttg gactccacat yttcccccct ctgttctgtt 120
gcataaatag attttttat acaaactatc tatacacact ctgcccgctt cctcttcttc 180
ctttcattct tcaacgtttt c 201

<210> SEQ ID NO 10
<211> LENGTH: 199
<212> TYPE: DNA
<213> ORGANISM: Homo sapiens

<400> SEQUENCE: 10
cctccaaaag gccctacctt cagctatcat cacattgggg ggattagatt ctaacatata 60
aattttgggg ggacacaaac atgcagtcca tagcagtgtc rgttcagcat gatttgagga 120
ataggaatcc cctctagact gcaggtaccc ctgactgttt acctaaaatt aaactattag 180
agattaattt ttctattca 199

<210> SEQ ID NO 11
<211> LENGTH: 201
<212> TYPE: DNA
<213> ORGANISM: Homo sapiens

<400> SEQUENCE: 11
ttcatattag agatcttttt aatgaaaatt agtggagaaa aaatttaggg taaggactgt 60
tgcctaggaa tatatttatt tttatgattt ccttaaatac raaaaaccaa ttctttgcgg 120
gtgttcacag ttggagaatg gttgtaagtt ctacctgcta ttttggtaag tcaaaccaat 180
atagtcttat tcatcccttt t 201

<210> SEQ ID NO 12
<211> LENGTH: 201
<212> TYPE: DNA
<213> ORGANISM: Homo sapiens

<400> SEQUENCE: 12
tcagtaaagc ccaaatttaa tgaacttcaa tttcctagat ttcacttaaa ggtggatgtt 60
gagagaatgt agatgtagaa agaaccagaa ctggaaaact rtaaatttag caaacactta 120
aacatacact atttggtagt gttttctagt cttcattctt gcaatacagt ttctgaatcc 180
ttctaaaatg ggtattttct c 201

<210> SEQ ID NO 13
<211> LENGTH: 201
<212> TYPE: DNA
<213> ORGANISM: Homo sapiens

<400> SEQUENCE: 13

```
ttgagaagcc ttctagatga tttgaaacag gtggtcctat gaccacactc tcatgatctc     60

ttgcctcaac tggtgccttg atgctggtac tcattcatat yttgtcctta gacttgtaat    120

ttaaaatttg cctgtttttt atggtaccca ttatgaattg gtacctctta ttcttagcag    180

atatttttac tttttatttt t                                              201


<210> SEQ ID NO 14
<211> LENGTH: 200
<212> TYPE: DNA
<213> ORGANISM: Homo sapiens

<400> SEQUENCE: 14

atacaaagct gtaaggggca agaggtacat gggccagccg taaagtttgt ttattcaaat     60

ggagcttgtt gatctgtcat atttttcaag ttgagctact mtgccagggc aacattctac    120

tgtattcaaa tcagctgttt tggaattggt acacctgcta gtgtctgttt ctgaacactg    180

aatgagttgc cataagggag                                                200


<210> SEQ ID NO 15
<211> LENGTH: 201
<212> TYPE: DNA
<213> ORGANISM: Homo sapiens

<400> SEQUENCE: 15

catatggact aggtacccac tcacctggat gactatttca caactttctt tcttttcaaa     60

attccagtcc ctttcctcat tttcaatttt agctgattga ytttttttaa aatgagacat    120

ttagaacaat ctagagagaa cttcccaaca ccatgtttga tcatcagcat tacattcctt    180

tactcttcct tccccccctca a                                             201


<210> SEQ ID NO 16
<211> LENGTH: 201
<212> TYPE: DNA
<213> ORGANISM: Homo sapiens

<400> SEQUENCE: 16

atgaacaagc ttttctcgaa acagttctgc catccagcac gatttttgtc ccctttgcaa     60

caaagcccct tgaaggagtt gtctatactt cttgttttca mttccattcc tcacattctc    120

tcttaaccca ttctaatcag ttaggcttct actgccctcc cctatggtct ccaatggcct    180

ctactttgct aaagactagt t                                              201


<210> SEQ ID NO 17
<211> LENGTH: 201
<212> TYPE: DNA
<213> ORGANISM: Homo sapiens

<400> SEQUENCE: 17

cttatactgt tccatgcata cagtttctca tctaatgagt agtattatag ataaatatct     60

acaaataaag tgagacttgt taaatgctta gcaccatgac ygtcactttg tataatctta    120

acaaatgtta gctattacaa ttataaccaa taatgataat tattaagttg ttagccagaa    180

gaaagatatc ttggttatag c                                              201


<210> SEQ ID NO 18
<211> LENGTH: 201
<212> TYPE: DNA
<213> ORGANISM: Homo sapiens

<400> SEQUENCE: 18
```

tctttttgag aaatgtgata agaatataca gagtgagaaa ttactagctg ttgtttgacc 60
ttttgatttc tgcctctgta acccaaattt acaaagggtg ygtgcataca cacacacaca 120
cacacataca cacacaagat ataccaaaaa caagtgtaat tcacatgaaa gaaattgtgg 180
tgggtatcta gcattttata t 201

<210> SEQ ID NO 19
<211> LENGTH: 201
<212> TYPE: DNA
<213> ORGANISM: Homo sapiens

<400> SEQUENCE: 19
aaaacagtag atatgatctc tcatgacttt agcaagattt tagatttagc ccagcatgat 60
agagtcatca atgaactgga aacacagtat gggtcacaca yactattgag ggctgcacag 120
ctattgagtg gttatcactg gctcagtgtc aaccgggtgg gaaatgaata gaaaatccca 180
aatgtaaatt tgtttaacat t 201

<210> SEQ ID NO 20
<211> LENGTH: 201
<212> TYPE: DNA
<213> ORGANISM: Homo sapiens

<400> SEQUENCE: 20
gtggttatca cagtacccaa taggtagttt ttctacccgt gcttctctcc ctccctgcca 60
tagtagtcca cagtgcctat tgttcccatg tttatgtcta yacgtactca gtgcttagct 120
ccctgttccc atgtttatgt ctgtatgtac tcagtgctta gctccctgtt cccgtgttta 180
tgtctatatg tactcaatgc t 201

<210> SEQ ID NO 21
<211> LENGTH: 201
<212> TYPE: DNA
<213> ORGANISM: Homo sapiens

<400> SEQUENCE: 21
ttgggtgttt taatttagtg attcttttga tgttttctgg gggatagaat ttccatttct 60
ttctgatttt gtatcaacct tgaatgtgga attaaaatag yaaatctcta ctttgtattt 120
tatatataaa taaaaattct acatattaca tatgtagctg atattaatat gtattatata 180
cacaatataa ttttattaca t 201

<210> SEQ ID NO 22
<211> LENGTH: 201
<212> TYPE: DNA
<213> ORGANISM: Homo sapiens

<400> SEQUENCE: 22
catccacagc catgaggcca cataacacaa gccctccagt ctcagctctg acaccacttt 60
ctcagagagg cattccctga gcacctaaga ggcctctcac mcttaccctc cttattctct 120
accctggctg ctttattctc tacctggttt ctatcttggc tcttatgaat tgcagttatt 180
ttttatttgt ttatgaaatt g 201

<210> SEQ ID NO 23
<211> LENGTH: 201
<212> TYPE: DNA
<213> ORGANISM: Homo sapiens

<400> SEQUENCE: 23

```
ttcttagtaa tttttataga aaatttagca tggatatcat acatctgtgt gtgtgtgtgt     60

gtgtgtgtgt gtgtgtgtgt gtgtgcattc caagtcttca yaaatggggt tgtattataa    120

atactgatat atacctggct ctttcactta atcagaaggc taagtgacca tctgtttgag    180

tccctagaaa tatactgttt t                                               201


<210> SEQ ID NO 24
<211> LENGTH: 201
<212> TYPE: DNA
<213> ORGANISM: Homo sapiens

<400> SEQUENCE: 24

tttacttttg attcagattg atacctttttg ctgattactt gtcattttat tttcatttct     60

ttgaattgct tatttacatt aattgatcag tttttttatta yctttttttct ggtccttttc    120

ttactaattt gtacaagcat tgtataaatt agaaaattag ctctcaactg tcaaaatatg    180

atgccaacct tttcttttttt g                                              201


<210> SEQ ID NO 25
<211> LENGTH: 199
<212> TYPE: DNA
<213> ORGANISM: Homo sapiens

<400> SEQUENCE: 25

tttagagtta atactagaga agaatctcac ttgaaaacat ttcacctata tgtatgcggt     60

gtcttggtag acagggtgcc tgaggacagt ggcatagcaa mtttccagtg aggtaattta    120

atttgttaaa ttaaataatt agatttattc ctcatgttgc cttggggtga tgaggaggag    180

ttaaggacat ggagaaaaa                                                  199


<210> SEQ ID NO 26
<211> LENGTH: 199
<212> TYPE: DNA
<213> ORGANISM: Homo sapiens

<400> SEQUENCE: 26

aaactgaaaa atagactcct attttgaaac ctagaaaaaa gttgtgcttt aaacttttct     60

ctgtcaaatg agaattgctt aattcttata cttaaggaac rtgggaaatg aaaaggcaga    120

atgtatagtg ttggtccttt gatggaattt ctgagaaaaa acaaactatt ccagatgatg    180

actaaatcac atagtttta                                                  199


<210> SEQ ID NO 27
<211> LENGTH: 199
<212> TYPE: DNA
<213> ORGANISM: Homo sapiens

<400> SEQUENCE: 27

atgaactagt gcatcacact gactgcctgc tctgtgtcag gttctacttg aggccccaga     60

tactagcaag ccctccaggt tctcacagtc taatgagatg yagcaatgta aacagctact    120

ttttatatga tgtgaaaaaa cagaagtatt aatgaaatgc tgtgggaaca taaactaact    180

agggagtagt aattctgcc                                                  199


<210> SEQ ID NO 28
<211> LENGTH: 199
<212> TYPE: DNA
<213> ORGANISM: Homo sapiens

<400> SEQUENCE: 28
```

```
tgatgtgaaa aaacagaagt attaatgaaa tgctgtggga acataaacta actagggagt     60

agtaattctg ccttggtggt acttgggttt tgattttgat yagagaaaat tagaacaggt    120

aatatttaag gtagttttga agaatgagta aaattttcca gaaagtttgg ggaatgtaat    180

tcctggtaga gggaagcct                                                 199
```

<210> SEQ ID NO 29
<211> LENGTH: 198
<212> TYPE: DNA
<213> ORGANISM: Homo sapiens

<400> SEQUENCE: 29

```
aatcctggaa tccaggttaa gaattctttc tctgggcagt gagtgccact gacaatattt     60

cagtaaaaga gggacaggag aaactttggt tatagaatga ygactgctgt aatttaaaca    120

atgaaatgga atggggagag gctgaagtta accacatcat gcaggaggtt ttgggattat    180

aaaataaaat agaacatg                                                  198
```

<210> SEQ ID NO 30
<211> LENGTH: 201
<212> TYPE: DNA
<213> ORGANISM: Homo sapiens

<400> SEQUENCE: 30

```
agtaaaagag ggacaggaga aactttggtt atagaatgat gactgctgta atttaaacaa     60

tgaaatggaa tggggagagg ctgaagttaa ccacatcatg maggaggttt tgggattata    120

aaataaaata gaacatggtg acacagaggt tgtgtgtggt gatcgaaagg gaacagaaaa    180

tgattccaag gtttctaact t                                              201
```

<210> SEQ ID NO 31
<211> LENGTH: 201
<212> TYPE: DNA
<213> ORGANISM: Homo sapiens

<400> SEQUENCE: 31

```
gattcaatag acagctattg aagagtgacg tgaaagtgac actgcaggag gtggaagaat     60

aaacaagaaa aagtggagat tgcgaatcta gattacttct ytaagggatt ggttaggaaa    120

agatagaaga ggagaaagag gcaaaaagaa tagggagatt gcttatttta ggacataaga    180

gactagcaaa catggtggac t                                              201
```

<210> SEQ ID NO 32
<211> LENGTH: 201
<212> TYPE: DNA
<213> ORGANISM: Homo sapiens

<400> SEQUENCE: 32

```
aaatataaat tatagcagca acatattgaa taattgcaac aagtataggt gttgcttatt     60

tcatgtctat catctaacta ttaattttta ccagataaaa ytagtacatt agggaataca    120

tttaatctac aatacaggaa agtcctgttg atatgatttt gcctgtgggc tgggtgactg    180

tattagtagt gatgatttc t                                               201
```

<210> SEQ ID NO 33
<211> LENGTH: 401
<212> TYPE: DNA
<213> ORGANISM: Homo sapiens

<400> SEQUENCE: 33

```
aattgccttc tgctggaggg taggaaaact ttcttgggag gtggttttac aaggaatggg     60

tcagaacatt aaaggtcaga gaatgggaag gggcaatcag atagaagaaa tcatgggaat    120

aaattcttag agggtaaaat acatggtaaa aatgggagtg gtgtgtagaa atatgagaat    180

tggaacttat agtggaagat racattggaa atgtaaattg tagctggatt gttgaagtcc    240

ataaagacaa cccaaggtct gagactttat tctgtaggca atagagagag cccctgaaag    300

cttttcaggt gggaagtatt attatcagag ctgaactcta ggcagggcag gttcagagag    360

gtgcactgat ggcaaaggaa gtacttgaag agcttgcaaa t                        401


<210> SEQ ID NO 34
<211> LENGTH: 201
<212> TYPE: DNA
<213> ORGANISM: Homo sapiens

<400> SEQUENCE: 34

gcagaatgta tagtgttggt cctttgatgg aatttctgag aaaaaacaaa ctattccaga     60

tgatgactaa atcacatagt tttaaatctt ctgtagattt ytaatggttt tttttcaaaa    120

acgcatattg ttcaatataa taaatatttg tagagtcagg aaaatgacaa attctttctt    180

cctaacaatt ttacaatgaa a                                              201


<210> SEQ ID NO 35
<211> LENGTH: 400
<212> TYPE: DNA
<213> ORGANISM: Homo sapiens

<400> SEQUENCE: 35

taatcactga gcctgctgta cttattctgt cagtcttttt gccaaaaaga tttcatgggt     60

agcaatatca gaagcatttt tgtaattaaa ttattgtcgc tttactggaa aatctcctta    120

catttgcaaa gggtgaatgt gttcttattt cccccactcc ctacttgact tgtagtttac    180

gcaggcactt ttggctgcgt rcgtttccag cctaatggcc tccttaccgc aatattcatt    240

ttggttgggt tactccagcc atcattttcc agagacagtc ataatccctc aatgatgaca    300

gaagtcattt gatcttgggg aacaagaaat aaaacgagca acaataattt ctttaggacc    360

attttacggg tttttaagag aataaattct gtgataagtt                          400


<210> SEQ ID NO 36
<211> LENGTH: 400
<212> TYPE: DNA
<213> ORGANISM: Homo sapiens

<400> SEQUENCE: 36

tctaggaccc tgggtgccca gccttctttg tacaggttcc tgttccttcc cttccagcct     60

gcatctggct gacttcagcc tgcaaatgct tcagaacaac ctttcttgtg cagcatcttt    120

gtgtgatggg ggaagcactg aagaagaagg taccacagtc tacctgcttg ggccttctgg    180

tgattatttc ttcaactcag ytgtcttgat ctgagggaga gttttatgag ctaaaaatct    240

gtcagtgttt ccatttacca agtagctatt caatcgtttt atagcctaac cattcccaat    300

taccctcaat taaaacttgg cacatatgtt gacaacctta gatgcaattt tttaattgaa    360

aattgttgat ggcttttgat tgaagtctaa aaccaaaagt                          400


<210> SEQ ID NO 37
<211> LENGTH: 400
<212> TYPE: DNA
<213> ORGANISM: Homo sapiens
```

<400> SEQUENCE: 37

```
ctctcttgct ttcccctgcc cttctggctt ccaccatgtg atgatgtatt aagaaggcac     60
ttgacagctg ctggcacctt gatcttggac ttcccacctc cagaactctg agaaaataaa    120
tttctgttct ttataattac ccagtctgtg atattctgtt ataggagcat aaatgaaata    180
agacaccgat gtttttctta ygattagatg ggggttatgt gttttggata tgatgactac    240
agaggtaaag tgcattatca tcacattata tcaagaatat gtactatcaa catgacttat    300
cactgttgag tttaaccttg atcacctaat tgaggtagtg tttgtcagtt tactccacta    360
actcattttt cctcctttct gaggtgtatt atttggaagg                          400
```

<210> SEQ ID NO 38
<211> LENGTH: 400
<212> TYPE: DNA
<213> ORGANISM: Homo sapiens

<400> SEQUENCE: 38

```
aaaccacaat gtgataccat ctcacactag tcagaatggc tattactaaa aagtcaaaaa     60
caatagatgc tggcgaggct gcagagaaaa ggcttttata cactgttggt gggaatataa    120
attagttcag ccactgtgga aagcagtttg gagatttctc aaagaactta aaacagagct    180
accatttgat ccagtaccca raggaaaata aatagatcat tataaccaaa agacacaagc    240
attcatatgt tcattgccac actattcaca atagcaaaga catggaatca acctgggtgc    300
ccatcattgg tggactggat aaagaaaatg tgatatacac atatacacca tggaatactc    360
tgcagcatta aaaagaataa catcatgttc tttgcagcaa                          400
```

<210> SEQ ID NO 39
<211> LENGTH: 400
<212> TYPE: DNA
<213> ORGANISM: Homo sapiens

<400> SEQUENCE: 39

```
ttgggcggct ctgtacctat cagaatgttt ctacaccctc ggtactgaag ctgaatgctg     60
agaaggagga aaggcaaaga ggttgctgta cctcttgctc ttctcctgtc cccgttattc    120
tacggctgaa ttaggtggct tttttcccct tcctatgtgg cagggacttt tcttgtgtcc    180
tatcttgagt tcttcagact ratagtaaaa ttgacggtta agccagccgg actggctttt    240
aatacattac tggaagttta agaaatttaa aaaatatttt ttctcttgac aaaccctgtt    300
tttaaaatag atggaattgc tagggattcg gctggtgtta attgcatttt tctattcctg    360
tgctatgtgt actaatcacc atcctatgcc cccttcacct                          400
```

<210> SEQ ID NO 40
<211> LENGTH: 400
<212> TYPE: DNA
<213> ORGANISM: Homo sapiens

<400> SEQUENCE: 40

```
tgcagggaac ataggtaagc ttagaatatg gctatttttta actgaaactg tactgacttt     60
ctttttgaag atgctgatac aacttctgac actgttggtg atgagtggtg cataacagcc    120
gtttcagctc tgaggctatc aaatagtgaa agagaatctt ctacatacaa atcccaggac    180
accagaacag ctcttaacag mcctcacttt cctgagtaag ctgaaggtgg ctaactaaaa    240
ggcctgagag aaattactgc ctaaacaatg aaggaaggag aaaacccccca aggaagacaa    300
tgtaaagatt aagtaacaag gtttcaattt gatacaatgt ggggaatttc agtttaattc    360
```

taatttatac taatttctca taattgtctt gatcctttac 400

<210> SEQ ID NO 41
<211> LENGTH: 400
<212> TYPE: DNA
<213> ORGANISM: Homo sapiens

<400> SEQUENCE: 41
agaataatca tacagcagga atgcaaacac gtgatttcca aagagaattt tattccatat 60
ggtatttttc ccctaactaa gaattaattg caactttaaa gaaggtttga ttgtgtctat 120
gaaaaacatt ttaactactg aggaattcta aatgacttca atttaaaatt ttcttttttt 180
acattgttag agtcaagaaa kaagtgcttt catcaagctc tgagttacag aatttattag 240
agtaaaggga agaggataac cttcagatgt cttctgtggt gaaatgttga agttaaaaat 300
tttaaatgtt tgcagactaa agacatcctc ggctgtgagg cctaaaagaa taaacaaaat 360
gtgacatgtt ttattttgtt acttaaccct tgtataaaaa 400

<210> SEQ ID NO 42
<211> LENGTH: 400
<212> TYPE: DNA
<213> ORGANISM: Homo sapiens

<400> SEQUENCE: 42
atatataaag cagctctttt gagtatatgt tcaagtgtgc tatacctctc catccagtgc 60
tctcttacaa atgctggatt tgggacttcc tgtcttaacc tgggatccca cattagggac 120
ttcctctctt gacctgggat ccgcacattt cagattgcct gtagagcttt tccagccttt 180
aagacaaact ctgaatccat raattgagcc agttgctgga aagctaaaat cctatctctg 240
tcaaagtgga gcagagagac aaaggtgagt ccacaaaaac agattttctt acctcagagt 300
gatgtgaagg acaaggtggc tccagtgtct aaactctggg agtgagagaa tagcgaagaa 360
ctgcccctga atccagtaag ttaaagaaac ggcagtgcta 400

<210> SEQ ID NO 43
<211> LENGTH: 400
<212> TYPE: DNA
<213> ORGANISM: Homo sapiens

<400> SEQUENCE: 43
tatatagtac tcatatattt cacaataatg tgactaagat gattgcctat ctgaaaaaat 60
aaatgcccat tataccttgt gcatagaggg aattcaataa atatggagtt tgttaaaggg 120
aactcagccg gcaactgtga aatcataagt taataaataa aatacaatga tgatttacca 180
taatcaaatt agccagtaac rtatatacat attacaagtc agctctcata aaaaggcctt 240
tgctactttt tctgacacaa ctgcatgatt ctttttattc agtgtacatt tatgtgataa 300
actctcatta gagtctaaaa agtttgatat tccccttata aaacatacag aaggagagct 360
cgttaaagta atggatttat ttaacaactg tttttttctt 400

<210> SEQ ID NO 44
<211> LENGTH: 400
<212> TYPE: DNA
<213> ORGANISM: Homo sapiens

<400> SEQUENCE: 44
ttatatggaa tgtaaataag gacatgaaaa agaattgtaa aagtcaacca agagctctga 60
tactaaattc attgaggaca ctgataccca ttgtcatgaa tggtgacact ggcactataa 120
aaatcatttt atgtataaga atgactgtga caaagtttta atttttgaaa atatagttgt 180
ataaggtttc tcatgtctgg yattttagct tttggtttga gaattatttt aaaagaatat 240
aggacaattt agttactgga ttggtattca aactactgga cttactcaat attcttccat 300
caaaatcaaa tccaaaagaa cagagattta ttctcatatc taataggaat ctagtagaca 360
atgctaaaat tagtgaacta agtaaggtga atcaaagtta 400

<210> SEQ ID NO 45
<211> LENGTH: 246
<212> TYPE: DNA
<213> ORGANISM: Homo sapiens

<400> SEQUENCE: 45
tcctcaggga ggtctaatca tatgttttct taaaccaaac tcttttcctt ttcattaggc 60
tttcttgagg caattggcta attaatgata ataaatagtt attgagcatc acagatattc 120
taaatcctcc agtgtcatac atttggaagg aaaaaagacc agtagataaa cttaggaaga 180
gtgtgtgtgt gtgtgtgtgt gtgtgtgtgt gtgtgtgtat gtgtaacaaa catgccttaa 240
aaccag 246

<210> SEQ ID NO 46
<211> LENGTH: 399
<212> TYPE: DNA
<213> ORGANISM: Homo sapiens

<400> SEQUENCE: 46
atattgagca acagccaccc tctctgggtc cctgcaaatg gtacccattt ttccaaccca 60
cagctctagc tgctcaacca tttgagattt ggggtaacta cctgggggaa cagtgttcag 120
atggcagtgg gagttaccac ctcacagtgg cctggggaag agaagagaaa gagattagag 180
gagggggcat ttgctaaaak cactcaacga acatgctgtt aatgcttcct cacatttgca 240
tgttactgcc acagttttcc taggtgtcac tgagtctcca gaaagcaact acttgccgaa 300
ctaagtaaaa taaggagaat ggtatagcac atgtgtttgg agaaggggaa ggaagggtgg 360
aatatgaaat tgagcataga tatccaggtc aggaaagaa 399

<210> SEQ ID NO 47
<211> LENGTH: 399
<212> TYPE: DNA
<213> ORGANISM: Homo sapiens

<400> SEQUENCE: 47
gcccccaaga agtgatgtgt ctgctagaaa agccctgaac atagaatttc ctgactttgt 60
ttttaattta gttctttcag gcatcacgct gcataaccag gtgtaactct ctaaaagtct 120
ctatgacaga attttccatc tgttaaatta ggctaataat attttcatct ttttttaggg 180
taaagatgtg aaatatttgk agaactctgg aaaacatgcc ccctactaat tagagctttt 240
tgatgtgaca tcattttctt cagtacttgg agtttagtca atagatatac agtgtagctg 300
tgaaattatg aagcatgaga atgcattacc aagggaccgt aggaggctct ttactgaaaa 360
gtgtagctgg ctatatttct ggaagtaatt taaacatag 399

<210> SEQ ID NO 48
<211> LENGTH: 399
<212> TYPE: DNA
<213> ORGANISM: Homo sapiens

<400> SEQUENCE: 48
acacagagca catagggctt gaagacctgt tatggggcat ggatgtgctt gacagggaag 60
cagggaagaa gtagcaaggc aaccgggagc acttttgagt ttcctctctt tgccaggcat 120
gagaagacca cttggtgtgc attttagatg gtgctgagat gggatcaaca aaggtggagt 180
gtgcaaaaga tgagagacay tgggcaatgt ggaaatgaag aataggatta ttgctcggaa 240
ggattatggt tgtgtttaat aggaataacc aaagcaaaca atgatcacat ttgttgtcct 300
tcaccttgtc aaatagtgat ttaggggcta gggaagtata tcacctctga ggttgctaca 360
acatcctttt ctgcccacct tctccagaac ttagtatta 399

<210> SEQ ID NO 49
<211> LENGTH: 399
<212> TYPE: DNA
<213> ORGANISM: Homo sapiens

<400> SEQUENCE: 49
tttaatttct ttggaaatta aatttgcttg gaaacagtgc tataaagagt tgatgtctcc 60
aaaggtgatt ttttttgttt tatataaata aggttttgct tttgctagtt gagcgcagtt 120
ctaggctttt cgcccttagc tcacacacac cccttctgcc tgcttggact ttaatggctc 180
aagacagcct tgagctcacy gggaaaagaa aatgactgtt aaaaattatc cttgaaattg 240
gttatttggc aacattctta attgtatgga aattcattaa ggcatatttc atatataatt 300
agctcaaggt tgttgattct acaggcttta tggatttaaa tctgattgat aataaagtaa 360
acaagagagt cgaatttaaa gcgtggctct ctcgggtta 399

<210> SEQ ID NO 50
<211> LENGTH: 149440
<212> TYPE: DNA
<213> ORGANISM: Homo sapiens

<400> SEQUENCE: 50
tcctttcttt tattaatgta gtgactgctt aggataggta actatcctaa gtaggagaga 60
gaactgagaa atgtgcccat aataatcact ttcaaactat cattaaaaca gacaataact 120
ctttcatcat tttttgtatc taaaggatta aattgataca atattcttac catgccaaaa 180
agtacacaat tatttagaga gcagagatca tatgtttcca tgaaccagta tttccctatt 240
gaatggtaat gtttctttta gtaacaaatg agttcttata cttaatatta gggcaagtgc 300
ttgctacaaa atgtcagtaa tatattcatg aggtgaatca ctttggaaca gtcttttaag 360
caatttctga gcttgtggct tgccctcttt agagtggcca gtgacttagt ccctcaaaaa 420
tgaggatgca gttcaggtag aacaggagcc ctgaaattat acaaagtgct agaaagtatt 480
aatagttgga gttgaattga ggagacaaga ggaaggcttg tcacaaatga ctttttagag 540
ttgggtctgt ggcagaaaca gccagttgtt ccctggtatc tcctctctcc tgtttctatg 600
gaagcagaat ttttagctgg gcctcttgtg caattggtgt atacatatga tggaattcta 660
gccaataaga tattagcaag gttgctgtgt gcaacttcta gattgtgttc tcaaagggag 720
aggatgtgcc tttctgttct cttcttgtcc ctgctgactg gaatgtgtta ggagaactgg 780
agctgaggca gctgtgattg agcaaaaagc tagaaggagt ccaggatcct ggcactacag 840
aactgctgta cttgcatgac ttctgggact gcacttgaga gagaaataca cttctatttt 900
gttcaagaca ccactatttc aggtctgtct attacaaaag ccaaactgat ataccacaaa 960
tacaggggac agagtccttc cattgggtca gtctccaagc cttttggttc agcaccacat 1020
gtgattaact tctgggataa tgggactcac tttatcatca tcatcatcac caccagatac 1080

```
ttccagctgg ggaggcatcc cttctcattc agttgtaggt ccaaactgaa tcctagcctc   1140
cacccatatt tttctactgc taacctggta aaaaccttcc caggtatttg gaggctgtta   1200
ttgactgaca aaattcatat taaaagccaa tctccattgt ggtggtatta ggaggtggtt   1260
aatttagggg gtgattaggt catgaggaat ccacaatcat ggatgggatt aatgccctta   1320
taaaagaggt taaagaaagc tgccttgttt tttctgccat ctgaagacac aaaaggcacc   1380
atctatgagg gatgggtcct caccagacct ggcatctgct ggcaccttga tcttgcactt   1440
cccagtctct tgaactgtaa gaaatacatt tctgttgttt ataaattact cagtcaaagg   1500
tattttgctt tagcagccaa aatagattaa aacagagggg ataagtagat ttacaagata   1560
aatactttaa gtattgagta gatttcacaa gactgatttt tcctgtccac aatcccttga   1620
gcctccttca gacttcagta gaaagtactg acctccaaaa tctgaaacct tcaaagaaga   1680
tgctctgctc ccactgtcat tttttaaagt ttattctttc tgaacctgag atcttgcata   1740
gcaaagaacc tattctagat atttagtggg gtattggaag cattagaaat cgaacttatt   1800
tgcatcatat ttatgtgatt caactacatt tatctgattt atctaactgg aagcccttgt   1860
tttttgtatt tagattttaa tctctctgct ttgtttcttc atacagtgaa gtgtcagagg   1920
caacatgttg gtagaagagc tctggtcagg aattaggaaa ctggagaact catcctgggt   1980
gtgctgttta ccagcatggc tctctgaccc tcaattttcc cagtcaagtt gggattttaa   2040
tattttctct cagtgcctca atttactatt ctgtgattaa ccctttggtg catggaaata   2100
atgagaaaaa aagtgccttg aacatcatga agtcttatat caccgtaggt tagaaggagt   2160
ctccgtgaat ttgcgctggc agtcttcgtg gtgaagttgg attgttaatt ctcagtcaca   2220
aatgtgaact tgcgttcctg ccaacagatg ctctcagcaa gtttctcaat aatttatata   2280
cttgtaccct tttctctgga caattgcctc ctcactttcc cccccaaata gctatctaga   2340
tatctagata atttctttta agttaccttt agttttgtct ataaaagatg attttacaga   2400
ttcaggtctt aagacatatc agtgtttacc caatggcaca taagaaatgt tttggtcatt   2460
tctggattta agtatagtta ctctcctttg aaggcaaaca catgttcccc ttggataaag   2520
gagttagtgt tggttgctcc ttcctttctg cttcctcact ttctattttc ctttttcata   2580
tcatttgcta cccagtattg tcataatggg gtcacagtga agagcagcag ggacttagtc   2640
tcactaactg ttgcacctcg ggcttggcac catgccaggc atctagcagt ttctcattcc   2700
atacatgttg aatgaatgaa tgagcaaatg tgaaggataa attttctatc tgggacaggc   2760
agtgtggcag taatacagta cagattagtg ttcagattgg ctggtgattg aatggcactg   2820
agtcagtctt gcctgtgtca ctgaaactga gacctcagaa gtttagcttg atagaataga   2880
catgggttag aggaaaaagt tactgatgtt ggagcaggaa atacagcatg gaaaacagaa   2940
gtaaatgtct gtggaaagga gctggggagc ttgaaacagg tctggtgctg tgtcaagctt   3000
actgctgcag ctctgggaaa tatcttgttc agaaccatac acttcaggct ctgtaagtaa   3060
atcactgaga attatttatt tctgctgtgt ctttaggctt ttttttgtt tttggccatc   3120
atataggaag agtggattcc tttagaatat gacattcata tcttcctctt ctcagacatt   3180
tgaacaagta atcatctatc tcagaagcat tactggtttt ttttttagcc agacaaaact   3240
taaaatatct tatctattac aaattgcttt caggataata atgttgttct gtaactttat   3300
ttgatgactc ttcacagtaa gtagacaaat aatttttacg tgccaggtca tttaaaaaac   3360
ccctcccgag tagggatctc tgtaggtaca taaaagtaaa caattaaggg aaattctcat   3420
taagaaaaat gtctaataga attagagaga acctactttt tgctacttta attccatgct   3480
```

```
cccctccccc agcttcaaca atgtcaccag gttgagaaac agaaggagaa aaagattaat   3540
cattagtaaa aacacaccct tctgcccctc cccctggcat cctgaaattt gagtgagtca   3600
aaaatatgta acatttaatc agaggagttg attttttccc attcgtgtac tatcccccct   3660
tcctctctcc attccctttt gaaaggggaa ggtgattttt ttggcttcac tcatgtctag   3720
tcaaccttta tcctctccct tctccctttt caatctctag ggtgtatttt ggagaaaacc   3780
ttccccgacc cccccttct ggcattcatt attttcttta cttttagaca ctaatggttt   3840
caaaaccaat ctcaacacat gactcagtta ttttagaaag gactgtacta tatcttttta   3900
gatccttttc aggcctcaca tacaaacttc caaatgtagg ctaaggacgt gttcctttct   3960
ttgtatgttt tcctgtacca atttttcagt agttggttag ctggccaaaa acgtttattc   4020
taataagtgt atcaaagtgg ctttctcccc atctcttact ccctcctttt ctttgttcct   4080
tcctttcctt ttttcttccc tccctttctc tctttattct ttcttctctg gttttactct   4140
cttccccact tagatgctca gaacttggat taggtgctaa gaataaaaaa aaatgatatg   4200
ataaaatccc agccctcagg gaactcacaa ttatcgatta actgtgaatt cccttgcaat   4260
ggaacaagtg tcctaaaagg ggggtggaat ggtgcccggg aaggaagacc agagaaagcc   4320
ctactgccag aggtggaaat gggaggggcc ctaaaggagg aaagagcatg cagattttgc   4380
aggggtggga tgggacagac aggcacatag aggaaacagc agattcagag ataaaaagaa   4440
atgagaagtt tagggcaatg cagactggaa tagatatgga gatgagtcag agatgagacc   4500
agaaaggtct tgaaaggcct gcttagggtt tagactttcg actgtaggca ctggagccgt   4560
tgatgatttt gtggaataga gggatctgcc tggatggagt tagaacagag gggagcaggg   4620
aagagaagaa acatagggcg acaaaataaa aatattgtga tagtctaggt aaacaattat   4680
aaaggactga actaaggcaa tgggcagagg ctgaaactga ggagacgaac ctgaggccta   4740
tttggaggtg cactggacag gacataatgg atgattagat gtggagtcga gggaggggga   4800
cgagtctcca agtctagcca gctttctgtt tcctgacctg gtgccgttca ttgagatagg   4860
taacactgaa gtgggagagg ttttgaggga ggaaagatga tgaattcttg gcactaattc   4920
agactgtatc attaagctaa cgaaccatct tgccagtaga agctgttgct agaaagaaga   4980
accaggaaag gcagttacat caacacagct cttctgatat attggtaggg agaaacttca   5040
gaactctaat ggaaaataca tggattagaa atcaaataag tgattttttt gaaaaaaatt   5100
gcaaaataca tatatagcta gtactttgca tgaaggtgaa aatactgatt aggcattagg   5160
gttaaaataa cattaaggat gaattttatt agtatatttc caaaacattt ctgggagact   5220
agggaactct atgccatacc tcctctaaat taaactgtac attatatgcc tcatttttct   5280
cttatagctt ctatcactgg aaagcagctc agccatgtta tctttaaact tcatttctat   5340
ggtaaagaga gctcttcatt tacaaaatat tttgtgatca ttaaactaca gaaacatgac   5400
tagcattgtt aaatggtcaa tagctgagga cctacaaaat atctttaaaa agcctcaaag   5460
catttgtgca ctgcgcctct agggctacat gctgcctaga gaaattatct aactagtttg   5520
gcatctctcc agaagactgg ttaccaaact gcattgggtt catgctgaac tagcagttat   5580
ttcacaagga ttttcactag tgctaatctg catgtgtgga attcctgttc agaggttgtt   5640
tttctgagct gtttagttga gccagattac aaattgactc tgtttggtgt gaacagaaac   5700
ctatttacaa tgcagatctc tcaagccaat tttctggtta aatttcatcc attaaatttt   5760
ttctattctt atataaaaaa cgtgtctaca gggcatttac ctttttacat ttcaaattgt   5820
aaagtggtga tgtggactgc cttgaaatct tggaaaagtt taaatttcct tctagaaatt   5880
```

```
aatcataaga tcacatagta tctttaattt ttaaattgtt attaattaat ttatttattt   5940
tagagatggg gtcttgctat attgcccagg ctgaactcaa gctcccggac tcaagcatcc   6000
ttccttacca ctgtttttaa ttaattcata attataaaaa gaagtactaa aaattcattt   6060
atatgcctaa gacaaacaga tttgtcggaa ttatgatttt aagtattggt aaattaggac   6120
agatttctaa aatttatgtt catagagttt tgttgttgtt gttaagggac ccacttttat   6180
gttggtcatt aatatgaatt aaatattact tcctcataga aaccctaatg atttttcttt   6240
tggtcaaaca tagacctagg tttgtttctt agactatgct attaattttg tgtcatcaca   6300
gaaagtagcc cagtcttatt ttgagattgg tttattttcc ctggacattt gggatgaata   6360
gctcagcata acagattatt ctatatactt tagtttcaag catttaaagt ggagtccaag   6420
ttttagcatc aggaaccaat taaatgatag ttaaatctga ctgaaaaatt aatggtccag   6480
aacagaaact gtgtagcttt tttttttca gcacttctgt tttaaataaa aatctggatg   6540
cttcccagta aaacacaaag cgtcattaaa aaaaaagcag ttgaatataa ataaaaccac   6600
acccagtctt aaaaatcatt taatgatgat tgtattctta gtctgctatt aaacacaagg   6660
tgtttatcag ccttcatggg ctgctaagag tttggctaca aaacacatag cactgtgggg   6720
caatgtagga ttgcagtgct actgtgcctc tttagggtga gtatggtttg ctcttcaatg   6780
tgattattct atagtcaaat catctagcat gattgtgata gcatctgatt tgtgccatag   6840
gcgtcaatca gatttatgct aatattttgt actaatgatc aatataacag cagagaaaag   6900
tgttgatgtt cagcccactg acttaaacct tactaacggg ccttgacaga acatagtggc   6960
cttagatttt atgtgagtag aagagttcag gcttgaacat ttggctgccg cttcaagcac   7020
cctacacaga aagtcagtat agtaccttta atctggctct aattcaaacc tatcagtaat   7080
cactgagcct gctgtactta ttctgtcagt ctttttgcca aaaagatttc atgggtagca   7140
atatcagaag catttttgta attaaattat tgtcgcttta ctggaaaatc tccttacatt   7200
tgcaaagggt gaatgtgttc ttatttcccc cactccctac ttgacttgta gtttacgcag   7260
gcacttttgg ctgcgtgcgt ttccagccta atggcctcct taccgcaata ttcattttgg   7320
ttgggttact ccagccatca ttttccagag acagtcataa tccctcaatg atgacagaag   7380
tcatttgatc ttggggaaca agaaataaaa cgagcaacaa taatttcttt aggaccattt   7440
tacgggtttt taagagaata aattctgtga taagttagac tctgtgcttc taacttgggt   7500
cacagcatct taacattttt cctgcgggaa ctaaagagca tactgtacaa tatgaaaagt   7560
agcctttcgt agaccgccac tcccttctct gagttctggt gtatcttatc acttctcacg   7620
aataggactg ccattcggcg cttatatatc tgcctctttc atggcatctt aacttctttg   7680
aggcccgtga cattagttac gtggttacgc agttgttagc gatgactgcc tggcccatag   7740
caggtgctca ttgtatgctt gatgcatgag tggataaaaa tactcattct ggtcctgggc   7800
cagatctatt tcttgctttc ctcagttttg gcctatgcct cagggaagct gaccccagta   7860
gcgtgcattt ctcaggctcc cacacatcgg gcattaggaa gcagtggcag gagacagaag   7920
ggaaggaaga agggaaaatc cagggtcttt ctctgctcga tctgcattgg ggtggggggg   7980
cggggtgcac aacctttgag acttaagctc acgctggata ggctgcagtg attccaactt   8040
cttttgggtg acaccattca ctgggctctg ataatagtgc ttccgccctt actcccgcag   8100
cactgggagt ggctccctcg tcttactgat ttttggcttt cttcactttc cccagtttgg   8160
tttctcagca attttatcac ctgtgtaacc cattccttgc acgaaattcc ttctgtttta   8220
aatacttatc gtctgttcag tgttgtattg tcatacaaag ttgaaattac acctcccaac   8280
```

```
cttaaacctt tttaataaag agggacttgc cttatacttt aggggcacat agttgcctgg   8340
gatctttgct cacactgcag agtctccaaa gtgtacctac actgagggga gagttaagag   8400
gttcctttgg ggatcttatg cctgcacttt ctggaaatac ctaatcctta catattgtga   8460
taatattctt gcttttgtcc tttatttgga attattgccg catattttaa gcgtgttctt   8520
atgatattag gggatatcct tccttcctaa tgtgaagggg catccccaat ctgccttagt   8580
aatttgacat agtagggcta tagagtcaca gaacaactga gagtggctct tacagacaga   8640
gaaaagacag gattctgtca ttggcagttt gtccaggttc tgaaggtgag aaaggcctag   8700
atcggtttta aatgtatgta atttctttaa aaatttctgt catacactac gtagttgtat   8760
agctcttgga ataagcacat ggagtggtga aattccccta gatagcaccc ccaaattctg   8820
gcactttaaa attctttgta aactttcaca atgagctgaa agttaattca aacctacata   8880
gattctatgc ctccctttc tcatctttgt agctctcctt tattcttcac agggggatgg   8940
gaagagaaag gaatccggct gacatcaaat tatgaatatt ggtttaagtt cttaacaagc   9000
ttgcatttca catgcacagc taacccacaa aagacactgg attttccaag ggttagttt   9060
caaatctaca agaatgaggg atttcagcac agccctctgt cttactttct tgcatggatt   9120
tggccatgca gccaggcaat ggtggtgtgg ttagctgtct gttgtcggga aaggagtcat   9180
ctaatggagg actccttaat aaaactcctt aataaaacgt gaaattttag tactgagtct   9240
gatttttatc attcataatc ctgtgtttat tcaggacatt caaatgcttt tgggggagaa   9300
aactgttatc tgtgtgggtt gaattgggct aaatgataaa aagaaattac cttactgaac   9360
tacttatttc cacaagaatt tcagaacttt agatctaaaa gggatttaaa aaatcttctg   9420
attcaatctt tttatttctt tcaggtaaga aaattcagac tcagacacat taagaacagc   9480
tggcttgtag cagaatagag attaaaatct agaatgattt tcatcttgct acctttaatt   9540
aaaaacttgt tactttcagt ttacgcacct tagctctcaa gcctgatttt ctttcctgta   9600
tcttgacctt aaacgtatca ggtctggccc agattcttta tgggagacaa tcaaaaatga   9660
aaagtgcaca cagagcacat agggcttgaa gacctgttat ggggcatgga tgtgcttgac   9720
agggaagcag ggaagaagta gcaaggcaac cgggagcact tttgagtttc ctctctttgc   9780
caggcatgag aagaccactt ggtgtgcatt ttagatggtg ctgagatggg atcaacaaag   9840
gtggagtgtg caaaagatga gagacattgg gcaatgtgga aatgaagaat aggattattg   9900
ctcggaagga ttatggttgt gtttaatagg aataaccaaa gcaaacaatg atcacatttg   9960
ttgtccttca ccttgtcaaa tagtgattta ggggctaggg aagtatatca cctctgaggt  10020
tgctacaaca tccttttctg cccaccttct ccagaactta gtattataac aatagacaca  10080
tgaaagctcc agtttgctta aacaatagca tctctattta aatatctatt cactaaagtg  10140
ataaatctcc tcatttggga aaggtaattt cttgtaagta caaggaaaca aacaagtatt  10200
tggaatatga gctactgcta ttatttcaga gtaaataatt cttttttgtt ttcatttttt  10260
tttttttaca tttttaacct agaatattac tccactgtat agtgaacatt tatggttaaa  10320
ttttcccatg actttctatg ctataggcct cgattaggta ttctgttctc attcaataaa  10380
agcttttcac tgaaaataaa tgtcattatg ttgtaatgag tttcaatatc tactgacctt  10440
acctggattt tggagggtga gttggctgtg agcgattcag cacctcttta tccttccctt  10500
gagacactaa ttactcatta aattttcttt ttatcctttt tgctatattt caaaaatgcc  10560
aaatataaag atttttgaaa aatgagaaac tagtggaaat gtctgcaagt gtttctttta  10620
acttaaaaat atagatagcc aagtgagaaa gatataatgc aaactttggg gtctttattt  10680
```

```
tagctggtta tatctagatc tgactgaaat tgggtattcc gagtttcatc ctgaagcaaa  10740
tttctatagc tgagttataa gtccctgaaa aatgaggttt atgatgaaaa tgttgaaaga  10800
ccctcaactt taggacaagg cacaactata attttacagg cattaggcac ctaaaataac  10860
tttgtatgaa gattactctg ggatttgtcc cccattgtgt agaaaatgct taatgttgaa  10920
ctatatttta tgcacacaaa aagacttact tcataagaca aggagcacag ggattttcat  10980
tccaatattc aacaatacta ttactaaagg gctctctcct tctactctca taattgagtg  11040
atcttaagtg atatttaaaa gaaaatatca ttccgctaaa cttacatgta aagatgatat  11100
gtggcagagc aatttaaaat tttcaagcag aatgtattcc agcaatgtat ttggtatgtc  11160
atgaaactga atggatggat cataataatg tcttaatatt ctattctata gcaacaaaga  11220
aaatgagtgt ttagttttgc ttgtgtagag caatagctga agtgcttata tctgagtctg  11280
cagtgcaata aaaaatatat atatatattt ttttcttaga gaccttgctt ttattgattt  11340
tggatacata cccaaaagtg ggattgtgcc tgttagattg catttctttt tttttaatta  11400
attaatttat tttttaaatt attatacttt aagttttagg gtacatgtgc acattgtgca  11460
ggttagttac atatgtatac atgtgccatg ctggtgtgct gcacccacta actcgtcatc  11520
tagcattagg tatatctccc aatgctatcc cttcccctcc ccccacccca caacagtccc  11580
cagagtatga tgttcccctt cctgtgtcca tgtgatctca ttgttcaatt cccacctatg  11640
agtgagaata tgctgtgttt ggttttttgt tcttgtgata gtttactgag aatgatgatt  11700
tccaatttca tccatgtccc tacaaaggac atgaactcat catttttat ggctgcatag  11760
tattccatgg tgtatatgtg ccacatttc ttaatccaga ctatcattgt tggacatttg  11820
ggttggttcc aagtctttgc tattgtgaat aatgccgcaa taaacatatg tgtgtatgtg  11880
tctttatagc agcatgattt atagtccttt gggtatatac ccagtaatgg gatggctggg  11940
tcaaatggta tttctagttc tagacccctg aggaatcgcc acactgactt ccacaatggt  12000
tgaactagtt tacagtccca ccaacagtgt aaaagtgttc ctatttctcc acatcctctc  12060
cagcacctgt tgtttcctga ctttttaatg attgccattc taactggtgt gagatggtat  12120
ctcattgtgg ttttgatttg catttctctg atggccagtg atggtgagca tttttcatg  12180
tgttttttgg ctgcataaat gtcttctttt gagaagtgtc tgttcatgtc cttcacccac  12240
tttttgatgg ggttgttttt tttcttgtaa atttgtttga gttcattgta gattctggat  12300
attagccctt tgtcagatga gtaggttgcg aaaatttttct cccattctgt aggttgcctg  12360
ttcactctga tggtagtttc ttttgctgtg cagaagctct ttagtttaat tagatcccat  12420
ttgtcaattt tggcttttgt tgccattgct tttggtgttt tacacatgaa gtccttgccc  12480
atgcctatgt cctgaatggt aatgcctagg ttttcttcta gggtttttat ggttttaggt  12540
ctaatattta agtctttaat ccatcttgaa ttaatttttg tataaggtat aaggaaggga  12600
tccagtttca gctttctcca taaggctagc cagttttccc agcaccattt attaaatagg  12660
gaatcctttc cccattgctt gtttttctca ggtttgtcaa agatcagata gttgtagata  12720
tgtggcgtta tttctgaggg ctctgttctg ttccattgat ctatatctct gttttggtac  12780
cagtaccatg ctgttttggt tactgtagcc ttgtagtata gtttgaagtc aggtagtgtg  12840
atgcctccag ctttgttctt ttggcttagg attgacttgg cgatgcgggg tctttttttgg  12900
ttccatatga actttaaagt agttttttcc aattctgtga agaaaggcat tggtagcttg  12960
atggggatgt cactgaatct gtaaattacc ttgggcagta tggccatttt cacaatattg  13020
attcttccta cccatgagca tggaatgttc ttccatttgt ttgtatcctc ttttatttcc  13080
```

```
ttgagcagcg gtttgtagtt ctccttgaag aggtccttca catcccttgt aagttggatt  13140
cctaggtact ttattctctt tgaagcaatt gtgaatggga gttcactcat gatttggctc  13200
tctgtttgtc tgttgttggt gtataggaat gcttgtgatt tttgtacatt gattttgtat  13260
cctgagactt tgctgaagtt gcttatcagc ttaaggagat tttgggctga gacaatgggg  13320
ttttctagat atacaatcat gtcatctgca gacagggaca atttgacttc ctcttttcct  13380
aattgaatac cctttatttc cttctcctgc ctaattgccc tggccagaac ttccaacact  13440
atgttgaata ggagtggtga gagagggcat ccctgtcttg tgccactttt caaagggaat  13500
gcttccagtt tttgcccatt cagtatgata ttggccatgg gtttgtcata gatagctctt  13560
attattttga aatatgtccc atcaatacct aatttattga gagtttttag catgaacggt  13620
tgttgaattt tgtcaaaggc cttttctgca tctattgaga taatcatgtg gtttttgtct  13680
ttggctcagt ttatatgctg gattacattt attgatttgc gtatattgaa ccagccttgc  13740
atcccaggga tgaagcccac ttgatcatgg tgggtaagct tttgatgtg ctgctggatt  13800
cgttttgcca gtattttatt gaggattttt gcatcaatgt tcatcaagga tattggtcta  13860
aaattctctt ttttggttgt gtctctgccc ggctttggta tcacaatgac gctggcctca  13920
taaaatgagt tagggaggat tccttctttt tctattgatt ggaatagttt cagaaggaat  13980
ggtaccagtt tctccttgta catctggtag aattcggctg tgaatccatc tggtcctgga  14040
ctctttttgg ttggtaaaat tctctaaaat tctctttttt ggttgtgtct ctgcccggct  14100
ttggtatcag aacgacgctg gcctcataaa atgagttaag gaggattccc tctttttcta  14160
ttgattggaa tagtttcaga aggaatggta ccagttcctc cttgtacctc tggtagaatt  14220
cggctgtgaa tccatctggt cctggactct tttggttgg taagctattg attattgcca  14280
caatttcaga gcctgttaat ggtctattca gagattcaac ttcttcctgg tttagtcttg  14340
ggagaatgta tgtgtcaagg aatttatcca tttcttctag attttctagt ttatttgcgt  14400
agaggtgttt gtagtattct ctgatggtag tttgtatttc tgtgggattg gtggtgatat  14460
cccctttatc atttttattt gcatctattt gattcttctc tcttttttc tttattattc  14520
ttgttagcgg tctatcaatt ttgttgatcc tttcaaaaaa ccagctcctg gattcattaa  14580
tttttgaag ggtttgttgt gtctctattt ccttcagttc tgctctgatt ttagttattt  14640
cttgccttct gctagctttt gaatgtgttt gctcttgctt ttctagttct tttaattgtg  14700
atgttagggt gtcaattttg gatctttcct gctttctctt gtgggcattt agtgctataa  14760
atttccctct acacactgct ttgaatgcat cccagagatt ctggtatgtt gtgtctttgt  14820
tctcattggt ttcaaagaac atctttattt ctgccttcat ttcattatgt acccagtagt  14880
cattcaggag caggttgttc agtttccatg tagttgagcg gttttgagtg agattcttaa  14940
tcctgagttc tagtttgatt gcactgtagt ctgagagata gtttgttata atttctgttc  15000
ttttacattt gctgaggaga gctttacttc caactatgtg gtcaattttg gaataggtgt  15060
ggtgtggtgc tgaaaaaaat gtatattctg ttgatttggg gtggagagtt ctgtagatgt  15120
ctattagttc tgcttggtgc agagctgagt tcaattcctg ggtatccttg ttgactttct  15180
gtctcattga tctgtctaat gttgacagtg gggtgttaaa gtctcccatt attaatgtgt  15240
gggagtctaa gtctctttgt aggtcactga ggacttgctt tatgaatctg ggtgctcctg  15300
tattgggtgc atatatattt aggatagtta gttcttcttg ttgaattgat ccctttacca  15360
ttatgtaatg gtcttctttg tctcttttga tctttgttgg tttaaagtct gttttatcag  15420
agactaggat tgcaacccct gcctttttt gttttccatt tgcttggtag atcttcctcc  15480
```

atcctttcat tttgagccta tgtgtatctc tgcacgtgag atgggtttcc tgaatacagc 15540
acactgatgg gtcttgactc tttatccaat tttccagtct gtctttgaat tggagcattt 15600
agtccatttt catctaaagt taatattgtt atgtgtgaat ttgatcccgt cattatgatg 15660
ttagctggtt attttgctcg ttagttgatg tagtttcttc ctagtctgga tggtcttcac 15720
attttggcat gattttgcag cggctggtac tggttgttcc tttccatgtt tagcgcttcc 15780
tccaggagct cttttagggc aggcctggtg atgacaaaat ctctcagcat ttgcttgtct 15840
gtaaagtatt ttatgtctcc ttcacttatg aagcttagtt tggctggata tgaaattgtg 15900
ggttgaaaat tcttttcttt aagaatgttg aatattggcc cccactctct tctggcttgt 15960
agggtttctg ccgagagatc tgctgttagt ctgatgggct tccctttgag ggtaacccga 16020
cctttctctc tggctgccct taacattttt tccttcattt caactttggt gaatctgaca 16080
attatgtgtc ttggagttgc tcttctcgag gagtatcttt gtggcattct ctgtatttcc 16140
tgaatctgaa cgttggcctg cgttgctaga ttggggaaat tctcctggat aatatcctgc 16200
agagtgtttt tcaacttggt tccattctcc ccatcacttt caggtacacc aatcagacgt 16260
agatttggtc ttttcacata gtcccgtatt tcttggaggc tttgcttgtt tctttttatt 16320
ctttttctc taaactttcc ttctcgcttc atttcattca tttcatcttc cattgctgat 16380
accctttctt ccagttgatc gtattggctc ctgaggcttc tgcattcttc acgtagttct 16440
tgagccttgg ttttcagctg catcagctcc tttaagcact tctctgtatt ggttattcta 16500
gttatacatt cttctaaatt tttttcaaag ttttcaactc ctttgccttt ggtttgaatg 16560
tcctcccgta gctcagagta atttgattgt ctgaagcctt cttctctcag cttgtcaaag 16620
tcattctctg tccagctttg ttccattgct ggtgaggagc tgcgttcctg tggaggagga 16680
gaggcgctct gatttttaga gtttccagtt tttctgttct gttttttccc catctttgtg 16740
gttttatcta cttttgatct ttgatgatgg tgatatacag atgggttttt ggtgtggatg 16800
tcctttctgt ttgttagttt tccttctaac agacaggacc ctcagctgca ggtctgttgg 16860
agtaccctgc cgtgtgaggt gtcagtgtgc ccctgctgga gggtgcttcc cagttaggct 16920
gctcgggggt caggggtcag ggacccactt gaggaggcag tctgcccgtt ctcagatctc 16980
cagctgcgta ctgggagaac cactgctctc ttcaaagctg tcagacaggg ccatttaagt 17040
ctgcagaggt tactgctgtc tttttgtttg tctgtgccct gcccccatag gtggagccta 17100
cagaggcaag caggcctcct tgagctgtgg tgggctccac ccagtttgag cttcccggct 17160
gctttgttta cctaagcaag cctgggtaat ggtgggcgcc cctcccccag cctcgctgcc 17220
gccttgcagt ttgatctcag actgctgtgc tagcaatcag cgagactccg tggggtagga 17280
ccctccgagc caggtgcggg atataatctc gtggtgcgcc attttttaag cccattggaa 17340
aagcgcagta ttcgggtggg agtgacccga ttctccaggt gccgtcagtc accccttttct 17400
ttgattgggt aagggaactc cctgaccctt tgcttcccga gtgaggcaat gcctcgccct 17460
gcttcagctc gtgcacggtg cgcgcaccca ctgtcctgtg cccactgtct ggcacttcct 17520
agtgagatga acccggtacc tcagatggaa atgcagaaat cacctgtctt ctgcgtcgct 17580
caggctggga gctgtagact ggagctgttc ctattcggcc atcttagctc ctccaatatt 17640
tttgtctaat gaaaaatccc taacactgga aaatccttgc ctatcttttg tttctttgtt 17700
tatttttggc tttgtttgtt ttcagagaaa aaggaatgct taaaacaata acaaatagga 17760
atgtttagat ttgacacaac tttcttggtg atttaggcca attttttttt taagaaggaa 17820
aaatattgat taacttctaa acttaagata cctggtttgg gtataattca gatgaaaaca 17880

```
taaaagcaag tttgctttaa aaaacctttt aaaaaagtta ttttttattg acaaaattta  17940
tatatttatt gcatacaaca tggtgttttg aaatatgtat acattatgaa atggctaaaa  18000
caagttactt aacataccat tacctcatat actctttttt tttttttttt gtggtggaaa  18060
cacttaaaat ctactctctt ggcaattctc aagaatatag tgtattgtta ttaactatat  18120
atacaataaa tctcttaaac ttcttccttc tgcttttgta tcctttgacc aacatcagcc  18180
caaccccatc ctcccacccc cctcctctgg taaacatcat tctactctct actctatgag  18240
ttcaactttt aaaaatttat taaaaaataa aagttagata atgtctttct tttctttttc  18300
ttgatcagat tggctagagg ttatccattt tattatcatt taaaagcatt agctttgagc  18360
tgggttgatt ttttgctatt ttttttctgt tttctattta ttgctttcta cttatttctt  18420
tattatctct tcctcctgct tactttggtg taatttcttc tctttctgtt ttcttaagga  18480
ggaagcttag atcctatatg tgtctcttat tttctaatac agttacttaa tgccatagaa  18540
atcccccgaa gccctgcttt agctgtgtac tacaattttt gtttaggttt agtttttagt  18600
ttcatttggt tcaaaatact ggtcttcttt gtgacttttt gacttatatt taatttagaa  18660
atttgttaat ttccaagtat tggaggtttt caaggaattt ttcggatatt catttctgtt  18720
taatttcctt gtgtcagagg ccatattttg tgtgatttca actcccttac attgttaaga  18780
tttgttttat ggcccagagt ctaataaatt gtagtttaaa aatgtgtgtt ctactgttgt  18840
tgggtggggt tggctggcag tgttggtcac atcttttata ttcttacgca ttttcattta  18900
cttattctct tacttactga caggtttttt tgaactctct aaccacactt gtggattttt  18960
ctatttcttc tttcatgcct accagttttc gcctgtgtgt tttaaagttc cattattagg  19020
tacctacata tttagtattg ttatgtcttc ttgattaatt ttattccttt agcattattg  19080
aatggtcctc tttatcttgg taatatttct tgtactgaaa tctacattgt ctttattata  19140
aaatcactct ggtattctct tgattagtat ttgcatagct tttcccatcc ttttactttt  19200
aataagtgtg gttctttcag gctgctttta ttttggtctt gcttcttaaa atccaaattt  19260
tagtatgata atctctgatt tttgtgtgta gaccacttga atttaataca attattgaca  19320
tgattgtaca cagatacaac agtttgctct ttttctgttt cttttctgct tctatttgtt  19380
ctgtttcttt ttttctcttt tcatttgtat tgcatatgtt tatgatttca ttttaacaca  19440
actattagct atatacatat ctttccaatc agagtgcacc tttaaatagt attgttctac  19500
ttcatatgca gtctaagaac cttaaaatag tacactttta tttcctccct ccaattcttt  19560
gtgctattgt cataaatttt acttctactc aggttataca tcctacaata cattgctact  19620
gcttttgctt tcgttatttt taaataattt aaataactat aaaaaattaa ataattaaaa  19680
attttaaata tttaccctaa ttctcctgtt ttgattctct caatttcttt gtgtagatcc  19740
aaattcccat ctggtttgac catatccttt ctgcttgaag aacttcattt aatatttctt  19800
gtggtacagg catttttggca ataaattctc tctgcttttg tttgtctgga aaaaattctt  19860
tatttcaaag aaatagtttc attggatata tagattctta atttacagtt tttcactttt  19920
ctgtacttta aagatggtac tccattgtct tctggtttgc ttatagtttc taataagaaa  19980
tctgtgataa ttctttattt gtttttctgt atgtagtttt tttttccagc tactttcaag  20040
atttttctct ctgtttttag tttttagcaa gttaactctg atgcttcttc ttcatttgtt  20100
ttttaaattt tgttaatcct gtttgggttc cccaagtatc ttgcattatg cattatgttt  20160
tttgttatct tttgtcagtt tagaaatgtg tgtgtatata tatacattta taaatacata  20220
aatatatata tgaaaatgtg tgtgtatata tatttacata tacattttaa atgtatgtgt  20280
```

```
gtatttacat atacatttta aatatatgtg tgtatatata cattcaaaat attttatata  20340
tacatttaaa atactatata tatatatata aaaactatat atatatagtt tttctttttt  20400
ttttgagaag gagtcttgct ctgttgccca ggctggggtt tagtggggca atctcggctc  20460
actgcaaact ccacctcctg ggcccaagtg attttcctgc ctcagcctcc ccagtagctg  20520
agattcaggt gccgaccacc acgcccggct aatttttgta tgttagtaca gatggtgttt  20580
caccattttg gccaggctgg tcttgaactc ctgacctcaa gagattggcc cacctcagcc  20640
tcccaaagtg ctgggattac aggtgtgagc caatgtgccc ggtctgaaat gtatattttt  20700
aaaatacttt ttttcctgtc atgtttttttc ttctcttttt aggaatctac ttatacaatt  20760
aaactctctg agattgaccc aagccttctg agttaaaaaa aacaaaaact gtattttcta  20820
ttcatgtttc actttggata gttactattt acctatcttt aattctttac tctgttgtgt  20880
ttgctgataa aactgacaaa tgaatttcca tcttcgatat tgtgttttta atttctataa  20940
tttgcatttg gctcttcttt atagtttcaa tctctgtgct gaaaatccta atttattgag  21000
gcatgtttcc catttttttcc tcttgatcct ttaacatatt aattatgatc tcaaaaatgt  21060
ccttgtctga tcgttctaat agctgaatca tctctggatc tggttctgtt gtctaatctc  21120
gacaaaggtt tttttttgg ttgtttttct tttcattttg tgcaaagtag attgtattat  21180
tttttaaatt gtatattgac aaattatagt tgtatatatt tatataaatg gtcttatgac  21240
ttttgaatac aatgtggaat gattaaacta agctaattaa catatctatt acttcaaata  21300
tttaacttct tttgtcatga gaacattagg aatttattct cttagtgata cggaaaggta  21360
caatatttaa ttattagcta tattcagcat gcggtactat tgatctaaaa aaaattaaac  21420
tcattcctct tatctaactg agactttgta tcctttgact atcatctccg gatttgtgtc  21480
tttgactatc atctcctgat tccccccaac cccctgcctc tggtaaccac cattctaccc  21540
tctgcttcta tgagttcagt tgttttagat ttcacatata agtgagaaca tgcagtattt  21600
atctttcaat gtttggctta tttcacttag cataatattc tctaattcta cccatgttgt  21660
tccaaacaac agaatttctt tctttttaaa ggttgaatag tatttcattt tgtatatata  21720
ccacactttc tttatccatt tattccttta tggacactta ggttgattcc ataatttggc  21780
tattgtgaat agtgctgcaa tgaacatggg gatacaggca ggcatctctt caacacactg  21840
atttttaaat ctttcgggta tcagaaattg tattactaaa tgatgtggta attctatttt  21900
tagttttttg aggaacctcc ataccatgtt ccatgtttgt actaatttgc attcccacca  21960
acagtgtaca aggattccct ttcctccaaa tccttgctaa cacctgtctt ttgttgcttt  22020
catagtagcc attctaacag ttgtgaggtg ctatctcatt gtggttttaa tttgcatctc  22080
tttaatgatt agtgatgttg agcatttttt catatatctg aagtcatttg tatgtcttct  22140
tttgagaaat gtctatttag atcctttgcc catttcttaa ttgggtaatt tgttttcttt  22200
ttagagggtt gtttgagttt cttatatatt ttatatattg atccattatt agatgtatgg  22260
cttgcagata ttttctccca atccataggt tgtctcttca ctctgttaat tgtttccttt  22320
gatgtgcttt ttattttaat gtaatcgcat ttgtctatct ttgcttttgt tgcctaacct  22380
ttggggtcaa acctaaaaaa taatcgccta gaccaatgtt gtgtagtttc tcccctgtgt  22440
ttttttttct agtagtttta cagttttaga tcttacattt atgtctttaa tctattttga  22500
gttagttttt ctatgtggtg taaaataagg gtccaatttc attcttttcc ctatagacac  22560
ccagttttcc caacaccatt tgttgttcca attggatatt cttggcacct ttgttgaaaa  22620
tcaagagacc acagatgaat gtgttctttt ctggattctg tatagtgtcc cattggctgc  22680
```

```
tatgtctatt tttatgccag taccatgctg ttttagttac tattgatttg tagtatagtt  22740
tgaaatctaa tagtgtaatg cctccaacta ttttcttttt gcaaataatt gacttagtta  22800
tttgtaattt ttttgagagg tttcataaga attttaaaaa ctttttctac atctgtgaga  22860
agtgacatta aaattttgat agagtttgct ttgaacctgt aggtcacttt gggcagtatg  22920
gacattttaa caatattaat ccttccaatt catgaacatg agagatattt ttatttattt  22980
atgttttctt gaatttcttt cattaatgtt ttatagtttt tagtgacagg tctttcactt  23040
cttaggttaa atttattcct aagtacattt ttttttgtag cgattgtaaa taagacggtt  23100
ctcctgattt ctttttcaga aacttcattg ttagtgtaga gaaacactac tgatttttgt  23160
gtcttgattt tgtatcctgc aactttactg aatttatcag ttctaagtat tttttctttt  23220
ttatagaatc tttaggtttt tttttaatat ataagataac atggtctgaa aatagggaca  23280
atttatctct tccgttttta tttccctgcc ttattgccct ggctgggaac tccagtacta  23340
tattgagtag aagtggtaga aatgggcatc tttgtcttgt tccaggtctt agagaaacag  23400
ttttcaactt ttctccattg aatatgatgt tagctatgaa cttgtcatat atgaccttta  23460
ttgtattgag gtacatttct tccatatcta attttttgag agttttttta atcataaaaa  23520
gatattaaat tttgtcaaat gcttttcctg tatctagtga gataatcata tgatttttat  23580
ccttcatcct attaatgtga catattacat tttataaattt gtgtgtgtta agccatcttt  23640
gcatcctagg aattagtccc aattgattgt agtgaataat tcttttaatg tgttgttgaa  23700
ttcagtttgc tagtgttttg gtgacagctt ttgcatctag atttatcaag gatcttggcc  23760
tgtagttttc ttttcttgtg atgtcctttt ctggctttgg tgtcaggata atgttggtct  23820
tgtaaaagga gtttggaagt atttcctctg ctctgatttt ttggaacaat ttgtggagaa  23880
ttggtattag gtctttaaat gtttgataga attcagcagt gaagccatca ggtcctgagc  23940
tgtttttttt gatggaagac tttatattac agcttcaatc ttctcttgtt attggtctgt  24000
ttggattttt atatttcttt gtgattcggc cttgataagt tgcatgtgtc tagaaatgta  24060
ttcatttctt ctagataatc taatttttttg gcacataatt gttcataata gtttcttatg  24120
atcccttcat ttccatgatg tcagttgtaa tgtctcttct ttcatttctg attttgttta  24180
tttgagtctt ttctcttttt ttcttggtta gtctagctaa agatttgttg attttgttta  24240
tcttttcaaa aaaacccaac tcagtttcat tgatcttttt tattgctttt ctagtctcta  24300
ttacatttat ttctgctcca gtcttcatta ttccattcct tctgctaaca tctaacaatt  24360
actttttgt ctggtaattt ttttgttgac tgtgaagctt ttttttttt tttttttag  24420
accagtagag tctgaagtaa gtagaattaa ctcctagaaa tggtctcctc ttttttcagg  24480
ctgttaatgt agggaagttg agccaatctg gttagtagct gagctgggct ttttgttgct  24540
aacattacct ttgtgcacta caggctgcag attcttctag ctctgggtgg ctgctacctt  24600
gtgcttactt tgggacctaa agtgcaggaa ggtttttctg tgttcttgct tcactctcag  24660
ctttcagcag accctaaata tctatgcata aacgggggtt ctttatgctc ttgcccctct  24720
ctcagttgca tattgctagg tacaaagctt atggtaggga aagtggagat tttctttgtt  24780
ccctggtctc agcctcagtc ttagttaggc cctatattct tggtcctctg tgatgagggc  24840
tttatcacca ctcctgcctt tccctgacat agtagccata tcttaccttg catctgtcaa  24900
aggtcttgaa taggagagac agtctttgtt cttcctcagt agtagaaggt ctctgccttc  24960
tattagtaca gttgaataga tttcctgttg tctgcctacc ccaatgggcc aatggatttt  25020
gctactagtt ctctctcagt agctgatggc tttgcctggg agtggaggtg tacagttttc  25080
```

```
tatactctcc taacagcctc tcactcagac agcttttgtg tctaccatct cccagaagca  25140
gtggatcttt gcctgggtag gagacttttc tgcttctctc tcagaggcaa aggcttttgc  25200
tttatttgag agcaggatca gaaatgcaga tacagtttca accctatggt tcaccaaggg  25260
ggaagagagg gctgcctcag atctcttgtc atgttccagt ctttcttgtg agcaacgagt  25320
agagaatcat ggaaaacaac tgaagaatgc atgtggattc cccacgggtt tgatctgcca  25380
agcagtctga attgtcctag cacacacttg gcttttgtaa aaaagtgttg cagttttctt  25440
cttatccact tttacgttgg cagattcttc cttactcttc caaagatgga acagttcatt  25500
atcccattta ttttcagaag ggtttattgc tctttggaat ttagttttag tttgcctgat  25560
ttattttgta actctgtgat tttagctctg atgggcttaa gaagagtgat atttttgtag  25620
attatctgcc tttttccttg ctgtaagggt aggagtgatg ttctcttgtg atgttttcaa  25680
tcctaagagg agcagaactc catgtcatat gatttttagt atgtgagtgt ggcctaggag  25740
ccagctttct caacaaacat aaaatactaa tataaaaaaa tggagattcc taagtctagt  25800
ttttagtttg agtttgtatt gacagtttgg aattgatatc caattctacg accactaaaa  25860
tgaaaagcac atccttttgg taataaaata attttgttgt agtaatgttt ttctttaaat  25920
taaaaagatc tgaaacctag agtggcttct tttcatgtta attagggtga aaatcaggaa  25980
ggatgtgata tactgtcatt tacttttact taacacttcc aattcatttt aataggatag  26040
gaaatacttg gaattcagat caacacttcg ctgtctgttt gctgatgaac tgaaatgctt  26100
atatgagaac agggattttt cccaaatgct tgaatttagt tccccatttc ccattatgta  26160
agaaaacatt gttccttgtg gtaggctgaa aaatggcttt ccaaaagaca tttatgtccc  26220
agtccctgga acctgtaaat gttacctttt tggaaaaggg tttttgcagg tgtgattgat  26280
tacttaagga ttttgagatg gagagattat cctagattat ctggatgagc cctgaatgcg  26340
atcacaaata ccttcgtgag aagagcagag ggaaattaga cacacagagc ggaaggtgga  26400
tatgaagata aggtaggtac tggaatgatg cagtactcca caggaatgcc ggcagccacc  26460
tggagcagga agacaggcaa ggagcagatt ctccactgga ggctccagag aatgtacggc  26520
cctgctgaca cgctgatttt ggcccagtga agcagattca gacttctggc ttccagaact  26580
gtgagataat aaatttccac tgtgttaagc caccatgtct gtagaaattt cttacagtga  26640
ccataggaca ctaatacatg tatcttagtc tttaaaaaaa atctatttgt gactgggcga  26700
ggtggctcat gcctgtaatc ccagcatttt gggaggccga ggcgggtgga tcacctgagg  26760
tcaggagttc gagaacagcc tgaccaataa ggtgaaaccc tatctctacc aaaaatacaa  26820
aaattagcca ggtgtggtgg catgtgcctg tagttccaga tacccgggag gctgagacag  26880
gagaattgct tgaacctggg agggagaggt tgcagtgagc cgagatcaca ctactgcact  26940
ccagcccggg cgacagagtg agactctgtc tcaaaaaaaa aaaaaaaaaa aaagatttgt  27000
ttttatttta ttattaaaaa aattttgagt acataatagc tgtatatatt gtcttgacag  27060
aagaatttta atttgtttca attatcttat ttgaaatgtc attgaataaa agtcagttgt  27120
acaaagtatt tatttttaaa tttatttatt tatttttgag atggagtctt gctctgtcgc  27180
ccaggctgga gtacagtggt acgatcttgg ctcactgcaa cctctgcctc ccgggttcaa  27240
gcaagtctcc tgcctcagcc tcctgaatag ctgagacaat gggcatgtgc cactacaccc  27300
agataatttg tatttttagt agagatgggg tttcgccatg ttggccaggc tggtcttgaa  27360
ctcctggcct caagtgatcc acccgccttg gcccttcaga gtgctgagat tccaggtatg  27420
agccactgag cccaggtgaa gtatttattt attatgatta cacccacaat tgcgaagttt  27480
```

taaaagtgtt aactcaattt acttaaaagc aataaaacat tagagaaaat tatgcttggc 27540
ctgagatgaa atacatatat ttacagatta ctcttatgag tgatttgttg gtagattttt 27600
ggatgcttct cattaatcct gacatgaatt gacaccaatg gtcatacagt catacatttg 27660
ggttcccacc aaaataatga cttaaaggga gtcacctatt cattgttgat tttcagacaa 27720
cttgacactc cttctggggt gccctaagct tcaccacctg cacacaattg ggtcttgttt 27780
actttctcag gtatcttcca gtcagttcac aagatccatt tatgagaaaa taagacaaag 27840
tatttgattg tggactaaat agaatgaaaa taaaagaata aatggaaagt tctagaaatg 27900
tttaactgcc taagaacatg gtgtattgat tatatttttc ttcttctaga cttattgtca 27960
catattgtat tatgtatctc caccataatt tctgtccttt tcatcctgct ttataatttt 28020
tggtgcatag cagttgtctt ctaccatatt atacaaataa ttttcattat gttttatatt 28080
tatctatctc ttctaattcg acataagctc caagagggta ggatctttct ttttttcagt 28140
cttgctccaa atgcctaaaa cagtgtctgg ggcgtactgg gcactcaata aatatttgct 28200
tagcgaatga aggaatgact aattctacag aatataaaga catcaatagt tttctcccag 28260
agaggtgtta gttgtgttaa attctaacct gttttaaaaa tttcaaagat aaaagaaaga 28320
ctttaatgac ctagagttaa aaaaattacc cttgccacca ttttttcctg ataaactaaa 28380
atgcttaaaa tgactcaatt gtctagagga ctctcatgat ctgaagttgt ctacctcttt 28440
gatactccct cctaccactc tcaccacagc tcaggaggct tcagccaccc cagccaatac 28500
acaaagcctt ttgccatgtt agggtgtttg cccttatcca tcccctagct tctacccccca 28560 aatccttcat ggctggccct ttcatatcac tttgcctcag atcagatgtc acctcttcag 28620
agaagactcc cataaccctt gaagccagta gttcccaact ggtggtaatt ttgtccctca 28680
aaggacattg ggaaatatct ggagacagtt ttgtttgtcg cacctgggaa ggagaggttt 28740
tgctactggg tctaatgggt aaatgggttg gggatgctgc taaacatcct acaatgcaca 28800
cagcaacccc cacaacagag aattatccag cccaaaaagt cagcagtgcc aagattggga 28860
aactctgccc tgggctaatg cagcccccac ctctgacact cactttcttg ccaccagtgt 28920
ttcacttcct catagcactt cctgcaagtc aaaaatactt tattaatttg ttcactttct 28980
tttgttctcg ctactctact agaatgtaag ctccatgaat gcaaaagcct tgtctgtctt 29040
attcacgtat tgtcctcagt gcacctagta gacatctaat tacttattgc ctagatgaat 29100
aaataaacaa tcatatactg accattttct ctccccacca cattattggt gttctcaact 29160
gtctttttgg ctacaacttt gagatagttt tacttttcag catggcttct tttccttata 29220
agtactttca cgaacacctg tggaagtcat tatacacggt taaacaacca cagactctaa 29280
aatcagaaca tctgggttca gtcagactga tacggtttgc ctatgtcctc acctaaatct 29340
catttcgaat tataatctga attgtaatcc ccaggtgttg agggagggac atggtgggag 29400
gtgattggat catggaggcg gtttccccaa cactgttctc ctcatagtga gggagttctc 29460
accagatctg atggttttaa aagtggcact ttcccctgtg ctcacttgct gtctcctgcc 29520
accgtataag acgtaccttg cttcctcttc ttctttgggc atgattgtaa gtttcctgag 29580
gtctctccag ccatgtggaa ctgtgagtca atcaaaccgc ttctctttat aaattactca 29640
gtcttaggta gtatctttat agtaatatga aaacagacta atacatagac ctttataatt 29700
tactagttct gtaagaatct attgaagaag ttactttatt aactcttgga aaagttgctt 29760
tatttttgtg gtccttagat ttccaaatcc tttagaagag ggtaatatta atacttcctc 29820
aaagagctac tttgaagact aaacgataat gcacataaag cacctggcac atgaagcaca 29880
tatatatttg tcattattat tattactact attattaatt tttattttat tatggtcaaa 29940
cgtatataac ataaaattta ccatcccaac cattttacat gtacagttca atgcattaag 30000
tgtaatcata ttgtgcaact gttattatta tttttatcct ctgaatctgt attttattgt 30060
ttaagcttcc ctttgtgctg tgtctcctac tctcataata gtattcaaga tagatcctac 30120
tgatgttgga tagaattaga tcgacccata attcttagat agtatgtacc atacatttta 30180
ttgctcaatg catctgcatg cttaagggtg tacattttcc ctatgtattg aataggttat 30240
ctgccatgtg tttatctctt cataagtgtt ttcccagtaa taatatagaa accttgtgct 30300
tcggtttgaa tgtgtcttcc aaattttagg tgttgaatac ttaatcccca aatatatatg 30360
ttgatggtat ttggaggtag ggcctttggg agataattag aattagataa gggcatgagg 30420
atagggcctc catcatgtca ctggtggctt tataagaaga gaaagagaga cctgagctgg 30480
tgtgctcttg cctttttgtc ctgtgatgcc ttctgtcatg ttatgatgca gtaagaaggc 30540
cctcaccagg tgcagcttct tgactttgga cttccagaat tgtaagaatt gtaagaatta 30600
aatgtctttt tgtcataact tagccagtct gtgatactgt gctatagtaa cagaaaacag 30660
gataagacat tggcacacat tttatttctg actgtgtgcc caataagcat acccactctg 30720
tatgtgtgaa atccttgcca ccttcaactt gatagtaaca agtcacagaa gatgaatatc 30780
tagttttata atcctaaaat acaggcttaa tagcaaatca tgaaagtaaa gatttgatta 30840
tagagattag aagaatagaa attgggtttt acagtaatcg aataactatt aagaatactt 30900
caaacgcctt gaaagaatcc ttaaaatacc aaggtttaaa acaagatcta gatatggact 30960
gagggttttt cccaaggaaa aaatatccta ctcacttaat taagcaattt ttaaaaattg 31020
tcatacaact gtttaaatac agtctcttag gtttctaaaa taacaaatta cgtgggaaaa 31080
ttagtgctaa gggctaagaa gaaacaaagg tgtttctcaa caatcacgtt tggattattt 31140
taaaaatacg attctaatca ctccacaatt tagaaaaggc taatggtcta ttagtgacct 31200
ttgctggaag cttttcaaga ggatagattt gttgtgatag atttcatctg tgaagtgaaa 31260
ttttgcaatg taagttttat agtctttatt catgaaaact tctcccaaag taattgaaag 31320
gctagacatc cagttatctg aaccagagtt ttataaatga gtgtgtgtag gctaggaaaa 31380
aatttttata cacggagttt tgttataacc tcagtacacg ggtgaggcac attaaaaaaa 31440
aaatcacctc attaggctgg gagcatacag cttccaaggg ggaaatgaat agtttggggg 31500
ttcagtagta caatccaact aacattttgt ccaaggatcc atagataact agtagtcaac 31560
catacctgaa acccaggtca tctgagctgg agacagtggc tttttctttc cctctaccct 31620
ctcttactac tctctaggac cctgggtgcc cagccttctt tgtacaggtt cctgttcctt 31680
cccttccagc ctgcatctgg ctgacttcag cctgcaaatg cttcagaaca acctttcttg 31740
tgcagcatct ttgtgtgatg gggaagcac tgaagaagaa ggtaccacag tctacctgct 31800
tgggccttct ggtgattatt tcttcaactc agctgtcttg atctgaggga gagttttatg 31860
agctaaaaat ctgtcagtgt ttccatttac caagtagcta ttcaatcgtt ttatagccta 31920
accattccca attaccctca attaaaactt ggcacatatg ttgacaacct tagatgcaat 31980
tttttaattg aaaattgttg atggcttttg attgaagtct aaaaccaaaa gtgcacaatt 32040
cccatgattc agatctttgg tgtggttctc agattattta ctgtcagtta tgatcacatg 32100
ataccaccac tttctaaagg ccagtaaatg tcatgggttg aaggcaggtt aaggcttggg 32160
agaaaccttt ttcaagtgtc gtatggtcta tatttttgtt cataggcaga tctgagactc 32220
aagtggcaga gggttatggg atgggaaaat gaagaatggt gtgttgtaaa aataaggaag 32280
aattaaatga cttcagaatg tagagtggag atggcaaaat aagaacttgc attgctcagc 32340
attattatct gaacacttgt ttaaggacag gcccagacct gtaaagaaat gtgaagcagg 32400
acaatttgtt ttgagatcca cttttctttc tcatcccagc ctttttctgt ttcttcctac 32460
gcttttccat cctctcttgt tttctatccc cagtgatgtc atatccacat tactggtatt 32520
aaggagtttc tttatttttc ttttaatttt actttaagtt ctgggataca tgtgccgaac 32580
atgcaagttt gttacatagg tatacatgtg ccatgtggtt tgctgcacct atcaacctat 32640
catctaggtt ttaaaccgcg catgcatgca ttagatattc gtcctataca ttaaagagtt 32700
tcctatttta gttccttatg gaaaaaacga tttcaagaat atttttggca tatcagaaca 32760
tagattctag agtcttaata cctaaggata agacaagcct tgctaaaagt tatcactttt 32820
tgaaaataaa attatcgctt catttcttct agcttccaac accaataagg gacagtcatg 32880
aaacatataa gctatgcaaa attaccgaag tatgtaaatt ttgcactgaa aaatagtatc 32940
attggatata tttaaaatgc gaactttgta tgcacttata aaattataaa aatggaagcc 33000
aagaattaga taaattattt taaatacttt aagcatagtt gtaaacatta ggtacctgat 33060
acagtttgaa tatttgtccc tgcccaaatc tcgtgttgaa gcattggagg tggggtctgg 33120
tgggaggtgt ttgggtcatg gaggaggatc cctcatggct tggtgttgtc cttgctgtgg 33180
tgagtgagtt ctcacaagat ctggttgtgt aaaagtgtgt ggcacctccc tgttaccctt 33240
gctccactct caccatgaga gacgtctgct ctcccttcac cttctgccat gattgcaagc 33300
ttcctggggc cttcccagaa gcagatgcca gtaccatgtt tcctgtacag cctgcagaac 33360
agtgagccaa ttaaacctct tttcttataa attaccctgt ctcaggtacg ttatagcaat 33420
gccagaatta cctaatacag aatcttacaa tggaaatata acagggactg ataaaagttt 33480
tttccttatt tctaaagtaa tctgggacca tttttagagt ttgggtagtg gcatgtatag 33540
tttaggagtc caaaaatatt aatatgaatt ctattttctg tatcattcca tgactgcttt 33600
ggagtgtgaa ctatataaat gaaatgctca aaagcagaga aaaagttaga taattggtat 33660
aattctccac acacaaaacc acctggccca aataactgaa gttgttgcta tagacaggaa 33720
atgtaaatgt gcatgcaaca attttcttgg taaggctgaa agctttataa aaatattttt 33780
tcccttaaat gctacaaaca tttttgcaag atcagttaaa aattatcatc catgtaaaag 33840
ttcacattta agaaaagtca ttcattttgt ttaataaaat ttcttttact gatttaatta 33900
attggcaggt agatgcccac tttctgtgtt gttctaaaac aaatacttta aaaatgtcat 33960
ctagatacat ctctatgttt tatactcaat ctatcccctc tttagtaaat aaagtataat 34020
taagattcca tcaaagtggt aaatggagat tatctacaat caatcttatg tacctatgtc 34080
tgccaggttt tattcttgtt cctgttgcat catgcctttg agagaccatt tctttagatt 34140
tcatttcatg tctgtcttag tgagtcactt ctgggacaat atattcttga gtgcctcgcg 34200
agggccccca gttaaatgcc attttgtaat gagagtttct ttggtcactg gactagtctc 34260
taaagttgtt aaagcctgca gaccttaaat acagtgctgg ctgatgcaac ttaattaaac 34320
tacagcaaat tgaatttagg taataaaact ttgcttggat tttatggttg tgattgtctt 34380
ttagttattt attttataag gatgataagc tatccatcct gtgactgcct agccattttt 34440
gatgagtcag aattactctg ggctggtccc cacaaaggaa gatttggctt ttctgcacat 34500
agtgaaaaat aaatatggtg cttaatctga gatatcatga tctttcagtc accccaagat 34560
tcttctggtc tgtttctgca ccattcattg ggtgtacact taggtaataa aaacttattt 34620
taatattgtc taagtgaaag ataatttatg cttatttcac aaaatttata tagtaatgat 34680
atatatagga catttgaatt atctgttatt acactttccc gttgacatta acaatggatg 34740
gttgacttta taagaagttt aaatttaact taattttcac atactagatg taaattaggt 34800
tttctgttta gtctacctaa gggaatttat caaactagga gaaattacaa gggtttaagg 34860
atgggttgta tgatgctgta gaatctgaga aatttgtgag ctccaattct agtgggtgta 34920
taaaccccag taccaaaggc cggtgggtga gtcccaactt ccctctgcag cagatgattg 34980
ttatttggag cagtggtctc aaggggacac cgtgactgtc acacacaaat aggatgtatg 35040
agtggttaca gcatcctcga gaggtgtggt ccttgagata tgagcctggt tctagattta 35100
aatattgact cctcctggac atctgaagga atgactgtag ttgctgttgg aactcccctc 35160
aacggtagcc aaaaataatt gcagcaacag aggcaggttt attttaacca catgccatga 35220
caggatggtc agcagtgatg cctacagata cttattaaag gtaccctgag aagtgagaat 35280
gcccttgttt tccagtgcct ttccttttca caattgcaag gatgagaata agggctgacc 35340
ttgtggtaat gacattttaa atgttctgag tctgaagact gctgtaaggt caagacgttt 35400
tctcctagaa ctgagcaaac cacagtgtgg acttacttaa gaagatttgt ggcattgtta 35460
agatctcttt ataatgaata tttatacttg caaaggattt atttctttcc aggatgccaa 35520
gaaatatgtt gatccagatt ctctgagttt caccaaacta cgttcccttt taacattttt 35580
ggaaaatgga tgaatttctt tctgtctcct gaatgttcgt tggtttgtaa ctgagcctat 35640
ccacagcacc tctgcggtct ttcaggcaca ttagatcttg gttttttttac tgctttgtgc 35700 tgtagggcag aaatgcatcc acaaaaggaa gtatattagg tatggaaaga cgctggctct 35760
ttcaatcagg gatgagtctc tctcgatgct atcttctttc atctaataac tagatttggc 35820
agtagtctca ggtgggctga aatgcaggtt tctgttgctt cttccaagtc tcttctgtgt 35880
gaactagaga aattacttca aagctgtaga acttgtcaga tttccatcaa ggctgcagaa 35940
ccagcttata acttttaaaa tgaactttta attttaggag aggtttagat ttacagaaaa 36000
actgcaaaga tagtacagag agttcctata tagcctatac cctatttccc ctattactaa 36060
catcttatat tagtatggta tatttattac aaatagtgaa cgagtattga tatatgagta 36120
ttaacttcat actttattca gattttcttc gtttttacct gatatggtct gactgctggt 36180
gttccactaa aattcgtgtg ttaaaatcta actcccagtg tattagtatt aagatgtggg 36240
acatttggga ggcgactagg tcatgagagc agagctcctt gtcaatgaca ttagtgcctt 36300
tataaaggag gcctaagaga ccttgttcac ttcttctatc atatgaggac atatataagg 36360
taccatttac aagataggcc ctcacgtgac actgaatctg ctggcatctt gatcttagac 36420
ttcccagcct ccagaactgt gagagataaa tttttgttgt ttataaatta accagtctat 36480
attgttatag cggcccaaat ggactaagac attactaatt gttttgtttc caggatccca 36540
ttgaggatac cccactgggt ctagttgtct tgtctccttt gactttcctt ggctatgaca 36600
gtttttcaga ctttccttgt ttatgatgac cttgacaatt ttgaggagtg tcagttaggt 36660
gttttgtaca attttcccct actagggttt gtctgattgt tatggcttga atgtgtcctc 36720
cagaaattca tgtgttggaa acttaatccc caatgcaaca tcgttggaag gtggcaggtg 36780
tttatgtcac gaaggggagg gaggtgttta tgtcacaaag gctctattct catgaatgga 36840
ttaatgctgt tataacaagg ggatgtgagg tggcatcatt ctctcttgct ttcccctgcc 36900
cttctggctt ccaccatgtg atgatgtatt aagaaggcac ttgacagctg ctggcacctt 36960
gatcttggac ttcccacctc cagaactctg agaaaataaa tttctgttct ttataattac 37020
ccagtctgtg atattctgtt ataggagcat aaatgaaata agacaccgat gtttttctta 37080

```
tgattagatg ggggttatgt gttttggata tgatgactac agaggtaaag tgcattatca  37140
tcacattata tcaagaatat gtactatcaa catgacttat cactgttgag tttaaccttg  37200
atcacctaat tgaggtagtg tttgtcagtt tactccacta actcattttt cctcctttct  37260
gaggtgtatt atttggaagg aagtaatttt aaacagccca catttaagaa gtgggaagtt  37320
attctccacc tcctggaggg tggagtatct acataaatta ttagaatttt tctgcagggg  37380
agatttgttt attctccccc atttacttat tcaatcattt atttatttat atcagtacag  37440
actcagatat tgattttcca ctttgggtta taatctaata ctactttatt tattttattg  37500
cacaaattat gctagctttg gctactggga gctctttcat ttggctcctg aaagttgccc  37560
ctgccactgt gttttccttt ttttttgagc acttatcttt tttcttgcac taaaagatgc  37620
tcctggctca tttcatatat ttcctaccca agtcctagag tcagccattt cttcaaagag  37680
tcctgttcag atcagttttt aaacagctta gtttttacat tctctctaaa tcttcccttg  37740
tgtttgtgta tgcgattatg ttaatgcttt ttgtttagtt ggcattgaaa taggtttttt  37800
aaatcttatt tttttgacaa gtgagaccta attaaactga aaaacttgca cagtaaaaga  37860
aatcatcaat agagtaaata gacaacttag ataatgggag aaaatattca taaactatgc  37920
atctgacaaa ggtctactat ccagagactg caagaactta aattagcaag caaaaagcaa  37980
cccattaaaa aatgggcaaa ggacatgaac agacacttct taaaagaaga catacaagca  38040
gccaacaagc atgaaaaaat actcaacatc actaatcaga gaaatgcaaa tcgaaaccac  38100
aatgtgatac catctcacac tagtcagaat ggctattact aaaaagtcaa aaacaataga  38160
tgctggcgag gctgcagaga aaaggctttt atacactgtt ggtgggaata taaattagtt  38220
cagccactgt ggaaagcagt ttggagattt ctcaaagaac ttaaaacaga gctaccattt  38280
gatccagtac ccaaaggaaa ataaatagat cattataacc aaaagacaca agcattcata  38340
tgttcattgc cacactattc acaatagcaa agacatggaa tcaacctggg tgcccatcat  38400
tggtggactg gataaagaaa atgtgatata cacatataca ccatggaata ctctgcagca  38460
ttaaaaagaa taacatcatg ttctttgcag caacatggat aaagcttgga ggtcataatc  38520
gaaagaaatt aatgtgggaa tagaaaaccg aatactgcat attctcactt ataagtgaga  38580
gctaaatatt gagcacacag ggacataaac ataggaacaa tagacactgt ggactactaa  38640
agtgaggagg gagggagatg tgtgttgaaa aactacatat tggaggctgg gcatggtggc  38700
ttatgcctgt aataccagca ctttgggagg caaaggtggg aaggtcactt gagtctaagc  38760
attcgaaatc agcttgggca acatcgtgaa actctgtctc tacataaaat acgagaatta  38820
gccaggcatg gtggcacatg tctatggttc cagctaatta agtggctgag gtgggaggat  38880
ggcttgagcc catcctcaag ccatcaaggg tgcagtgagc caagattgtg ccactatact  38940
ccagcctggg tgacacagtg agaccctgtt taaaaaacaa aaacaaaact acctattgaa  39000
tactatgttc actacctggt acaatatacc catgtaacaa tcctgcgagg atttagatac  39060
aagttaccct cttatctaaa ataaaagctg aaattaaaac aaaacagaaa acagagtaag  39120
ttttaaaaaa tattaaagaa tttttttttt aatatagaga agtgcaaaca cttacaaata  39180
ggggaattta gctgtcatcc agcttcaaca atatcacctt tttgttaatc ttatttcttg  39240
tatatccgga tccacttacc cttatatccc aaacatcata ttatttcatc tataaatatt  39300
tcagcacata tctctaagta ataatatctt aaaaaacata aatattatgt agataaaaga  39360
aacaataaca atttgtttgg tgatagattg aaggtggtaa caattatttg actctttcat  39420
cacatggtgg ggtctatgtt cctatcctta aatcttggca ggctctgtgg ctacaatatg  39480
```

```
gcagaagtga aattgtacca gttttggggg ctacacctta agatcttcca cttattgcct  39540
cttagaatac tttctctggg agccttgata cacgtgtaat ttcaactacc ttgagacagc  39600
tgtggagagg catgtgttag tgctccagcc aacagtccca gctgagctta gccttctagc  39660
catatctgca aaggcaccag atgtatgggt gaagccatct tggatgatcc agaccagccc  39720
atctgccacc tcagttgaca acacgcagag cagacaaatt gtccagccta ctcctgttgc  39780
aattgttaac tcaacaaaat gtgagatata acaaaatgat tatagtttaa ttcactaagt  39840
tttggggtaa tttgttaagc agaaataaat aactaaaatg gtaggctttt aaaatttgca  39900
ttcccagtgt ttctggatga gcagtgcatc ttttgggagt gtgagttagc ctgtcgtcaa  39960
aggtcttttt gaaattgtgt tgtcccattt gccatgaaaa tatttttgat tatttcctac  40020
ctttgttctt aatatgattt attcaattat atatttatat aatgcaattt ttaataatga  40080
ctattacagc atttttgaac atttaccagt tgacttttcc aagctggtat gatctgactc  40140
tagcacgttt ctgatggaca gtccctcctc gatcagtttc tgattttacc tcaatactca  40200
gctatggtag aagagttaaa tgacctagtt tgggagtcag agttcagtta acattttggt  40260
tttgtgactt actggtagtg tgagcttgag taagtgactt agtgtttcat cccgttgcct  40320
catgtgcaaa atggggatca tcataactac cttaaaagtt tgctgtagaa gattgtatga  40380
gggaaatatg aacagaactt tgtacattgt cagctctaat atttttataa ttctttggtg  40440
ttcttgtaaa atatatgggc tcacataggt agtaattcta ttgacattca cagtaataaa  40500
aagaaaggta gcctttcttg agaaaattag ggagattttc cctagtcttt ggtccttgtt  40560
ttgactgtac tggggactct gggctttaat cttcacagag aggtgtggtg ggtgtgggtc  40620
gtggcaacat gaaggcttgt gcatactttt attcaaaaag gatgttagca gaaagaagca  40680
ccaactttcc tagcatgagg attcctgaca tgcccatctt ctgtgacacg gttgagaaag  40740
tatatgattt cccttttgcg gactggcaaa cagaagataa aagagattac aactttcccc  40800
aggattatag tagcaaggct ggaaaaaaaa tggcagaaat attcagtaca gctttttgtt  40860
agtggattcg ctccaatacc cagaccatga aggttcttta atttccccca aactatactc  40920
ttaaatgagg cctatttcag gcagagacac taatccagcc ctgaggtgga atacttcctc  40980
ctcagcgccc ttctttgatg tgtagctgat atggaactga gtgccaacat atgtttgtac  41040
aaatatattg gcaaatgtaa gcagcctact gctaattact acactctgaa cctcatgtga  41100
agtttgaatg atgcctcaag gaatttgaat gtaagaaaat aatatatata catatttttc  41160
aaatcttagc aaaaaagggt taacttcttt atggttgaaa ctggaagaca ctcgagaatt  41220
atcttgtctt ctcaaacctt tggcaataac atgtttattt aaggaactca ggtcaaacag  41280
ttgctagaaa agattaagtg ttttggacac ttttaaaata aaaaagggcc gcttaaatta  41340
aaaaaaccca aaattgctta atattttaca aatgaaaata agaacaatat aatttaaaca  41400
gatgctatac aaaacaacag agtactatag gccaaaggtc acaaattaaa gaccatttat  41460
gggctgagaa caaagctact gggttcaaaa cataaagcga atactgtggg aacttcagag  41520
gggcttgccc tgcctaaagg tattcaaatt caaataattt tggagtacta tgctggctta  41580
gcataattgg gaaggccaga tcaggctttt gtactcaacg ttgtggtcct tgatttagac  41640
aatattggtt aaaaagatgg tactttaatc agtttactac atatttcaaa ctaaaacatt  41700
atttttaaac atgaattata tgaacacatt tcttctacta attttgtaaa tattaagggt  41760
tgattttaac taaaccaaat ggagggtttt tttttaactt ttagtgatgg atatatagaa  41820
ttattctgtt gatcagcttc tgaacatctc aaattttaaa tatagaaatg ttatcagaat  41880
```

```
acttcctttt taagaatacg aaatgtttgc attctgtgga gatgtggaga aaactaaagc  41940
caaaccgaag gagtggctta atctctattt ctgtgatgaa ttgacttctg ctagtcagat  42000
gggaaaaaat tagaatgttt aatcactgtg tttaattgaa aggaatttgt aatgattcaa  42060
tttggttatc tctatatcta gatatttaga ctaatttttt tctaatttgg tttagttaca  42120
ggggagatgt ctaaattgat aatatagaaa aaacaaaagc agtgttattt ttttaaaatg  42180
taagtaacgt agtagaataa attcaactag ctaacccaat aattaaccaa ctaagtaatt  42240
tgataaaaat ttggtttagt ttcttaggac acctgtatta atgaaaagaa aaggtcgatt  42300
tgtaattagt acttaagtgt tgttatttac atggttgttt ctaaatttcc tagtgtgctt  42360
caacttagaa tttcttctta aatattttaa ataattttaa ataatttcct gaattgttat  42420
taaaaattca ctttattaaa tttctttttc cctgtagtca ggaagagtta aataaatact  42480
attaagtatg tgaatgtact tggtaaattg tacataatta gaacattgtg agtgacacca  42540
ccacctttga aatctttaag tatcccatgc tgtgatgccc atgtcttatt cttccagctc  42600
aattgctcta gtacacccac tgcaacaatt cttcaatgtc atagagacct ccagtccagg  42660
gaccctgtgt attccatcca tcagtttcct cccgtcttca tttcctttct tgttcagcgt  42720
aatgtcatgg tccatcatta ttattactcc cttgctaatg ccctaaacct ccttgctcct  42780
cttttccttc ttcacatttg actggcaaaa gctcaaccct gattgaaccc aaccatcgcc  42840
ttttcatgaa cgctgtttgg ggaaaaaatt cacacacgga ggctgactga tggctaaatt  42900
tttggtctca aacttcacat aggctcaacc aaaatctaga aattcactga ttttttttcc  42960
tcctgttttt gggacaaaat tttacacatt gtaacagagc aaaagctgct ggtggtggtg  43020
gtgctgaagc agtagggtag gagaaactta gatataaatg taatgaatgg agtcttaatt  43080
ttagatccca ttgctttagg taacttttgg gtgttttgtc ttctagatct cttcactttc  43140
tctagctcct cttcatggat gatatctaga catatggggc agctaactta attttatgat  43200
ggtgggtaag gaggcctcag atatgcttaa taaactggtc agctgctgtg tttgcggagg  43260
aggaggggtc ccctatcttt actgatagtt ggcccttggc attggtaccc actgaggtat  43320
gtccgctccc ctgtggcctt ttggaggtct tgtgtgtgca gctgtttctg aaatttgcag  43380
tcttagctgt ttgtcctggt tgcatagatc ttgtacttat gtgtcccttt tttttctggt  43440
gccggatctc ttttggttaa ctagccctct catcaccttt atgtccactc atactccaca  43500
caagctttaa gaagccagtg gcatatgggt gctattggtt ctgtgcccat tggacattgg  43560
gttctgtccc agtgagggac ttctgctaat ggtttatatc tcttctaggc tctgcctgga  43620
gaagcagtcg gctagctcta atgttcttgg gcggctctgt acctatcaga atgtttctac  43680
accctcggta ctgaagctga atgctgagaa ggaggaaagg caaagaggtt gctgtacctc  43740
ttgctcttct cctgtccccg ttattctacg gctgaattag gtggcttttt tccccttcct  43800
atgtggcagg gacttttctt gtgtcctatc ttgagttctt cagactaata gtaaaattga  43860
cggttaagcc agccggactg gcttttaata cattactgga agtttaagaa atttaaaaaa  43920
tatttttct cttgacaaac cctgttttta aaatagatgg aattgctagg gattcggctg  43980
gtgttaattg catttttcta ttcctgtgct atgtgtacta atcaccatcc tatgccccct  44040
tcacctgctc tctaagtccc ctgtagatga atgcctctga gtagaaagaa ggtcacgtct  44100
atagagatgc aaaagagaaa agcacattaa tatatatcaa aaattgttat ccttgttaca  44160
ctactaagtt tacttttcca ttctatgaga tgactacttt gtctgcttgg tccttagagc  44220
tctcattact cttccccctc tttcttaccc agttctcagc agaagacccc atctcatgaa  44280
```

tcactgagaa aaattatagt cattggagaa ctctcactgc tgagtctatc cataatctgc 44340
atctttttct tctttacaga aaagatgtaa gaagagtcaa ttctactgaa gaccaatccc 44400
tccagctttg cttgcgattc tatttcctct tatcttctaa acatttcagt ccttcccttt 44460
atcttttaca ttatgagtgt ctttttctac tgaattattc tcatcagtat aagaatatgc 44520
tgtagtattc ctctttttta ttgtagaact taataaaact ttatttattt aatttaaaaa 44580
tttttaatat ttgtgggtac ataataggtg tacatattaa tggggtacat gagatgtttt 44640
gatacaggca tgaaagatga aataatcaca tcatggaaaa tggggtatcc atcccctcaa 44700
gtattcctct tcttgaagga aaaaaaactc accccatatc ttccccaccc tcaatttact 44760
aattcctttc tctgccaccc ttcctggcta agttctttag aaaagtagtc tatatgctgt 44820
cacccttttct atgcagtttc aaaccactca aatatggctt tcttctctct accatttcac 44880
tgaaatcact tgtgccaaat ccaatgttta tgattatgct cttgtcttac ttaatttccc 44940
ggtagcattt agcatagctg attattttct cttttgggaa aaaaatttcg atgtctctta 45000
gcttccacac tcttctggct ttcttcttgt ctcattagca actcaatctc attctttact 45060
ggcttttcct cttttttttgt aattttaatt ttatttaaat tattttcaat ttcaatagtt 45120
tttggggaag aggtggtgtt tggttacatg gatacattct ttagtggtga tttctgagat 45180
tctggtgcac ccgtcacctg agcagtgtac atggtagcca tcgtgtactc ttttaaaccg 45240
caaccccacc catcctttcc cccaagtccc cagagtccat tatatcattc ttacgccttt 45300
gcatcctcat agcttagctc ctatttacaa gtgaaaacat acgatgtttg ttctcccatt 45360
cctgagttac ttcacttaga ataatgctct ccaatttcat ccaagttgat gtgaattcca 45420
ctattttatt cctttttatg gctgagtagt attttatggt atatttacat atattatata 45480
tatatgtata tatacacata attttcttta tccactggtt aattgcttga tgggcattta 45540
ggctggttcc atatttttgc aattgggaat tgtgctgcta caaacatgca tgtgcaagtg 45600
tcttttttat ataatgattt ctttttctgt gggtagaacc agtattggga ttgctggatc 45660
aaatggtagt tctactctta gttctttaag gaatctccac actgttctcc atagtggtcg 45720
taccagttta cattttctcc agcagtgtaa aagtgttcct ttcttaccac atccatgcta 45780
acatctatta ctttttgatt tttaaattat gccattcttg caggagtaag atggtattgc 45840
attgtgattt tgacttgcat ttccttgatc attagtgatg ttgagcattt tttcatatgt 45900
gtttggccat ttgtctatct tcttttgaaa attgtctgtt catgtcctta gcccactttt 45960
tgatgggatt atttgttttt tttccttgat gatttgtttg agttccttgt agattctgga 46020
tactaatcct ttgtcagatg catagtttgt gaatatattc tcccactctg tgggttgtct 46080
gtttactctg ctgattattt cttttgccgt acagaagctt tttagtttaa ttaagtccca 46140
cttatttatc tttattttttg ttgcatttgt ttttgggttc ttggtcatga actctttgcc 46200
taagccaatg tctagaagag tttttctgat gttatctcct agaattttta tggtttcagg 46260
tcttatattt aagcctttga ttcatcttga gttgattttt gtataaggtg agagatgagg 46320
atccagtttt attcttctac gtgtggcttg ccaattatcg cagcaccatt tgttgaacag 46380
ggtgacaggg tgtcttttcc tcactttact tttttgtttg ctttgttgaa gattacttgg 46440
ctgtaagtat ttgactttgt ttctgagttc tctattctgt ttcattggtc tacatgtgtg 46500
cttttatact agtaccatgc tgttttggta actatagcct tgtagtagta tagtttgaag 46560
tcaggtaaag tgatgcctcc agatttcttc tttttgctta gtcttgcttt ggctatgtgg 46620
gccctttgtt tggttccata tgaattttag agttgttttt ttctagttct gtgaagaatg 46680

```
atgatggtat tttgatggga attgcattga atttatagat tgtttttggc agtatggtca  46740
tcttcatgtt attgattcta cctatccatg agcatggtat gtgtttccat ttgttagtgt  46800
catctattgt ttctttcaac agtgttttgt agttttcctt gtagagatct ttgacgtctt  46860
tcgttaggta tattcctaag tatttttatt tttttgcagc cattgtaaaa ggggttgagt  46920
tcttgatttg attctcatct tgattcctgt tggtgtatag cagtgttact gatttatgta  46980
tgttgatttt gtatcctgaa actttgctga attcatttgt cagatctagg agctttttgg  47040
atgagtcttt agggttttct tcctatagga ccatatcatc agtgaatagc aacagtttga  47100
cttcctcttt accaatttgg atgcccttta tttctttctc ttgtctgatt gttcaggcta  47160
ggacttccag tactatgttg actagaaatg gtaaaagtgg gcatccttgt cttgttccac  47220
ttctcagagg gagtgctttc aacttttcct cattcagtat aatgttggct atgggtttgt  47280
catagatggc ttttgttacc ttaaagtatg tcctttcttt gctgattttg ctgaggattt  47340
taatcataaa gggatgctgg atttgtcaa atgctctttt ctgcatctat tacgatgatc  47400
atattatttt tgtttttaat tctgtttaat gtagtgtatc acatttattg acttgcatat  47460
gttaagccat ccctgcctcc ctggtatgaa acccacttga ccatggctta ttagcttttt  47520
gatatggtgt tggatttggt tggctagtat tttgttgagg atttttgcat ttatgtttat  47580
cagggatatt ggtttgtagt tttctttttt tgttatgacc tttcctggtt ttggtattag  47640
ggtgatactg gcttcataga ataatttagg gaggattccc tttttcttta tcttttggaa  47700
tagtgtcaat agggttggta ccaactcttc ttcgaatatc tgatagaatt cagctgtgaa  47760
tccatctggt cctgggcttt ttttgttggc aattttttta ttactgcttc aattctcact  47820
acttcttatt ggtctgttca gagtttctat ttctgtctgg tttaatctag gaaggttgaa  47880
tatttccagg aatttaccca tttcctctag gttttctagt ttgtgtgcat aacagtgttc  47940
atagtagcct tgaataatct tttgtatttc tgtagtattg gttgtaatat ctcccatttc  48000
atggcttttc ctcttaactc aaactctaaa tgttggccat cttcagggct tagtccagcc  48060
tttatttttt tttaaatatt ttttccaaag ttccctctcc caactttatg actttaaata  48120
ccacataatt agaattttcc acatttgtat ctcctcagac ttctcgtctg agctatggac  48180
tcaaacattc aaactatctt cttgatgtct ctgtttgaag gaatcacagc catcttaaac  48240
ttaacatggt taacacaatt attgatttcc tgtctctcat tccccagtaa tcctcttcag  48300
tcttccatat cttagtaata gtaccatcat cctctaggtc cttaatctgt aaatctagta  48360
gtctttctgg atttcccagc tacttctttt cagtgtcttg catggttact tttttgatg  48420
tattctttaa acagtggtgt tttggcttag catctactca cttttcattt gaatttttct  48480
ccctaatcaa ttggatctac ttctatggct tcattgtcat catatgctga tgactttctg  48540
aatttatctc taaccttgga tttgcttctg aaattgtggc ccttatattt aaatacttag  48600
tcaacatctt tatttcgatg ttccacagga aacctcaaat tttcctatcc agaatggaat  48660
ttgctacatt cccaataact catgcttcct tcttgtcccc tctctcagtg aataatatga  48720
gcatctaata gagtcacaag ctagaatcct ggataccact cttggtaagt tgtccctttt  48780
tcattcacat taaatccatc aggttttgtc acctcgatgt ctaaaatatg gcacaaattt  48840
gttaactcat cttcctttct catgaaacta ccttggaaca ggtctttcta atttttgtct  48900
agactgttgc agcagtctcc tcattttcat ttttactcac ttccattcta ttcttcaaga  48960
agtcagaatg atttctgaga aagcaaataa gaccatgtca ttgtcctgtg taaagccatt  49020
tattttaata ttatgcttca taaatctgca atcattttgt ttatccattt gtttatctat  49080
```

```
gattgtcatc cctcattggg attcatgctc catgtgaaga aggttgtgtc tgcttatctt  49140
ttgtttctta agcatcttgc acagtttccc aagcaccatt tcttaatgat aatagtaatg  49200
atgaaaaaca acaaagggac tcagtaatca acatagaggt ctggtcacca gaaatcccaa  49260
aatagtgcag ttcagttttg tactaaaatg acattttagt gaatttaaac taagacattt  49320
tagtaaataa atctagtatg gaattccatt tttcagcttt gttttcaagg gattgtgaat  49380
ctaggcacat gagtgagtag ttttccctgt tactctatat gaggcctaca gcttgctcaa  49440
gcaagttcag gaccacagct aggccctttg aagaaatcca tatgtgtaga actctaacca  49500
ggtcagacgt aagttacaga tattcttaaa gtgacttttt gtctttctgg ctggatatga  49560
tactgtagtt tctgtaaaac aaaggaggac catttagttt caaaaataca atatgggtaa  49620
atacaatata gataacttgg taataaaagg attttaattt aatttaggta tttatgttta  49680
gataccagct actagtaaaa taccacctcc ccccacaaca aacacatata ctctagtagt  49740
ttctaatgct tatagaaaaa tggacttaat gatttttgga ttaatctttc ttaattttca  49800
tttgcttttc aatcttcttt gggaaaaggg taacctgtgt ctcaactttt tatgatgatc  49860
aatttacaca tcatatatat atatattttt ggatatatac cctaatggga ttgctcggct  49920
gattggtagt tctaagttct ttgagaaatc tccaaactgc tttccacact ggccaaacta  49980
atttacattc ccaccagcaa tgtatataca catcataatt tgaatatgct atgttccaga  50040
ttagttgcca gcaagaaggg gtgagatggg ggctaagaaa aagatgatag caatataaaa  50100
agagatttga aataaatata tatatcagtt taaaaatata tatttattct gggtgatact  50160
gatgcgtcaa tgtgagttca tcaattgtgt ggtaacaatg tatcacttcg gtgggggatg  50220
ttggtaatgg ggaggcccac acatgagtgg aagcaaggga tatgtgggaa atctctgtat  50280
cttccactca tctttgctat gaacctaaga ctgctctaca gaataaagtc tattaaaaaa  50340
tatatatctt accagtggca ggggtgtggg tagagtggag agtggggcta gggagtttca  50400
gggcataagg gttaagccgt gtcttcattc agatacccca tggaaccact gaagggcttt  50460
cccaggtatc ctacagtagc atggcataca ctcaaggtta gtggagagaa ctcttaactg  50520
gtaaaatgtg tgaattctgt gtttctaggc aattatgaac accaggtaaa acaatgtcag  50580
ttctttaacc tcagaacctt tgcggagtgg tcagctaaag tgaactagac agtgactcag  50640
gaaatctaag catttctgtt tttttttct tcattatttt tgtgtcagaa acttggtggt  50700
taattgtgta gttaacccgt ggctggctgt agagggattc tattctctaa atgcaatccc  50760
atataaaatg agtcttacca gcttataaaa gaaaaagttc cctatatcat taatttttat  50820
aagtgtaatc acatcagaaa tatactaatg gagttcttta ttgaaagaaa acatatataa  50880
gaatcttctt aatataagaa taatatctgc tccatcaact gcatctcaaa atttgtgcta  50940
ggatttagca agttgtacaa agaacacaag cctttatctc aataggtctg ggttcttttc  51000
ccaattgtca ctggctgtgt gacatcaaga aaaactccta acattgcagg ggcacttttc  51060
ttatctctag aaagagttgc actagatgat gcccaagaat ttctctggct ttagaatttt  51120
ctgtttcatc ttccaaactt ggaaattcat tgattttgat gtttttatgg ttgcatgctc  51180
atattatata accaagatga ctgtgtgcta aattaatgct aatccccagg actaaataaa  51240
agttatttga aaactgtggt gcattgattg ccatctctta atgaaacttc cgggaccttg  51300
attaacctag atgttcgttt ttgttgttgg agaatctggc tgttggtatg gtatcaatat  51360
gcatggcaat aactttagaa ttattggtga gataagaaat agtttcaaaa tccatgtaac  51420
tcctcttgtg cagtgaaagg aatactaaaa ttttaaagat acattttgaa ttttggcctt  51480
```

acctttttaa tgactctgtg acattgctaa gtcacttaat ttctctgata tttaattttt 51540
tgcgtctttg aagaaaggga taatgcctgt tctgcataca ttataagtcg actataagtg 51600
aaaatagttt tataggagaa ttctctttga gttattgcaa aatgcaaaac attctaaaga 51660
ttgtagttta atcttttgcc atggcaaaga taaattactt ccaactgcta attttgggaa 51720
gcgagcaata atattttatg aatgtctctc tgggttggag acctgcagca tttgtaggaa 51780
atcacataca ggcggcatca tttgataatt ctgctatcct gatcctgctt actgcaatat 51840
ccatcagtag agtaagggta tgtctgagga atactgtatg gcactctgca ctcttcatag 51900
aagtgattac ttgttgaaac aaaggctatg gcagacacag tatcatcaat cttctgactt 51960
ggtacttcat ttctttgggt ctagtctttt ttatcctggc tctagcactt actggcatgt 52020
gaacttgtaa catgctacct aaccctgatg agcttataaa aggaaaagtt gtatagatca 52080
ttaattttta taaactaggc accagttttc ctctccctca aaaatggtag ctattgtatt 52140
tgctactctt acattattat tctctaagtg cagagatttg caggcatata catcctaaag 52200
aaagggtatt aaaagtccca aagtttataa atcactgctt tccccaaatc ctctattgcc 52260
aatgggcatt attatttagg attagagatt actgagaata acagagaccc aaaatatact 52320
gtcttaagta aaattgaaat ttatttctct gacactgaaa ggtttgtaga taagtagttt 52380
aaggctgatg tggtgggtca gttccacaga gtcctcaggg ccccagctcc gtctattgtg 52440
ttgctctttt gtgtgtggct cctaatttac caaggtcatc tcatggctca acatagttgc 52500
tctagctcca gccatcaagt ccacattcta gctagcagaa aagaggaagg gacaacagaa 52560
aaggaaaatg gtgtgcatta tttaaagaag gtccccagaa tgttgtataa aatttgtcca 52620
ctggatgaaa atgtatatac ttaccaacaa aggaggttgt gacatatagt ctgtccatgt 52680
tcatgaggaa gaggagaaca aatattggga aaaagctagc ttcttagaca caagaacaat 52740
gacagaggca tttaaaaatg tgtcccagat aattgagaaa aaaaccagca aaaaaaggaa 52800
ggggagtgaa cccgggaggc ggagcttgca gtgagccgag attgcgccac tgcagtccag 52860
cctgggcgac agagcaagac tctgtctcaa aaaaaaaaaa aaaaaaagga aggggatata 52920
tgtagctatg ttagtctgag ttaggtggtt attatgagga ttttgttgtt gttgttgtta 52980
catgtaatta tcaaacatac cgaagcctaa tttgcagtct tgagcttttg ttttttttagc 53040 tgttattgag aggaaaacaa tctcctggat tcttttctca tcctggaagt atggatgcct 53100
tctctagtaa gtaagtttat tttgctttca gtgaagcata tgtattacct ttaaaaaaac 53160
attaattata ttctgttatt tttttgacta gaaaaccata tactttaaga aggatttaat 53220
aacttggtcc ctgggtgtca atcaataaag cacgtgaata accagtgcaa agtggtcact 53280
cggctgccca aggggaggtc atccaagaat gaaatcagtg taacaacagc tgaattgcat 53340
ccttcatcaa atgcatgtaa aacagaccag aaagacatca attcccaatg ctggtatggg 53400
tggtctttct actgcatgta taatttccaa tttaacaaag gttaatacca tgttgtaatt 53460
tgaaatgtca aaataataaa tcctatgtgg gtaaactaga tggtggtttt aaaatttata 53520
atgaatattc agttgaaata gtaaagtcat ttaaatcaca tcagcagagt ttttctcttt 53580
ttcaaactag tgatacacac acacatatat atatatatat atatatatgt gtgtgtgtgt 53640
gtgtgtgtgt gtatcactag tttataccag aatagatata tattctgggt aacagctttt 53700
atgggtctga tatcagatca gataactaac atctgatacc ttgtctttta ggtcagcatg 53760
gcccagtatg attggaggca atgacatatt attaagtaaa aaattctaga tagagtgttt 53820
ccttttgaca gcttttaatc acctgttact ttctttcagt tttttattcc ttgaggtaac 53880

```
ttattttaga ggctagtttg aatatttaat ctgttcttgt cttttactgt gaatttcctt  53940
ctaaatttta attcacaata ttattcatat taaatctgtt cataagataa aatgtgttag  54000
taatttcgtc tttttaaaat tgaatttatt ttaataattt tctttaatca aaaaattaaa  54060
attccctcct aggaacaagg cacaaaaggc tcaagagctt caatttactt ctcttcttct  54120
tctttttttt ttgtcttgtt tttttgtttt gtttatctta ttttacttta agttccagga  54180
tacatgtgca gaacctgcag gtttgttaca taggtaaacg tgtgccatgg tggtttaatc  54240
cccacatgca ttagctattt gtcctgctgc tctccctccc ctccccaccc cgacaggccc  54300
tggtgtgtgt tgttgccctc cgtgtgtcca tgtgttctcg ctgttcagct tccacttatg  54360
agagagaaca tacttctctt ctttacctat ggtaaattca cttttgatgg gtgtgcttgt  54420
caatactgaa aatgttctcc attgctttta aaaaagaaat agtcacatca gcaaaatggc  54480
tacctttcat tttgggtatt tcattactct tttttggata cctgttagtt taattcattt  54540
aaacaatcat gtattgaaag gctacttggt tccaggtgtt tgccaagatt gggaaatata  54600
aacatgagtg aagtatggtt cctgaccttg agaagttcag agtctagagt ctgaactttc  54660
taatttgaat tgcttttaga aaacaaaaat agaatatcaa tcattctggg agatttaaat  54720
gatggattta agataagaaa tgggtaattt aaacataata gaaagcaatg tagagatctg  54780
ttttgtttta aatctctatc cttgtattga acttgcatgt gagttttcca tctctctata  54840
ttactaatgt tccagaagaa gccgaccttg gcaacaaaaa gatcacttta ccaccaatat  54900
attacaaaga ctgatttgga tgcaacttag aacctgtgaa aatctagtcc tcttttattt  54960
actcaaagat cctttccatt ttacggtact ttgcctataa gaatagtgtt aaaattagat  55020
gtgatatcca aatcttctga tttgggtagt ggtgcatttt cacccaaagc taaattgcaa  55080
agaaagtgga caatgatcaa gcatagatat tgatcccata tttcttaacc tttatgaatc  55140
tattatcttc caaaaatcca tttaggattt agatagaaag caggatttcc ttttgactct  55200
acagtgtata aaacacagaa catctgagaa acagaaacat ccaaccttaa tcatgttcca  55260
ctttaagtga aggtaaaagt aataaagttg tgttggtaca aatctttaat agaattttta  55320
tgtaaatagg ggattcttat gttactttaa tgcaaaatag aaagaaaaca aatgaaattt  55380
tatatgaaaa ttaaaaacct aagagtcaaa aggtagatgt atgtagaatc ctccacagtc  55440
ggcctatcaa tgaattcctt tctcattttt ctcttggtct gcattcagca gtgtcatctt  55500
ttctttcttt ctttactctc ccctttcttc tcctttgctt ccttctcagt ttcttgctcc  55560
ctttctgcca gctttttgaa aatgccatac tgtaccccac ctttccctgg ttggactcct  55620
ctgacttctg agagttcctc tggtaggaag tagtccagtg attgcctgtt gacttcacaa  55680
ggaagagttc ttaaatatgc tgttttctta gcagcttgga gaaaagcaag tgaatggctt  55740
tcatcttaga gggaaatctg tagggacaat gtgggtgcac ttccttgcat agagctaccg  55800
tttgcactgc atgggctctg aggttctttt acttcccttt tcatacctct ttaagagagg  55860
cccctagaga accaactctc tgatttttgt gcttgggaag ctcttggaaa actgatgttt  55920
ttctccctga tgtaaagtca gtagtcttag gactgaaagc ttagattcca gctttgagct  55980
ctgatttatt gttctctgat gtatgtggat ccagctagga ctttaatact tacttcagtt  56040
catttcctgc attgatttct caggtaatct caagatgccc tataaggtcc ttgaaggctc  56100
tgaaacccct gacgtcccag gcctatgcca ggtttgccct aaggaccttg gtcaatttcc  56160
tttacaacca catcccagcc cctacactcc tgatcttggt cgtccttgta ttacttggta  56220
atgctttctt tctattttat ttggacttgg cccttcagat gtcccagtgg ggtctcagca  56280
```

```
tgttctacca ctggctaata aatgaggtgc tcagtgtagt gggaaaggtg taggttatga  56340
aatcacacaa acttgtgttt gtgtcctagc tctaaacctt tctccctatg taatgtggac  56400
aattcactat tttttttttt tttttgagat ggagtctcgc tttgttgccc aggctggagt  56460
gcagtggcgt aatcttggct cactgcaagc tccacttcct aggttcacgc cattctcctg  56520
cctcagcctc ccaagtggcc gggattacag gtgcccacca ccacgcccgg ctaatttttt  56580
gtatttttag tagagatggg gtttcaccat gttagccagg atggtctcaa tctcctgacc  56640
tcgtgaccca cccgccttgg cctcccaaag tgctgggatt acagacatga gccaccgcgc  56700
ctggccaaca attcactatt taaccttagc ttccttagcc ataaaatggg cataataatt  56760
tcaatcccct gggaattgtt gtgagaatta tatgaaatat tcacgtaaat cacctgcccc  56820
tttgtctgaa agcagtggga gctcaatcaa gttgattccc tttctctcct ctgtatgtat  56880
gcatgagtgt atgtgtacaa acatgcgagt atagatgtat gcgtgtgtgt atgcatacaa  56940
gcatgcatgt atgcatgtta tcctgatgcc gcttttgtgt tctttttctg tttttctctc  57000
ctgcaagaca tgtactctga cagttttctg tattttctgg ttgtttctga gatttaagaa  57060
aacaagccat ttctgcagaa acccgcaaca aagggtaggt tgatttacat cagtatttgg  57120
tcctaccaac tcttccagaa tagaactatg ttcccttttt atgctctaca actctggaga  57180
taaagaaaca catgaaaaat aaccctagtt ctcaattcct ttagttattt ttcctggtat  57240
ccattccctt aatatttcca aatggtaggt acttcttgat gtatctattt agacaccact  57300
tattaactta cacttaacta taagatgagg agttaacttt tttcaactac cccacactcc  57360
ccttcacagt ctatcacagg ttggggtaca aactactcaa tgttttcagt attatgactt  57420
tgtagatgtt cactgaagtg aactagtaga gtactatgat aatttattct ttcttgaaca  57480
atatattttc ccctggggtt aatatttcct ggaatgaaaa acattttctg tttaatttgt  57540
ttaattttta atatatctac taaaagtcct tcccagatac agagatttgt tcatcagatc  57600
aaagcctcct attaccccac aattaaatga atcagttaat atactgctgg cacacctcca  57660
tttgttttca gtcttccaaa aatgtgttga taattcccac ccactgtttc ttctttctca  57720
ctcgttcatt cctatgccat taaaaaaatt cctttattca ttaacatgta tgtttctgag  57780
caggactgtg gggaggactg tggctggagt gggcatgttc agctggcttc cggggtttgc  57840
tcttcgtgtg gacaacagtg ctggtggctg agctccacat cggaggcctg gcacaggtca  57900
atctgtctca atgataatgc tgtgggacaa ggcttttgca gtgaactgaa gttctatccc  57960
attaactccc atctactttt tctcttgtta tttagcatta tggagactat ttactttttg  58020
tactcatttc ctgttgctgc tgcaataaaa atgaccacaa atttagtctt ttgaaacaac  58080
cgcaattttt tatcttattg ttctggaggt cagaagttta aaaagggtgg gcagagctat  58140
gtttcttctg agtgctctag gacaaatccg tttctttggt ctttccagct tttgaggcca  58200
cttatattcc tcggctcatg gccccacatc actctaactt ctacttttat tgtgacaact  58260
cctttcctga ctctgatctt ctgtcttcct ctttcatctt ttaaggaccc ttgtgattac  58320
attgggtcca catggatatc cattgtccca tttggataat atggataatc cattgtccca  58380
tttgaatata cttaacttag tcacacctgt aaagttcctt ctgccatgca agataactta  58440
ttcacaggtt tccaggattg ggatgtggac atctttgggg gccattaatt ctgcttgcca  58500
caatcttctg tactttacaa acatttgaac aaacgttatg tcttctgata tggtttggct  58560
ctgtgtcaaa tctcatctct aattgtaatt gtcatgtgtc gagggaggga cctgtaatcc  58620
ccatgtgtca ggggagggaa gtgatgggat catgggggcg atttacccta tgctcttctt  58680
```

```
gtgatggtga gtgagttctc tcacgagatg tgacggtttt ataagcactg gcatttcgct  58740
gcttgcactc actctctcct gtagcattgt gaagaagatg cctgcttccc cttttgcctt  58800
ccatcatgat tttaagttcc ttggggcctc ccctgcaacg cagaactgtg agtcaattaa  58860
accttttttt ttctttatga attacccagt ctcaggtatt tctttatagc agtgtgaaaa  58920
ctgactaata aatctcctct aaaacttctt tttaggttat cataagaatt gttttcactt  58980
gcttggtaat tgatgtggct tccagattca tcaccatcct tattgcctcc atctgctttt  59040
actccacttt accaatgtct tttttaagta tcccaaactg aacatagata tgatcagact  59100
caggaagatt caatgaagac aacatttccc tggttctgga cacctggctt ataaaacagc  59160
tcaagaattc attattttcc tgggaacatt tttgactaat atcgatcttt tcaccaacta  59220
taatccctca gttttttttc atgtaaagta ctggtgaggt tttcccatc  ctgtatttct  59280
gtaggattgt taagttttaa aaatattaat gcgctatatt caagtcctat taggggtcag  59340
aaactggaca ttgttacact taggtaagcc cagtgtcagc tgcctacatg tcctcagttc  59400
ttcagctctc tggggtcaca ttttaaattt aaacaaatta ccatgggtcc tatctcaaga  59460
gtggaggaac tcacatcttc cctcttaata tgttcaaggc ttcttgggga agttggcact  59520
atgactggtc atctctggct aatcatctat ttctactgag ctctcaactc ccaatctgca  59580
tcctatgttc cacgccactg tcactttttt gcattttgtt gtcctaggct ggatacctca  59640
atttctatct ccaccaaagt tctaccaacc caggtttata tatgtagact tttactgaag  59700
gtctgaagtt atgaaaagag atagcatgca gcttagatag taacaaaaca aaacaaaaat  59760
gaatattaga cctcagaagt atctttatca ttcttgcctc tgtgaactcc tcccagggcc  59820
cattcctggc acagagccca ggttgacatc aggctggtgg attcctcccc ttctgctctc  59880
tcaggctttc agggccaacc ttcccttctt tattttctgc tgcagagcca ggtgtcctca  59940
ttggagactt cacctttttg ggggtaaaga aactatgaag gtatttggct gaacagaaat  60000
agcttttcta cctataaagc aggggcgtac aatcttttgt cttccctggg cagcattgga  60060
agaagaaaaa ttgtcttggg ccacacataa agtacactaa tgctgacagt agctgataag  60120
ctaaaaaaaa aaaaatcaca caaaaaaaat ctcataatgt tttaagaaag tttacaaatt  60180
tgtgttgggc tgtgtgtcag aaaagacttg agtcttgcta taaagagttc catcccagga  60240
ttttaacata agaaaaaggt tcaacctttt ttccatttat ctctgtgaaa aattcatgtc  60300
cttatgctag tttattataa tttttgaaag gcgattccac tgcacagtgt ttttgttctc  60360
actcttagca ttctcatctt tttaaagcca caaatttcat agatattttt ctacattttc  60420
ctgtaattat ttaaaattaa gcggttaatt ttaaataatt aactaatttt aaataaaata  60480
attaatctta aaataggata gagaataaag agcaattcta taaactttac ttggtgttgg  60540
tactagtacc tcaataaaaa ttttggcaaa aatgccacta cttttgtggc acaaggatag  60600
aatgagaact tatgcatgtc aaatgccatg ctggattgaa gatatgcttt gctgaagaga  60660
ttttctctta ggatttgaag agattttctc ttaggacaat tttatgttct tggtgttctc  60720
tttttccttc taagatatgt ttttaacaat aaattataca tttttaaaga tttttttccc  60780
tttaaaaaca aggcaattta ggctattata tttgtcaggg atcagagatg ttgactcccc  60840
tgcaatgtaa actttcatga attagtttaa gaattaagac taaggcctgg tgcagtagct  60900
cgcacctgta gtcccagtat tttggaggcc aatgctggca gattgcttga gtccaggaat  60960
tcgagaccat ccttggccac atggtgcaac cccgtctcta caaaaaaata caaaaaaatt  61020
agctggtgtg gtggtgcacc ctgtagtctc agctatgcag gaggctgaag tgggaggatc  61080
```

```
acctgagtcc aggaagttga gggcgcaagt gagctgtgat ggcgccactg cactctagcc  61140
cgggtggcag aatgagaccc tgtctcaaaa aaaaaaaaaa agaaactcaa ggctactatt  61200
tattgcaaaa aagaaaagtg aagtgcagtt catttttgt atctgtagct ataattttta  61260
tataacatca aagtttaact ttctaatatg acctgagtag ctattttatg tgttctgtta  61320
ttacttgaat tgctcacagg tctcagtaag ttaatacata aaatattaaa tgcagattca  61380
aaatttggtc tgctcttgac tatgcagtgg aaatttataa cattttcttt catacaccct  61440
agaattgaaa tggacatagc atctttaact ctatgagagc ttataaactc cttcgttaca  61500
cagaactatt aatatatatt ttatatttat tatattttat gaaaataaca tatacatata  61560
tttaaaaact tcatatttta caaaaagcaa ttattataaa ttatcagtct caaaataaag  61620
attacaatgt gttactctga atttccagct acatgaataa tctagggtac ctgcaaggtt  61680
ttgcttccca caatgtgcat cctacagttc ttggacccac agaagtcagc ctgtataaga  61740
actgtgggat caaaatctga ccaaatacca tgaagctaaa gatatcgccc acaaaagtgg  61800
tttttctctc tttcactaag aagaggaaag gctgtttgtg tttaagtgca tcgtgggggt  61860
taaactgtgt cctcctaaaa cccccagtac tccagaatgt gaccttattt ggaagtaagt  61920
gaggtcagta aggtggtgta ttggtcaact ggtatattcc aatacgactg gtgtccttat  61980
aaaaaagaag aatttatttt tatttatttt ttttcaagac aaggtctcag tctgtcaccc  62040
aggctggaat gcagtgatgc catcacaact tgactcactg caccccttgac ctcctgggct  62100
gaagcgatcc tcttacctca gcctctgaat agctggaact aaaggtgcac gtcaccacac  62160
ccagcttatt aattattatt atttttttt ggtagaggca gggtctcact attttgccca  62220
ggctggtctc aaactcctgg actcaagtgg ttctcctgcc ttggcctccc aaagtgcttg  62280
tattacaggc atgagccact acgcctggca aaagggaaaa tttacacaca gagacagaca  62340
cacacacagg gagaatgcca tgtgaacaag aaggtagaga tcagtgtcat gtgtctataa  62400
tctaaggaat gccaaagatt gccagcaact ccctagaaga tagaggacag gtctggggca  62460
gatccttata gccctcagaa ggaatcagtc ctcccaacac tttgatcttg gactgctagg  62520
ttctagaact gtgagataac acatttctaa agccacccac tttgctaaaa tgaagacttt  62580
attaataatt tcttaactcc ctgatctatt tctaaactaa aatatggtgg gaaaacactt  62640
tatttagggg gaaattttct tactacagga agaccgttgg tcaatattaa ttaacatatt  62700
tttgtcaaat aaaccattcc ttttaaatgc caaatatcca tctggaaaag atacttctgt  62760
gtcaggaagt caaattgacg tttaccaatg agtcttgtgg ttcttcttgg aagaactgtc  62820
ttcttgtgaa tgaactgaat gtttatgaat gtggaccaga tccagaaatc agaaacgaat  62880
gccctgggaa gactggggca gcaccgactc ccacaatccg ttccaccaat tcaccctacg  62940
acacaaacta aacagcaagc aaacaaaatc ctctttggac tccacatgtt ccccccctctg  63000
ttctgttgca taaatagatt tttttataca aactatctat acacactctg cccgcttcct  63060
cttcttcctt tcattcttca acgttttcca atctggcttt atccctggca ttcaattgaa  63120
actgcccttg ccaagggtct aagactccat gccagcaaca tttccccctc atcttactcc  63180
tcccattggt agcatttggc actgttaacc atttgctcct tgctggaatg cctctctggc  63240
ttctgtgata ccatactccc cgggtcttca ccatatctta ctgaacattc ctctgtcttt  63300
gctggctctt cctgctctat ctgttcttta tttgttgttc ctttgagctt tgccgtaggt  63360
cctcctttct tttctgtttc tactgtctcc ctgggctgtc tcattcaatc tcatggattt  63420
aaatattata tataggctga tgaattttct gagttccaga cttttatatc caactaccta  63480
```

tctactcgac gtctgtattt gtaaatgtca ttgtatcttg taaacaacat cttccaaact 63540
gaattcttta ttcccatgca accaagcctt tgtttcttcc aacactttat catctcagta 63600
aaatccacca gaagtctaca agtcagccct tattcctctc ttcccctaat ttaccatcca 63660
tttctctcca tctgcattcc tgctactata gcccaggcta ccatcattta atatggaact 63720
aatttaaaca gcctctatct aatcactctt ctgcccctct tgccttcccc tccctcatta 63780
attctccaca tagtatccag aaatatctgt atatatgaaa ataggatcat ttaattctcc 63840
tgcttaaaac tcttctatga attcctattg cacttagatt aaaatccaga cctattctag 63900
tgaccttcaa ggccctctgt aaccatgtcc ctgcctccct ctctacttgt agaacagcat 63960
cctgggaccc ccattcctta ctcactgctt tccatcatac aattggcttg aatttcttga 64020
atagaccaag gctttttctg tgtcaggaca ttttcacatc ttccttctgt caaaaatgtt 64080
aacctaataa catggtataa ggaaagacat agttaaatca tattgtggac tgggccactt 64140
gggaagctct ttttgtggca gggaagttgg gatgctctcc tggtccagtc atttggggtt 64200
cagtgaagtg gagtcggcca ggtggaggat ttctaatcta tacatgtgta tggactgaaa 64260
ctatagctgg tgggtggacc tgcagcatta aagagtcctc ataagggtga tttcatgcag 64320
ataattattc cttggaaaga ggatatggtc aaaattcttt ccacttaaac cattgattcc 64380
tttgagtttt atacccattc tgaggagaat tgatttagta acatataggt gaaaaagaca 64440
tgctagaagc tgctttgcat gcaaaataat aagtgaaaat gaattgtatt aattgatgtc 64500
cctgagatta ccctttgctt ttttaaaaaa ataatgcaac ttttaaatat atattttcca 64560
atatcatagc ttttatttca gaccttttct tttgtgatca tattctcatg tcctaaactt 64620
tagtcatttg catttcatct ttaggatttt tgaaatattt ctgtctcatt tgttttagtg 64680
tgtatgtgtg agagtgtgtg tgtatttcta acttaatatt aacatctgga aaagcatgag 64740
tttgatgttt taagttacac ctttctattt ataacaaaat gcataaataa taccataaat 64800
tatttatcta ggtaccatgt aaaattgtga ttcatcagta tgtaagtacc actttttgaa 64860
aaagctatta tataccatcc ttaaacttag ccctacttag ctgacataat ttgacaacac 64920
atttacctca tttaatttg tcttatttaa gctaagatta aaaggaatta gtattttctg 64980
agcatgcacc agttgaagac atcaaagata ctatggaaag catgaagcca ggctgcaatt 65040
aaaatttgc cttatgtaac agaaaagatg taaaatatac cagtgaataa taaaggaatg 65100
tagtttacca agttatatct atctctctat atttatgttt ggagttttgc ccttattgat 65160
gaccctgtat ggaaaagact ggtcaatcct acttagcatt aatcctttgc acggggagac 65220
tactcttgga gactgagtgt attttcagtc tttacaaatg atgaactatt gaatagatca 65280
cacacacatg cagatgaacc caatttcatg tctaacagca tatattcatt ttatttcata 65340
tattaatcta tatataaaat atgaaagttg cttttcaata gaatgatgga tggctgatga 65400
tctatttatt attccttagt cttccttttg atgaactaca cctattcact actcagacaa 65460
catagttcgg ttgggacctc tggtaataga acagatcaaa gttaattgga ctacatggga 65520
attgaattga agatcgactt tgacctcatt agcacaatga tatagtcagc taaggttgta 65580
agatccaaca ctcatggaaa cactcaaagg aaaaactcat ttcaaaggga agttggatgt 65640
atggttaata taccatgcag ctttgtagat gaaagattaa aaaagaatta tagaactatc 65700
agagagcaga tcagaaagca ggatttttat ctttgcatat atttgactca gtttcccaac 65760
taatactaag tgttgggaaa atacttagga agcagggcta attcatcatg gtattagaag 65820
atacggtcag acagaatgac actgcaaact gtcgtaatca ctctacaagc atcattgaaa 65880

```
ctatgctaat tgcatctgta ccagtcacat aatgagaatg gccaatgcta tgcagtggat  65940
taagggccaa ttgtaagtgg agaaggtaag aaaaccctgc agaggcatat ttaagttatg  66000
cacattacca taatattatc acagaatgga aataaatagc aagccaacct tttctgaatg  66060
cagtaaccag atactctggc tattgttgtt tgacatggat atttaacttc agcaaaaaga  66120
ctatgttaaa tggtaaagtt aggaggaata ggatttccaa agcaacatgc tatagggggt  66180
aatggaggct gcctttattt aggaacaaga tacaagtgta tagaagtctg tggagtgtat  66240
ttggccacat ttgcagacac aggaaatagc atgagtgcag agtcatcaaa tggcaattct  66300
ctatatagtt ctgaccacat ctgaaaactt gtctttcctc tttaaagaca ggaaacttca  66360
gtttttcttc ccttccttct ctcttattcc ctgtttcctt ccttcaagac atgttattca  66420
tccctatttt tttcaaaata attttattgt tgaattcttt ctccaatata tcttgacctt  66480
gacttccctt gtttggtagc tatgagtttg tattaatgat atgctactgg taacaatggt  66540
tcacattcac agtctaggct ggacctttga gtaagttgtc tgtcttaatc agtttgggct  66600
actataacag aataccatag attgggtgac ttaaagaaca aacatttatt tctcacagtt  66660
ctggaggctg ggaagtccaa gatcaaggtg tctgcagatt tggtgtctgg taggcgccca  66720
cctcctcgtt cgtggatagc catcctctca ctatgtcctc acatggtaga aggaaggaga  66780
gcactctctg gagtctattt ttaaagggca ctaatcccac tcatgagtgc tttgcctcca  66840
tgacctaatt gcctccaaaa ggccctacct tcagctatca tcacattggg gggattagat  66900
tctaacatat aaattttggg gggacacaaa catgcagtcc atagcagtgt cggttcagca  66960
tgatttgagg aataggaatc ccctctagac tgcaggtacc cctgactgtt tacctaaaat  67020
taaactatta gagattaatt tttctattca gttaatattt attaaatggc tattgcatgc  67080
tatgccctgt gataggtaat aaaaataaaa tatgcaaaaa acaaagtata gtctttgtgt  67140
cacggcagtt ttagttaacg caatagtagc agcaattatc ttttggactt ctaggctccc  67200
attcaaaagc aaatatctct tggagtaaat atcaagactt tagccattaa cgctttagag  67260
gggatttgac ttcaatctaa gaggaaggct ctgtagaagc agcttttgac ttaggcactt  67320
ggaagctagg acactggatg agaggaaatg ctattttgct taaagcactg atttgcgggg  67380
gtgcaaaagt ggtgagggtg acttgaagac ctgatctaca tactgagaaa taagaagcta  67440
gaaccttcat ttatttgcca ttttttgccc attattattg tttagttgag gatgtgaaaa  67500
ttagatttct gagtcactga aaattcacct cagttgtcct gttttagtca ttaacattgt  67560
gttcattttt cagataatct gttatggctt ttcattttct aatgtatgct tcccaaaatt  67620
gactattttt ttgactgttt acatattaat gcatattttc aaaaactata attttatctt  67680
aagtgtgtaa gatcactata ctaacagatt tgagttagag tttgcaaaat ttttagctta  67740
tttaccattt ttaatcacaa aaatatatgc tactttgaat atttacttct ttttatacca  67800
atatctaaat aattcaagag ataaagaaat aaatagaata gaataaataa tagcaaatat  67860
gttgaattca gtgactttag atcattgaat attttgatat aaaacaatgt ttttttttag  67920
ttgataaaag cacaattgtt tgcaattata tgcttattat tttgattata ttatcttaat  67980
gagttattat cctattgtat tattttggag cccagcacaa tttgtactac gtccagctaa  68040
tcaaattggt tatttcccct gaactatggg ataggtaatc taaataaatt cacttagata  68100
ttataatcat ggtaaagatc agtagcaaac ctttacaatg ttcaaattca aggccttcat  68160
ctccatttgt cacattccac aaaacctccc cttccttctc tctgacttta ttgggactca  68220
cctactcatt cattttcttc aaacctgcct cttttttct ctcagttgac tatgttttgt  68280
```

```
caattgtacc ataaagatgt tttttcatgc tcattggttc atttccatca tctctgacac  68340

tgttataatt tagctcttta tttttttcaa ccagaaattt gcaagctctt caagtacttc  68400

ctttgccatc agtgcacctc tctgaacctg ccctgcctag agttcagctc tgataataat  68460

acttcccacc tgaaaagctt tcaggggctc tctctattgc ctacagaata aagtctcaga  68520

ccttgggttg tctttatgga cttcaacaat ccagctacaa tttacatttc caatgttatc  68580

ttccactata agttccaatt ctcatatttc tacacaccac tcccattttt accatgtatt  68640

ttaccctcta agaatttatt cccatgattt cttctatctg attgcccctt cccattctct  68700

gacctttaat gttctgaccc attccttgta aaaccacctc ccaagaaagt tttcctaccc  68760

tccagcagaa ggcaatttcc cttttctctc tcctattatt tcataaatta tgaaataatt  68820

ttatttcaga gtagctgaag ctgttctgtt agttaaatgt atccagacat gttattaatt  68880

aggtgagggc atattatgct gtggtaacaa aaaactccac caaatcttaa tggcttagct  68940

gtgctccatg ttgcagttca actttcaagg ctgcttttga cacctctatc tcaagaaatg  69000

ctttcgcagt tgtcacagca gaaggagcta catgggaatc acacaccagc tcttaagtgc  69060

ttctttctgc ctggaattga tacacatctc ttcactcata tttcattggc caaagcaagc  69120

tacctttaag tcgatagaaa agtgtaaaac ctttgaatgt gcagaaaaga gagaaccaga  69180

aatattggtg agcactatta attttttcct tcccaatctg tataccttgt ctttccttta  69240

gttgtattat ttcattgggt aggacttcca ataaaatatt ggctaagagt ggtaagagat  69300

aagagagaac atccttttg tcttgttcct gatcttaggg ggaaagcaac tattttttt  69360

ttaaccattg aatatgatat taactgtggg cttttgcaga ttctctaaaa aaaaaaaaac  69420

tcaagttgaa gaagctccta tctaatccta gtttgctgag aatttatatc ataaacggat  69480

gttgagtttt gtcaaacttt tttactacat ttacggatat gatcatatga ttttaattta  69540

ttctcttggt gagatggatt acattagcta atttctgcat gttgaaccag ccttgcatac  69600

ctagaataaa ttccacatgg tcatgatata taattcattt tgtacattgt ttgattcaat  69660

gtgttaatat tttattgagg attttcacat ctgtgttcat gagagatatt gacatatagt  69720

tttcctgtct tgtaatatct ttgtctagtt ttggtatttg ggtaatgctg atcttataga  69780

atgagttagg acgtgttccc tctgtttttta ttttcaggaa tagattatag ggaatctgtt  69840

accatttctt ccctaaatat ttggtagaat ttaccagtga aaccatcaga atctggtgct  69900

ttctgctttg gaaggtaatt aattattgat tcaatttaaa acacaaatat aggcctattt  69960

agatgattta tttccccttg tgtgagtttt cacagactgt gtctttcaag gaattggtct  70020

atttcaccta ggttatcaaa tttgtaggcc tacagttatt cataatattc cttcattatc  70080

cttttaatgt gtatgggatc tatagtgaat gttctcactt tcattcctgg tattagtaat  70140

ttgggttttc cttcttttt tcttgcttag ttggtctgga ggtttatcaa tttcattgct  70200

cctttcaaag aactagcttt tattttcatt tgttttctcg aattttttt gaaaaatttc  70260

tttgatttct gctctaattt ttattttttg tcttctgctt accttggatc taatttgttc  70320

ttatttttcc agcttcctaa gatatcttag attattgatt ttagatattt cttcttttct  70380

aataacacta ttaatttcta tcataatata tgtgaaaact atcgtagact gtacattttt  70440

gaagtcagca tttgtgattt attcttcact gtatttttct aggtcaaaga gaagcaccca  70500

taaactagtg ttttccaaac ctcagtcatt cccagtccat cttcacattt ttgccatagt  70560

cttgtgccat ttatgataat acttaactaa ttcttaaaaa ggaatcactt ttaaaaaact  70620

aaatcaacat ttttagaatg ggatttttaa tacaactata aatggaaatc aggatctctt  70680
```

```
cccatgtagg aatcttgaaa aatatatatt aaactctata aaatatttac tgaaaatatg  70740
aaatgaaaat attacttggc tactatctga agtcctctta aataccagag ttatctttgt  70800
ggtattttgg aaatcagtga aacaaataca aatgaaagag gatacaaatg tatgccaaag  70860
ttctacacca gagattttaa actttttact ttattttctt ggggttaaat ataggaactt  70920
agggtaagca ttaatagaac ggttacctta atgtgaaggg aaaaaaatat tagatttata  70980
gtaagaagac atgaatttaa atgccctgtt tttctacctc cttgctgcat gagacagaaa  71040
gttccacaga atttttgttg gtagaaagaa tcaatgatgt tcgcttgatt atattgtcag  71100
atgtaaatga gataaattac aattatgttt taaaattgtc tagttttatg ggaaaaggat  71160
tatgattctg cacagatatg cctgtatcta ccccttttata atgtagtatt caaagtgtag  71220
cataggcagt ttttttaag caacatttgt gcaacttttt tttgaaatga gtacttgacc  71280
aggggcatag gtagagttac taaatatcaa aaaacaagat tcatattaga gatcttttta  71340
atgaaaatta gtggagaaaa aatttagggt aaggactgtt gcctaggaat atatttattt  71400
ttatgatttc cttaaatacg aaaaaccaat tctttgcggg tgttcacagt tggagaatgg  71460
ttgtaagttc tacctgctat tttggtaagt caaaccaata tagtcttatt catccctttt  71520
tctattttcc aagtgttcat tttttgctcc ttttttattg ccagaatttt ctaaagagtt  71580
atttcagaat tgcatacaaa caacatgatt caccattgtt tggtaccata taagcaaaaa  71640
gccctaactg attaagtgct ttatccctta actgaaggat tgacttctga gccaccatac  71700
taagtagttg gagtaagagg taaagtaaat tagcaaatac ttcatgagcc aaatgggagt  71760
acctcataag ataaaaattt attttagtta aagttccttg aaatattttt ctaagaatca  71820
agttttaaaa aaagatacat tcaggagatt atttaataca gaagcattgg aagattttgt  71880
cctcattgat ataatgaagt cactctttgg gctggatgtc agtcactgta gtttttgagg  71940
atacagaaat gtctgcattc tgaagtgtaa acaaaggagt aaataaattt attttttaca  72000
tggcttgatg taatagtata gaatctagac atggataata gatgcaactc agtcaacatg  72060
gataaccaaa gttcttaaaa ctacgctttc aatgaacaca tatcctttga gcaagactaa  72120
taatgaggaa tgggagccag ctcctgtgat atttatgcaa ctactaaatt ctcactgaag  72180
tcaatgggag tttgcttacg taagggctgc aaactttagc ctccagagat taaaggggaa  72240
aaaaatcctt aaactctttc aacattaata ttgcctgtaa ggaatccagc catgacctaa  72300
gccatggagc tttctgaacc tagcaagtag aagggtaaac agtaaacacc agttatttta  72360
agcacaatct aatcagagtt caatgagaag caatattata tttgatctct aaggtattaa  72420
tacttgtata tcactattag acatctttat gtagtccatt atccaaacaa tggcttaagt  72480
ctgtggtatt taataaatca agtttccatg gccgtgagac tgagtgggag tggggatgaa  72540
gcctttttc ttcattttt tttcctcagg tgcaattctg tgttaatata agagaagtgt  72600
ggccttcctt ctcatagcac taaaagtgag ataatccctg tgtaagaaat cagtaagtac  72660
ggtctgctta atctagtccc agtgtgaaac tgttgacatt tgttcttttt tctatcatta  72720
tgtgactggg cctgttttgt gctggattag gcacaaatct cctatgcagc acatttggca  72780
tgttactagt agtttaactt cattaataat gtatgaagaa aatgtaatcc atgacaagga  72840
agcaaagaaa agtatttttt tttttttttg cttctcccaa atcctttgga atgagtaatt  72900
attcaacatt ttatgtttga tgttatattt tacaattcaa cttccatagt gatatttaaa  72960
aaagaaactt tggcaaatgc ttgcaaaaaa cacacctttt acaattttaa atgtgattta  73020
ctgatggcca gaacttgtta aacatagtag gaaattaaat atttattcat cttatttcat  73080
```

tttcagggcc gtaaacgctc cttctgagtc attcccaata acaagaattt ctaccagtaa 73140
agctattaac aggcatcaaa ataggggagt gctaaattaa gatgagattg taaaagcaaa 73200
taagaacata cgcagactcg cataggagtg caaatgatcg tttctgattg aaatgtttat 73260
agctaaatga gtttggctga attaaacaca aatgttccaa aagataagcc gtagctggtg 73320
cttctttttt ctgtttttta agctgcttta cagacgaaaa tggaactata tttggaacaa 73380
tgctttctgt ttttccatac tattgatatt tgtggaaagt cacaaaatgg cctaaggaag 73440
ctaagctcgc cccaagcagt ggtcacttac aagtactttt gtactctgta ctcctgtcac 73500
atttgggcga tcagagcaac agctggggag actttttcaa caaagatgag tgtcagataa 73560
tcctgatgag attccacatc caacatcttt tgtaattatg tcacattcag ctgtaatgga 73620
ataattcaag ctgaaagaac aagctttgat cctttcttaa acctttccct gtggactggc 73680
tatctaaaag atttaaagat atttctgtta caagatctag tgtttcctca gagaagtcat 73740
gcttctgaag catcgtgatc tacaagaaca atatcaagtt tgccaaacac atttctgaaa 73800
gcatcgtgtt ttggggggag gggttgtatt taatgaagat atcaataata tgctatgctt 73860
caattttcat ctaggtgatc aagattcatt ttcttgttct gtcatccaaa taggcagaca 73920
gaaaagtgat tgaaatacat tatggagatg tgtcattgca catataaagc atctgtgtgc 73980
aaattcatct tttttatgc ctgtgcttat taagttgtgt tttaatagaa actgacctag 74040
tgaaatacta gctatgttgt agaaattaaa aaataaagtc atcaagatac tagcaagttc 74100
caaatttctc atctataggg gaatttttgt gcaaaatatt tatattttac ttttattagg 74160
ttttgtatta aactaattaa acggacagat tgaacctaac acaagatttt tgcataatca 74220
tcaagattag tcatgttaaa aatcactttt acttgtttat agtaatcata tttctccaag 74280
ttatcattgt aattctttct gtattttact cttacattat ttttttttctt catttctttt 74340 tcctttctaa tcccaattat tattttttttc ctgagactaa attcgtcaca acaggaaaga 74400
atgtgatggg gaagaaaacg tagacctgat tttaattttg acttgaagaa aattattact 74460
aaaattaaaa ccagtgttag aaaataaaca ttcttcaaat ttaattttta aaagtgaatc 74520
tgtatgactt ttaaagcatg aaggtttagc tgctgtttgg tttattgagc aaagaaaaga 74580
taatcagcgt gtgaatgctc ccaaaggaaa atagcttgat ttggtagaaa tgaaaagagg 74640
caagtctgta ggactaagtg gtacaaatat taaaactatt tttgcccaaa ccagtgaagt 74700
aacctttaat gcatgtgata aaggtcatct ggaagatcat ctttcccaca gaacatttcc 74760
tctatgcccc cattagggat agcgagtgat cccagtgcta aatagaacat gctctaacct 74820
ctatttgtgt ctttagctta cactttaata gtgttttcca ttaaaattat gtatttgtaa 74880
atgaaacata attatagatg ttgttttatt tcatttaggt ctttaaatgg atgtctgatt 74940
taatcttaat attctcagct ctgaagtagg tatcattatt actattttgt agatgagaaa 75000
actgaggttc agagtgatta aaggactttc acaggtatga gacaatgctg ggactgaaaa 75060
ttggagtttc tacttgaaag tttagtactc tttctgctgt actatggttt ctttttctga 75120
tttggttaat ggtgggagag gaaacagtaa gtaatacagc cactcaaaac tattttttttc 75180 tatacattat taattttact tgtaatttga taataatttt taaaaatcta aacttattgt 75240
taagaatata ttttgtctct gttagaggga gttggctgaa gtggatggaa attgtactct 75300
gactgtgact caccaaaaat attaaaggga acagagtaga catttccgtg cttgccttta 75360
ggcctaaagt ttaggttgta actctacaga tatatattca aagggtttga atattcaatt 75420
gaatatgact caattttctc ctcctttgtt aggtttggtt atttctgatg aaacgacaag 75480

```
ttggttttta aacaagcgag aaatttagaa tattgaaaaa cctgaccact atcactgtcc  75540
tccagaagag atgttccttg ctggtgaata tgacaaaggc cagtacacat ttccccaaaa  75600
gataaaaagt ctggtgggct gacagatctt agatttttac ccggtaccca cttcaccgta  75660
tataacttta cagtcttttt ccctttattt aaaatagaca ttttatcatg cctatcattt  75720
acatattaga attgaacaca taggtcacat tcctaacaaa ttcatcaagc gagccttcct  75780
ggaaattcta ggtctctaac attacttaat tcttgggaga caaaaaattc ccacaatata  75840
taacccatat tatgtgtttt gggtttttat aagaaaataa gaaatgtgtg aattaaactt  75900
attcccttat tggcagtatt tacctagtat tttcttgata tttttccaat tcagtatttt  75960
caaagatgtt ttggggaaaa agtcctctgt attttatacc tttaaaacaa gttattggct  76020
aaaaaattag aatcttctgt ttattgcagt tgactaggtt ttaatgcttt gtgtgtgagg  76080
caaaaacacc cattttcttc attttagtca ccatataaat ccagggaagc actctagaga  76140
tgcagctgtg gttttgagga caatttcaac atagctaatg gtacggcatg ttttactttt  76200
taaacgtggc tgtagaaaaa tcactgtctt atattgcagt aactttttca tttagggagc  76260
catatattta aagatgcatt tcattcatgg gaagcacaat ggtttatatg gtttatttat  76320
tgtggagact gtctagaaaa ataagtctct gtcagtgaca catgcacaca catacgtgta  76380
tatttatata gaacacacac actttttgtg ttatgtatac acacagtttt ttttcagtta  76440
ttttaagggg tatgttaaaa acatatttta tcatttccaa gtacaagaaa agtagaataa  76500
atagtattat aattctccgt gagctcatta tttaacctca ataactatca tgataccttg  76560
tttcacgtat attccccaca ttactgaatt atttttaagc aaatcagaca taatatttca  76620
tctgtaaata ttccatatat atctctaaaa gtaagagtgc ttccttaaat atgtaaaaca  76680
atctactgac acacctgggc ttattaatca tagttgttca gatgtcatca aatttaaaag  76740
acagactttt cacatttatg gaacagtcat tacatttttg gttacttata tattttttca  76800
tttcaatcca caagagctaa taaagttaat tccctttctt aaactcacaa agtataaaat  76860
agtggttagg agtataggct tgaaaaacta gaagtcaagg ccttcccttg actttatta  76920
gctacgtggc tgggggcaca ttaataagcc tcaatttcct catcagtaaa aatgggaaca  76980
atactactta gatcatacca ttatgagtgc tgtatgattt atatatggaa agtggcctta  77040
gcttagtgcc tggtatgtag gatggtcttt gtaaatgtga actatttttt gaaaacttgg  77100
agttggaatt tgaacccagg tctgactgat cccaaagcct gcgacctttc cacagtgcca  77160
tgctcaacta gcgtggtgac aacactggca gcaccccagc ctggacactc tttaaagagt  77220
atttaatgtg tacttattaa gagtccactc cttgatagcc ccaaactttc catcatgatt  77280
ggcaagctag tgactggaat tctttagttg tggcaatcac tggtcacaga aaacagctga  77340
gcctaaacag gtggttctga aggtgagcag agccagcatg ggcatggaga aaggctgagc  77400
tgaacaccct gtgggcagag gggtctgatg ggagaaaatg agacctgaga aatgtcccct  77460
ccactcctca taaagaacaa gttgccagga gccagcattc tgcattcgtc ttaatctttt  77520
agaggagaat tgttattctg agccatgtct tagatgccac aagaatgagg ccggtctttg  77580
tgtttgattt gtgctcatga ttacagctct tgtgtcttcc aacttcattt ttttttacgt  77640
caagaaatat tttagtctag attttgctca aagcagaaca cacacatcaa gttttgagac  77700
tgattgtttg ccaaaatgtt gtggattaaa aaaaaagagc aggaatgcag cattttcacc  77760
aagctagaaa atttagcaga ttgggccaaa gactgtacaa ttattaagca cctaatacag  77820
atcaggagct gagggacata taaaagacta cttgtcccgt ccccccgggt tctcactgtg  77880
```

gtaaggagta atagctgaag caggagactt ttgttgaatc tatgttatta ttgatgttta 77940
gtgcttctac actttaaatt tttccacgat tatacaagcc tgtcctctct gtgcttcaga 78000
agcaagtgat gaaagttaat tccttcttct attaattcaa caaacatcta ttgacctctt 78060
actgtatgcc atgtactttt gaaagcactg gggccatggc aatgaacaaa acagacaaaa 78120
aatctctccc ctcatggata acatggggag atagaaaata aacaagaaaa atataaagca 78180
tgttagcaaa aaatgctaag aagaaaaata aagcagggca ggcgggttgg aaggttcaag 78240
gagagttatg aaatgttaga taaggccgac agggaaggcg ttcctgagaa ggtgacttag 78300
gaatagcgac ctgaaggaag tgaggggaca accatgcagg tgtctgagta tgaatgtttc 78360
tagacaaaag tgacagcagc tgtaaagacc caaaagcaga ctgtgatggg cacattggaa 78420
gaatggcaag gaggctcctg tgcccgagtg agggtaaaag gaaatgaagc aagggagaga 78480
atgtgtgtac gcatcgtggc cttgggggcc acagtgagga tgcttgcatt aggctattgt 78540
aggggtatga gcagagcaga ggcgtgatct tactgagact gtattagaat cacttctgtt 78600
gctgtgtaca gaacagaggg ataatttgga caaggcgcct gatatgtagt aaggcaaaat 78660
aagtgtaaat tgttattgct aattttacaa ttactgtggt ctttacctgt tgcttgactg 78720
tgcctgttga atgaattgac aaggagattc atgaaacatg acacggtcac ttattttact 78780
gaaatgacta cataaaaatg attaactctg ctacacatgt cttcttttat tttgaagtga 78840
tgatctatag agagctggct caagcggaaa aattccttgt ggttgtggtc tatctcttga 78900
gaaactttag gattaaattt ttattttgga tgcttaagtg tgtcaacttt aaattggcta 78960
taagtagtat tttttaaaaa accaacataa attgtggcta gggagatcag agtccagaat 79020
acctttagaa tattaaacaa atctatttat tgcccaaaac atatttctta acaaataaaa 79080
caacatgtaa atgtacgtat gccagttatt cacaatgaat aatacagctt cgaattaaat 79140
attagaatgt agttttctct attgttactt atagaaatac ttctgcagta tgtcctagtg 79200
gaaaaattta aaaacatttc ttatagtagg tcttgttttt aaaaattctg gattagatag 79260
tgatgctatg ccttgaatat atagtatatt ctaaacaaat tattattgcc attaaaattt 79320
aaagggcaag aataaagaat aaaggtaata ctttgtggag acaatttaat gaaccaactt 79380
ttctgtacat tttaatttaa atttatcaaa cgtttacatt tctctctgtt tctttctctc 79440 ttttttttt ttgagaccaa gtctcactat gtcaccttct ttttcaacat gaacagattt 79500
ataaatatgc tagaattcac atttcaatag aaataaatac ttgtgtatct ttatctatac 79560
ttatctatca gaccatttat tttgttgtaa caaatccaat tttaagaaag ggtggctatt 79620
agtcactgaa aacaatagtt ttctaggaga ctattccctg tagatcttca ctacactatc 79680
cattttgttt ggcatttgat gctgtctgtg aaattcaaga atttcactta cagacgcctt 79740
gtcaactttt cctcacttga ggtttcccac acccacttaa ctgtcagttg cttttcagta 79800
aagcccaaat ttaatgaact tcaatttcct agatttcact taaaggtgga tgttgagaga 79860
atgtagatgt agaaagaacc agaactggaa aactataaat ttagcaaaca cttaaacata 79920
cactatttgg tagtgttttc tagtcttcat tcttgcaata cagtttctga atccttctaa 79980
aatgggtatt ttctccttga aaagccaaaa aatgctttgc acatgtaaaa ccatttacag 80040
ccacagatga aggaattacc ttcttattcc ttgttacttg caacaatttg aagagagcat 80100
ataatagaaa aaatctttta aaaaagtatt gagatgaagg agggaaagtg taaccgtaaa 80160
gatctgtgcc tatagattca attaaacaca ttcaaaagca aattctttgg aagaaattta 80220
gattatgaaa tttgatgctg ggtcttgaca gaaacttgaa acgtagtaag gattagccca 80280

```
atggcatcag ggctgcttga attctggtga gcataggaat ttcctgaatt acttaccaaa  80340
aaacgtagct ccttggccta ccaccaggga ctctgattta gttggtctct ggtagagttt  80400
atgcagaaat catgtttgag aagccttcta gatgatttga aacaggtggt cctatgacca  80460
cactctcatg atctcttgcc tcaactggtg ccttgatgct ggtactcatt catattttgt  80520
ccttagactt gtaatttaaa atttgcctgt tttttatggt acccattatg aattggtacc  80580
tcttattctt agcagatatt tttacttttt attttttag atgataaaaa gctgtaatcc  80640
ataatctccc taaatgctgc ctccccttgc ctcagaaagt cattacatct tgctcttccc  80700
tctttcttct tcccatctta gaggataatg catttcccac ttttttctaa gattgtattt  80760
ctgcctattt tcttctattt acttgctcaa tgtctggttc tttcattgta ttcccagctc  80820
catgagaaca cagactgtga ctgttttctt gatcattgtg tcttcagaat tgagcacagg  80880
gcttatagac actcaggaaa tgtctgtgtt ctgaagccat gagagatagc ttgtcttcct  80940
tttcctacga atctatttca tctgttattt ttttacctcc agttctccag cttcttctcc  81000
ctaaactcca gaaccttacc tttgtgtatg ctctctcttt cctatggcta cttcttttta  81060
agctacaaac atacatattt ctgaaaatta aaaactacat ttcccagtgt tatggtctga  81120
atggttgtat cccctcaaaa ttcatatgtt gtagtcctaa ctcccaaggt gatagtatta  81180
ggaggtgggg cctttgggga ggtattagat catgagagca gagccccatg aatgtgatta  81240
gtgccttaga gaagaagccc aagggagctt ggtggccccg cccaccacat gaggacacag  81300
tacgaaggca ccagctatga aaaattggga ccttatcaga tagtgaatct ttggatgtct  81360
tgatctggga cttcacagat attacaactg agagaaataa attcctgttg tttattttat  81420
tttattttta ttttctttta ttgttattat actttaagtt ttagggtaca tgtgcacaat  81480
gtgcaggcta gttacatatg tatacatgtg ccatgctggt gtgctgcacc cattaactcg  81540
tcatttagca ttaggtatat ctcctaatgc tatccctccc ccctcccccc accccacaac  81600
agtccccaga gtgtgatgtt ccccttcctg tgtccatgtg ttctcattgt tcaattccca  81660
cctatgagcg agaatatgcg gtgtttggtt ttctgttctt gcaatagttt actgagaatg  81720
atgatttcca atttcatcca tgtccctaca aaggacatga actcatcatt ttttatggct  81780
gcacagtatt ccatggtgta tatgtgccac attttcttaa tccagtctat cattgttgga  81840
catttgggtt ggttccaagt ctttgctatt gtgaatagtg ccacaataaa catatgtgtg  81900
catgtgtctt tatagcagca tgatttataa tcctttgggt atatacccag taatgggatg  81960
gctgggtcaa atggtatttc tagttctaga tccctgagga atcgccacac tgacttccac  82020
aatggttgaa ctagtttaca gtcccaccaa cagtgtaaaa gtgttcctat ttctccacat  82080
cctctccagc acctgttgtt tcctgacttt ttaatgattg ccattctaac tggtgtgaga  82140
tggtatctca ttgtggtttt gatttgcatt tctctgatgg ccagtgatga tgagcatttt  82200
ttcatgtgtt ttttggctgc ataaatgtct tcttttgaga agtgtctgtt gatgtccttt  82260
gcccactttt tgatggggct atttgttttt ttcttgtaaa tttgtttgag ttcattgtag  82320
attctggata ttagcccttt gtcagatgag taggttgcaa aaattttctc caattttgta  82380
ggttgcctgt tcactctgat ggtagtttct tttgctgtgc agaagctctt tagtttaatt  82440
agatcccatt tgtcaatttt ggctttggtt gccattgctt ttggtgtttt agacatgaag  82500
tccttgccca tgcctatgtc ctgaatggta atgcctaggt tttcttctag ggtttttatg  82560
gttttaggtc taacgtttaa gtctttaatc catcttgaat taatttttgt ataaggtgta  82620
aggaagggat ccagtttcat ctttctacat atggctagcc agttttccca gcaccattta  82680
```

```
ttaaataggg aatcctttcc ccattgcttg tttttctcag gtttgtcaaa gatcagatag  82740
ttgtagatat gtggcgttat ttctgagggc tctgttctgt tccattgatc tatatctctg  82800
ttttggtacc agtaccatgc tgttttggtt actgtagcct tgtagtatag tttgaagtca  82860
ggtagcgtga tgcctccagc tttgttcttt tggcttagga ttgacttggc gatgcggggt  82920
ctttttggt tccatatgaa ctttaaagta gtttttcca attctgtgaa ggaagtcatt  82980
ggtagcttga tggggttggc attgaatcta taaattacct tgggcagtat ggccatttcc  83040
acgatattga ttcttcctac ccatgagcat ggaatgttct tccatttgtt tgtatcctct  83100
tttatttcct tgagcagtgg tttgtagttc tccttgaaga ggtccttcat atcccttgta  83160
agttggattc ctaggtattt tattctcttt gaagcaattg tgaatgggag ttcactcatg  83220
atttggctct ctgtctgtta ttggtgtata agaatgcttg tgatttttgt acattgattt  83280
tgtatcctga gattttgttg aagttgccta tcagcttaag gagattttgg gctgagagga  83340
tggggttttc tagataaaca atcatgtcat ctggaaacag ggacaatgtg acttcctctt  83400
ttcataattg aataccctt atttccttct cctgcctgat tgccctggcc agaacttcca  83460
acactatgtt gtataggagt ggtgagagag ggcatccctg tcttatgcca gttttcaaag  83520
ggaatgcttc cagtttttgc ccattcagta tgatattggc tgtgggtttg tcatacatag  83580
ctcttattat tttgagatat gtcccatcaa tacctaattt attgagagtt tttatcatga  83640
agggttgttg aattttgtca aaggcctttt ctgcacctat tgagataatc atgcggtttt  83700
tttctttggt tctgtttata ttctggatta catttattga tttgtgtata ttgaaccatc  83760
cttgcctccc aggtatgaag cccacttgat catggtggag aagctttttg atgtgctgct  83820
ggattcagtt tgccagtatt ttattgagga tttttgcatc aatgttcatc aaggatattg  83880
gtctaaaatt ctctttttg gttgtgtctc tgcccggctt tggtatcagg atggtgctgg  83940
cctcataaaa tgagttaggg aggattccct ctttttctat tgattggaat agttttagaa  84000
ggaatggtac caattcctcc ttgaacctct ggtagaattc ggctgtgaat ccatctggtc  84060
ctggactctt tttggttggt aagctattga ttattgccac aatttcacag cctgttattg  84120
gtctattcag agattcaact tcttcctggt ttagtcttgg gagggtgtat gtgtcgagga  84180
atttatccat ttcttctaga ttttctagtt tatttgtgta gaggtgtttg tagtattctc  84240
tgatggtagt ttgtatttct gtggggtcgg tggtgatatc ccctttatca ttttttattg  84300
catctatttg attcttctct gtttcttctt ttgttagtct tgctagtggt ctatcagttt  84360
tgttgatcct ttcaaaaaac cagctcctgg attcattaat tttttgaagg gtttttttgtg  84420
tctctatttc cttcagttct tctctgattt tagttatttc ttgccttctg ctagcttttg  84480
aatgtgtttg ctcttgcttt tctagttctt ttaattgtga tgttagggtg tcaattttgg  84540
atctttcctg ctttctcttg tgggcattta gtgctataaa tttccatcta cacactgctt  84600
tgaatgtgtc ccagagattc tggtatgttg tgtctctgtt ctccttggtt tcaaagaaca  84660
tctttatttc tgccttcatt tcattatgta cccagtagtc attcaggagc aggttgttca  84720
gtttccatgt agttgagcgg ttttgagtga gtttcttaat cctgagttct agtttgattg  84780
cactgtggtc tgagagacag tttgttataa tttctgttct tttacatttg ctgaggagtg  84840
ctttacttcc aactatgtgg tcaattttgg aataggtgtg gtgtggtgct gaaaaaaatg  84900
tatattctgt tgatttgggg tggagagttc tgtagatgtc tattaggtct gcttggtgca  84960
gagctgagtt caattcctgg gtattcttgt taactttctg tcacgttgat ctgtctaatg  85020
ttgacagtgg ggtgttaaag tctcccatta ttattgtgtg ggagtctaag tctctttgta  85080
```

ggtcactcag gacttgcttt atgaaactgg gtgctcctgt attgggtgca tatatattta 85140
ggatagttag ctcttcttgt tgaattgatc cctttaccat tatgtaatgg ccttctttgt 85200
ctcttttgat ctttgttggt ttaaagtctg ttttatcaga gactaggatt gcaacccctg 85260 ccttttttg ttttccattt gctcgataga tcttcctcca tccttttatt ttgagcctat 85320
gtgtgtctct gcacatgaga tgggtttcct gaatacagca cactgatggg tcttgactct 85380
ttatccaatt ttccagtctg tgtcttttaa ttggagcatt tagtccattt tcatttaaag 85440
ttaatattgt tatgtgtgaa tgtgatcctg tcgttttgat gttggctggt tattttgctc 85500
gttagttgat gcagtttctt cctagcctcg atggtcttta caatttggca tgattttgca 85560
gtggctggta ccggttgttc ctttccatgt ttagtgcttc cttcaggagt tcttttaggg 85620
caggcctggt ggtgacaaaa tctctcagca tttgcttgtc tgtaaagtat tttatttctc 85680
cttcgcttat gaagcttagt ttggctggat atgaaattct gggttgaaaa ttctttagga 85740
atgttgaata ttggccccca ctctcttctc gcttgtagag tttctgccaa gagatctgct 85800
gttagtctga tgggcttccc tttgtgggta acctgacctt tctctctggc tgcccttaac 85860
attttttcct tcatttcaac tttgatgaat ctgacaatta tgtgtcttgg ggttgctctt 85920
ctcgaggaat atctttgtgg cattctctgt atttcctgaa tctgaatgtt ggcctgcctt 85980
gctagattga ggaagttctc ctggataata tcctgcagag tgttttccaa cttggttcca 86040
tcctgcctgt cactttcagg taccccaatc agacgtagat ttggtctttt cacatagtcc 86100
catatttctt ggaggctttg tttgtttctt tttattcttt tttctctaaa cttctcttct 86160
cacttcattt cattcatttc atcttccatc actgataccc tttcttccag ttgatcgcat 86220
cagctcctga ggcttctgca ttcttcacat agttctcgag ccttggcttt cagatccatc 86280
agctccttta agcacttctc tgtattggtt attctagtta tacattcgtc taaatttttt 86340
tcaaagtttt caacttgttt gcctttggtt tgaatttcct cctgtagctc ggagtagttt 86400
gatcgtctga agccttcttc tctcaactca tcaaagtcat tctccgtcca gctttgttcc 86460
gttgctggtg aggaactgcg ttcctttgga ggaggagagg cgctctgctt tttagagttt 86520
ccagattttc tgctccgttt tttccccatc tttgtggttt tatctacttt tggtctttga 86580
tgatggtgat gtacagatga gattttggtg tggatgtcct ttctgtttgt tagttttcct 86640
tctaacagac aggaccctca gctgcaggtc tgttggagtt tgctagaggt ccactccaga 86700
ccctgtttgc ctgggtaaca gctgcggtgg ctgcagaaca gcggattttt gtgaaccatg 86760
aatgctgctg tctgatcgtt cctctggaag ttttgtctca gaggagtacc cggccgtgtg 86820
aggtgtcagt ctgcccctac tggggggtgc ctcccagtta ggctgcttgg gggtcagggg 86880
tcagggaccc tcttgaggag gcagtctgcc tgttctcaga tctccagctg cgtgctggga 86940
caaccactgc tctcttcaaa gctgtcagac agggacattt aagtctgcag aggttactgc 87000
tgtctttttg tttgtctgtg ccctgccccc agagatggag cctatagagg caggcaggcc 87060
tccttgagct gtgttgggct ccacccagtt caagcttcct ggctgctttg tttacctaag 87120
caagcctggg caatggtggg cgcccctccc ccagcctcgc tgccaccttg cagtttggtc 87180
tcagactgct gtgctagcaa tcagtgagac tccataggcg taggaccctc tgagccatgt 87240
gcgggatata atgtcctggt gcgctgtttt ttaagccggt cggaaaagcc cagtattagg 87300
gtaggagtga cccgattttc caggtgccat ctgtcacccc tttctttgac taggaaacgg 87360
aactccctga ccccttgcgc ttcctgagtg aggcaatgcc tcgccctgct tcggctcatg 87420
cacggtgcac tgcacccact gacctgcacc cactgtctgg cactccctag tgagatgaac 87480
ccagtacctc agatggaaat gcagaaatca cctgtcttct gcgttgctca ctctgggagc 87540
tgtagaccag agctgttcct attcggccat cttggctgct tcccgccaaa tttctgttgt 87600
ctataagcaa cccagtttat gctattttgt tatagaaacc tgaatagact aagtgactca 87660
gtttcttatg ctatgtagtg tctttgttca gtaaaaacag ttagcgatgt cctgctattg 87720
atattgaaaa aaggttgagt tattttcctt ctttcagtgg acatttggag gtctatacaa 87780
agctgtaagg ggcaagaggt acatgggcca gccgtaaagt ttgtttattc aaatggagct 87840
tgttgatctg tcatattttt caagttgagc tactctgcca gggcaacatt ctactgtatt 87900
caaatcagct gttttggaat tggtacacct gctagtgtct gtttctgaac actgaatgag 87960
ttgccataag ggagaaaata taattctctt catcaactag aaaatataat tcaaagtagc 88020
aataagatct gtaagatacc tacaatcaat gtaataaaga acacatttat tttatgtgga 88080
aaaatttaaa actgtactaa agataaataa taataatctt tagtaaactg tacgaaagga 88140
aataaataat aatctttctg attagagaga catttcatgc ttctggctgg aatgacttaa 88200
tattgtgaaa ataccacgta cttcttgaat taatctataa attcaatata atttcaatca 88260
aaatatcagt tatatttttc gtgtactggg aagaataatt gttcacaaat aataaattta 88320
aatttaataa caataaaaag tatacgtggg tgaatcttgc ttgctctatc aaatattgag 88380
aaattagccc aagaacagac aaactgaccg acaaaatgga ataaaaagtg caaagacaga 88440
ttcgtgtgta tgtgtaaata tatttaattt acaataaaat gacactgcaa gtcaaggggg 88500
aaaagatgga ttattaggaa aatgttggga aaactggttt accatatgca gaaagataaa 88560
cttgattgct aactaacagc attcaaaagt agactctaga tgtgacaagt aaaactatac 88620
agttaacaga agaaacagta gaagaaagcc tttgatccta gagaatgatt tctcagactt 88680
tcctggagaa tgatttctag aactttcaaa gaacaaactg taaggcaaat gttggtgaat 88740
ttgtttatat ctaaactaat gatttctaat taatgaatgg aaaatgttaa gagctaacaa 88800
aatgggtgca tctatatgtt caagatatta atatctaaaa acggtaaata tctagaatat 88860
ataagaaata cttgcaaatt aataaggaaa agacaacaat ctcaacagaa aaatacataa 88920
agcataagaa taagcaatgt acaaatattt taagaaacac aaaataatgc actttttttg 88980
gcaagaaaac acacaatgca aaatcttaaa gacattagaa tgcctgtgga ggggaatttt 89040
aatatttaaa aatagttatg taccatacta gattttggat attgaagaca gaaatgaatt 89100
taattcctcc atgttcagct atgctaagca ataatgtttg aggaaaaaaa aacacatcct 89160
aatagccata aattagatta taatagaaat cagtaggagg ccgtggcacc tgtctagata 89220
tgtgctgctg aatacctgga cttgggtggt ggcaagggaa tggagtgatg ggtcagcagg 89280
cttttgtatt ggcatggatg tttgagggaa tgaaataaat aaataaacat gagttttaaa 89340
gccaagtgaa ggtccaattt ccagtagtac tgcttagaat catttgaact aattgttcaa 89400
ctaaaaatgt tggataaact ttaaaaaaat tcttaaaatg taaacaactt ggcaagacat 89460
aaagccattt cagatcaaaa tgtataattc ctttatccca ctgtgactcc caatctactg 89520
atcctaccca catttcagtg tccctcaccc ccatgatatc ctaattttcc tctttgatta 89580
cttaaattgc atagacaatt aatataaatc actcccttgt atatttcctt gattcctttg 89640
tccttcttgg gttttactat agtggcttgg ctcaacttaa ttaaacccaa gtttctcccc 89700
ctatacttgt gtagctgagc atggttgatg caaaacataa aacatacaac cacattgaat 89760
ggcatcactt taaatttaac gttatcaagc aaacatactt tctgtcccta gtccattcat 89820
atggactagg tacccactca cctggatgac tatttcacaa ctttctttct tttcaaaatt 89880

```
ccagtccctt tcctcatttt caattttagc tgattgactt tttttaaaat gagacattta  89940
gaacaatcta gagagaactt cccaacacca tgtttgatca tcagcattac attcctttac  90000
tcttccttcc cccctcaatg aaatatacat gcttttatca aaagccaatc cctctatttg  90060
tgccgtagat gtgatccctt ctcacctttt ccatgacatt tctccagcaa ttctccccac  90120
tgcttcttat gacatcaatt tttcacttta ctgaagtatt ctcctttagc atacaaatct  90180
gctgttattt cttccatatg aaacaatatg aacaagcttt tctcgaaaca gttctgccat  90240
ccagcacgat ttttgtcccc tttgcaacaa agccccttga aggagttgtc tatacttctt  90300
gttttcactt ccattcctca cattctctct taacccattc taatcagtta ggcttctact  90360
gccctcccct atggtctcca atggcctcta ctttgctaaa gactagttct tgcccctcat  90420
tttagtcttg acccatcagt aacatttact tctgattatt gattgttcaa ttctttttaa  90480
catatgcttt cttttggctt ctaggacatc acacactcct tttccctcct gctttgctgg  90540
tcttctattc ctctgtcttc ttcactggtt ttttcttttt tctcgtatat tttagagttg  90600
gaaagtatcc tagagtgttt tcgttttttt ctcttttttc tttgtactca ctatctcagt  90660
gatcccgttc tcatctgatt ttgaggcctt gaataccatc tgtatgttta tgactcccaa  90720
atttatatct tccgctcaat ctctttccaa ttagctactt gatattttta cttgtacatc  90780
tgatagatta ttttaaactc aacatattaa aaacagaact tctgaaacct tccacactgt  90840
caaacaaaca tataaaaagt ataacaatac tactttggtt gatgacaact caggccataa  90900
gcctttgtct aatatttgac tattctctga ctcttatacc ccacatccca tactttatta  90960
attgcattgg aaattcagtt tccatctatg taaagctcca tgttgatctg ctgcaaggat  91020
agttgtgggc cccagtgcaa taaaaatgtg gggctcctga tagggaaggg aagtcaatga  91080
ttccttctta cgggtccttc ttctaatcca tggtgaacag atgaccctcc atagattgtc  91140
gcctcctctc tcagatgtgc ttggtacccg gattgggagt ggtaagaggc tcttgccaaa  91200
ttgtccatga aatgctctgt gttgctgcca gcctagagta gagaatcact gccttgatct  91260
gccctaagat atcacgtggt gtgcacccaa cactgaccct ctctgtgctt gcatccaggc  91320
cctcttgggg ctggaaggta aacaacagaa tgtgagtctt tccttgccga aggtgagggt  91380
gttagtggtc acagggatgg tgtagggagg aggaggctgg acagggccta ggtggccaag  91440
aacccatatt aagttggtgg gaaggtggag aaatggtagg aggaggctat ccatgaatga  91500
gtttccaacc acctgtgcat gctcccttgt cccatcaaac ttcacttaaa aatgcaaatt  91560
cagatgatca gattcaatgg ataatcttag ccaagttatt taacttctct aagcctgttt  91620
tccttagatc atcatttcaa tatggtggct gcagagtact aaattgcaaa tgcagggctt  91680
ttttgagcat tgagtcttgt gtgactgcat tgattacgct cccatgaagc cagccctgat  91740
ctggtgatat tgcctagcca aaaataagac tccatttaat gattgccttt tgcctttctt  91800
actggtactt ctgacttctc ttccttctga ttgcccaatt ggcatctttt ctaggctgtc  91860
aaattttacc cagagcctcc aggatttgtg atgacttcga agaaggtttg gactctgatc  91920
tccgatcttc agttttcaga acccagttag ttatgagtta gggatggtct tttttttttg  91980
cacgtaacac ttaaaagcat gaattttgaa gacaactaga ccagagttta agtcctgtgt  92040
ttgctcttac ttgatgggtg aacttgggca agttatttaa cctcgctaag gcttgctttc  92100
cttagatcat tcatttagaa gactgtgtgg ttaagagtgt atgctgtagg cagtctttaa  92160
cctctctgtg cctcagtttc ttcctctgaa aatgggaatg ataatactac ctaccctata  92220
ggattgtatt gaagattcag tgagttagta catgctaaag tacttggaaa atgctcagaa  92280
```

```
caggctggca ccattgcaag ggtttagtaa atgctaacta ttctattcat ttattcattg  92340
aaaaaatgtt tatgtagcac ttatactgtt ccatgcatac agtttctcat ctaatgagta  92400
gtattataga taaatatcta caaataaagt gagacttgtt aaatgcttag caccatgact  92460
gtcactttgt ataatcttaa caaatgttag ctattacaat tataaccaat aatgataatt  92520
attaagttgt tagccagaag aaagatatct tggttatagc tgtttgatgg taatgagagg  92580
tgaaagctgc gtggtaaaaa acatattcaa agaatatcct agtcctattc cttgaggaca  92640
ttctattttt ccatgcagag tgagcagcat agatctcaga tgacaacttg gtctccctac  92700
catttgatca agataaaatt gaattggacc ccctatctca taacctgcat acaccattag  92760
acctcccaag atttcttcaa aagatccacc caaggattta tgctttcata atcctctttt  92820
cttgtgagtg gttttttccc agcaacatgt ctaacaagga aagagaccac agatctaggt  92880
tttctaaaag aataccctca cattagtgaa aaacatagaa tttagtgtat attttgcagg  92940
agggcagaag aagcgttgat tacatggcac atggtagaac aaacaattat taaactccat  93000
gttagtgatt cttgttcttc taaacccctc tgttactctg ctgccatact gggcattttt  93060
tcccttcttt attgagcacc tccttccttt cacattgtct cttatccact ccaggaatcc  93120
cccaattttc ctggaaaata attggatgtt ttctggctta cactcccaaa cttatattta  93180
gacatttatc aagtgctcaa ctcatcaatg gccttctagt aatataattc attcttcaga  93240
gaaaattcag tggtgaaata tttccttatt atatttgctt tatatgtttg gcaatatgta  93300
ttccttcatt tacgtgttta tttgaaaagt atctgttgaa tgcaaccttt ggttcaggca  93360
ttaggctttt agtaatatga tgggagtccc tgacctcatg ggtatttaat taaaaagtta  93420
aaacatagat atacatatct atatcataca ctgacattgc tttggtgtta tagcatacat  93480
tttaaaagag ccttgtcaga attaaacttt gtttttcagc tactctgtac tcactctctg  93540
gtcctcccac ttagatctag gaaccgagta aggactggca gtatatgcaa tggggagtag  93600
tggctggaag gtgagtctcc agatgacatc cgggatctag tgccttcatt tctctgatga  93660
agccatgcaa ataaccataa gagaaaaagt taattgaggt gatgagtgga tgaagagagt  93720
gagtcatggt taccaagaat aaaagtgctg agttgttgat gaggtacaga aataattagt  93780
aacatattta caattgctga catttcctaa ctactttcag ctggttcttt ggtgtggact  93840
gtatgaaact taataattgg tactcattta atcttaagta gggtccaaaa tgttcttctg  93900
cttggtctga ttctttcttc ttttgttcaa actcctttga tagacaaaca gaggaaagag  93960
aaggaggcaa ctgttccaag atagattctt ccccaataca gaaaagagag acaagaaaaa  94020
tcataatttt caatgccata tatttgtatg taatgcagac caaacttctt gtttaaaaat  94080
gataaagtaa gtcatgctta taaggctcat ggcttggtgt tttctcagca agaaaaacag  94140
atccaaaggt tgatatagtc tagaggatct actagattga tcttaaaatg aaaaactata  94200
taatgctaaa gaacaatgtt agaaaatcgt ctagataaaa agtagttcct ttctaaataa  94260
aaaagctact tcccacatac gttctcttga ttatgctcca aattctaggt cctaaataca  94320
attcaataaa tatatgaaca ataagcgttg aaatggaaga cgagcaatca ataatttatc  94380
atagcccatt tacatgatct tgtagagtat gaacccagat atattgtttc cactaatcta  94440
tggtactatc ttaatgaact aagaggagat atacagattc agtacgttag gccttcaaat  94500
aacattttta aagcttcctt tttcttagtt tattgcaaaa ggaaatattg gttcctcctg  94560
aatagatgta gtggttagat aaatttcagc actcaagaga ccaaaaaaaa aggccatgag  94620
agaaaatatc tttcttagac tcacttaagc ttgttatctt ttggctgttg cctgtattct  94680
```

```
tttgcattct ttagccacat tggttattca aacacagtga attaaagcca ttagttttag  94740
ttttgatgat cttgtataga aggttagttg atacggggtt ttgcatgtaa aatcagggtt  94800
agctgatatt cattctataa attcagcatt ttgtgagaat tttgatggag tcttaaagcc  94860
ctttttaaat atttcattga attgatagga gtcttgtgta agtaaagaaa ctctattccc  94920
aagctgatcc actgatttgt ggacttgtca cttggtagta gatacttgtt tttggcatca  94980
catatccatt tacccttcat ctgggtaata agaggttaat gtttatttag aaatcaattt  95040
cttccctatt tttagctaca cagttagaat tgactccact actgatccta catgtgtggt  95100
ttgtgagttc aggcttgact cagagcttct ccttctggcc atgataatca gcatgaacat  95160
atgattcggt cagagacaag aagacacaaa gagaattttg caggtgattg tgagaaattt  95220
tttttcctat tggacttaaa tcgagtggga taaaatcaac aagaaaaatg cagagctcag  95280
taatgtagaa aaactttgtc ctatgacgtt gcttcagccc tgaatccagc cagacatgcc  95340
cccaaccagt cttaccttta gacttttcaa ttacaggagc caatacattt cctttttggt  95400
taagccaaat ataggttggg ctttctctca cttgcaacca aaagagttct cattgacatg  95460
ggcttcttct ttatcttctt cttttttaa ttctaagaca aacttgagtg aatctgtttg  95520
gatggtggct tgcctatcat tgttttcatc ttacccaagt tgaccacacc cacagagaca  95580
tgctctgtta ttttcagttt actcagatga ttttttttta acataaagaa ttttctgcat  95640
aaagaaaagc tttacaatgg tgctttgagt tgaattgtgt ggtctctgca tctcccttat  95700
ttgcatgtgg aagtcctaat ttctagtgct tcagtgtggc cttatttgaa gggtctttac  95760
agaagtaatc cagttgaaat gacatcatta gggtaggccc taatccaata tgactggcat  95820
tcttataaaa aggggaaatt tgaatacaga cacacataca gggagaatgc catgcgaaga  95880
tgccggaaga agatggccat ctgcaagccc aggagggagg cctgaaacag cacgttccct  95940
cacagccctc agaagaaaac aaccctgtgg ataccttgat cctgaacttc tagactgtgg  96000
aactgagaga caataatttt ccattgttta agccatctaa tgtgtgatac tttattacag  96060
caacgctggc aaatgcatac aattggcaaa agggactcgc attaaaacct gagtgagtaa  96120
ataaaaagaa gtacaatttt atttgattta atttgataga gcattcacta caagttgttg  96180
ttatttgtag agctagaaat ggattaagaa agcacttggg aaaatcaagg atggcaaagt  96240
tataaactaa ataaaggaag agattcaatg tatttaatat tcaaagctga tttcagggaa  96300
gattgctttt ggcaagaaaa tgaatgcgcc atatttacag catgtgtggc aatttctatg  96360
tttctatact tcgatattta gaaaattaat gtaatgtgat atggcatttc atgctttctt  96420
aaaatatttc aaaacatata tttttctgca aatccttcaa taaaaaaact aagaaatttc  96480
agaataatcc caatgtttat acattttcat tgctgccttt ctttaaaatc tgtcataaaa  96540
taatcattaa aaattattac aattttcttg aattataatt gtcctaaacc acttactttc  96600
ttttatggaa ctacaagaaa aaatataaaa acgccagtta aactcttact taaagccaaa  96660
cccctttaca tttaaattct ggactaatag ccaaggattt agattcagag gttggctaat  96720
tacaagaaag aaaacagaac tctagtgaaa ggtatcccta tcatttacat acatgtttat  96780
attaatatgt gtatatatat gtatatccac acagacacaa agtattatat aaggtttgtt  96840
ttaaaatgaa tatatttgat ttgaaaggct aaaaaagatt acagatctca gaatgttttg  96900
tcacagaata gatatgatac ctccaaatta agtggacaaa tttttaagta gcctgatcta  96960
tgaaaactat ataaatgtaa actttttctt actagatatt acataaaatg acagacaact  97020
ctttaatttt cttaaaactc tgacacattt tacagttgtc tgtcttggtg ttggatgaag  97080
```

gagcaaagag aatgctgttt tacagaggtt acatttctcc tactatatga cagagatttt 97140
aaaaaaagta ttgtcctttt gccctccctc ttcaaagagt gaaatcctac tcataagcaa 97200
aaattgattt tttaaaaata aaagacgtta ttgtttgccc tttctaccag aactgcatga 97260
tattgccatg gtctcaattt atactccata tggtttgtag gaatatttca tataaagtat 97320
ttgtgggaat tcttaggaaa aagatgtttt gccaatagac aataaaatac tcttcagttt 97380
ccaaatttag agatcaaaag ttttatgtga ttcgttgcct ctagcatcta ttctatttca 97440
tggtttgtca tattctaaca ttttgcatta tttaaaaaaa tctttcttag aatgaggctg 97500
aataaagcat gcagaattgt ctgcttggaa attgtacaca tagcattaaa caacttttta 97560
acacgttgtt gtgtgcttaa ttcctcgata atctcatcct aattatttac tgctttacat 97620
ctttttattt tttaattttt taaaattaat acatagtatt ttgcatatgt atgagctaca 97680
tgtgagtatt tgttacctgc atagaatatg taacaatcaa gtcagggtgt ctggggtgta 97740
acttaccttg agttcttact tttatgtctt agtaatattc aagtcctctt ttctagctac 97800
cttaaaatat acagtatatt attactaact atagtcaccc tactctgctt tagaacattg 97860
gaacgtatta gtacttctgt ctgtttacat ccatttaaga acctgtcttc atccccctct 97920
ccccaacctt catacccgtt cccagcctct atcctccacc tcccgttctt ttgtgttacc 97980
cagggcagta cacaacttca aaggatatag cctgtgttaa attggaggac acacacacaa 98040
gaacaacaac actttaagga aaagtgttct ttcactagcg gcttctgagt cttattaaag 98100
gaaaatgaag tttctatata aaatgctaga tacccaccac aatttctttc atgtgaatta 98160
cacttgtttt tggtatatct tgtgtgtgta tgtgtgtgtg tgtgtgtgta tgcacacacc 98220
ctttgtaaat ttgggttaca gaggcagaaa tcaaaaggtc aaacaacagc tagtaatttc 98280
tcactctgta tattcttatc acatttctca aaaagactgt actgttctat gtgatattga 98340
tcttgattat ttctgtgaac acattttctt agttaataat atgcagaatt ctgactctat 98400
tgtatctctt ctcttcattt ttgagaattt tagtgccaga aaggacattt attttatcca 98460
gctgcaaact taaataagct cttcatttct ctaggtcact gatggcaaat gttaaacaaa 98520
tttacatttg ggattttcta ttcatttccc acccggttga cactgagcca gtgataacca 98580
ctcaatagct gtgcagccct caatagtatg tgtgacccat actgtgtttc cagttcattg 98640
atgactctat catgctgggc taaatctaaa atcttgctaa agtcatgaga gatcatatct 98700
actgttttcc ctttgtgtcc caagagtgac ttcctttgaa aaaatgtgaa aaagagtttt 98760
cactgtagtc agtctagatg ttaaaacttt atttgagcac gagtttctgt aaaatagaac 98820
ttgaagatcc tgtaaagtta aaacatatag gcacactttt tcttcctggt cactttgggc 98880
ctgttctgta gcagtgtctg cccataattg gtatagtaaa ctgttctcta gttatgagct 98940
tcttatcaag ctctcaggag tgcattgatt ctatttttgg ttaattttta attatttata 99000
cttatgtcac taagctgatt aaagtggaga attaacctca agcttagccg agtggcagct 99060
tctctcagtc aaagacaagg atactgactg gttgtcagaa tatttgggtt ctcttgtcaa 99120
ttaccaccca aagctacatg ttctccagga agatccttta cctttatatc agtttcatca 99180
tctgaaaggt gaagataaca atatgtattt tactgaacat gaagggcttt cccaactatc 99240
aaatgagata aaatatatgt aagttgtttt aacactctaa atatttgaat tatttactta 99300
ataacatatt tgcatttttt taggattcat atattagtaa catatttttc aaaataatac 99360
cttaaacaat atgtttcacc atgataaaca tttccagatt ctgattatat attttctact 99420
ttatggctga ggctatggtt taaaaatata ttgtgtgata tattgctaat aaattaaaat 99480

```
tttttattc atatgaattg gattgaaaag aaatgaaagc aagtatttca gtaattcaag  99540
ataaaaacta ctcccatcca aactctccaa atttcttttg tgtatttgaa attgacttgg  99600
aggaccaaag aactgatatt ttgatgttgc acataaagga atggaacaat aacatcaaat  99660
tgtacttctg ttgaaaatat atatgtgaaa ttaaatgttt ttgtataatt aaattgtttt  99720
gtaaaaaatt ttaatcttct attatttgtg ttttagtcaa attaaagtgt gtgtgtatac  99780
catatccaga gaatgtattt cctctgaagt gatcaggaga tttcatttat ttccctatgt  99840
taccttggag aaaattactt ttagaatagg taaaatgtaa ataaggggta gtgaaattaa  99900
atttttactt gcctatgact tttcctacta tttactttat atcttatatt gtttaaacaa  99960
gttaagtggg gaagaatagg aattattttg ggaacagcag agcaggtgaa ggtgtagggt 100020
ttgggcagct ggtaagactt taacattttt atccttcaag tgtactagcc accttaaaat 100080
tgcaaaatca cacttgccta gagcttggta atcatcatat gttaaagaaa catacttgac 100140
atcaacctga gatcttttct ttatttaata atcttaaatt ttgcttgaat ttgagttaat 100200
ttttcattga aaatttatat ctattttctt catctgttat gatttttttt ctgaaagtga 100260
cattgtctct gttgataaat ctggaaataa aaatgttaag accagcaatg gctatttcta 100320
agtttattct atagggaagc agaaataata gcttgggatt tataattact tctgaaataa 100380
cttcatcctc tgaatactgt taatttttc tttttttgtt ttttattttt attgagacag 100440
ggtctccctc tgtcgcccag gctggagtgc agtggctgga tcatggctca ctgtagcctt 100500
ggcctcctgg gctcgaatga ttctctcagc tcagcttccc aagtagctgg gactacaggt 100560
gcgcactacc atgcccggct aattttttat ttttattttt agtacagatg gggtctccc 100620
tatgttgccc aggctggtct tgaactcctg ggctcaagca atcctcctgc ttaaactcca 100680
aaagtgctgg gtttacaggt gtgagtcaat tcaccttggc agtattttct acattctcac 100740
ttacgagcac ttcattgcag tcataccatt ggaccatgag taatcttata aatgacatac 100800
attattttac agtcctatta aaattgttta ctttctattt tagggaaata tttcataaat 100860
gattatttca aatcaaagaa cttagtgaac agagtaacat atctaaaaat atgaaactcc 100920
aggatgctgc cttctaaggg ttgagcaact aatatgttat ttatgttact actttgagct 100980
ttctgttggg attttcataa tttagtatta tatattgtag aacaaaaatt agatggacaa 101040
gcactctctt ggtccatgta atttattttt catcttattt cagtagcttt gtagaggact 101100
atggttacaa taataataaa aataaactaa tctgaaacaa ttttaaagat gtaaagtttt 101160
ccagagcatc aaaagcacgt tctgatagtc tacaaccact ctaggtggtg tggaaatgta 101220
tataaacaga taaacaagtt ttgcatctgg gactttataa tttaaagtgg caggaaatga 101280
aagaaacagg taggtaacag aaaaacatgg tattgatgtt gaatatgttt tcctacaggt 101340
gtgtgtgtgt gtacgtgtac gtttggaagg tgaagaacat agtggggaga caggaagctc 101400
agtactcagg cagatcagcc agataccgtc catgttgcaa ctaagttccc atcaacacca 101460
ggcaaggata aacaatacta gggttatgga tgataactct agtcatttta aatagtattt 101520
tttcctaatt attagctgaa taattagagg gaatataagt ttcccttggg tgtcctccta 101580
gatgctgaag ctagtcacta agcagggtgc tgagagctgg atgcaggatc caagggccat 101640
cacgctggac ccgtcttcac tcatgcccct tagctgaagt gctcagatcc acacatatca 101700
ccggccagtg aaaacaggaa tagccaattg gacagcctac acatggttac ccatggctcc 101760
aagtgcaagt gctccaaatt ataatgagga agctgcatct tcttttctga cctagccatg 101820
ctgtgttatc tcccctacat tcttttggtt gtgactcaaa aacccaccca gattcaagag 101880
```

```
gttaggatat aggctccatt tcttcttctt ttttaataac ttcaactttt tagattcaag 101940
ggtcgtacat atgcaggttt gttacacagg tgcattgtgt gatgctgagg tttagggaat 102000
ggatgatccc atcatccagg tggttatcac agtacccaat aggtagtttt tctacccgtg 102060
cttctctccc tccctgccat agtagtccac agtgcctatt gttcccatgt ttatgtctat 102120
acgtactcag tgcttagctc cctgttccca tgtttatgtc tgtatgtact cagtgcttag 102180
ctccctgttc ccgtgtttat gtctatatgt actcaatgct tagttttaaa tgagaacacg 102240
tggtatttgg ttttttgttc ctgtattaat tcatttagga taatggcctc cagctgcatc 102300
catgttgctg caaagtacat gatttcattc ttttttttata gctgcatagt atcccatggt 102360
gtatatgtgc cacattttct ttatctagtc cactgttgat gggcatctag gttgattcca 102420
catctttact attgtgcagc aatgaacata ggggtgcata tgtctttttt tttaaacaac 102480
ttattttcct ttggatatat acccaataat gggattgttg gattgaatga tagttctgtt 102540
ttaagttctt tgagaaatct ccaaactgct ttccacagtg gctgaactaa tttacattcc 102600
cattaagaat gtataagcat tctgctttct ctgtaacctt gccaacacgt gttgtgtttt 102660
tggcttttta ataatagcca ttctgactca tgtgagatgg tatatcattg tggttttgat 102720
ttgcatttct ctgataatga gtgatgagaa gcagttttcc atatgtttgt tggccgctta 102780
tgtgtctttt gagaagtgtc tgttaatgtc ctttcccatt tttaaatagg gctgtttgtt 102840
tttttgcttg atgatttgtg taagttcctt atagaccctg gatattagac ctttgttgga 102900
tgcatggttt gtgaatattt tctcccattc tgtaggttgt ctgtttagtc tgttgatggt 102960
ttcttttgct gtgtgaagtc tctttagttt aattaggtcc cacttgtcga tttttgtttt 103020
tgttgcaatg acttttggga acctagtcat aaattctttg ccaaggtcaa tgtcaagaag 103080
agtatttcct aggttgtctt ctaggatttt tatagtttga gcagacttca cttcttaaag 103140
ggagacatat caaggtcaca ttgtatatga gacatgggat gggaaatatt atagccatct 103200
ttggaaaacg tgatgtacta tggagcttat gtaagtattt atatgcactc acatctgagg 103260
taatctcttt cagtctcata aatttaatta aatgccatat acaaactaat gagttccaag 103320
tctatatctc cagtcctgac ttccgccctg agttctagat ctatatattc aactgcctac 103380
ttgagatttc cactgaatgt tatggcagag atttttagtt gtctcacaac atccaatctt 103440
attctacagt gttataattt tggatgaaca catggtaact cagaataaag cttatcattt 103500
acccctaccc tcactcctga tgtttggtgt agttatgtca caaaattttg gctaagagga 103560
taaaagggag tgctgttgga cagcttctga gaccctttgc tcattcttct acctttctcc 103620
attctgatgc ttggactaga gcttaatctt gaactaggag atgatgtcca cactccagat 103680
ctcatagaga agaaagttgg aatgattttc ttcctccagg ctcttatgcg gaagagatta 103740
aaaactctat cttatttaag ctacctaact tacagttaaa cctaatcatt tcagactgga 103800
catggcaaaa cagaactcct aatttccctc tgttaatctg cctgttactt ggatgtcttc 103860
atattcgtaa atcacaccca tattcactca attgcttaga aatctaggag ttaccactaa 103920
ttccttcctt tctcttggag tccacatata tgacacatgt aaatcccaac atctctacct 103980
ttaaaaacct aactacttct actatcatgg tttaagccga catcatcttt tacttaaact 104040
actcctgtcc ctaactgtgt ctctgcttcc acttttgctt ccttataacc cataaataca 104100
tcagattata tcactagctg cttcaaaacc atctactggc tttctgtcac acttgggaag 104160
acatcttaaa ggcttaccat ggtcaaagaa tcctacacca tgtaagacct gggtatctcg 104220
aatcccatct cctacctgtc tcctccttgc tcactccatt cccttcccag tgatcttctt 104280
```

gttgtgcctt aaatattcct gcatcaaggc ctttgcaaat gcagttcttt ctgcctgata 104340
ctccctcaaa tttctacttg gttcactcct ttactttctt aaaacttctg cttggatggt 104400
acattgtcag aatgagcttt cttgactatt ctttctaaaa cttcactcta ctctctatca 104460
ctctccactt cttacccagt gttatttcat ttattgctac ttaatgtgta tgtggtagat 104520
gctgtgatgt gccacacaaa tttctcccct tcagaactga agtacacatt cctccagcta 104580
cttggagtgt tggtggtact tcttagctga atgtcccact gagtcctgtt agccatgaaa 104640
ctcttagcct tgatggaaga ctgttgcctt gcccatcttc acttcccctt tctggaggca 104700
gcacacatct actggctgtt gatgtggaag aataaaagcc tggccatttt gcttcaatgg 104760
agagccactc tgaagagccg cttcagcttc agagctcccc atgggacctg ctaaggctcc 104820
tgtggagact catcacagcc catcttctcc ctttgccact cctgcttaat ttacttctcc 104880
ctcagcactt cataggaatg ggctctgaga gtgcttctta gtaaatgtca gtctcctccc 104940
tgaagaaaat aacctaggac acatattttt acttgtctct tgtttattgt tgatatctcc 105000
cagtagaatg caatctcaat gagggcaagg atttttatc agttttgttt gctactgaat 105060
cccagtacct agaacacaga gcttcaaaaa tatttaataa ataaatggcc ttgtttagga 105120
tgacaaaact agtaatcctt gaagctagag ttcaaactaa atttggaatt cagagctgtt 105180
cctctctcac actataagtg gaatgcaggg tttctcaaca gaagaaccag ataatcttgg 105240
accagataat tttttattgt gggagcactc ctgtgcctta taggatgctt agcaacatcc 105300
ctggcctctg cctactagat gcctgtagca ttcccacctc acccccaagt tgtgataaca 105360
aaaactgtct gcaggtattg acaggtattc ctcgggggca aaattgtgcc caattgaaaa 105420
tcactggcct acggtggttt tgactgattg gcaataatat tccactcact aatattaaaa 105480
agttctaata gtagttcatg tttcctgctg aaagtttgtt tctttggttg tttcacatcc 105540
ataaatacac tttaatggag atctgatttc acagagtcat gtgaataact actgttttta 105600
caaatgggga tggctagcat gattttcagg gctgatgtga gtgaagccac tgggtaacag 105660
aaagaaacac atatgcactg ttataattag tgtgtctgtt ttaggctgca tatcagttta 105720
cagagctttg cccatgtgtg ttgaagacaa aagaaagact ttaggaatga gaatccagca 105780
atgaattgta ggatattttt gtcaaggtaa attaatcttc cttttgcttt catccttttg 105840
tttcaattca ttcttattaa actttcatag aaaatatcct gtgtttttgt attatcatcc 105900
atactacctt cttttattga aaaatccata aagtaaaggg aatcagtttt catgctgtct 105960
ttgaaaacac cgggcactat gcttcagaat tatttttgtt gcttctgctg atgataatgg 106020
ttacactata taacctcatg ccagatataa atagtgaagt gacaattata ctgcatacaa 106080
tggaatgtat caccgttgct tttggcttca cggagtcctc tgtattcaca caaaagagtg 106140
aagctactta caggattttc ggaaaaaaat gatgtacttt tccaaagaat ggtgggagaa 106200
ggatatcctt tctcattagt caccagaaat gtgcttcctc cttccatgtc aaaggagaag 106260
tagaattggg tgttttaatt tagtgattct tttgatgttt tctgggggat agaatttcca 106320
tttctttctg attttgtatc aaccttgaat gtggaattaa aatagcaaat ctctactttg 106380
tattttatat ataaataaaa attctacata ttacatatgt agctgatatt aatatgtatt 106440
atatacacaa tataatttta ttacatatta tattattaat aatatatata tttccttttt 106500
tcctcattag ttgggtatga ctttgatcaa gttatttaat cattttatgt ctcggtttcc 106560
tcatgcgtaa aataggaata agaatagaat ttatctcata aagttgtttt ggacatggca 106620
tgaatataat gcataggtac ttagaatatt atacacagtg tatacactca ataaacctag 106680
caattgttaa tattatattc tttctctctc tctttctata tatatgcaca cacacataac 106740
tatgattttt aatttatact acataggttt attgaatatt aattacgtgc catgatttta 106800
ctaggtgagc attagaaaca tagtggtaga caagtttact ttggtccttc tgtcacagag 106860
catacattcc aatgaggatg acaaaccaaa accaatttca taaacaaata aaaaataact 106920
gcaattcata agagccaaga tagaaaccag gtagagaata aagcagccag ggtagagaat 106980
aaggagggta agggtgagag gcctcttagg tgctcaggga atgcctctct gagaaagtgg 107040
tgtcagagct gagactggag ggcttgtgtt atgtggcctc atggctgtgg atgaatgagt 107100
acagttatca tggatttgcc tgaccaaatg caggtgacat atcttccata gctcttgtta 107160
ttctccatat cccttttgcc atcacaatgg gaaatggggc ttagaaatat atacagacac 107220
tttctcacca attgacttaa ctgggggcta accattaagt agtgaatccc ccagaccact 107280
cacttttggt tagggtttga gttattttga gttagggttc atggaagtca tttgggatgt 107340
gaaaatgcaa tcaggttttt tttttttttt ttttttgaga cggagtctcg ctctgtcacc 107400
agtctggagt gcagtggtgc gatctcggct cactgcaagc tccgcctcct gggttcacgc 107460
cattctcctg cctcagcctc ccgagtagct gggactacag gcgcccgcca ccacacccgg 107520
ctaatttaat ttttttgtat ttttagtaga gacggggttt caccgtgtta gccaggatgg 107580
tcttgatctc ctgacctcat gatccgcccg cctcggcctc ccaaagtgct gggattacag 107640
gcgtgagtta ccgcacccgg cctatgcaat caggtatttg taataatgaa agcagtaatt 107700
cagaaatatg ttaagcctga caaaagtctt ttcttgctgg cagctgcagc tgtctgggtc 107760
cctagaggtt catcttactt actgaaatgt ggtttttaat tttaaaccaa gaaaaacaaa 107820
actccaatgt atttgatttt tcaaaagaaa aagttattta acaagtcaaa atgaaagtaa 107880
tatatgcata aagagtacag aaagtttaat atgagaacta aaactcacct ttttcttcag 107940
gccaccactc cttgtcccca gtgatctctt caagggtaac cacttagatt cttagtaatt 108000
tttatagaaa atttagcatg gatatcatac atctgtgtgt gtgtgtgtgt gtgtgtgtgt 108060
gtgtgtgtgt gtgcattcca agtcttcaca aatggggttg tattataaat actgatatat 108120
acctggctct ttcacttaat cagaaggcta agtgaccatc tgtttgagtc cctagaaata 108180
tactgttttt ttatgattgt acaatgtctt tttttatgac agtatcacaa aatattgtat 108240
tttagtctta tcaataagtc tttggattat tttcctgatt atttttatta taaataattc 108300
tgtaaagaac attctagtca gtgggaatat tatctgttca gtaggctcaa tttctaacaa 108360
tggaatcgct gagtcaaaga atgtttattc attgttgatt ttgatcatta ctaaatttta 108420
ccaatctgta aggtgaaaac ttatatgtga tttgaatttt ttttactttt gattcagatt 108480 gataccttttt gctgattact tgtcatttta ttttcatttc tttgaattgc ttatttacat 108540
taattgatca gttttttatt atcttttttc tggtcctttt cttactaatt tgtacaagca 108600
ttgtataaat tagaaaatta gctctcaact gtcaaaatat gatgccaacc ttttcttttt 108660
tgttattgat cttttaactt tctatttttt ggcatttttc ttaatagttc cttggttttg 108720
tgtcatgttt aggaaggcct ttcatattac aaaattaaag aaatatttcc ccatgttttc 108780
ttttgataca tttatggttt cattttgtaa ttcaaaattt cagatccatc tggaatttat 108840
tttggcataa ggagtcattt ccttttcaaa atgatgaagc agttgtcacc atattattta 108900
ttgaataata tgttaatgac tcattattac tctaataaag tgtatggctt agatttcgga 108960
atcagaaata actaaattca aatgttggtg tgaatgttct tttgttagat ttaatatagg 109020
cttaatagtg tagagtcaca atatcttaac tgaagctctt ggcaccacat gcattatact 109080
tcactatgaa ggatctctac ctgcattccc tggttgaacc tgctaattag gaggtttaca 109140
gggtgtcagg tcatggtggc tgtcatctct tcctattggt atccactgaa atccccatat 109200
ttcataaggt ttctggttgt tgatctactt agatctcttt ccaagccctg aatagtcttc 109260
attctctcag atactctcag ctctcattct ctcagctact tctgaacccc ttcccttgcg 109320
caggacatat ttctctattc ttctgaatct ttatgggtgg gactatgggg aactttctgc 109380
agttatctca gacccctatt gcccagaatt tccatgcagc catctttatt acagtgttcc 109440
ctgtggcagg ctggtgtctg gggatattct gtgaggctta ccgcctctct gacctccgcc 109500
catggtatct ctcccttctc agatccacta aagttatctg gaggctccag tcttatcaac 109560
catcctcttg ttcagacacc cagagcatct caaaccccgt ttttaccttt tgcatgctcc 109620
tcttctttcc gtcccagtgg caaacttcag ctctgtctgg ggatggctgg gtaggaaaaa 109680
ctggttctga gaaacttacc attaaagatc tttttgtcct atgcctggat atcagccttt 109740
ggtaatccaa aggcaaggat ttaattcttt tgttctcttc actaaagtat caaccctacc 109800
ctaaagcaag agacatctca aagtctttga tagggaagag acacaggtta agaaggaatc 109860
actgaagaga aagcacatta gttaatatgt tggaattcta gtcctctatg ttactatgat 109920
attcaatact atagaaaaac caactttcag agttaaaaaa aaagattaaa caaagccaaa 109980
tttattactt ttccaggttt aataaaacaa ttttaagggg tttcatagtc atcattataa 110040
aaaatgtcaa catagccatt caatgaactt agttggactt tagccaattg gtgaatatta 110100
taaatacctg caaatatgtt tcattattag gtgttgccat cttggccctg cttcctacag 110160
agttataaat tctctcatca ttgactcctg gtccacagaa tatctttgtt atacctaata 110220
gaaacacccc taggtatcca ttattgtgat gtatttttcc ttttctcctc cagcattcca 110280
atatcctggt ctctcatagt caaaattttc tattgggaga aagcaattga agggctgcct 110340
taattattca gatttatttt tccttgaaat gtattttgaa gattttgatt ttggcagtaa 110400
tgaatttcat acgaacattt tactggttat caaaataatt tgcaagaacc aactagggcc 110460
ataatgttga ataaaaagta tttaaaatat tctatagtac attaagattt ttcacttgaa 110520
attattatgc agtatgaaat ggataatttt tgactgcttg aaaatatttc agtcactaaa 110580
ctaagtttag atttagattt cccaaagcca agaaaatgtt aacatgatgt tccacctaca 110640
attttaggag gaagtctata taattcttga atttaaatgt ggatcactaa ttatagttat 110700
aacactaaat tattcctgag tgggtttgtt tagtattcaa atgtcatccc agaggaggaa 110760
tcttttatct atagagctgt catagataag caatataatt cgaaccctct ttctaactaa 110820
aatttatttt taacttgaaa gaacacatca cactgcccac ccacttactc actgagaatt 110880
gtgccagtgt gtggaatccc tgctacaaaa ttagctaaat tattttgcca ggaattcagg 110940
gtaagctaag ttcattttgg accttgtcca acaaaattta tttagagtta atactagaga 111000
agaatctcac ttgaaaacat ttcacctata tgtatgcggt gtcttggtag acagggtgcc 111060
tgaggacagt ggcatagcaa ctttccagtg aggtaattta atttgttaaa ttaaataatt 111120
agatttattc ctcatgttgc cttggggtga tgaggaggag ttaaggacat ggagaaaaaa 111180
gggcacagta aattttggtg gttattttta agtctgatta atgatgtttt aactgcaggt 111240
catagattta gccgatggac tttcgcaatt caggaaaact gtcagagaag actcattctc 111300
actgaaggtt catttaggtt gtcagtagca aagaaaaaga tattgtacga agctgccttg 111360
gaggcactcg cataaaaatt atgttaccat ttatctatag ttgcattgag ttattcttat 111420
aaactgatga tactaccaac ccaaattgac aattcttgag aatacacaca cacacacgca 111480
catgaaaagt tttcataaaa atgctgtttg ataatttgtg tcctgttatc tctaacaagt 111540
aaacaggtaa aaataaaata ccttcatgcg gtgaagaagt ataaactgaa aaatagactc 111600
ctattttgaa acctagaaaa aagttgtgct ttaaactttt ctctgtcaaa tgagaattgc 111660
ttaattctta tacttaagga acgtgggaaa tgaaaaggca gaatgtatag tgttggtcct 111720
ttgatggaat ttctgagaaa aaacaaacta ttccagatga tgactaaatc acatagtttt 111780
aaatcttctg tagattttta atggtttttt ttcaaaaacg catattgttc aatataataa 111840
atatttgtag agtcaggaaa atgacaaatt ctttcttcct aacaatttta caatgaaaag 111900
taatggtagt ccaactaccg aaaattctaa gaaatttgtg gctttcagtt gtgactatga 111960
caaagaaagt gactacagaa tgtgtcacat tccatcaaag tcactcaggg ctttgttact 112020
ctttaaaaat gcttcttggt ggattcacaa atgtgcagta tgatacaaaa aagaaaaaaa 112080
tcacaccagt tagtatcttt gctagagttt tgtagaaatt taagattatg ataatcccca 112140
ccattcatcc ttttgaacca caaaattata gaaacttgat ttatactcta cagtatattt 112200
tttgatggct taaagtatag aatgcaactt atttatctgt gattcttcta gaagggtagg 112260
gaagagaaat cattttaaaa agtgtatcag aaaccaagct gagaagagtt gaggagcaca 112320
tctgggctgg attcacgtct atgtaattca ctgtgagaat tcccattgaa ttacacagga 112380
caataattag acccagagaa acagatcagt acttttctaa cttaacattt ttatcgtcat 112440
ttcccccacc acacacactc ttttaagtag ttatttgcag gcttaccaat gataattttt 112500
aagtatttga atatgttaaa ttaaatattc agttatgata gttaagtaaa taaagctgtt 112560
gagttctgtc ttgcatgtac gactcccttt ctgactttca taaacattca gaagactcca 112620
gctcattcag agaattttca ctaagaattt atttgctttt taaaatacag aaaagtcata 112680
aaatagaaaa agtttaggca aagacttccc tttgcctgct tgggtggatg aatgaatgaa 112740
ctagtgcatc acactgactg cctgctctgt gtcaggttct acttgaggcc ccagatacta 112800
gcaagccctc caggttctca cagtctaatg agatgtagca atgtaaacag ctacttttta 112860
tatgatgtga aaaaacagaa gtattaatga aatgctgtgg gaacataaac taactaggga 112920
gtagtaattc tgccttggtg gtacttgggt tttgattttg atcagagaaa attagaacag 112980
gtaatattta aggtagtttt gaagaatgag taaaattttc cagaaagttt ggggaatgta 113040
attcctggta gagggaagcc tgtgaataaa tgcagtggca ggagcattca cagtgtgaga 113100
ttctaaccgg tgtggacatg tagagagtca agtgtgaggc gatgaaggga gtgagagagg 113160
agtaggtagc atggggacct ggaaggtagg tggaggccag atgaggaggt tctatcctca 113220
gcattttttt cctctgtcct ctaggctcct tacctatttt gggtcatgga cctcttaggg 113280
cagtggtttg caaaattcat tgcgtattag aatcacctac ggagatttaa aaaatcgttc 113340
agaaacctag gccacatccc atagagcctc tgggaatgag atccaggact caataattta 113400
aaaatctcca gatgctttca gtgtaaaata gtgcttctca gagtgtggtc ccatgatcag 113460
cagcattagt atcagccaag aacttggtaa aaatgccaat tcccagacca aaattcagac 113520
ctagtgaatt tgaaactatg atggggtcca gcaatctgtg ttttaaaaag ctctccagga 113580
ggttttcatg tatgctaaag tttgagagtc actgtcatag agaatctaat gaagctgata 113640
gtttttccag aacatgtacc gcatgttgaa ttttaaacat aattctaggt ggtagatgga 113700
aattccctct gatccctttc cattttctcc cccaaatcct ggaatccagg ttaagaattc 113760
tttctctggg cagtgagtgc cactgacaat atttcagtaa aagagggaca ggagaaactt 113820
tggttataga atgatgactg ctgtaattta aacaatgaaa tggaatgggg agaggctgaa 113880
gttaaccaca tcatgcagga ggttttggga ttataaaata aaatagaaca tggtgacaca 113940
gaggttgtgt gtggtgatcg aaagggaaca gaaaatgatt ccaaggtttc taacttgagc 114000
tcagagtgaa tgaaaactac ttgggagagg gactataaaa agagaaggct tggaggcaaa 114060
taatggtaat tactggacat gtatggggag tgcattaaaa acaggtctag agcttagttg 114120
agagatgtag gttgtggata actatatagc cacatatata aacaggtaga tgtagaccat 114180
ttctcatcct ctgttgacat tttgggtctg ctaattcttc attttagagg gatattttgt 114240
gcattttaag ctatttattg gcattccagc tctctatcca ctagatgcca gcagccaata 114300
ccctctgcag tgatgacaac caaaaatgtc ttcagacatt gcctaatgtc ttttggtggc 114360
aaaatcatcc cccattgaga accacaggtg taaatgaaac ctggcgagta gatgagatta 114420
ttattgacta agtggagggc aagtggtgaa ggaggatcca ttaagtgttc ataaagattg 114480
ggagaaagtg gcatcaagac agcacaaaaa ggctgagttc cccaaagaag gtggttgggt 114540
atcaaacact acccaggaga ataagaattg agaagaggcc tttggatttg gtgatccggg 114600
gattattgtg aaacagattc aatagacagc tattgaagag tgacgtgaaa gtgacactgc 114660
aggaggtgga agaataaaca agaaaaagtg gagattgcga atctagatta cttctctaag 114720
ggattggtta ggaaaagata gaagaggaga aagaggcaaa aagaataggg agattgctta 114780
ttttaggaca taagagacta gcaaacatgg tggactgata gggaagtgcc agtgtttcca 114840
gataaatata gagctttagg ctggcccaga atcttttctt tactaagagc tcaaaataca 114900
gataatatta attatgaagg agagtatgga aatataaatt atagcagcaa catattgaat 114960
aattgcaaca agtataggtg ttgcttattt catgtctatc atctaactat taatttttac 115020
cagataaaac tagtacatta gggaatacat ttaatctaca atacaggaaa gtcctgttga 115080
tatgattttg cctgtgggct gggtgactgt attagtagtg atgattttct tttttctttt 115140
ttagcttctg tctttaatct tttcttttgc ttcttcataa ccagcatgag tgcaggggac 115200
acacatacca tttggtacaa gccttatttg tcttgccttg ggtctggaac cacttttgca 115260
gtaacacatt tagaaaagag aaatcaagag caaaaaaggc ttcaatatag tttatttttt 115320
tttgccagta actttcttgt tgcacaacta ttatatatga aattattctt tctaaacatg 115380
tgtgtgtgtg tgtgtgtgtg tgtgcacgta ctcatgtgtt tcagttccca ggttcttttc 115440
atggctgcac aacttagctg caaggcctta ggtgccttat ttattctttc cagatttcat 115500
gtccatcatc tgcacaatga gcagggggga atctatgtgc tttgaggttg tttctggctt 115560
taaaattcta taattgtatg attttctttc tgcattatct ttgtttggtg agagcttgcc 115620
ttaatctgat ctattccaga gcaaaatctc tcaggttgac ttgaagcttt aatttttact 115680
ctggttttca caccttttg tttattaggt cataagtaat gagctctgaa tgcttaagaa 115740
cctgttcaag ttcacattag tagcttatca gggttgtaga tagagtgaaa acaaattcgg 115800
gctttcctat tttctcattg cagtatttaa atccaggaga acatgttacc tatgaaaatg 115860
tagaatcttt gcatgtctgt cttttcttca agagattaca aaacattttc caagtgtaat 115920
aaatgaatcc tttccttatg aatcccattt gtaaacaact ggattgatag gttctaagca 115980
ccttaataga gagtgatgtg tgagtttatt tctaccacta gatattgtaa ctgtgataaa 116040
tgaatcaact atttataatg gtaagttgat tctccagaga ttgcatttaa atttattagt 116100
ataatttgca ttagcactcc taactttaaa actcttctta aattccctca cccttgtgac 116160
tgatactcag taggtgggaa ggattatcac aggggaatga ttggctagac aatgggttgt 116220
cctaaataat atagtttttc ttgggataag aagtgaacaa agtttctttt gtcctggaag 116280
ttaaatggga cttttttttc aatctaagat ataaattgca ttcctacatt aagttatgtg 116340
tatggcaacg aaggcacttg cttatatttt taaggtaatg atttcattct ttgcatgaca 116400
ttctgtccat tgaaattgag taaaatgttt tgttatataa aatttgttcc tcacagcacg 116460
ctgactgtta ggtgttatag ttgtgtaaac tgagtccaag atattagcag gcttatgttt 116520
acatggcaaa ttcgaagcag gattgctttg agatataaaa aacgttctga atatatgggt 116580
gtattatcca ctcatccttt gactatgagt gggaaaggga aaagcgggag aaaaatagga 116640
gaggggaaat gaagaaaggt acacagctga gtaaggagga ctaaagaggt atttacaccc 116700
actgagaaaa caatgattta aaggtgctaa aaacaaactg gagaagtgtt cctacttcag 116760
gatctggagg aaaaggaaaa gatttaaatc attttaagca aacatttcaa gcaggaccag 116820
gacttcagtg aatactactc cagggctagc ttttattatc ttttcaattt tattattatg 116880
acttattagc actggctgga ttcatacttt ttggagaatt atttaactgt tttgtgtcaa 116940
catatctatg tataaaatct ggaatagtct aaaacttggg ggatggacca gtataaccac 117000
agcttcagct cttcttcgtt atataaaaga gctggcagta cccttttttt gtttctcttc 117060
tcatggcctt cttatttatc atttttttcct ttctgctttt taaaaaaatc tagaatacat 117120
ttctttatcc aaattctgta ttttcttctt aacagagctc caaacttaca ttctccatga 117180
aaactttgat ggataaacca aatgcataaa tatctttgcc ttatttctaa cctctttgac 117240
cctgatatat tcagttcata tcaacaagtt gtcattgtct tccagattgt ctagttatgt 117300
cataaatatg tgtttcaact ccccaagtag gaactgattt tcctcctttt tgttcatctc 117360
ctataacatt gagcacagtg ctgggcccca aatacttccg gaatgaatca tgacaagctg 117420
aagactgtgt aaagataaaa agaaaatcat actgaagctc ttctggcaaa aggtcagttg 117480
aaatttatga caaatgtcag tagctgaaga cgagatatgg gtgttgttcc cagatatgaa 117540
agggagatga caccaacaca gagaaatgtg aagcaattgt tctgtattct taacagtctg 117600
tgtataatcc taaatgatac acatgggttg gcatagtgtg ctcagtttga ttccagggat 117660
atctcaggct tatttaacaa tgctaccctt agaacaacat tagcatacta atctatacta 117720
ctggccgcga accacattcc ttggtatctt ttaactggat ggattgagac tattgcccca 117780
gatagccagg ataatattta gcatggtggc ctaggatttt aaaagggcag tatcaggggg 117840
gaaagtcatg gatttaaatc atttttcttt tccagggttc ttaccaacaa cacacccagt 117900
aaaaaaaaaa aaaaaaaaaa atcatcttct gaagtttaaa tatctctttc ttttctcttg 117960
cttgtgctgg attatcactc ctgtgcactt cactgagctt gaaaattgca aaagaaagac 118020
acagcttccc cacccccag ctcctaaact actctgttta tagtcagttt gcctccctgg 118080
atcttatgtt ttaacacatg ctgtagtgtt cagattgcaa acacagcgaa gggatgttta 118140
aatcctaaaa acaaactgtt ttcattgcaa tgtgcaaaac agcattccat gaagacattt 118200
caattaatat tagctgagtg aggggagtcc tctctctgtg gcctgttcag tgtttggcct 118260
ctctctgctg agactgccaa ccagggtgct gccaattaat gccagctgtg atctattgtt 118320
tgcttctgac acctgggaag tcccagatca tcagactcct gcaaacagca gctggcttag 118380
tggaggctgc cagacttcgg ggattctgag atctctcagc gaaggtaggg ggccgtcttg 118440
ttttagttaa ggggatagtc cggaatagcc agcttaaaac cccagatgac ttacattaaa 118500 caaccccaa atttggggag gatcagccca agtctgtaag cctcgtatct tactctaggt 118560
tcccataggg cagtctttta aaaaataaac aaatgttcct aatcctttct tataaagtcc 118620
caacaagtcc ctgttatgct gtaaaggtat tttcaggact ccatacttct acaggaggtt 118680
ctcaatttgg tccaattgtg ctataattta attttacacg tgttgaaaat gtgtatgccc 118740
tttctttgcc taaaacccta gccttctatt acagtactca ctctgatctt cttactgata 118800
agacctaaga gccaaccttt actgagtgct tattatgtgc taggcactga gccctttaca 118860
agttttatca ttttatttca tttattttta ataagcatgt ttgatcatag taatgatgtc 118920
aagtggatga aaagtcagtt gggtacaagg gtttcttttt ttaaccttca aatattattg 118980
ttcttaaatg ataaccatgt tttattctga cttgggcccg ctttgaggaa gaacttgagc 119040
aagttatgct gcctgactgt atttcactgt ggtggggttg ttagatgagc tgtctcattc 119100
tttctttttt ggggggtttt gagagagttc tgatgttttt gcctagtcct ctggaattat 119160
aaatgtcagg aagacagaag ctacctgtct gtgtcatatt agtgcccttc ctacaatctg 119220
taaattctaa taaggccctg taggaatagc agaaaatacc atagactctt tctcctgaga 119280
gagacaatgt tgagacgggt ggtaaccggc ccagtaagtc tggcccaaaa atatgactag 119340
atcttctgtc tcctgatgcc ttctttgcat cctgaattct tttcatatgg atgcccttca 119400
aagctggctg gtagccctcc ttctactcgg ggctcctagg cttcagggtt ggagcctgct 119460
gatggtgtta aacacacagt gactttatgg tgctggtcat tgaggctaag gtgaagccag 119520
ttgcacttga tttattcagt acatgattcc atgtctcaag aagtgaaaat ccagtgaact 119580
gagcctgtgc cctagttctc attaacaact taatccaaat ccacttgaaa tgctcactct 119640
tgaagtcgtc agtgatgatg gcatgatttg tttgctgagg tctgttagtt caataggata 119700
attataaata gaatttataa acagttccga ataatactct atttcttgta aatcaatgta 119760
aaatttccca aggagttgaa attaatttta cgtttgtgcg atatacaaat aagtgagagc 119820
ccttcagtgt tcagtgctca gtgtgcaaaa ctacagagtc atctcacatg tttctttgaa 119880
ataaactatg taaaactaag aaagtgggaa agaaaaatta gaacaaaaga tattctaggt 119940
gatttcttat agtcatatca tgatcaggtt aatttatata agacacttga tacatttcat 120000
ctacatcagc ttgtttagaa gtctagagtc aaagccttct ctgatccaga cttggtggac 120060
tatctgagca gaagaatgtg ctggcaggct gattgagcta tgtcatttta ttgagggttt 120120
gatccaggaa agaattaaaa ccatactttg ctctaccccc tatacagtca tttagtacta 120180
gaagtttgct tctataaaca aaaggccgtc atcacttctt cctctgttct ttagatcttt 120240
gaaaatcaag ccaattcaca gtggccctat atgtaatttt tatagcctaa agaacatatc 120300
agaagtatct gtctaatctc cctatccacc ctccactatt agatctagaa aaggcacgag 120360
catcatataa aattcatgcc agaaaactat ctttatatta actataatta ttctaactat 120420
aattattctg tgttggcatt tttcttctgc tgccctttat tacataagtg ggaaaactat 120480
gattttaagt aaatgaaata gccactgaac taaaataaat gtgacttgat acatattctc 120540
ttaatgaaat gtctgttgga gactagaata acgttttggg atactagcca agtcaaacct 120600
taagactttt taggtttgac tgatgctagg gagctgctgg attctggaaa taaaacaaag 120660
gtgttttaca cctgatagaa attattgaac atgtcgaaga caggttcaaa ggtattttca 120720
tttcaactta aaaaaagtag tgcagggaac ataggtaagc ttagaatatg gctattttta 120780
actgaaactg tactgacttt ctttttgaag atgctgatac aacttctgac actgttggtg 120840
atgagtggtg cataacagcc gtttcagctc tgaggctatc aaatagtgaa agagaatctt 120900
ctacatacaa atcccaggac accagaacag ctcttaacag ccctcacttt cctgagtaag 120960
ctgaaggtgg ctaactaaaa ggcctgagag aaattactgc ctaaacaatg aaggaaggag 121020 aaaacccccca aggaagacaa tgtaaagatt aagtaacaag gtttcaattt gatacaatgt 121080

```
ggggaatttc agtttaattc taatttatac taatttctca taattgtctt gatcctttac 121140
gtagagatcg gtttggataa aggaatcata gctatgagaa ggcagttagt tactcagtga 121200
atccaaatgg caaattctct gatgagaaag gggatgtcct cagggaggtc taatcatatg 121260
ttttcttaaa ccaaactctt ttcctttca ttaggctttc ttgaggcaat tggctaatta 121320
atgataataa atagttattg agcatcacag atattctaaa tcctccagtg tcatacattt 121380
ggaaggaaaa aagaccagta gataaactta ggaagagtgt gtgtgtgtgt gtgtgtgtgt 121440
gtgtgtgtgt gtgtatgtgt aacaaacatg ccttaaaacc aggaattgtg gttgtaaact 121500
gggaagacat acataaaaga tgggatggct taagtcacag agacagacag aaacttcact 121560
ttgtgtgatc atgcagagct ctccttatat ataataggtg taagaataat catttccaca 121620
tctgtatttg gactttggcc ccatctctta aatcagagtt ataaattctg tgaagctgat 121680
taatcttatt ttatgggtag ctgtaaataa agagaaaggc tgtctttcag ccttacttaa 121740
ggaaaaacaa gaaatctttg caaaatagaa atttgggaaa ggatgttgag agggtatgat 121800
ggtaggtaca cgggagacat actgggtttg ctcttgttat ctagggaatg gaatgagggt 121860
gtcttttcaa agcagggggt aataaaaaga gcttaggctt tggggtgcag cagctctgac 121920
tttggatcct ggctctccac tgaccagctt tgtgactttg gacatgttac ttaacctctc 121980
tgacgccaag ttttatttgt aaaaatggag ataataccca gattacagaa ttattttggg 122040
aattagggat gattataaaa gtacacaggg atgattagta aagtacacag tgtttggcac 122100
ttaataatcg gtagctgtta ttattgatat tactgtttga ttgcaaagct gaaaaggcct 122160
cagaaatcac aatcagatgg ctcatgtgag atcatgatgg ggtcctctct tctgaaaaca 122220
catgctactt aagtctgtga gaggaattat ggatgaattg tcacagatta aactttatga 122280
ggtagctctc gttggtgcgt gatggtttgc actttgctat tcttcctttt cgcatgagag 122340
aatctcatct ctggaatgaa atttacctgg atttatcaca agagcacatg cttcgagttt 122400
gatttggatg cgatcacctg ttaccctgaa atgaaaactt ctttttcttg ttttgggaga 122460
atctccctgg cttaattgaa gaagtttccc ctcaaagatt cattcagatt cactcagatc 122520
agagggtaat cttctaattt aaaagccaat ttatgacgaa aatcctaatg caaagaggca 122580
aacgtgtcta ctagagttgg gcacaataga tttgtgtagt tgtaacattt tttgctactt 122640
tttttcccca agcaatctca aaaacaacaa caaaaaagta tgttaacaag actagttgaa 122700
attaatactc tgctattaga gtgtacgcgg accggctcac tcccttcttt tccaccgtgc 122760
tgcacgctgc agttcctaga agacacgaca cgctccttcc ttaacgaatt ccatccctga 122820
aatcagtgac gattggcatc aggccaggtc gacttctttt ggactcctta caagaccttg 122880
ttcgtatttt gtttttatta gttcttacta ttctaatttc tctcactgtc gcatttttca 122940
ttggtttaag ctctcagcag tcttgctttc ttgccaactt aaaaacaaac aaataaaacc 123000
aagttagcac tggggcgggt ttcccccaac tcacagcact aattgtataa tcaccactca 123060
aaagtcaaca gactaagtcc aatttgtttt taaacacggg caactcttga gcctttgcat 123120
ttggaaatgt ctttctgccc atttgttgga tttagaataa taaactgcct atgtaaatga 123180
gagggtgcca gccttcagca gcccacaccc tcaaactgcc actcgacgat tcaaacatac 123240
agttcttgag gaaaagcctg ttgtgaaagt taatggttat aaaaagcact tatttacatc 123300
tgttttagtg tagccttgaa gagtgcaatt aattaagaag tttctggtgt ggtaagaata 123360
atcatacagc aggaatgcaa acacgtgatt tccaaagaga attttattcc atatggtatt 123420
tttcccctaa ctaagaatta attgcaactt taaagaaggt ttgattgtgt ctatgaaaaa 123480
```

```
cattttaact actgaggaat tctaaatgac ttcaatttaa aattttcttt ttttacattg 123540

ttagagtcaa gaaataagtg ctttcatcaa gctctgagtt acagaattta ttagagtaaa 123600

gggaagagga taaccttcag atgtcttctg tggtgaaatg ttgaagttaa aaattttaaa 123660

tgtttgcaga ctaaagacat cctcggctgt gaggcctaaa agaataaaca aaatgtgaca 123720

tgttttattt tgttacttaa cccttgtata aaaaagcaca acaaaaaatg tatataaatc 123780

atatttttat ttctttctga aaacacggac atggattttt ggtgatgatc ttctatgtag 123840

tggcatcatg ccataggtta aagagtggtt agtgtgtatg caaatagctt tattttggta 123900

tggcagtttc ttaaagcaga aagttttaaa ggtatacaac ataaattctg tgaagatatg 123960

ttcttctcct tctgttgcaa tatgctacgc attccagtat tttgctgtag cccagcaatg 124020

aacaatgcaa agagatgaag aggggaaaaa caaaaacatg gcagctgaaa gcaagactgg 124080

tggagaaagg atgctcgttg ctgcctaggc acagaaagag aatgtgacat cctagaggag 124140

ggaaaaagaa taaaaacaac ttggatacag gcagagaacc tatttctatc aaatgcagtt 124200

acaacagttg ctgagaagaa aatttcaatc aataacaaag agctcttatc acatgcaact 124260

ttaatttgat tggcatgaca tttccattat atgctaatga attacagatg atgagaacgg 124320

ctgttgcctt ctgagtgcaa ttgaacattc atcaatcagt tacttaaatg ccagactgtc 124380

tgaaatatta aaggaagttg ttgctatttt ggagatgaaa gtaaacaaac tggaaatctt 124440

gaattaattg agaaaaggat acacgttgat aagtaggatt tggcaagtta ttacttctct 124500

gagtggatgt cagtgcaggt atcttattct cagtggaata agtgtgtccc tgcaaagcta 124560

actgaaaaac aaattctctt aagtgaatcc tgtttttctg ttgactagca ttatacaatt 124620

attgactatt actctgggga aaaaaaggct gatcctagaa tgtaataaga tcactctcaa 124680

gtatgcaaca tttttgacaa ttcaagttta aaggaaaata actatccact aaaatattaa 124740

caataatcct caaaatagca ggaacattga aattatcaca attgagtaac agtactaaat 124800

aaagttgttg caaaagaaaa atgcaaaaga aaaaacacat gatataaaat tactaaattt 124860

tcatcctttc cccatcaaaa aaatccaaaa tgtttggagc tttagaattt taattaaggt 124920

tttcatcagt ctcaagccac ctaaagatgt ctaagtttat tttttcatca tcctttccac 124980

ttccctttta cttgtcctta gcattttact ctagatggtt ttcctattaa tttaaaaaat 125040

agttatgctg ctttacatgt gaggaaatgg aacattcagc taagtgctaa aatatctaat 125100

ctttgcaaaa cacgaatttt gttctgcttt ctgcagagac atggtcagct ggggtattta 125160

ggtaatggca aagatgatca atttgcaaac tttttgtgct ataaaaattg atttgttacc 125220

actacctcac accaattagg atggctgcta ttaaaaaagc cagaatgtaa caagtgttgg 125280

caaagatgta gagaaattgg aacccttgtg cactgttggt aagaaagtaa catgccagct 125340

tctgtggaaa acagcacgat agtttctcaa aaattaaaaa taggattacc ataatcataa 125400

ttatctagca attctacctc tgcatatgta tcccacataa ttgaagagat atttatatac 125460

ccatgctcat agtcttaaaa tatgctagtt ttggtggaaa acttgagtta aaatttctta 125520

aatattgaaa cgtcttgtca aaactttcca agctattaac ttttcccttc ctgaagtctt 125580

attcatatcc agccaaaatg tggaggcaac ccaagtgtcc actgactggt gagtggataa 125640

acaaaatgtg gtctatacat acaacaaact attatccagt ctttcaaagg agggaattct 125700

gacacatcat cagcatggat aatccttgag gacattatgc taagtgaaat aagccagtca 125760

caaaggacaa atactgtagg attccattta tatgaggaac tagaatagac aaatttacaa 125820

agacagaaag taaaatgatg gttgccaggg gctagagtga ggagggaatg ggaattactg 125880
```

ttttatgggt ctgaagtttc tatctggaaa gatgaaagat gttctggaga tggatggtgg 125940
tggtagttac acagcaatgt gaatgtactt agtgctcctg aactgtatat ttaaaataat 126000
caagatggta aatgttatgt gatatgtaat taattaattc acaattaata atgaaatttt 126060
aaaagttgta aaaaatggat ttgttgccaa atgactagat ttacgaatta aagcaatgtc 126120
tgctatacta attaggatgt attactgaat caacacagtt ttttgagaat tattagactt 126180
ttctgcaacg tacatagaga gaaaatgtca aatagatttg gctgcctctg ttcgaacaag 126240
cagaggtggc actaaatgtt ccaaattcta ttcatatgag ggcacttctt cttaaaacac 126300
ataactttat ttctttgtag ctctcttagt aaattctcca gagagtaaga gcaaaagctg 126360
ggggtgtttg aggaatagcc aggggtctga gtgactggag aaacatgaag aaggtggggc 126420
agagggagga ggttagttca gatgaagtca gagagccaac tagggaccat ggctttttcc 126480
ttgcacagga tggggaaacc atggcagggt tttgaataga agagtattgt ggggtttttt 126540
ttgtttgttt tttttgagac agagtctcac ttactctgtt gccctgtgca gtggtgcaat 126600
ctcagctcac tgcaacgttg gcctcccagg ttcaagagat tctcctgcct cagcctcccg 126660
agtagctggg attacaggca tgcaacacca caccctggat aatttttgaa tttttagtag 126720
aggcgggggt ttcactgtgt tggccaggct ggtctcaaac tcctgacctc aagtgatctg 126780
cccgcctctg cctcccaaag tcctgggatt acaggtgtga gccactgcac ccggccatgt 126840
gatttgatat atgtttaaaa agtacacaaa ctgtgtacta caagggagat gaaatggaag 126900
tgcagaaatg gaattctaga ggtgagagat tactttcacc tgggggaatc ctggaaacaa 126960
aaatctgagg ctgagctaca gaggagaaag aaatgtattc cttttcacat ttgagtatgc 127020
ttgagaatct ctaaacagca caactgcacc aagaattctc ttgcattatt actctgtact 127080
attaatttgt ttgttgatag cagcaaatga gctttcactt actgagtcct gtgtgagccc 127140
agactatttc agcacttaag agtccttcaa tgactacctc agaggtggat ctcagggtgt 127200
ctggggctcc tatgcacata tgtttcttgt tgtttacaaa gctctttgga cttaatctga 127260
atgagagttg ccctaaaaag ctggagacaa atgattagcc ataaagtttt atttttcaac 127320
atttaatttt tagaataatt aatttaataa cagattttag ggcatgtatt ccttgctact 127380
tagtggttta tgtctctttt aggagaatac ctcattatgt tctctatatt gtcacataag 127440
agatgctggt tctgcttttg attctaggag tcagtttaag tgaccataga tgatatacgt 127500
agtgtatatc atctagggct ggaaggtaat caattaacaa acggtttaaa ttgcttgggc 127560
ctgaagattc tagagtttct gcaagaacaa aatcaagcct gtcttctata tccttgagaa 127620
aaccttctat atttatagta gtgctttcct caaattcaac ctgactgtaa aaatgcatga 127680
tgatgtgcca aataaaggaa gtgtgcgtgc acacacacac acacacaaaa ttagtaagaa 127740
ttagtaacaa caaattctaa acacaagcct tgatatgcta aaaactataa tatggtaaaa 127800
aaataaaaat aaaaaaatca aatgctttca gcttaaaatg ccctgccaag gttttttttct 127860
tcaacccaaa atgctcactt aagtaatctt ctaccacaaa gttaaagcta tacagagtaa 127920
acagaaatag aactcaactg tgcccttcct tggtatattc aaataacttt cttcaacact 127980
tatgcaattc tgtgaattgg taacgtcatt gaaaatatgc tagttttggt ataagttgag 128040
ttaaaatgtc tcaaatattg aaaagtcttg tcaaaagttt ccaaactatt ttttctctcc 128100
ctgaagtctt tatttggtgc aaattcagca tttaaatatt tgtgctaatt taagttttca 128160
ttacattttt tctttggaaa aaaaatttgg ttgaatgatt gactaattat aaaagatatg 128220
gcccaaatta aaaataactg aagtttatga cattgaagga agatatgctt tatctctgta 128280
ctctaaatac aattctattc tttttcctga aattatatct gtgaatttct gtattctttc 128340
tattttgtta aaaaatttat ttgaaaaatg ctgaaaaacc caaaatgcaa aaactactta 128400
gaattaaaca atttaggaaa caacacagat gtacaagtga gagccatccc taggcactgc 128460
ccctgcttca ctaattctac aacagagtgg taacccagtt aacctatgtt tttcaatttt 128520
catgtgttta taggcagtcc tatgtataca tatctaccaa acaactgact ctgctattca 128580
ttggtcctgt aatttaactt cgtttttctt tatatctatg gctagctttc tatctatcta 128640
attctatctt tctatctaat tctacctcag atgtcacagt ctggaggtct gctggggaaa 128700
gggactacac ataaatttg cttggtttga gccatttaat gtgtttgaaa aaatggaatt 128760
tgcatccctt ttgatgacag gccttctgat tcctattaat ttcactcaac tctttattat 128820
catatctgct tagtgatctg aagcatttat atttgcggct tccaaataat attccattat 128880
attgttatag tctcatttat ttagcccctc ctcatattgg aacttgaagt ggctcttcct 128940
ccccaccttt ttttttatta ttaaaaacaa tgctgtcctg atcattctta agtacctact 129000
ctatgttatt tctttggtat aaatttttga aagtggggtt gctcagttgt agaatattac 129060
atatttaaaa cttttataga cagtgcaaat tactctaaaa cacaaaatta ccatttatac 129120
ttccaggaat agtatatagg agttaaattt tcttataccc tttaccaata ggttgtatcg 129180
acttgttaaa ttttttcat tctgaatagc gataaaatta ttatggcttt aaaaagtatt 129240
ttttaaacta ttgatgaaat tgaccttttc atatgtttat tgctatatgt atatatatat 129300
gtatatatat agtctgtgaa tttcacaatc ctatgctatg actgtttttc atatggataa 129360
tctgtctgaa atgtaaaata ttaatctttg ctttaaatgt tgaagataac tttttttagt 129420
ttttggatgt cttttaactt tgttctttta ccttttgaca tataggaatt taagatttgt 129480
atttaattaa atttcttatg tgtcgcttta aaaacttctt tgtcttagta agtttgaggg 129540
gcaatttatc aatttgtact cttatacagt gttggtggga atgtaaggaa tagtacacat 129600
aagcaatggt aaaatttggc aaaaaaatcc catatataca cacacacaca cacacacaca 129660
cacacacaca cacacacaca tgcatatatg gcatagcaca agaatgtgca attcacagaa 129720
tatatattat atagcaacaa aatatggaaa gaggtcaatt attatatatg tgtagaaata 129780
cacacagcac tgtttaacac agctttaagt gtaagaacaa agcccataag atgttcattt 129840
cttcaatatt tagtaaatat atcaaacatt ttctgtacac aaagcacatt tgaaagcttg 129900
aaacttaaaa tctaactagt ttctaaaata ccttaaaaaa tactgtggca tggaagctag 129960
tgttcttttg gaattttcat tttcgattta tatgtgtttt ctgaaaacaa cagaacacat 130020
acaacacctc tccctgccgt attgttgtat taagcaatgt tgggattgat gtgaagatta 130080
aatcttcatg tctgccttta tctgtctcct actttacat gtttgacctg tgaattgaac 130140
tgattttgtt tacttctatt cttttatctc ttttatttgt gataaatttt caatattaat 130200
ttacctaaag gaggtatctt atttgtaatt gaaatctcaa ccatagcagt aaggtgtgga 130260
tttattctga ggatgataca atggcctaaa ttaatgtggc aatggattcc agcagttttt 130320
ctgttttaag tttgaaaaac tttgtaagtc ttacttcttg atgatcagag aggttgttgt 130380
gggttttgtg tggcacttct ctcccttaag ggatctgact gatagaatcg acgtttaaag 130440
aaaagtacat gtgtgtgtat atacatatta tatataatat aatatatatt atatgttata 130500
tagtatgtat tatatataat ataatatata tgttatatcg tatgtattat atataatata 130560
tattatatgt tatatatatt atgtattata tatattatat acatgataat aatttgcaag 130620
gagtgtcaac ataataaagc tttagtgcag catcctagag atatttgcag attaacacct 130680
tgtttgctaa ttgtgtcagt gctcaactta agttgcaaaa tatgaatgta aagagtatga 130740
gagtcttgca gatgggattg ttaaagcaaa catctgcaca tatgtttcag cttcagctca 130800
tagaaataag gcttctactg tctctccata tggaaaatca ttgaagagag catatttgtc 130860
ccctctcttg ctggcccact tttcactcct atctactcct ataaccagaa aaattatgta 130920
tattatatat attatatatt atatgagata tataatatgt atatataata tgttacatat 130980
tataacatat aatatgtata tataatatgt tatatattat aatatataat atgtattata 131040
tattatataa tatgtattgt atattatatg tatatatata catatatatg tattatatat 131100
tatatataat atgtattata tataatatat aatatgtatt atatatacta tatgcatatg 131160
tattatatgt attatatatt atatataata tgtatataca cacacatata tataaagcag 131220
ctcttttgag tatatgttca agtgtgctat acctctccat ccagtgctct cttacaaatg 131280
ctggatttgg gacttcctgt cttaacctgg gatcccacat tagggacttc ctctcttgac 131340
ctgggatccg cacatttcag attgcctgta gagcttttcc agcctttaag acaaactctg 131400
aatccataaa ttgagccagt tgctggaaag ctaaaatcct atctctgtca aagtggagca 131460
gagagacaaa ggtgagtcca caaaaacaga ttttcttacc tcagagtgat gtgaaggaca 131520
aggtggctcc agtgtctaaa ctctgggagt gagagaatag cgaagaactg cccctgaatc 131580
cagtaagtta aagaaacggc agtgctagcc tggttcctgc ttttgaggca cagtagccct 131640
gcccattatt agcaaatgaa cccagctctt gtcaattgga tcaggaactc atttttctgg 131700
gagtagatag gagtgaaaag caggccagca agagagggga caaaaatgct ctcttcaatg 131760
atttccata tggagagaca gtagaagcct tatttctatg agctgaagct aaaacatatg 131820
tggagatgtt tgctttaaca atcccatctg caagactctc atactcttta cattcatatt 131880
ttgcaactta agttgagcac tgacacaatt agcaaacaag gtgttaatct gcaaatatct 131940
ctaggatgct gcactaaagc tttattatgt tgacacttac tccttccaaa ttatttttaa 132000
ttacagcaat agtaagaatg gacaatggaa accctaactg cattgtttta gttaattaaa 132060
catgggtctc ccagttgtgt ttttgttact tgttgcatgc aggtaactat aggttagatg 132120
ctttgggaac ataaatatga atatgatgga ctgtagctac agaaagatca taatacaata 132180
caattattga gcatgaagct ttgaaattat actgcctgag tttgggtatt tgttgtccca 132240
cttaatgtct ctacacttca gtttctttag ctataaaatg gggacgataa taaggttata 132300
taaagattaa attagatagt atatataaag catttggcat agtgcctgga acttggtaag 132360
tattcaaaaa atgtttgtta ctatggtaat gacgactgta ctatgactgc taccactatc 132420
ggatagtgga tgaattactc aacattgact tccaaatcac ccttctgagg aatagagccg 132480
taaatgttac ctacggtaaa agttgtcatg tgactctact gtcctgccca caattgattg 132540
aactggcagt tggtacctac aaccaatgat tctgagttat cgtgttgaca tacttttgaa 132600
tagtagaact tttgccaacc tcagagagac tgaagtctat tcacagttat agcaccagtg 132660
actggctcac cttgggcacc atgtggctgg gtaattattt gtgatactca ttccaccttt 132720
gtgctcatga gtcacggttc cagtactgaa ctgaaactag tctatgtctt cctcacagtc 132780
acctacaccc agaatatccc atagcctacc catgcagttt agtgatttaa cccacaggca 132840
ttgccttaat aatatgtttt gcagttgtgc ctgcagactt gagagtgact gaccatcaca 132900
ggggggatta tttgccttct atttgagagc tgccacttcc tctaggaaag tcatgtatta 132960
caatggatcc cagtgcttgt gtatgtgcac atgggatgga atgggaatga atgtgtcaga 133020
attaccttca ctcccaacaa gacatcctga aaataccacg tgggtaagcc agtgatttat 133080

```
tccattatga cttttatatt tccccttatt aaggttcaag attattcgta acatgggaag 133140
tataattgca cagacaggta gagattttgg agtctttatt gtttagtata tagctaggcc 133200
actgaaatat cgagatccta taagagtgtg gcttaaaaga acaaagctgg aggcatcacg 133260
ctacctgact tcaaactata ctacaaggct acagtaacca aaacagcatg gtgctggtac 133320
caaaacagag atatagacca atggaacaga acagagccct cagaaataat accacacatc 133380
tacaaccatc tgctctttga caaacctgac aagaacaaga aatagggaaa ggattcccta 133440
tttaataaat ggtgctggaa aaactggcta gccatatgta gaaagctgaa actggatcca 133500
ttccttacac tttatacaaa aattaattca agatggatta aagacttaaa tgttagacct 133560
aaaaccataa aaaccctaga agaaaaccta ggcattacca ttcaggacat aggcatgggc 133620
aaggacttcg tgtctaaaac accaaaagca atggcaacaa aagccaaaat tgacaaatgg 133680
gatctaatta aactaaagag cttctgcaca gcaaaagaaa ctaccatcag agtgaacagg 133740
caacctacag aatgggagaa aatgtttgca atctactcat ctgacaaagg gctaatatcc 133800
agaatctaca aagaattcaa acaaatttac aagaaaaaaa caaccgcatc aaaaagtggg 133860
tgaaggatat gaacagacac ttctcaaaag aagacattta tacagccaaa agacacatga 133920
aaaaatgctc atcatcactg gccatcagag aaatgcaaat caaaaccaca atgagatatc 133980
atctcatacc agttagaatg gcgatcatca aaaagtcagg aaacaacagg tgctggagag 134040
gatgtggaga aacaggaaca cttttacact gttggtggga ctgtaaacta gttcaaccat 134100
tgtggaagct ggtgtggcga ttcctcaagg aactagaact agaaatacca tttgacccac 134160
aaatcccatt actgggtata tacccaaagg attataaaac atgctgctat aaagacacat 134220
gcacacgtat gtttattgca gcactattca caatagcaaa gacttggaac caacccaaat 134280
gtccatcaat gatagactgg attaacaaaa tatggcacat atacaccatg gaatactatg 134340
cagccataaa aaggatgagt tcatgtcctt tgtagggaca tggatgaagc tggaaaccat 134400
cattctcagc atactattgc aaggactaaa aaccaaacac tgcatattct cactcatagg 134460
tgggaattga acaatgagaa cacttggaca tgggaagggg aacatcacac accagggcct 134520
gtcatggagt cgggggaggg ggagggatac attaggagat atacctaatg ttaaatgacg 134580
agttaatggg tgcagcacac caacatggtg catgtataca tatgtaacaa acctgcatgt 134640
tgtgcacatg taccctagaa cttaaagtgt aattaaaaga aaaaaaaaga ctgtggctta 134700
aaaataagga attttatttc tttttcacat tagagttcca acatgacagg gaaaccatgt 134760
tctttatgta catttaagga ctcagttttg ctcaaagtca tttttctgac ataccctagg 134820
gaactgtcat catctgcatg gtctatgctg ggtcaccacc atgtctgtgt tcaggctcgt 134880
ggaaggagga ataagaaagt gaaaatggca agcttgatgc taggagggaa gcttataggc 134940
cagtcccaga agtggcaaag accacttccc ttcagttcca ctggtgggga cctagttcat 135000
ggctgctctt caatggagag agactgagaa ttgtaggtac tctaactgca cagccatgtg 135060
tcctagatga agaggagaag gggtttttgg agggtaacct ccagtctcac cacagaggcc 135120
ttgttgagaa acatgagatg tacaactgta ttatcaaaca ttaactgtga ccaggagaca 135180
ctaagaaaat acctattctc actgagtttt tgggaaaaag cttgtgattt ccaaagatta 135240
taactttata ctcaattaat atacttacat atacacatat tcataaatat attttgaata 135300
aattctcaga gatgatattg caagacatac actgtaaatg tgggacatga tgtgacacac 135360
tataacagtt gctgtactat aaggacttta gatttatgat ttgggatacc tgagatttag 135420
tgctgtcact gccattaaat gggtaacttt gtccaatgtg tttaacattt ctgggtctca 135480
```

ctgcccaaga tatcttaagt tttaacagta cagtcctgtc ctgttgattc tacctctata 135540
atagatctta acagcatcca ttcttctggt cataattcct tccagagttt ataatccaac 135600
ttcttttcct tctctagccc cactgaggtt attcctccca gattgatccc actgatgttc 135660
ttccagtccc tagacctctc taaacgcttc ttgctcatga cctctgcatc tggtagtctc 135720
tctgactgcc ccttggtctt ctctcttttg tgtggccatt tccttctcat ccttcaggtc 135780
tcagctttga tgtctcttct ttagaggaac ttctcctacc actctgtcta aagtttttta 135840
gtttatctca aactcagttt atttcttcaa ccatacttgg tattgtcttt tgtatctatt 135900
tatttgtttt ctttctgttc ccctcattgc actattaact tcactgaact attaaggtaa 135960
tgggatatat ctgtattttt catcctttta atcctatcac ctggcacagt gccctgcacc 136020
tagctggtgc tcagtaaata tatgttgaat aaattaatac aggaatttag aaatgtgtgg 136080
tctaaatagg taagtacatt atttaatgta attaaaaaat tcatacttct tcaaaatttt 136140
atggaaaaac ttaaaaaaat cagcgaacct tatttgaaa caaatatttc ataatatgaa 136200
tttctctcta ttaattgtgt ttctttttaa ttttagattt actatcctat ctatctttaa 136260
atgttctttg atttgaatac ttctgcaatc cagttaagat ggaaggtttg ggggagagaa 136320
ctcactatac ttaggctatc attttgtttt gtataatttt aatcatgaca gtctttatca 136380
aatccatgtc tatttaaata tttattttct tttgcatatg ttgggatgga atatgttgtt 136440
ttaattagcg gcaccgcttt cttgttgcta aatgtattgc tctggcattt gaccaaaagc 136500
aaaacagaat caacacagtg taatctatgg aaagggaact gaatctcact gcacatagta 136560
tttcatcagc tgtaggttaa gggatagtct atccagtaaa gaatgtatat agcaactata 136620
cctctatact ccatgacagt cagagctgcc atttctggtt ctcagaagaa actttttttat 136680
ttgacttgga tcagcctaca gctagatgac aataacataa aataaagttg aagaaaaaaa 136740
cagttgttaa ataaatccat tactttaacg agctctcctt ctgtatgttt tataagggga 136800
atatcaaact ttttagactc taatgagagt ttatcacata aatgtacact gaataaaaag 136860
aatcatgcag ttgtgtcaga aaaagtagca aaggcctttt tatgagagct gacttgtaat 136920
atgtatatat gttactggct aatttgatta tggtaaatca tcattgtatt ttatttatta 136980
acttatgatt tcacagttgc cggctgagtt ccctttaaca aactccatat ttattgaatt 137040
ccctctatgc acaaggtata atgggcattt attttttcag ataggcaatc atcttagtca 137100
cattattgtg aaatatatga gtactatata attatcttca aaaggaaatc ctgaatattt 137160
aatattaata tttaatgtca ttaaagtcaa atttatctct attgcctgtc tttttttttt 137220
tttctaaagc agagcaattg aaagctgaaa ggtgaaaagg agtgggaaaa gctggttcac 137280
catggctcaa acacagctca aactttaccc agcaatgagc tttctattgg cttgacttgg 137340
aaaatacaat ttatatgtgt catgtaaaag gggaaatgat acatcagaac tttattataa 137400
cactattctc tctaaagtgt aatttagcac aagatatgac ttgtaaaggt taccactaaa 137460
actctatcaa aacatcattg ttttatatct gtgagatata aaatatccct gaaatcagga 137520
agccttccca cagatttaca gattaactct aaactttaga tctttttttct ctttttttagt 137580
acatacatgc gtgtcactaa aatgtctgta tataacatgt gaaatattgt tactcaagaa 137640
atttcttaag agcaggttaa ttttataaga caatggcctt atgtttctac gtataaaata 137700
tctacaggcc ttctctgcta aaatcccagt tttgtttagt tccaagtaat gtgatagaag 137760
ggtctattat aaaactattt gcaaatgtgg aagccgtaga ttttactatg gatttaagaa 137820
gggagcttac tttaagattt tctggcatag ggtgtttttt tttcccttaa aaaaaaccat 137880
atttaggaaa gtaaataggg agacaaaggc taagaaaaca aaaattattt aagattttag 137940
gctgtacaaa taaaattgta gaaacaaaat tattaaaaat agcttactga ccaaattcag 138000
ctgagattta cagccacacc ccacatcatc atagtatcat attggtaatt gtaacattct 138060
tttcatatga aaaaaaatca agcacgtgta aagttatcct aattgaaaaa catttcagga 138120
caatatgttt attacttctt attcatgtac attttcaatt acagcccaaa tttatacaca 138180
tgttgcttgc aaaatgccat ttggatataa tatggtaaat tttaaaaacc acaaaatcct 138240
tagctttata acacattcac agtaagtata aacctaagct atggcttagt atgtaccact 138300
gctacctctg ggaaaaaaaa ataaaagtgt tggggaattt ttatgcaatg gattcagtta 138360
gctcaatttt tattgaagat agcattaaaa aatccatagt taagcaatca ttactataat 138420
agtgattgtt tttctaagtg ttgagagttt gggctgagag agagtgtatt tgaagacatc 138480
taaaagatgt ttcctcctct ctggaaatta tatacttatg tagttgtttt tggttgactt 138540
ttattgtaca attacatatt tattttaatt attgtgtagt tatatatata tatatatatg 138600
cttctctttc ttatgtgtat ataaatgagg gaatattata atcactcttt tctgaatcat 138660
ttcctcttta ctgactagat ggtaggtacc tctgggcctc ctaataaatg gaaacaaggg 138720
ggaataatac acatcaagtc agtgtggaat ttggagaaaa cttatagttc taaatgcttg 138780
tcaacatcat catgaaaatg ttaactgtgt ggccattgca tgtgatgcat tgctgcctca 138840
cttataactt ctagaactct atagttgctc accaaccaca tccacacaga ctgacataaa 138900
aggtatacac ccgacagcat aagcacatag tgagaaaata aaagaaataa taaaaaccta 138960
cacagtagcc tggtgtatca ctattgggtg gtaactgaga gtctgtgaaa agtgtttcat 139020
gtttagtcag ggtgaggcca ggaggagctt gtcaatgcct ttcagttgtc tagaaagact 139080
tcatggagac agagattttt aagaagggag tgaagtcatt aagtttgcag agaaagagta 139140
tgttaggtgt aaggtatgtg gtcatgaaga tggcttatta ttattagagt aagaagatta 139200
aataaggaag gcaaagggta gatttgcttc ctgggagtgg cgtataaaaa cacaatgata 139260
tgttttcatg agctaatgca agcaaaagcg attgatgagc agaaaaataa cctcagcaaa 139320
agtgtcaaga atcaaataga gagaagtgta cctgagtggg agagagtcag ctgatattgt 139380
ctagctcata ggattgagaa gagatatttg aggtgtgaag aaagttggga caggggttag 139440
aaatgtcggg atgtacactg aagtagcttg aatatgaaac aagtaagaga ggaacaaaaa 139500
ctcaagggga aaacatgtgt actgaaatat tccttataca tagagggaat ttttatcaaa 139560
agctgtgcat tcatatgatt tggtctttga ggaattaatt ttaaagaact gttaaaatgt 139620
gttctttgtg atccagtgta ggccacgggg aattgataat gttcctagaa gttgtaatca 139680
gctcaattga gtaaagaccc tttaccctag gaccatatcc attatcatag cccaaaacac 139740
ctccaagtgc ccattggcca tttggcccag ttctaggtac tgtgtagcca agcttttggg 139800
acacagtttt caaaagcaga tcaaaatatt tttgaggcat agcaatcatc taatctgcct 139860
gaagaattat gttaccgtga aaagtgatgt cttaaaccca taaatttgcg atgttagaat 139920
gagtcatttt ttatatcctt tacaagcgaa aaagtactca ggcctgttga caaagcaaag 139980
aaatggtgtc aaaaataatt ttaaaacctt ttgacctata aggtttaaaa gaattaggca 140040
cagattcttt gctttaagcc tcttggtgac aagaaatatg gtactctgcc agactgtttg 140100
attgacagta gcgtttgtag tttcagctgc taatacagta tgcttcttgt atattctggg 140160
tgggtaaata tagaagacta tttgtcacct gggttgatgg attacaaata agtaagacaa 140220
tgtgtttagg attctgaagc ataaatgaaa agtcaaaaac cttatattat ttacaatata 140280
acgtttatgc tttcagattt gttatcccta ttacatcaat aaaaatgatt gggttttaaa 140340
ataagcatgc aactcatttt taaccatctc ttttcattac atagttattt gctgcaagat 140400
agtatcaatt aagcatagaa aaaaactgat tagaatgaag aacttattat agatagctgc 140460
atttattttt aaagatcatg attcaagtat cttaaaattt ttccactcat aggacctatg 140520
actaatgaca tgtttctcca cccatgaaaa gctggttgtt ttcagtacct aattaatgtt 140580
caagcttatt gtacacactt atgcttagaa cggtggcatt tctgaaaaat cttcttggtc 140640
aacagccctc taataatatt gatttctctt tgtacaacat tttgaatttg ctaaggtgtt 140700
acaagtagta taacataatt tcaaaatgat atcgtgaatg gctcagtaat taatattttc 140760
aaagaaccgt gctattcaag atgaaaagat tattaaggtg atattactgg gtctttggat 140820
ttagaaagaa aatttgcttt ggaaagcaca ttatcacctt tcaggacaag aagcaaaatt 140880
ggcattttta gcatgctact cttatcttta tttgctgata aagaaagaat ccagagtttt 140940
tcaaaacttt aaataaaagc ctatggtgag gttcacatta cccaatgttt aaagaagaaa 141000
taaaaactcc agacataaaa ggatgggaac aaaatagaaa caatagtctt gacattttat 141060
tttagagctt ttaaaaaata ttactattca aaacaaaact caacatatga agtctatttg 141120
ctttcatcta cataattaat acagaattat actgaagtac atggaagtgt aaaagctaat 141180
gttctttaac ttcatgtcat aacactatca tttcataatg gatattcagc ttctttttga 141240
gtaggttttc ttttgatgtc tatgtttgaa gaccacatat gctaaatggg aggaaacaca 141300
cttaattctt attgttataa cttgtggttt ggtttagaga attgtgaaga ggcaaacagc 141360
attttcttgt gaatctctgt tatgagataa ttgttactta aaactagctg catttgactg 141420
tatgtgctat cagaataatg ggacaagtca gcttaagttg tattaagtaa attataattc 141480
aatactttaa aatatatagt atttaaaaaa tcaatactat ataaattaga actctatgcc 141540
aatagtacac tcttggttaa atacaacagt taaaaattct ttccatgtga atttatcttt 141600
ctttataaat tgtttctatg tgctacaaaa attcttttat attttttttcc acaagcatag 141660 aaccataatc cagacaggaa ttgttaattg ctacattatt gaatatcagt ttggttactg 141720
acatgctcag agaaatgtta gattagttta taagcttaag ttggatggct gacaataaat 141780
tctctgtata tcttgttaaa atttgaaacc agaggcttta agttgtatgt taggatttca 141840
aactaatgag atcaaaccag aatagctaat aaactcagat atcaacttct tattttgttt 141900
cttagaaaaa acagtgatta ggtattacaa tgttaaagat cttacagtcc agtctcttta 141960
ctatatggat aaagaaatgg aggtgtgagg taaggaagta ctgtgatgaa ggtaacataa 142020
cagtgagtgg ggcaatggaa ctcaaaagca atgctgcttt tactacacaa catggctact 142080
aatggaccag gataatttaa cctagtattt cctggaactc tgtagtcagg attccctgat 142140
tctcttcgca gaaatactac actatatgtt gcttacagat aatagtattt tggggataca 142200
acaataacaa caaaaagaat ttttaattga aaaagcacaa tttgtagatc tttagcagac 142260
acagaacatg gacaccaaag gaaccacctc tgtctttgct cttgacacat ttatggtaga 142320
aagagtggag ggggggctat gaggcatttc cagctgcatt cactctttaa tcttacagga 142380
gattaaaata caaagtattt ctcttatttt tgctcatgga gatgctttta agaagttaaa 142440
aattgatgat gtttcatatt tgtgtagcgc ttattgtcta aataatttga aaacacttaa 142500
gcaccattcg atttcatagt ttccaacaat ttgacacgac tctgagagaa agcactgagc 142560
agcctagcca gtctcggggt gaacacccac agaacaagtt ttccaattta ggtaaaaatt 142620
tagcctccta ggaatctacc aaatgaagtg caaggacaat tatatgaggt ataaattaaa 142680
gcttgtgtac ccaattagga agacctcttg ttagtgttat tgttagtgct tcttgaaaac 142740
atagaaattc ccattgcttt actcatgagt ttgtttgtgt tttgaatgtg atgtgttaac 142800
tattaaaata tgaggtgtga aatattgtta tacaaatgta aatgattaca attttaatat 142860
aataccttta aagtattgtc aggtagggtt aaattaattc acttgtgggt agtggtgaat 142920
ctagagccag cctgtgcctc tagatttcta gttcattatc ctcttaagtt ccaagttagg 142980
cgcactttat gacacacaca gaaattagaa gatgtttgca ggtttagaag ctgaagaaaa 143040
tgaggggaca ttatatggaa tgtaaataag gacatgaaaa agaattgtaa aagtcaacca 143100
agagctctga tactaaattc attgaggaca ctgataccca ttgtcatgaa tggtgacact 143160
ggcactataa aaatcatttt atgtataaga atgactgtga caaagtttta atttttgaaa 143220
atatagttgt ataaggtttc tcatgtctgg tattttagct tttggtttga gaattatttt 143280
aaaagaatat aggacaattt agttactgga ttggtattca aactactgga cttactcaat 143340
attcttccat caaaatcaaa tccaaaagaa cagagattta ttctcatatc taataggaat 143400
ctagtagaca atgctaaaat tagtgaacta agtaaggtga atcaaagtta gaacccaaat 143460
tatgttcaat gcaagcaaag ctttacttat tgcttttggt aagtacaatt caatgtgata 143520
atgtatgtca attaattgaa gcagtctgat agatgagctt ctggtaaatg tacccaattt 143580
tatatgagag actcagggtt ttacggactg tcaaagtaag acttagtaag aaatgcatcg 143640
tgattaaatg agtatacgat gtgtgaagaa tgtttacacc agtacaagga aacctagttg 143700
gtcatctgct agaaagtcaa attggcagtg gttgtttcta atgtatcttt ttcttgtgtg 143760
atgtgtcata tgtataatga ttacatttta gataaagtga atggatctat caaacattta 143820
tcagactcct tcactgtaag gtgctgtgga ggtgcctcat ttaaaccacc atagttaaac 143880
ctcaaagagc agccctatgg atctggcaat tttattctca acttcgtttt agaggtgagg 143940
aaattaaagc aaagacaact taagtaattt ttccaaggtt ctaagactgt gctcaaagac 144000
aggattttaa ttccactgtc ttttttcttt ctatcacatc acacagtggt tgcaacttgc 144060
ttttctgtaa atgtaatgaa ggaaacatcg cagaccttgt ataaaactca tctacagatt 144120
ctttggtagt taggtctttt tagtgctgct ttgataatga attctggtaa aaaaaattct 144180
tttataataa taaaatgttt ttaaaaatcc tccttgaatt ttctgaagtg caatagcaga 144240
taacgcagct gtgaatgata aaaatacctc actgcactgt ttctatttgt cattgctcag 144300
ctgaagagaa acagggccaa ctgcgaccat aactgagaga cttctgaaag ttattttcca 144360
attttaatct accatatatt cagtggttac tttgtgccag ctagtaagcc agttagacac 144420
tgtgtattca ttttttaaaa agtagtgtag ctttattatt ttctggtttt gccatttgaa 144480
aaattattct ccccctccc cgcctacatc aggccatctt cctctcacac cactgaatca 144540
gggaagaatc tgctaccgaa cagtagtatt tactgaccaa gagataactg tacctcattt 144600
tgaaggtgat tcctctttct acctaaactg tattagtatt tttaaatctt caggtagtgt 144660
atatcggaat cactagtgaa cttgtaaaaa ggcatatttt taagcaccac ctaagtattt 144720
taaatcacta cattttaaat agcatcccag tttactgcat gtaaagaagg cttccctctt 144780
gaaggaaagg catcttttcc acaaacagaa tctagagacc agttggggat cctagtggga 144840
ggattgtttg gaacagaagc atcccgagaa tcgtaacttt ataggctttc cacctccaga 144900
attatgcttt tctttttctt ttccttatct attcatttat ttattcatcc attcttcagg 144960
catttatgat ttgctggcaa caatggataa gaagcagtct tggcaaataa ggagctcaca 145020
gtctagcagg gagacataca catcattcct aaaaacagca tcacccttag gcccaggcaa 145080
gaagaggccc tgccttggcc tgtgtgcttt agaaagctta ccttctggtc tgccatttgg 145140
ctgtgcccct tgctatggga gtgggaattt ggagagacaa aataatgtaa tcaactgcag 145200
ttcacgtctc ctagatgaca ggattatctg ctggtctagt ccccggcctg tgcctctttc 145260
ctgagtccat tccttggact ctgccactgg tttgcacaca ccaaagccca agggatcgtc 145320
caaataccta gctgtttgca gggacaatgg atggaacgtg gacagggctg agatatctat 145380
gtgtacacat gtgaagctat tgtagtgtgg aatgaagata gaggtggcag gactggttca 145440
gaagagaagc ttatgttctg ggattgaagg gtagatctcc cagtgtggca agttctggct 145500
cagagaagta caaggagttt gagaattcta actttgaacc taaccgtcta gaagaaatat 145560
ttcgcagggc aggaggagat aatatatttt atttaacagc ttgtcagctt gatttataac 145620
ctttaaatat atgagtatat aacaagtgag cttccatttg tactgttgcc ccagaccctg 145680
aaaatgttaa gggagggctg cacttggaat taagagagtc ctgaggagtg gagtcaccca 145740
gcttgtctga atcaggcaac acttgagcta gatattaagc aatggtcaat tgggaattat 145800
ttaggcaaga taaatggatc aaagatgaga gaaaatggca gggcaacgca gggcaggaca 145860
tggaattgac aactgcattt aatgcacgag ccaaggcaaa aaggcagcaa atcgcatgaa 145920
gtgtgtttgg gccttaaaat gcaagtagag cagagtttac taaaagctag ggagcttcca 145980
cctttaggtt ttctcacttg aacagtccct gatgagttct gaggatttct aggggttgta 146040
agggttttag gtagaaagag gatgccagat tgcaatctgg aatcatttct gtgtaaacat 146100
ttctatttaa tcgcctaagg agatttcaaa gaaagagacc catattttta agtcccagta 146160
tatgttgtga tttctttttt tgtcctagat aaatatttac ttttgtatct aattttgtat 146220 ccttttctt caatagaatt ctctcctaaa ttataggtgc ctcagatctc acccaaagtg 146280
gattcacctc tgagttcaat atatcttgga aagatgaggc tagagaaatt gcagagaacc 146340
aggcttgatt ctttgcaggc cacagagcca tgagatttag tcagggaagt gacctgggta 146400
tttatacatt gggtattttc cacatgatgg gccatttgga gacaatagac atattggaga 146460
ttcttctaac aatcccacag agtaaaaatg tagttttgaa ccagggcagt ggagaaaaaa 146520
tatttattga gtaaaattgg caagactgag tgtttgatta gaaatgcata gtggaagagt 146580
tcaaagaaga gtttgcaatt tctaattttg aggtcttata aattacatcc agttttaatt 146640
gtgttgagtt tatatctgca taggatatgc aagtagagac atccagcagt cagttaagag 146700
tgtgattctg aagcttgggg gagacagctg ggctggctgg gaatatctat gaatgtgtgt 146760
gtgtctgtgt gtgtagtgac ataccttcac acacacaaat acctatgtac atttgcatct 146820
gcatttatat atacatgcat atctttttga gcccaaatat gtatttggga gttatcagta 146880
tacagttgaa accaccagaa tgaatgaagt caatcaggaa aagcatttaa aatgggtaca 146940
ccagagagct gatgacagaa acctgagaaa cacaaatgtt tcagtaacga acagaggaag 147000
aggacaatag aaaggacaca gcaaagtgag aattttctca aaatcttaaa aatcatagga 147060
gggcagtttt ttaaatgagg gaataattga cagtgtcaat aaagcaatga taattaaaaa 147120
gtgcaatttg gtaactagga agtcattgga gattttctgg agtttaagag ggaatggaaa 147180
gcagctttca gtgggatgag aagtgacttg gaaatgagga atggagacgg tatctttctt 147240
gaagaataca gttactctta aaagttaaat tgtaaacata tgaaaaattg tttgtattct 147300
gaagggaact ggaaatcaag tgaggtatct ctttttgtct ctctccattc tctatcttcg 147360
ggctgagaga ggcttgggca tgctcacgat gactcatgaa gtcaggtccc agggggcagg 147420
tatgattcaa gagccttatt gggactcact atctgctgtg catgaaggaa ataagatgat 147480
catgatgctt acagtgaagt aaaagtgttg gtaggtggtg tttcaggctt tgctagagca 147540
agatatgaaa acagtgagtg agtggcaaca aattactctg gtatgatttc ttcaggtgca 147600
ctcattcctt tacacagcta atagatttga gtttggtatt cagctgggag gcataataga 147660
ggttaatggg taatatggtt tggctgtgtc cccacctaaa tctcatcttg aattgtagtt 147720
cccataattc ccataattgt gggtgggacg cagtgggaga taattgaatc atcggagtgg 147780
tttcccccat actgttctcg tggtagggaa taagtctcat gagatctgat ggtttataag 147840
gggaaactcc ttttgcttgg tttttttttt tttatatata tatatataaa gaggagttct 147900
cctgcatatg ctctcttctt gcctgctgcc aggtaagaca tgactttgct tctccttgcc 147960
ttctgccatg attgtgaggc ctccctagcc atgtgaactg tgagtcaatt aagccttttt 148020
cctttataaa tacccagtct cgggtaagtc tttattagca gcatgagaac agactaatac 148080
aatgggtaca ataaatggaa tgttctagag caaaaaggtc cccaaccttt ttggcaccag 148140
ggtctggttt cgtggaagac agtttttcca ccaatggggg ttatagtttt gggatgattc 148200
aagtgcatta tatttattgt gcactatatt tctattatta ttacactgta atatataagg 148260
agataattat acaactcacc ataatgtaga atcagtggga gccttgagct tgtttcctgc 148320
aattagatgg tcccatctga gggtgatagg agacagtgac agatcatcag gcattagatt 148380
ctcataaaga gcatgcagca gagacccctc acatgtgcgg ttcacaagag ggtgtatgct 148440
cctatgaaaa tctaatgccg cggctgatct gacaggaggt ggaactcggg tggtaatgca 148500
aacgatgggg agcagctgta aatacagatg aagcttcact cacttaatgg ctgcccacct 148560
cctgctgtgt ggccccctaa caggccacag actggtactg gtctgtggtc tgggggttgg 148620
ggacccctgt tctagaggtt aaagaatact tagcaaatca acaatgagga ttgagagaga 148680
aaccaagaga tagtcgacaa tctcagaaga acttgaaaag ctcaggactt tgataagtta 148740
atggagaggg gtgaataaag aaaggatctg agggagctgg ggtggtagaa catggggtta 148800
gttttgagag tttatgattg cagagatgta atgatgtgtg atgataacag aattgagaat 148860
ctagctgaag tgttttgaag tctatggttg aaattggttg aaagtgaaaa ttattcaatt 148920
taacaaggtt tagaaacctc agacagagaa taaaaaattc tagacttccc aagatacatt 148980
taaaaaagat aatttcaact tctctttaga tttagggggt atgtgtgcag gcttattaca 149040
tgggtatgtt atgtgtttgt ggtatggatg atcctgtcac ccaggtagtg agtatagtac 149100
tcaataggta gttttttagc ccttactccc tcctctctct acccaccagt agccccaggt 149160
atctattgtt tcgatctttg tatctatgtg tacccagtgt ttagcttcta ctcacaagtg 149220
aaagtatgca atattcagtt ttctgcttct gtgttaattc acttagaata atggccttca 149280
cctgcatcta tgttgctgca aaggatatga tttcattctt ttttatggct gggtagtatt 149340
ctatgatgtc tgtgtaccac attttcttta tccaatctac agttgatggg cacctaagtc 149400
atgtctttgc tattgtgcat aatgctgcag tgatgcaaac 149440

<210> SEQ ID NO 51
<211> LENGTH: 599
<212> TYPE: DNA
<213> ORGANISM: Homo sapiens

<400> SEQUENCE: 51
gagaattatt taactgtttt gtgtcaacat atctatgtat aaaatctgga atagtctaaa 60
acttggggga tggaccagta taaccacagc ttcagctctt cttcgttata taaaagagct 120
ggcagtaccc ttttttgtt tctcttctca tggccttctt atttatcatt ttttcctttc 180
tgctttttaa aaaaatctag aatacatttc tttatccaaa ttctgtattt tcttcttaac 240
agagctccaa acttacattc tccatgaaaa ctttgatgga taaaccaaat gcataaatak 300
ctttgcctta tttctaacct ctttgaccct gatatattca gttcatatca acaagttgtc 360
attgtcttcc agattgtcta gttatgtcat aaatatgtgt ttcaactccc caagtaggaa 420
ctgattttcc tcctttttgt tcatctccta taacattgag cacagtgctg ggccccaaat 480
acttccggaa tgaatcatga caagctgaag actgtgtaaa gataaaaaga aaatcatact 540
gaagctcttc tggcaaaagg tcagttgaaa tttatgacaa atgtcagtag ctgaagacg 599

<210> SEQ ID NO 52
<211> LENGTH: 20
<212> TYPE: DNA
<213> ORGANISM: Artificial Sequence
<220> FEATURE:
<223> OTHER INFORMATION: Synthetic primer

<400> SEQUENCE: 52
acaaccccat ttgtgaagac 20

<210> SEQ ID NO 53
<211> LENGTH: 22
<212> TYPE: DNA
<213> ORGANISM: Artificial Sequence
<220> FEATURE:
<223> OTHER INFORMATION: Synthetic primer

<400> SEQUENCE: 53
tttatagaaa atttagcatg ga 22

<210> SEQ ID NO 54
<211> LENGTH: 20
<212> TYPE: DNA
<213> ORGANISM: Artificial Sequence
<220> FEATURE:
<223> OTHER INFORMATION: Synthetic primer

<400> SEQUENCE: 54
ctaagttgtg cagccatgaa 20

<210> SEQ ID NO 55
<211> LENGTH: 20
<212> TYPE: DNA
<213> ORGANISM: Artificial Sequence
<220> FEATURE:
<223> OTHER INFORMATION: Synthetic primer

<400> SEQUENCE: 55
tggaaccact tttgcagtaa 20

<210> SEQ ID NO 56
<211> LENGTH: 19
<212> TYPE: DNA
<213> ORGANISM: Artificial Sequence
<220> FEATURE:
<223> OTHER INFORMATION: Synthetic primer

<400> SEQUENCE: 56
ctggttttaa ggcatgttg 19

<210> SEQ ID NO 57
<211> LENGTH: 20
<212> TYPE: DNA
<213> ORGANISM: Artificial Sequence
<220> FEATURE:
<223> OTHER INFORMATION: Synthetic primer

<400> SEQUENCE: 57
tcctcaggga ggtctaatca 20

<210> SEQ ID NO 58
<211> LENGTH: 1211
<212> TYPE: DNA
<213> ORGANISM: Artificial Sequence
<220> FEATURE:
<223> OTHER INFORMATION: Synthetic polynucleotide

<400> SEQUENCE: 58
tcctgctcca gcttgtggat attttgcaaa aaagctctcc atctgccaca gttgcagttc 60
agtgttgaat ggctctgcta ttgtgacaat tcggccaagg tttctgttat tgagtgtata 120
tctgttgact agatagtccc agttgagttg tatccaattc caggccatgt tcttcccata 180
gctgttatat gagatatatc gaatgactgt aaacacatcc tgagttttaa taaggttcgt 240
gtccttgagc aaatccaaat accttgacaa aagagtaacg ttcttcactg atgctaatcc 300
atacagcagt tttcttttt cttgagctaa tgaagtttct ggtattgctc aagagtgtag 360
ttccatgaaa tctcattgcc agagttctgc atcccatacc gatacaccag aagcctgaga 420
tttacgggaa ggcttacagt cccatttagc cactgctcaa ataacgagga agcattgttc 480
aaggcttctc tgtctcccat cttgcacgca aaccctaaca cggaggaacg gagtaacttt 540
gtgacatggt ctccagcatc attccatccc agagaatctg caataggctt cacttgacct 600
tggaagtatt cctcaatcat aggatatagc tctttatcat cttcaaacat gctaatgatg 660
taggttacag ctgaaattac tctctgccat ggtaaaaaat tctcttccct tttgagatac 720
ttggtcaagt tcaaagccac cttataatct agaagttgag ctcttgccaa ggcaaaagca 780
tcatcaataa gacttgcacg atctgctgaa gaaaatgtct tgtggttcaa ggagagcgct 840
gtagctatcg agtcccaagt tgctacttca taatttacac gataaaaccc aatatgatct 900
gggtttattt tgagaaaagc atttccacta ggattagagg agttcaaagt gattccttct 960
ttttctgacc tattaaataa cacactgctt gttatattat cttcagtcca tttaactggg 1020
atattccatg tataaccaag atctgaaggg ggctgagaag ggttagctct tgggtccaac 1080
aaaaagcgtt tctgtgtgat gttcttgaca ccgttcacgt taagcacagg ataacccatg 1140
tggtctggtc caggtgtcca ttacttcttt cactggtagc ctacttgcct cttccagtgc 1200
tgcccaaaaa t 1211

<210> SEQ ID NO 59
<211> LENGTH: 20
<212> TYPE: DNA
<213> ORGANISM: Artificial Sequence
<220> FEATURE:
<223> OTHER INFORMATION: Synthetic primer

<400> SEQUENCE: 59
agtggaggct gccagacttc 20

<210> SEQ ID NO 60
<211> LENGTH: 20
<212> TYPE: DNA
<213> ORGANISM: Artificial Sequence
<220> FEATURE:
<223> OTHER INFORMATION: Synthetic primer

<400> SEQUENCE: 60

-continued

```
tgcaccactc atcaccaaca                                                 20


<210> SEQ ID NO 61
<211> LENGTH: 23
<212> TYPE: DNA
<213> ORGANISM: Artificial Sequence
<220> FEATURE:
<223> OTHER INFORMATION: Synthetic primer

<400> SEQUENCE: 61

ccgaggatgt ctttagtctg caa                                             23


<210> SEQ ID NO 62
<211> LENGTH: 23
<212> TYPE: DNA
<213> ORGANISM: Artificial Sequence
<220> FEATURE:
<223> OTHER INFORMATION: Synthetic primer

<400> SEQUENCE: 62

atcatacagc aggaatgcaa aca                                             23


<210> SEQ ID NO 63
<211> LENGTH: 24
<212> TYPE: DNA
<213> ORGANISM: Artificial Sequence
<220> FEATURE:
<223> OTHER INFORMATION: Synthetic primer

<400> SEQUENCE: 63

tgagattcca catccaacat cttt                                            24


<210> SEQ ID NO 64
<211> LENGTH: 23
<212> TYPE: DNA
<213> ORGANISM: Artificial Sequence
<220> FEATURE:
<223> OTHER INFORMATION: Synthetic primer

<400> SEQUENCE: 64

tggcaaactt gatattgttc ttg                                             23
```

GENETIC MARKERS FOR RISK MANAGEMENT OF ATRIAL FIBRILLATION, ATRIAL FLUTTER, AND STROKE

Incorporated by reference it its entirety is a computer-readable nucleotide/amino acid sequence listing identified as follows: One 221,884 byte ASCII (Text) file named "44319 SubSeqListing.txt, created on Dec. 4, 2012.

BACKGROUND OF THE INVENTION

Cardiac arrhythmia is a group of medical conditions, in which the electrical activity of the heart is irregular, or is slower or faster than normal. Some arrhythmias are life-threatening, and can cause cardiac arrest or sudden death. Others cause, or predispose to, other aggravating symptoms or disease, including stroke. Fibrillation is a serious form of arrhythmia, in which the heart muscle presents with irregular or quivering motion due to lack of unity in the function of contractile cells. Fibrillation can affect the atrium (Atrial Fibrillation (AF) or Atrial Flutter (AFl)), or the ventricle (Ventricular Fibrillation (VF)).

Atrial fibrillation (AF) is an abnormal heart rhythm (cardiac arrhythmia) which involves the two small, upper heart chambers (the atria). Heart beats in a normal heart begin after electricity generated in the atria by the sinoatrial node spreads through the heart and causes contraction of the heart muscle and pumping of blood. In AF, the regular electrical impulses of the sinoatrial node are replaced by disorganized, rapid electrical impulses which result in irregular heart beats.

Atrial fibrillation is the most common cardiac arrhythmia. The risk of developing atrial fibrillation increases with age—AF affects four percent of individuals in their 80s. An individual may spontaneously alternate between AF and a normal rhythm (paroxysmal atrial fibrillation) or may continue with AF as the dominant cardiac rhythm without reversion to the normal rhythm (chronic atrial fibrillation). Atrial fibrillation is often asymptomatic, but may result in symptoms of palpitations, fainting, chest pain, or even heart failure. These symptoms are especially common when atrial fibrillation results in a heart rate which is either too fast or too slow. In addition, the erratic motion of the atria leads to blood stagnation (stasis) which increases the risk of blood clots that may travel from the heart to the brain and other areas. Thus, AF is an important risk factor for stroke, the most feared complication of atrial fibrillation.

The symptoms of atrial fibrillation may be treated with medications which slow the heart rate. Several medications as well as electrical cardioversion may be used to convert AF to a normal heart rhythm. Surgical and catheter-based therapies may also be used to prevent atrial fibrillation in certain individuals. People with AF are often given blood thinners such as warfarin to protect them from strokes.

Any patient with 2 or more identified episodes of atrial fibrillation is said to have recurrent atrial fibrillation. This is further classified into paroxysmal and persistent based on when the episode terminates without therapy. Atrial fibrillation is said to be paroxysmal when it terminates spontaneously within 7 days, most commonly within 24 hours. Persistent or chronic atrial fibrillation is AF established for more than seven days. Differentiation of paroxysmal from chronic or established AF is based on the history of recurrent episodes and the duration of the current episode of AF (Levy S., *J Cardiovasc Electrophysiol.* 8 Suppl, S78-82 (1998)).

Lone atrial fibrillation (LAF) is defined as atrial fibrillation in the absence of clinical or echocardiographic findings of cardiopulmonary disease.

Atrial fibrillation is usually accompanied by symptoms related to either the rapid heart rate or embolization. Rapid and irregular heart rates may be perceived as palpitations, exercise intolerance, and occasionally produce angina and congestive symptoms of shortness of breath or edema. Sometimes the arrhythmia will be identified with the onset of a stroke or a transient ischemic attack (TIA). It is not uncommon to identify atrial fibrillation on a routine physical examination or electrocardiogram (ECG/EKG), as it may be asymptomatic in some cases. Paroxysmal atrial fibrillation is the episodic occurrence of the arrhythmia and may be difficult to diagnose. Episodes may occur with sleep or with exercise, and their episodic nature may require prolonged ECG monitoring (e.g. a Holter monitor) for diagnosis.

Atrial fibrillation is diagnosed on an electrocardiogram, an investigation performed routinely whenever irregular heart beat is suspected. Characteristic findings include absence of P waves, unorganized electrical activity in their place and irregularity of R-R interval due to irregular conduction of impulses to the ventricles. If paroxysmal AF is suspected, episodes may be documented with the use of Holter monitoring (continuous ECG recording for 24 hours or longer).

While many cases of AF have no definite cause, it may be the result of various other problems (see below). Hence, renal function and electrolytes are routinely determined, as well as thyroid-stimulating hormone and a blood count. A chest X-ray is generally performed. In acute-onset AF associated with chest pain, cardiac troponins or other markers of damage to the heart muscle may be ordered. Coagulation studies (INR/aPTT) are usually performed, as anticoagulant medication may be commenced. A transesophageal echocardiogram may be indicated to identify any intracardiac thrombus (Fuster V., et al., Circulation; 104, 2118-2150 (2001)).

Atrial Flutter (AFl) is characterized by an abnormal fast heart rhythm in the atria. Patients who present with atrial flutter commonly also experience Atrial Fibrillation and vice versa (Waldo, A., *Progr Cardiovasc Disease,* 48:41-56 (2005)). Mechanistically and biologically, AF and AFl are thus likely to be highly related.

AF (and AFl) is linked to several cardiac causes, but may occur in otherwise normal hearts. Known associations include: High blood pressure, Mitral stenosis (e.g. due to rheumatic heart disease or mitral valve prolapse), Mitral regurgitation, Heart surgery, Coronary artery disease, Hypertrophic cardiomyopathy, Excessive alcohol consumption ("binge drinking" or "holiday heart"), Hyperthyroidism, Hyperstimulation of the vagus nerve, usually by having large meals ("binge eating"), Lung pathology (such as pneumonia, lung cancer, pulmonary embolism, Sarcoidosis), Pericarditis, Intense emotional turmoil, and Congenital heart disease.

The normal electrical conduction system of the heart allows the impulse that is generated by the sinoatrial node (SA node) of the heart to be propagated to and stimulate the myocardium (muscle of the heart). When the myocardium is stimulated, it contracts. It is the ordered stimulation of the myocardium that allows efficient contraction of the heart, thereby allowing blood to be pumped to the body. In atrial fibrillation, the regular impulses produced by the sinus node to provide rhythmic contraction of the heart are overwhelmed by the rapid randomly generated discharges produced by larger areas of atrial tissue. An organized electrical impulse in the atrium produces atrial contraction; the lack of such an impulse, as in atrial fibrillation, produces stagnant blood flow, especially in the atrial appendage and predisposes to clotting. The dislodgement of a clot from the atrium results in an embolus, and the damage produced is related to where the circulation takes it. An embolus to the brain produces the most feared complication of atrial fibrillation, stroke, while an embolus may also lodge in the mesenteric circulation (the circulation supplying the abdominal organs) or digit, producing organ-specific damage.

Treatment of atrial fibrillation is directed by two main objectives: (i) prevent temporary circulatory instability; (ii) prevent stroke. The most common methods for achieving the former includes rate and rhythm control, while anticoagulation is usually the desired method for the latter (Prystowsky E. N., *Am J Cardiol.;* 85, 3D-11D (2000); van Walraven C, et al., *Jama.* 288, 2441-2448 (2002)). Common methods for rate control, i.e. for reducing heart rate to normal, include beta blockers (e.g., metotprolol), cardiac glycosides (e.g., digoxin) and calcium channel blockers (e.g., verapamil). All these medications work by slowing down the generation of pulses from the atria, and the conduction from the atria to the ventricles. Other drugs commonly used include quinidine, flecainide, propafenone, disopyramide, sotalol and amiodarone. Rhythm control can be achieved by electrical cardioversion, i.e. by applying DC electrical shock, or by chemical cardioversion, using drugs such as amiodarione, propafenone and flecamide.

Preventive measures for stroke include anticoagulants. Representative examples of anticoagulant agents are Dalteparin (e.g., Fragmin), Danaparoid (e.g., Orgaran), Enoxaparin (e.g., Lovenox), Heparin (various), Tinzaparin (e.g., Innohep), Warfarin (e.g., Coumadin). Some patients with lone atrial fibrillation are sometimes treated with aspirin or clopidogrel. There is evidence that aspirin and clopidogrel are effective when used together, but the combination is still inferior to warfarin (Connolly S., et al. *Lancet;* 367, 1903-1912 (2006)). (2) The new anticoagulant ximelagatran has been shown to prevent stroke with equal efficacy as warfarin, without the difficult monitoring process associated with warfarin and with possibly fewer adverse haemorrhagic events. Unfortunately, ximegalatran and other similar anticoagulant drugs (commonly referred to as direct thrombin inhibitors), have yet to be widely licensed.

Determining who should and should not receive anti-coagulation with warfarin is not straightforward. The CHADS2 score is the best validated method of determining risk of stroke (and therefore who should be anticoagulated). The UK NICE guidelines have instead opted for an algorithm approach. The underlying problem is that if a patient has a yearly risk of stroke that is less than 2%, then the risks associated with taking warfarin outweigh the risk of getting a stroke (Gage B. F. et al. *Stroke* 29, 1083-1091 (1998))

Atrial fibrillation can sometimes be controlled with treatment. The natural tendency of atrial fibrillation, however, is to become a chronic condition. Chronic AF leads to an increased risk of death. Patients with atrial fibrillation are at significantly increased chance of stroke.

Atrial fibrillation is common among older adults. In developed countries, the number of patients with atrial fibrillation is likely to increase during the next 50 years, due to the growing proportion of elderly individuals (Go A. S. et al., *Jama.,* 285, 2370-2375 (2001))(3). In the Framingham study the lifetime risk for development of AF is 1 in 4 for men and women 40 years of age and older. Lifetime risks for AF are high (1 in 6). According to data from the National Hospital Discharge Survey (1996-2001) on cases that included AF as a primary discharge diagnosis found that 45% of the patients are male, and that the mean age for men was 66.8 years and 74.6 for women. The racial breakdown for admissions was found to be 71.2% white, 5.6% black, 2% other races, and 20% not specified. Furthermore, African American patients were, on average, much younger than other races. The incidence in men ranged from 20.58/100,000 persons per year for patients ages 15-44 years to 1203/100,000 persons per years for those ages 85 and older. From 1996-2001, hospitalizations with AF as the first listed diagnosis, increased by 34%.

Stroke is a common and serious disease. Each year in the United States more than 600,000 individuals suffer a stroke and more than 160,000 die from stroke-related causes (Sacco, R. L. et al., *Stroke* 28, 1507-17 (1997)). Furthermore, over 300,000 individuals present with Transient Ischemic Attack, a mild form of stroke, every year in the US. In western countries stroke is the leading cause of severe disability and the third leading cause of death (Bonita, R., *Lancet* 339, 342-4 (1992)). The lifetime risk of those who reach the age of 40 exceeds 100%.

The clinical phenotype of stroke is complex but is broadly divided into ischemic (accounting for 80-90%) and hemorrhagic stroke (10-20%) (Caplan, L. R. *Caplan's Stroke: A Clinical Approach,* 1-556 (Butterworth-Heinemann, 2000)). Ischemic stroke is further subdivided into large vessel occlusive disease (referred to here as carotid stroke), usually due to atherosclerotic involvement of the common and internal carotid arteries, small vessel occlusive disease, thought to be a non-atherosclerotic narrowing of small end-arteries within the brain, and cardiogenic stroke due to blood clots arising from the heart usually on the background of atrial fibrillation or ischemic (atherosclerotic) heart disease (Adams, H. P., Jr. et al., *Stroke* 24, 35-41 (1993)). Therefore, it appears that stroke is not one disease but a heterogeneous group of disorders reflecting differences in the pathogenic mechanisms (Alberts, M. J. *Genetics of Cerebrovascular Disease,* 386 (Futura Publishing Company, Inc., New York, 1999); Hassan, A. & Markus, H. S. *Brain* 123, 1784-812 (2000)). However, all forms of stroke share risk factors such as hypertension, diabetes, hyperlipidemia, and smoking (Sacco, R. L. et al., *Stroke* 28, 1507-17 (1997); Leys, D. et al., *J. Neurol.* 249, 507-17 (2002)). Family history of stroke is also an independent risk factor suggesting the existence of genetic factors that may interact with environmental factors (Hassan, A. & Markus, H. S. *Brain* 123, 1784-812 (2000); Brass, L. M. & Alberts, M. J. *Baillieres Clin. Neurol.* 4, 221-45 (1995)).

The genetic determinants of the common forms of stroke are still largely unknown. There are examples of mutations in specific genes that cause rare Mendelian forms of stroke such as the Notch3 gene in CADASIL (cerebral autosomal dominant arteriopathy with subcortical infarctions and leukoencephalopathy) (Tournier-Lasserve, E. et al., *Nat. Genet.* 3, 256-9 (1993); Joutel, A. et al., *Nature* 383, 707-10 (1996)), Cystatin C in the Icelandic type of hereditary cerebral hemorrhage with amyloidosis (Palsdottir, A. et al., *Lancet* 2, 603-4 (1988)), APP in the Dutch type of hereditary cerebral hemorrhage (Levy, E. et al., *Science* 248, 1124-6 (1990)) and the KRIT1 gene in patients with hereditary cavernous angioma (Gunel, M. et al., *Proc. Natl. Acad. Sci. USA* 92, 6620-4 (1995); Sahoo, T. et al., *Hum. Mol. Genet.* 8, 2325-33 (1999)). None of these rare forms of stroke occur on the background of atherosclerosis, and therefore, the corresponding genes are not likely to play roles in the common forms of stroke which most often occur with atherosclerosis.

It is very important for the health care system to develop strategies to prevent stroke. Once a stroke happens, irreversible cell death occurs in a significant portion of the brain supplied by the blood vessel affected by the stroke. Unfortunately, the neurons that die cannot be revived or replaced from a stem cell population. Therefore, there is a need to prevent strokes from happening in the first place. Although we already know of certain clinical risk factors that increase stroke risk (listed above), there is an unmet medical need to define the genetic factors involved in stroke to more precisely define stroke risk. Further, if predisposing alleles are common in the general population and the specificity of predicting a disease based on their presence is low, additional loci such as protective loci are needed for meaningful prediction of disposition of the disease state. There is also a great need for therapeutic agents for preventing the first stroke or further strokes in individuals who have suffered a previous stroke or transient ischemic attack.

AF is an independent risk factor for stroke, increasing risk about 5-fold. The risk for stroke attributable to AF increases with age. AF is responsible for about 15-20% of all strokes. AF is also an independent risk factor for stroke recurrence and stroke severity. A recent report showed people who had AF and were not treated with anticoagulants had a 2.1-fold increase in risk for recurrent stroke and a 2.4 fold increase in risk for recurrent severe stroke. People who have stroke caused by AF have been reported as 2.23 times more likely to be bedridden compared to those who have strokes from other causes.

There is a need for an understanding of the susceptibility factors leading to increased predisposition for AF and stroke. Identification of at-risk variants for AF can, for example, be useful for assessing which individuals are at particularly high risk for AF and subsequent stroke. Furthermore, preventive treatment can be administered to individuals suffering from AF and who are carriers of at-risk susceptibility variants for AF and/or stroke. Finally, identification of at-risk variants for AF and/or stroke can lead to the identification of new targets for drug therapy, as well as the development of novel therapeutic measures.

SUMMARY OF THE INVENTION

The present invention relates to the discovery that certain genetic markers have been shown to be associated with cardiac arrhythmia, in particular atrial fibrillation and atrial flutter, and stroke. This discovery can be utilized in a variety of methods, procedures, apparatus, media and kits, as described herein, relating to methods and procedures of diagnosis and/or determination of a susceptibility, methods of genotyping associated variants, methods of predicting response to therapeutic agents, methods of predicting prognosis, methods of monitoring progress of treatment, and systems and kits for use in such methods.

One aspect of the invention relates to a method of determining a susceptibility to cardiac arrhythmia or stroke in a human individual, the method comprising determining the presence or absence of at least one allele of at least one polymorphic marker in a nucleic acid sample from the individual, wherein the at least one polymorphic marker is selected from the polymorphic markers set forth in Table 5, and markers in linkage disequilibrium therewith, wherein determination of the presence or absence of the at least one allele is indicative of a susceptibility to cardiac arrhythmia or stroke in the individual. In one embodiment, the at least one polymorphic marker is located within the LD block C04, set forth in SEQ ID NO:50 herein. In another embodiment, the at least one polymorphic marker is selected from the markers set forth in Table 9, and markers in linkage disequilibrium therewith. In one embodiment, the at least one marker is selected from marker rs2220427 (SEQ ID NO:1) and marker rs10033464 (SEQ ID NO:41), and markers in linkage disequilibrium therewith. In another embodiment, the at least one polymorphic marker is selected from the markers set forth in Table 19. In one embodiment, the method further comprises a step of assessing at least one haplotype comprising at least two polymorphic markers in the individual.

In another aspect, the invention relates to a method of determining a susceptibility to cardiac arrhythmia or stroke in a human individual, comprising determining whether at least one at-risk allele in at least one polymorphic marker is present in a genotype dataset derived from the individual, wherein the at least one polymorphic marker is selected from the markers set forth in Table 5, and markers in linkage disequilibrium therewith, and wherein determination of the presence of the at least one at-risk allele is indicative of increased susceptibility to cardiac arrhythmia or stroke in the individual.

The genotype dataset comprises in one embodiment information about marker identity, and the allelic status of the individual for the at least one polymorphic marker, i.e. information about the identity of the two alleles carried by the individual for the marker and/or information about whether an individual is a carrier of a particular at-risk allele for the at least one polymorphic marker. The genotype dataset may comprise allelic information about one or more marker, including two or more markers, three or more markers, five or more markers, one hundred or more markers, etc. In some embodiments, the genotype dataset comprises genotype information from a whole-genome assessment of the individual including hundreds of thousands of markers, or even one million or more markers.

The invention, in another aspect, relates to a procedure comprising a step of analyzing a nucleic acid from a human individual to determine the presence or absence of at least one allele of at least one polymorphic marker or haplotype associated with the genomic sequence with sequence as set forth in SEQ ID NO:50; and a step of determining the status of a genetic indicator of cardiac arrhythmia or stroke in the individual from the presence or absence of the at least one marker or haplotype. Thus the genotype and/or haplotype status of the individual is used as in indicator of cardiac arrhythmia, including atrial fibrillation and atrial flutter, as well as stroke, in the individual.

The invention also relates to a method of assessing a susceptibility to cardiac arrhythmia or stroke in a human individual, comprising screening a nucleic acid from the individual for at least one polymorphic marker or haplotype in SEQ ID NO:50 that correlates with increased occurrence of cardiac arrhythmia or stroke in a human population; wherein determination of the presence of an at-risk marker allele in the at least one polymorphism or an at-risk haplotype in the nucleic acid identifies the individual as having elevated susceptibility to cardiac arrhythmia and/or stroke, and wherein the absence of the at least one at-risk marker allele or at-risk haplotype in the nucleic acid identifies the individual as not having the elevated susceptibility.

The procedure or methods of the invention in one embodiment entail at least one polymorphic marker or haplotype comprising a contiguous nucleic acid fragment of LD block C04 as set forth in SEQ ID NO:50, or the complement thereof, wherein the fragment is less than 500 nucleotides in size and specifically hybridizes to a complimentary segment of LD block C04. In one embodiment, the fragment is more than 15 nucleotides and less than 400 nucleotides in size, and wherein the fragment specifically hybridizes to a complimentary segment of LD block C04 as set forth in SEQ ID NO:50.

In alternative embodiments, the susceptibility conferred by the polymorphic markers or haplotypes is decreased susceptibility, i.e. the markers and haplotypes of the invention confer decreased risk of an individual develops cardiac arrhythmia, including atrial fibrillation and atrial flutter, and/or stroke. In one such embodiment, the decreased susceptibility is characterized by an odds ratio (OR) or relative risk (RR) of less than 0.8. In another embodiment, the decreased susceptibility is characterized by an odds ratio (OR) of less than 0.7. In another embodiment, the decreased susceptibility is characterized by an OR or RR of less than 0.6. In another embodiment, the decreased susceptibility is characterized by OR or RR of less than 0.5. Other embodiments relate to other values for OR or RR including values of 0.9, 0.85, 0.75, 0.65, 0.55, etc.

Another aspect of the invention relates to a method of identification of a marker for use in assessing susceptibility to symptoms associated with cardiac arrhythmia and/or stroke in a human individual, the method comprising at least one polymorphic marker within SEQ ID NO:50, or at least one polymorphic marker in linkage disequilibrium with at least one marker within SEQ ID NO:50, determining the genotype status of a sample of individuals diagnosed with cardiac arrhythmia and/or stroke and the genotype status of a sample of control individuals, wherein a significant difference in frequency of at least one allele in at least one polymorphism in individuals diagnosed with cardiac arrhythmia and/or stroke as compared with the frequency of the at least one allele in the control sample is indicative of the at least one polymorphism being useful for assessing susceptibility to cardiac arrhythmia and/or stroke. In one embodiment, an increase in frequency of the at least one allele in the at least one polymorphism in individuals diagnosed with cardiac arrhythmia and/or stroke, as compared with the frequency of the at least one allele in the control sample, is indicative of the at least one polymorphism being useful for assessing increased susceptibility to cardiac arrhythmia. In another embodiment, a decrease in frequency of the at least one allele in the at least one polymorphism in individuals diagnosed with cardiac arrhythmia and/or stroke, as compared with the frequency of the at least one allele in the control sample, is indicative of the at least one polymorphism being useful for assessing decreased susceptibility to, or protection against, cardiac arrhythmia and/or stroke. In preferred embodiments, the significant difference in frequency is characterized by a statistical measure. In one embodiment, the statistical measure is a P-value. In particular embodiments, a significant P-value is less than 0.05, less than 0.01, less than 0.001, less than 0.0001, less than 0.00001, less than 0.000001, less than 0.0000001 or less than 0.00000001. In other embodiments, the significant difference is characterized by an odds ratio (OR) or relative risk (RR) with particular confidence interval (CE) values.

In another aspect, the invention relates to a method of genotyping a nucleic acid sample obtained from a human individual, comprising determining the presence or absence of at least one allele of at least one polymorphic marker predictive of increased risk of cardiac arrhythmia and/or stroke in the sample, wherein the at least one marker is selected from the markers set forth in Table 5, and markers in linkage disequilibrium therewith, and wherein determination of the presence or absence of the at least one allele of the at least one polymorphic marker is predictive of increased risk of cardiac arrhythmia and/or stroke in the individual. In one embodiment, genotyping is performed using a process selected from allele-specific probe hybridization, allele-specific primer extension, allele-specific amplification, nucleic acid sequencing, 5'-exonuclease digestion, molecular beacon assay, oligonucleotide ligation assay, size analysis, and single-stranded conformation analysis. In a preferred embodiment, the process comprises allele-specific probe hybridization. The process of genotyping preferably comprises amplifying a segment of a nucleic acid that comprises the at least one polymorphic marker, by Polymerase Chain Reaction (PCR), using a nucleotide primer pair flanking the at least one polymorphic marker. In a preferred method of genotyping, the following steps are performed:

1. contacting copies of the nucleic acid with a detection oligonucleotide probe and an enhancer oligonucleotide probe under conditions for specific hybridization of the oligonucleotide probe with the nucleic acid; wherein
   a) the detection oligonucleotide probe is from 5-100 nucleotides in length and specifically hybridizes to a first segment of the nucleic acid whose nucleotide sequence is given by SEQ ID NO:50 that comprises at least one polymorphic site;
   b) the detection oligonucleotide probe comprises a detectable label at its 3' terminus and a quenching moiety at its 5' terminus;
   c) the enhancer oligonucleotide is from 5-100 nucleotides in length and is complementary to a second segment of the nucleotide sequence that is 5' relative to the oligonucleotide probe, such that the enhancer oligonucleotide is located 3' relative to the detection oligonucleotide probe when both oligonucleotides are hybridized to the nucleic acid; and
   d) a single base gap exists between the first segment and the second segment, such that when the oligonucleotide probe and the enhancer oligonucleotide probe are both hybridized to the nucleic acid, a single base gap exists between the oligonucleotides;
2. treating the nucleic acid with an endonuclease that will cleave the detectable label from the 3' terminus of the detection probe to release free detectable label when the detection probe is hybridized to the nucleic acid; and measuring free detectable label, wherein the presence of the free detectable label indicates that the detection probe specifically hybridizes to the first segment of the nucleic acid, and indicates the sequence of the polymorphic site as the complement of the detection probe.

A further aspect of the invention relates to a method of determining a susceptibility to cardiac arrhythmia or stroke in a human individual, the method comprising determining the identity of at least one allele of at least one polymorphic marker in a nucleic acid sample obtained from the individual, wherein the at least one marker is selected from the group of markers associated with the PITX2 gene, wherein the presence of the at least one allele is indicative of a susceptibility to cardiac arrhythmia or stroke in the individual.

Some embodiments of the invention relate to a further step of assessing at least one additional biomarker for atrial fibrillation, atrial flutter or stroke, wherein combining the genetic information from the markers provides risk assessment for atrial fibrillation, atrial flutter or stroke. In some of these embodiments, the biomarker is a genetic marker or haplotype, i.e. genetic risk factors shown to be, or contemplated to be, related to increased or decreased risk of atrial fibrillation, atrial flutter or stroke. In other embodiments the biomarker is a protein biomarker. The protein biomarker is in some embodiments selected from fibrin D-dimer, prothrombin activation fragment 1.2 (F1.2), thrombin-antithrombin III complexes (TAT), fibrinopeptide A (FPA), lipoprotein-associated phospholipase A2 (Ip-PLA2), beta-thromboglobulin, platelet factor 4, P-selectin, von Willebrand Factor, pro-natriuretic peptide (BNP), matrix metalloproteinase-9 (MMP-9), PARK7, nucleoside diphosphate kinase (NDKA), tau, neuron-specific enolase, B-type neurotrophic growth factor, astroglial protein S-100b, glial fibrillary acidic protein, C-reactive protein, serum amyloid A, matrix metalloproteinase-9, vascular and intracellular cell adhesion molecules, tumor necrosis factor alpha, and interleukins, including interleukin-1, -6, and -8). In one embodiment, the at least one biomarker includes progenitor cells. In particular embodiments, more than one biomarker is determined. In a preferred embodiment, the biomarker is measured in plasma from the individual. Other embodiments further relate to combining non-genetic information to make risk assessment, diagnosis, or prognosis of atrial fibrillation, atrial flutter or stroke in the individual. The non-genetic information can comprise age, age at onset of disease, gender, ethnicity, previous disease diagnosis, e.g., diagnosis of cardiac arrhythmia (e.g., atrial fibrillation) and stroke, medical history of the individual, family history of disease, biochemical measurements, and clinical measurements (e.g., blood pressure, serum lipid levels). Analysis of such combined information from various genetic markers, or genetic markers plus non-genetic markers is possible by methods known to those skilled in the art. In one embodiment, analysis is performed calculating overall risk by logistic regression.

The invention further relates to a method of diagnosing increased susceptibility of stroke in a human individual, comprising the steps of (a) determining whether the individual has experienced symptoms associated with Atrial Fibrillation, Atrial Flutter or a Transient Ischemic Attack; (b) determining whether a nucleic acid sample from the individual comprises at least one copy of an at-risk allele of at least one polymorphic marker selected from the markers set forth in Table 5, and markers in linkage disequilibrium therewith; wherein the presence of symptoms associated with Atrial Fibrillation, Atrial Flutter and/or Transient Ischemic Attack and the presence of the at least one copy of the at-risk allele is indicative of increased susceptibility of stroke.

The invention in a further aspect relates to a method of assessing an individual for probability of response to a therapeutic agent for preventing and/or ameliorating symptoms associated with cardiac arrhythmia and/or stroke, comprising: determining the presence or absence of at least one allele of at least one polymorphic marker in a nucleic acid sample obtained from the individual, wherein the at least one polymorphic marker is selected from the markers set forth in Table 9, and markers in linkage disequilibrium therewith, wherein determination of the presence of the at least one allele of the at least one marker is indicative of a probability of a positive response to the therapeutic agent for cardiac arrhythmia and/or stroke.

In one embodiment, the therapeutic agent is an anticoagulant, an anti-arrhythmic agent, a hear rate control agent, a cardioversion agent, or a heart rhythm control agent. In another embodiment, the therapeutic agent is selected from warfarin, heparin, low molecular weight heparins, factor Xa inhibitors, and thrombin inhibitors, sodium channel blockers, beta blockers, potassium channel blockers, and calcium channel blockers.

In another embodiment, the therapeutic agent is selected from warfaring, ximelagatran, heparin, enoxaparin, dalteparin, tinzaparin, ardeparin, nadroparin, reviparin, fondaparinux, idraparinux, lepirudin, bivalirudin, argatroban, danaparoid, disopyramide, moricizine, procainamide, quinidine, lidocaine, mexiletine, tocainide, phenyloin, encainide, flecainide, propafenone, ajmaline, cibenzoline, detajmium, esmolol, propranolol, metoprolol, alprenolol, atenolol, carvedilol, bisoprolol, acebutolol, nadolol, pindololol, labetalol, oxprenotol, penbutolol, timolol, betaxolol, cartelol, sotalol, levobunolol, amiodarone, azimilide, bretylium, dofetilide, tedisamil, ibutilide, sematilide, N-acetyl procainamide, nifekalant hydrochloride, vernakalant, ambasilide, verpamil, mibefradil, diltiazem, digoxin, adenosine, ibutilide, amiodarone, procainamide, profafenone and flecainide.

Yet another aspect of the invention relates to a method of predicting prognosis of an individual diagnosed with, cardiac arrhythmia and/or stroke, the method comprising determining the presence or absence of at least one allele of at least one polymorphic marker in a nucleic acid sample obtained from the individual, wherein the at least one polymorphic marker is selected from the markers set forth in Table 9, and markers in linkage disequilibrium therewith, wherein determination of the presence of the at least one allele is indicative of a worse prognosis of the cardiac arrhythmia and/or stroke in the individual.

Methods of monitoring progress of a treatment of an individual undergoing treatment for cardiac arrhythmia and/or stroke are also within scope of the invention, the methods comprising determining the presence or absence of at least one allele of at least one polymorphic marker in a nucleic acid sample obtained from the individual, wherein the at least one polymorphic marker is selected from the markers set forth in Table 9, and markers in linkage disequilibrium therewith, wherein determination of the presence of the at least one allele is indicative of the treatment outcome of the individual.

In particular embodiments of the invention, e.g. in the various methods, uses, procedures, apparatus and kits of the invention, the cardiac arrhythmia phenotype is further characterized as being atrial fibrillation or atrial flutter. The inventors have determined that the risk conferred by the AF at-risk variants described herein is greater for individual with early age at onset than for individuals with late age at onset. Thus in one embodiment, the atrial fibrillation or atrial flutter is further characterized by an age of onset in the individual of less than 80 years. In another embodiment, the atrial fibrillation or atrial flutter is further characterized by an age of onset in the individual of less than 70 years. In yet another embodiment, the atrial fibrillation or atrial flutter is further characterized by an age of onset in the individual of less than 60 years. Other age cutoffs are possible in alternative embodiments of the invention, and are also contemplated, including, but not limited to, age cutoff of less than 75 years, less than 65 years, and less than 55 years. Furthermore, age at onset or diagnosis above age 55, 60, 65, 70, 75 or 80 are also contemplated and within scope of the invention, as are age ranges within which diagnosis or symptoms or onset of the disease occurs, including, but not limited to, age 50-80, age 55-75, age 60-80, age 65-75, etc.

In certain embodiments of the invention, the stroke is further characterized as ischemic stroke. In other embodiments, the stroke phenotype may be characterized as one or more of the ischemic stroke sub-phenotypes large artery atherosclerosis (LAA), cardioembolic stroke (CES) and small vessel disease (SVD).

In particular embodiments of the invention, linkage disequilibrium (LD) is defined by a specific quantitative cutoff. As described in detail herein, linkage disequilibrium can be quantitatively determined by measures such as $r^2$ and |D'|. As a consequence, certain embodiments of the invention relate to markers in linkage disequilibrium by a measure within a certain range specified by particular values of $r^2$ and/or |D'|. In one such embodiment, LD is characterized by numerical values for $r^2$ of greater than 0.1. In another embodiment, LD is characterized by numerical values for $r^2$ of greater than 0.1. In another embodiment, LD is characterized by numerical values for $r^2$ of greater than 0.5. In yet another embodiment, LD is characterized by numerical values for $r^2$ of greater than 0.8. Other cutoff values for $r^2$ are also contemplated, as described in more detail herein. In certain embodiments, LD is characterized by certain cutoff values for $r^2$ and/or |D'|. In one such embodiment, LD is characterized by values for $r^2$ and/or |D'| of greater than 0.2 and 0.8, respectively. Other combination and permutations of these or other measures of LD are possible to practice the invention, and are also contemplated and within scope of the invention.

The procedures, uses, or methods of the invention in some embodiments further comprise a step of administering to an individual determined to be at increased risk for developing cardiac arrhythmia or stroke a composition comprising at least one therapeutic agent effective to treat or prevent cardiac arrhythmia or stroke, or prevent symptoms associated with cardiac arrhythmia or stroke. Thus, the invention can be used to determine whether an individual is suitable for a particular treatment module.

Kits for use in the various methods and procedures described herein are also within scope of the invention. Thus, in one aspect, the invention relates to a kit for assessing susceptibility to cardiac arrhythmia and/or stroke in a human individual, the kit comprising reagents for selectively detecting at least one allele of at least one polymorphic marker in the genome of the individual, wherein the polymorphic marker is selected from the group consisting of the polymorphic markers within the segment whose sequence is set forth in SEQ ID NO:50, and markers in linkage disequilibrium therewith, and wherein the presence of the at least one allele is indicative of a susceptibility to cardiac arrhythmia and/or stroke.

In one embodiment, the at least one polymorphic marker is selected from the markers set forth in Table 5. In another embodiment, the at least one polymorphic marker is selected from the group of markers set forth in Table 9, and markers in linkage disequilibrium therewith. In another embodiment, the at least one polymorphic marker is selected from marker rs2220427 (SEQ ID NO:1) and rs10033464 (SEQ ID NO:41), and markers in linkage disequilibrium therewith. In one preferred embodiment, the at least one polymorphic marker is selected from the markers set forth in Table 19. In another preferred embodiment, the at least one polymorphic marker is selected from D4S406 (SEQ ID NO:45), rs2634073 (SEQ ID NO:33), rs2200733 (SEQ ID NO:28), rs2220427 (SEQ ID NO:1), rs10033464 (SEQ ID NO:41), and rs13143308 (SEQ ID NO:51). In one embodiment, the reagents comprise at least one contiguous oligonucleotide that hybridizes to a fragment of the genome of the individual comprising the at least one polymorphic marker, a buffer and a detectable label.

In another embodiment, the reagents comprise at least one pair of oligonucleotides that hybridize to opposite strands of a genomic nucleic acid segment obtained from the subject, wherein each oligonucleotide primer pair is designed to selectively amplify a fragment of the genome of the individual that includes one polymorphic marker, and wherein the fragment is at least 30 base pairs in size. The at least one oligonucleotide is in preferred embodiments completely complementary to the genome of the individual. In one embodiment, the oligonucleotide is about 18 to about 50 nucleotides in length. In another embodiment, the oligonucleotide is 20-30 nucleotides in length. In one preferred embodiment, the kit comprises:

a. a detection oligonucleotide probe that is from 5-100 nucleotides in length;
b. an enhancer oligonucleotide probe that is from 5-100 nucleotides in length; and
c. an endonuclease enzyme;

wherein the detection oligonucleotide probe specifically hybridizes to a first segment of the nucleic acid whose nucleotide sequence is given by SEQ ID NO: 2 that comprises at least one polymorphic site; wherein the detection oligonucleotide probe comprises a detectable label at its 3' terminus and a quenching moiety at its 5' terminus; wherein the enhancer oligonucleotide is from 5-100 nucleotides in length and is complementary to a second segment of the nucleotide sequence that is 5' relative to the oligonucleotide probe, such that the enhancer oligonucleotide is located 3' relative to the detection oligonucleotide probe when both oligonucleotides are hybridized to the nucleic acid; wherein a single base gap exists between the first segment and the second segment, such that when the oligonucleotide probe and the enhancer oligonucleotide probe are both hybridized to the nucleic acid, a single base gap exists between the oligonucleotides; and wherein treating the nucleic acid with the endonuclease will cleave the detectable label from the 3' terminus of the detection probe to release free detectable label when the detection probe is hybridized to the nucleic acid.

The polymorphic markers described herein as predictive of risk of cardiac arrhythmia (e.g., AF and Atrial flutter) and stroke are useful as diagnostic markers. In aspect, the invention therefore relates to the use of an oligonucleotide probe in the manufacture of a diagnostic reagent for diagnosing and/or assessing susceptibility to cardiac arrhythmia and/or stroke in a human individual, wherein the probe hybridizes to a segment of a nucleic acid whose nucleotide sequence is given by SEQ ID NO:50 that comprises at least one polymorphic site, wherein the fragment is 15-500 nucleotides in length.

In one such embodiment, the polymorphic site is selected from the polymorphic markers set forth in Table 5, and polymorphisms in linkage disequilibrium therewith. In another embodiment, the at least one polymorphic marker is selected from D4S406 (SEQ ID NO:45), rs2634073 (SEQ ID NO:33), rs2200733 (SEQ ID NO:28), rs2220427 (SEQ ID NO:1), rs10033464 (SEQ ID NO:41), and rs13143308 (SEQ ID NO:51), Computer-readable medium for storing information about disease-associated markers as described herein are also within scope of the present invention. In one such aspect, the invention relates to a computer-readable medium on which is stored an identifier for at least one polymorphic marker; an indicator of the frequency of at least one allele of said at least one polymorphic marker in a plurality of individuals diagnosed with atrial fibrillation, atrial flutter and/or stroke; and an indicator of the frequency of the least one allele of said at least one polymorphic markers in a plurality of reference individuals; wherein the at least one polymorphic marker is selected from the polymorphic markers set forth in Table 5, and polymorphisms in linkage disequilibrium therewith. In a preferred embodiment, the at least one polymorphic marker is selected from D4S406 (SEQ ID NO:45), rs2634073 (SEQ ID NO:33), rs2200733 (SEQ ID NO:28), rs2220427 (SEQ ID NO:1), rs10033464 (SEQ ID NO:41), and rs13143308 (SEQ ID NO:51).

The invention also related to an apparatus for determining a genetic indicator for cardiac arrhythmia and/or stroke in a human individual, comprising: a computer readable memory; and a routine stored on the computer readable memory; wherein the routine is adapted to be executed on a processor to analyze genotype and/or haplotype data for at least one human individual with respect to at least one polymorphic marker selected from the markers set forth in Table 5, and markers in linkage disequilibrium therewith, and generate an output based on the marker or haplotype data, wherein the output comprises a risk measure of the at least one marker or haplotype as a genetic indicator of cardiac arrhythmia and/or stroke for the human individual. In a preferred embodiment, the routine further comprises determining an indicator of the frequency of at least one allele of at least one polymorphic marker and/or at least one haplotype in a plurality of individuals diagnosed with cardiac arrhythmia and/or stroke, and an indicator of the frequency of at the least one allele of at least one polymorphic marker or at least one haplotype in a plurality of reference individuals, and calculating a risk measure for the at least one allele and/or haplotype based thereupon; and wherein a risk measure for the individual is calculated based on a comparison of the at least one marker and/or haplotype status for the individual to the calculated risk for the at least one marker and/or haplotype information for the plurality of individuals diagnosed with atrial fibrillation, atrial flutter and/or stroke. In certain embodiments, the risk measure is characterized by an Odds Ratio (OR) or a Relative Risk (RR), as described in more detail herein.

The polymorphic markers discovered in the present invention as predictive of a susceptibility of cardiac arrhythmia and stroke, as described, as well as markers in linkage disequilibrium therewith, are all useful for practicing the various aspects of the present invention. Thus, although particular polymorphic markers were used by the present inventors do detect an association of a particular region on chromosome 4 to cardiac arrhythmia (e.g., atrial fibrillation and atrial flutter) and stroke, it is equally useful to assess markers in strong linkage disequilibrium with those markers. As a consequence, in one embodiment of the methods, uses, kits, procedures, apparatus and media of the invention, the at least one polymorphic marker or haplotype useful in the methods or procedure of the invention comprises at least one of the markers set forth in Table 5 (e.g., Table 5A and Table 5B) and markers in linkage disequilibrium therewith. In another embodiment, the at least one polymorphic marker or haplotype comprises at least one of the markers set forth in Table 9, and markers in linkage disequilibrium therewith. In one embodiment, the at least one polymorphic marker or haplotype comprises at least one of the markers set forth in Table 5. In another embodiment, the at least one polymorphic marker or haplotype comprises at least one of the markers set forth in Table 9. In another embodiment, the at least one polymorphic marker is selected from the markers set forth in Table 4. In one embodiment, the at least one marker is selected from marker rs2220427 (SEQ ID NO:1) and marker rs10033464 (SEQ ID NO:41), and markers in linkage disequilibrium therewith. In another embodiment, the at least one polymorphic marker is selected from the markers set forth in Table 19.

In one embodiment, the at least one marker or haplotype comprises at least one of markers D4S406 (SEQ ID NO:45), rs2723296 (SEQ ID NO:35), rs16997168 (SEQ ID NO:36), rs2723316 (SEQ ID NO:37), rs6419178 (SEQ ID NO:38), rs1448817 (SEQ ID NO:39), rs2634073 (SEQ ID NO:33), rs2200733 (SEQ ID NO:28), rs2220427 (SEQ ID NO: 1), rs13105878 (SEQ ID NO: 40), rs10033464 (SEQ ID NO:41), rs13141190 (SEQ ID NO:42), rs3853444 (SEQ ID NO:43), and rs4576077 (SEQ ID NO:44). In another embodiment, the at least one marker or haplotype comprises at least one of the markers D45406 (SEQ ID NO:45), rs2634073 (SEQ ID NO:33), rs2200733 (SEQ ID NO:28), rs2220427 (SEQ ID NO:1), rs10033464 (SEQ ID NO:41), and rs13143308 (SEQ ID NO:51), In yet another embodiment, the at least one marker is selected from rs10033464, rs2200733, rs13143308 and rs2220427, and markers in linkage disequilibrium therewith.

In a further embodiment, the presence of alleles −2, −4 and/or −8 of marker D45406, allele G of marker rs2723296, allele T of marker rs16997168, allele T of marker rs2723316, allele A of marker rs6419178, allele G of marker rs1448817, allele A of marker rs2634073, allele T of marker rs2200733, allele T of marker rs2220427, allele C of marker rs13105878, allele T of marker rs10033464, allele A of marker rs13141190, allele A of marker rs3853444, and/or allele T of marker rs4576077 is indicative of increased susceptibility of cardiac arrhythmia or stroke in the individual.

In particular embodiments of the invention, the susceptibility conferred by the at-risk variant (i.e. a particular allele at a polymorphic marker (e.g., a SNP) or a particular haplotype) is increased susceptibility, i.e. the markers and haplotypes of the invention confer increased risk of an individual develops cardiac arrhythmia, including atrial fibrillation and atrial flutter, and stroke. Susceptibility is typically characterized by the measure Odds Ratio (OR) or, alternatively, by a Relative Risk (RR). In one embodiment, the increased susceptibility is characterized by an odds ratio (OR) of at least 1.3. In another embodiment, the increased susceptibility is characterized by an odds ratio (OR) of at least 1.4. In another embodiment, the increased susceptibility characterized by an odds ratio (OR) of at least 1.5. In another embodiment, the increased susceptibility characterized by an odds ratio (OR) or relative risk (RR) of at least 1.6. In yet another embodiment, the increased susceptibility characterized by an odds ratio (OR) or relative risk (RR) of at least 1.8. Other embodiments relate to other values for OR, or comparable values for RR including values of 1.25, 1.35, 1.45, 1.55, etc.

Certain embodiments of the invention relate to individuals of a particular ethnicity or ancestry. In one such embodiment, the human individual has ancestry selected from black African ethnicity, Asian ethnicity, Caucasian ethnicity, Hispanic ethnicity, and Arabic ethnicity. In particular embodiments, the ethnicity is self-reported. In other embodiments, ancestry is determined by the assessment of particular ethnicity-specific genetic markers.

BRIEF DESCRIPTION OF THE FIGURES

The foregoing and other objects, features and advantages of the invention will be apparent from the following more particular description of preferred embodiments of the invention.

FIG. 3 Is an overview of a 200 kb genomic neighborhood of rs2200733 and rs10033464. It includes predicted ESTs, the locations of the three main classes of equivalent SNPs in the CEU HapMap samples and an overview of the LD structure of the region in the various ethnic HapMap samples.

Figure 1:
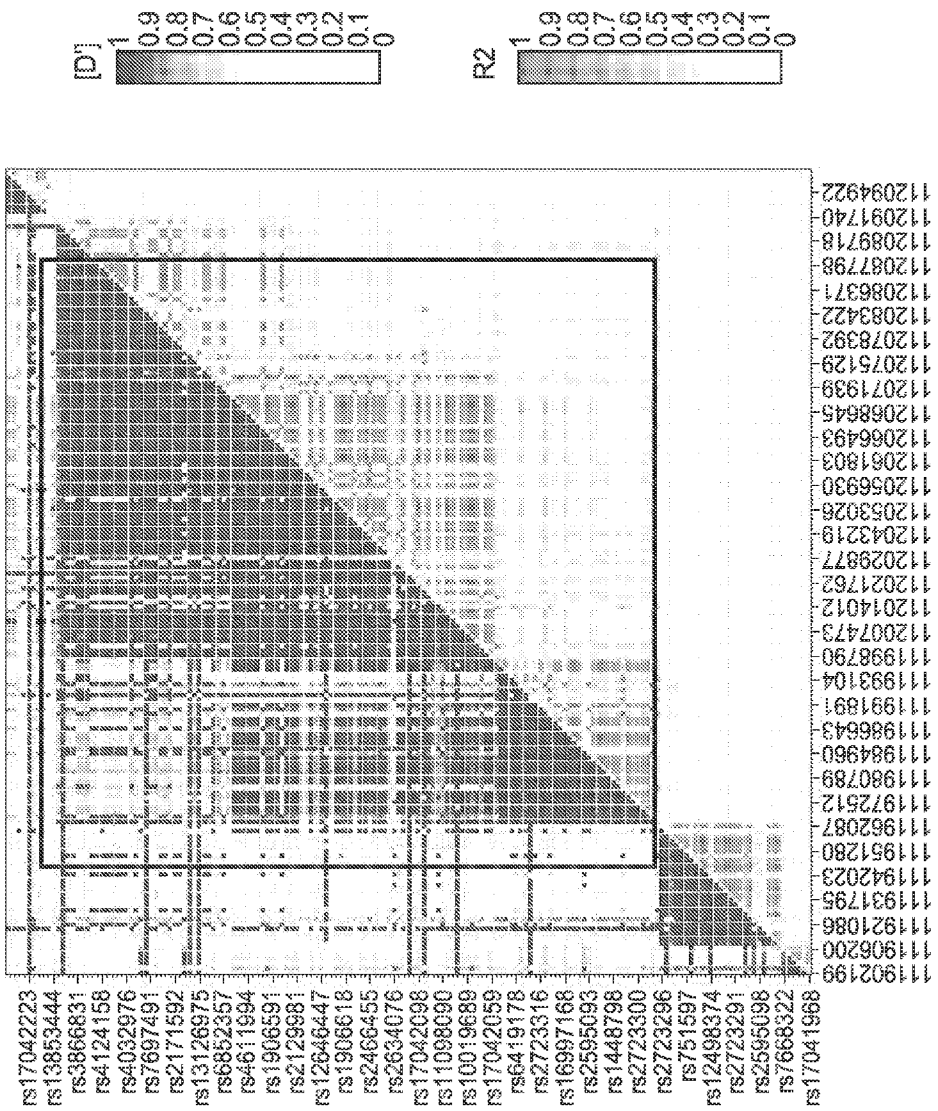
FIG. 1 Shows a plot of linkage disequilibrium (LD) in the region comprising variants of the present invention for the CEPH population (HapMap data). The LD block C04 (111, 954,811-112,104,250 on Chromosome 4, NCBI Build 35 positions) is indicated on the Figure by a black box. The plot shows two measures of LD, i.e. D' in the upper and left part of FIG. 1 and $r^2$ in the lower and right part of the figure.

The PITX2 cDNA clone HU3_p983E0327D was used as a probe and detected 1.8, 2 and 3 kb transcripts and 2.2 and 3 kb PITX2 transcripts in left atrium and aorta respectively. Lane 1: Fetal heart, lane 2: Whole heart, lane 3: Aorta, lane 4: Apex of the heart, lane 5: Left atrium, lane 6: Right atrium, lane 7:

Left ventricle lane 8: Right ventricle. Blot probed with PITX2 cDNA clone (HU3_p983E0327D).

DETAILED DESCRIPTION OF THE INVENTION

A description of preferred embodiments of the invention follows.

Definitions

The following terms shall, in the present context, have the meaning as indicated:

Atrial fibrillation (AF), as described herein, refers to AF as commonly defined according to established medical criteria. AF classified by ICD-10 in class I48 and by ICD-9 in class 427.3

Atrial flutter (AFl), as described herein, refers to AFl as commonly defined according to established medical criteria. Afl is classified ICD-10 class I48 and by ICD-9 in class 427.32.

A "polymorphic marker", sometime referred to as a "marker", as described herein, refers to a genomic polymorphic site. Each polymorphic marker has at least two sequence variations characteristic of particular alleles at the polymorphic site. Thus, genetic association to a polymorphic marker implies that there is association to at least one specific allele of that particular polymorphic marker. The marker can comprise any allele of any variant type found in the genome, including SNPs, microsatellites, insertions, deletions, duplications and translocations.

An "allele" refers to the nucleotide sequence of a given locus (position) on a chromosome. A polymorphic marker allele thus refers to the composition (i.e., sequence) of the marker on a chromosome. Genomic DNA from an individual contains two alleles for any given polymorphic marker, representative of each copy of the marker on each chromosome.

A nucleotide position at which more than one sequence is possible in a population (either a natural population or a synthetic population, e.g., a library of synthetic molecules) is referred to herein as a "polymorphic site".

A "Single Nucleotide Polymorphism" or "SNP" is a DNA sequence variation occurring when a single nucleotide at a specific location in the genome differs between members of a species or between paired chromosomes in an individual. Most SNP polymorphisms have two alleles. Each individual is in this instance either homozygous for one allele of the polymorphism (i.e. both chromosomal copies of the individual have the same nucleotide at the SNP location), or the individual is heterozygous (i.e. the two sister chromosomes of the individual contain different nucleotides). The SNP nomenclature as reported herein refers to the official Reference SNP (rs) ID identification tag as assigned to each unique SNP by the National Center for Biotechnological Information (NCBI).

A "variant", as described herein, refers to a segment of DNA that differs from the reference DNA. A "marker" or a "polymorphic marker", as defined herein, is a variant. Alleles that differ from the reference are referred to as "variant" alleles.

A "microsatellite" is a polymorphic marker that has multiple small repeats of bases that are 2-8 nucleotides in length (such as CA repeats) at a particular site, in which the number of repeat lengths varies in the general population. An "indel" is a common form of polymorphism comprising a small insertion or deletion that is typically only a few nucleotides long.

A "haplotype," as described herein, refers to a segment of genomic DNA that is characterized by a specific combination of alleles arranged along the segment. For diploid organisms such as humans, a haplotype comprises one member of the pair of alleles for each polymorphic marker or locus. In a certain embodiment, the haplotype can comprise two or more alleles, three or more alleles, four or more alleles, or five or more alleles.

The term "susceptibility", as described herein, encompasses both increased susceptibility and decreased susceptibility. Thus, particular polymorphic markers and/or haplotypes of the invention may be characteristic of increased susceptibility (i.e., increased risk) of atrial fibrillation or stroke, as characterized by a relative risk (RR) or odds ratio (OR) of greater than one. Alternatively, the markers and/or haplotypes of the invention are characteristic of decreased susceptibility (i.e., decreased risk) of atrial fibrillation or stroke, as characterized by a relative risk of less than one.

A "nucleic acid sample" is a sample obtained from an individuals that contains nucleic acid. In certain embodiments, i.e. the detection of specific polymorphic markers and/or haplotypes, the nucleic acid sample comprises genomic DNA. Such a nucleic acid sample can be obtained from any source that contains genomic DNA, including as a blood sample, sample of amniotic fluid, sample of cerebrospinal fluid, or tissue sample from skin, muscle, buccal or conjunctival mucosa, placenta, gastrointestinal tract or other organs.

The term "atrial fibrillation and/or stroke therapeutic agent" refers to an agent that can be used to ameliorate or prevent symptoms associated with atrial fibrillation (AF), atrial flutter (AFl) or stroke, as described in more detail herein.

The term "cardiac arrhythmia (e.g., atrial fibrillation or atrial flutter) and/or stroke-associated nucleic acid", as described herein, refers to a nucleic acid that has been found to be associated to cardiac arrhythmia, e.g., atrial fibrillation (AF), atrial flutter (AFl) or stroke. This includes, but is not limited to, the markers and haplotypes described herein and markers and haplotypes in strong linkage disequilibrium (LD) therewith. In one embodiment, an atrial fibrillation, atrial flutter or stroke-associated nucleic acid refers to the LD-block C04 found to be associated with atrial fibrillation and stroke. In another embodiment, the atrial fibrillation, atrial flutter or stroke-associated nucleic acid refers to the PITX2 gene.

The term "LD Block C04", as described herein, refers to the Linkage Disequilibrium (LD) block on Chromosome 4 between position 111,954,811 and 112,104,250 of NCBI (National Center for Biotechnology Information) Build 35, with the genomic sequence as set forth in SEQ ID NO:50.

The term "fragment", as described herein, refers to a segment of a nucleic acid or protein sequence. Fragments are of size smaller than their reference point, i.e. a fragment of a reference nucleic acid molecule that is 1000 nucleotides in size is smaller than 1000 nucleotides in size. Nucleic acid fragments of the invention are commonly more than 5 nucleotides in size and typically more than 15 nucleotides in size, with an upper limit as defined by either their reference nucleotide or by the practical utility of the nucleotide fragment. For example, nucleotide fragments useful as hybridization probes in some embodiments of the invention are more than 15 nucleotides and less than about 500 nucleotides in size. Other size ranges will apply for other nucleotide fragments and protein or peptide fragments of the invention.

The term "PITX2", as described herein, refers to the paired-like homeodomain transcription factor 2 gene on chromosome 4q25. This gene is also referred to as pituitary homeobox 2 (PTX2), rieg bicoid-related homeobox transcription factor 1 (RIEG1), solurshin, and all-1 responsive gene 1 (ARP1).

The present invention relates to the observation that certain polymorphic markers on chromosome 4q25 of the human genome have been found to be associated with cardiac arrhythmia an stroke. In particular embodiments of the invention, polymorphic markers at chromosome 4q25 are associated with the cardiac arrhythmias Atrial fibrillation (AF) and Atrial flutter (AFl), and stroke. These observation have important and unforeseen implications for the development of diagnostic and therapeutics methods, uses, kits and systems, as described in further detail herein.

In a genome-wide scan for genetic variants conferring susceptibility to AF, several markers on chromosome 4q25 were found to be associated with AF. The most significant association was found for markers rs2220427 and rs2220733, both of which gave p-values close to $10^{-9}$ (Table 2) for AF, and smaller, but nominally significant association to stroke (Table 3). A large number of markers were identified as perfect surrogates for these markers, including the microsatellite marker D4S406 (Table 1) and a number of SNP markers (Table 4).

Further refinement of the results revealed that the association signal appears to center, in genetic terms, to markers of rs2200733 and rs10033464 (Table 7) and markers in linkage disequilibrium with those markers (including, but not limited to, the SNP markers listed in Table 9).

The original observation in the Icelandic population was replicated in an independent Icelandic AF/AFl cohort, in a Swedish AF cohort, and in a US AF cohort (Table 7). When combined with the Icelandic samples, the association to rs2200733 was unequivocal (OR=1.72, $P=3.3\times10^{-41}$), and the significance of rs10033464 was well beyond the threshold of genome-wide significance (OR=1.39, $P=6.9\times10^{-11}$). Assuming the multiplicative model, the population attributable risk (PAR) of the two variants combined is approximately 20% in populations of European ancestry. Furthermore, the association replicated in a Chinese AF cohort from Hong Kong (Table 7).

The inventors have also found that age at diagnosis of AF/AFl for the Icelandic samples correlates with the two SNPs rs2200733 and rs10033464. Thus, diagnosis occurs 2.28 years earlier per T allele of rs2200733 and 1.10 years earlier per T allele of rs10033464 (joint $P=1.29\times10^{-6}$). This effect is manifested by the association of the two variants being strongest in those diagnosed at a younger age, although the risk remains significant even in those diagnosed after reaching 80 years of age (Table 8). A similar age at onset effect is observed in the US cohort (Table 8).

The inventors have also observed a strong association between the variants and AFl, that appears to be even stronger than for AF. Thus is revealed by the association to the subset (N=116) of the Icelandic patients that have a diagnosis of AFl (OR=2.60, 95% confidence interval (CI)=1.83-3.68, $P=7.5\times10^{-8}$ for rs2200733, OR=1.94, 95% CI=1.26-3.00, P=0.0028 for rs10033464). In fact, for rs2200733, the OR for these definite AFl cases is significantly higher than that for the cases with an AF phenotype (P=0.0026), and close to significantly higher for rs10033464 (P=0.084). These results that both AF and AFl have significant genetic risk factors that are illustrated by the association to SNPs rs2200733 and rs10033464.

The inventors have furthermore established that the variants associating with AF/AFl also associated with stroke, in particular ischemic stroke (Table 21). Marker rs2200733 replicated significantly in Ischemic stroke and in the Ischemic stroke (IS) subphenotype cardioembolic stroke (CES). Both this marker and marker rs10033464 were found, after genotyping additional Icelandic IS cases and controls (total 1,943 cases/25,708 controls) and four large IS case/control replication sets (4,294 cases/3,709 controls), to associate most strongly with the CES, of which AF is the primary cause, (rs2200733: OR=1.53, $P=1.5\times10^{-12}$; rs10033464: OR=1.27, $P=5.9\times10^{-4}$) (Table 21).

There is no known gene present in the LD block containing rs2200733 and rs10033464 (FIG. 3). The LD block contains one spliced EST (DA725631) and two single-exon ESTs (DB324364 and AF017091). RT-PCR of cDNA libraries from various tissues did not detect the expression of these ESTs (Table 16). The PITX2 gene located in the adjacent upstream LD block is the gene closest to the risk variants. Several markers within the LD block containing PITX2 gene are correlated to the markers showing association to AF and Afl, as shown in Table 18. It is therefore possible that variants within the PITX2 gene are the underlying causative variants. Alternatively, it is possible that the variants of the present invention, as described herein, affect the function, stability, expression, post-translational modification, splicing, message stability of PITX2, or by other means affect the gene so as to predispose to the symptoms associated with atrial fibrillation, atrial flutter and/or stroke. The protein encoded by this gene, the paired-like homeodomain transcription factor 2, is an interesting candidate for AF/AFl as it is known to play an important role in cardiac development by directing asymmetric morphogenesis of the heart (Franco, D., Trends Cardiovasc Med 13: 157-63 (2003)). Furthermore, in a mouse knockout model Pitx2 has been shown to suppress a default pathway for sinoatrial node formation in the left atrium. There is very little mRNA expression of PITX2 in all easily accessible tissues, such as blood and adipose tissue, hampering the study of correlation between genotypes and expression levels. The next gene upstream of PITX2 is ENPEP, an aminopeptidase responsible for the breakdown of angiotensin II in the vascular endothelium. This gene is expressed more widely, but the variants associated with AF showed no correlation to its expression in blood or adipose tissue. No other annotated genes are located within a 400 kb region upstream and 1.5 Mb regions downstream of the associated variants.

Assessment for Markers and Haplotypes

The genomic sequence within populations is not identical when individuals are compared. Rather, the genome exhibits sequence variability between individuals at many locations in the genome. Such variations in sequence are commonly referred to as polymorphisms, and there are many such sites within each genome For example, the human genome exhibits sequence variations which occur on average every 500 base pairs. The most common sequence variant consists of base variations at a single base position in the genome, and such sequence variants, or polymorphisms, are commonly called Single Nucleotide Polymorphisms ("SNPs"). These SNPs are believed to have occurred in a single mutational event, and therefore there are usually two possible alleles possible at each SNPsite; the original allele and the mutated allele. Due to natural genetic drift and possibly also selective pressure, the original mutation has resulted in a polymorphism characterized by a particular frequency of its alleles in any given population. Many other types of sequence variants are found in the human genome, including microsatellites, insertions, deletions, inversions and copy number variations. A polymorphic microsatellite has multiple small repeats of bases (such as CA repeats, TG on the complimentary strand) at a particular site in which the number of repeat lengths varies in the general population. In general terms, each version of the sequence with respect to the polymorphic site represents a specific allele of the polymorphic site. These sequence variants can all be referred to as polymorphisms, occurring at specific polymorphic sites characteristic of the sequence variant in question. In general terms, polymorphisms can comprise any number of specific alleles. Thus in one embodiment of the invention, the polymorphism is characterized by the presence of two or more alleles in any given population. In another embodiment, the polymorphism is characterized by the presence of three or more alleles. In other embodiments, the polymorphism is characterized by four or more alleles, five or more alleles, six or more alleles, seven or more alleles, nine or more alleles, or ten or more alleles. All such polymorphisms can be utilized in the methods and kits of the present invention, and are thus within the scope of the invention.

In some instances, reference is made to different alleles at a polymorphic site without choosing a reference allele. Alternatively, a reference sequence can be referred to for a particular polymorphic site. The reference allele is sometimes referred to as the "wild-type" allele and it usually is chosen as either the first sequenced allele or as the allele from a "non-affected" individual (e.g., an individual that does not display a trait or disease phenotype).

Alleles for SNP markers as referred to herein refer to the bases A, C, G or T as they occur at the polymorphic site in the SNP assay employed. The allele codes for SNPs used herein are as follows: 1=A, 2=C, 3=G, 4=T. The person skilled in the art will however realise that by assaying or reading the opposite DNA strand, the complementary allele can in each case be measured. Thus, for a polymorphic site (polymorphic marker) characterized by an A/G polymorphism, the assay employed may be designed to specifically detect the presence of one or both of the two bases possible, i.e. A and G. Alternatively, by designing an assay that is designed to detect the opposite strand on the DNA template, the presence of the complementary bases T and C can be measured. Quantitatively (for example, in terms of relative risk), identical results would be obtained from measurement of either DNA strand (+strand or − strand).

Typically, a reference sequence is referred to for a particular sequence. Alleles that differ from the reference are sometimes referred to as "variant" alleles. A variant sequence, as used herein, refers to a sequence that differs from the reference sequence but is otherwise substantially similar. Alleles at the polymorphic genetic markers described herein are variants. Additional variants can include changes that affect a polypeptide. Sequence differences, when compared to a reference nucleotide sequence, can include the insertion or deletion of a single nucleotide, or of more than one nucleotide, resulting in a frame shift; the change of at least one nucleotide, resulting in a change in the encoded amino acid; the change of at least one nucleotide, resulting in the generation of a premature stop codon; the deletion of several nucleotides, resulting in a deletion of one or more amino acids encoded by the nucleotides; the insertion of one or several nucleotides, such as by unequal recombination or gene conversion, resulting in an interruption of the coding sequence of a reading frame; duplication of all or a part of a sequence; transposition; or a rearrangement of a nucleotide sequence. Such sequence changes can alter the polypeptide encoded by the nucleic acid. For example, if the change in the nucleic acid sequence causes a frame shift, the frame shift can result in a change in the encoded amino acids, and/or can result in the generation of a premature stop codon, causing generation of a truncated polypeptide. Alternatively, a polymorphism associated with a disease or trait can be a synonymous change in one or more nucleotides (i.e., a change that does not result in a change in the amino acid sequence). Such a polymorphism can, for example, alter splice sites, affect the stability or transport of mRNA, or otherwise affect the transcription or translation of an encoded polypeptide. It can also alter DNA to increase the possibility that structural changes, such as amplifications or deletions, occur at the somatic level. The polypeptide encoded by the reference nucleotide sequence is the "reference" polypeptide with a particular reference amino acid sequence, and polypeptides encoded by variant alleles are referred to as "variant" polypeptides with variant amino acid sequences. A sequence or a reference sequence can either represent the (+) or (−) direction of double stranded DNA. Such sequences are related as being the reverse complement of one another, as well known to the skilled person.

A haplotype refers to a segment of DNA that is characterized by a specific combination of alleles arranged along the segment. For diploid organisms such as humans, a haplotype comprises one member of the pair of alleles for each polymorphic marker or locus. In a certain embodiment, the haplotype can comprise two or more alleles, three or more alleles, four or more alleles, or five or more alleles, each allele corresponding to a specific polymorphic marker along the segment. Haplotypes can comprise a combination of various polymorphic markers, e.g., SNPs and microsatellites, having particular alleles at the polymorphic sites. The haplotypes thus comprise a combination of alleles at various genetic markers.

Detecting specific polymorphic markers and/or haplotypes can be accomplished by methods known in the art for detecting sequences at polymorphic sites. For example, standard techniques for genotyping for the presence of SNPs and/or microsatellite markers can be used, such as fluorescence-based techniques (Chen, X. et al., *Genome Res.* 9(5): 492-98 (1999)), utilizing PCR, LCR, Nested PCR and other techniques for nucleic acid amplification. Specific methodologies available for SNP genotyping include, but are not limited to, TaqMan genotyping assays and SNPlex platforms (Applied Biosystems), mass spectrometry (e.g., MassARRAY system from Sequenom), minisequencing methods, realtime PCR, Bio-Plex system (BioRad), CEQ and SNPstream systems (Beckman), Molecular Inversion Probe array technology (e.g., Affymetrix GeneChip), and BeadArray Technologies (e.g., Illumina GoldenGate and Infinium assays). By these or other methods available to the person skilled in the art, one or more alleles at polymorphic markers, including microsatellites, SNPs or other types of polymorphic markers, can be identified.

In certain methods described herein, an individual who is at an increased susceptibility (i.e., increased risk) for any specific disease or trait under study, is an individual in whom at least one specific allele at one or more polymorphic marker or haplotype conferring increased susceptibility for the disease or trait is identified (i.e., at-risk marker alleles or haplotypes). In one aspect, the at-risk marker or haplotype is one that confers a significant increased risk (or susceptibility) of the disease or trait. In one embodiment, significance associated with a marker or haplotype is measured by a relative risk (RR). In another embodiment, significance associated with a marker or haplotype is measured by an odds ratio (OR). In a further embodiment, the significance is measured by a percentage. In one embodiment, a significant increased risk is measured as a risk (relative risk and/or odds ratio) of at least 1.2, including but not limited to: at least 1.2, at least 1.3, at least 1.4, at least 1.5, at least 1.6, at least 1.7, 1.8, at least 1.9, at least 2.0, at least 2.5, at least 3.0, at least 4.0, and at least 5.0. In a particular embodiment, a risk (relative risk and/or odds ratio) of at least 1.2 is significant. In another particular embodiment, a risk of at least 1.3 is significant. In yet another embodiment, a risk of at least 1.4 is significant. In a further embodiment, a relative risk of at least about 1.5 is significant.

In another further embodiment, a significant increase in risk is at least about 1.7 is significant. However, other cutoffs are also contemplated, e.g. at least 1.15, 1.25, 1.35, and so on, and such cutoffs are also within scope of the present invention. In other embodiments, a significant increase in risk is at least about 20%, including but not limited to about 25%, 30%, 35%, 40%, 45%, 50%, 55%, 60%, 65%, 70%, 75%, 80%, 85%, 90%, 95%, 100%, 150%, 200%, 300%, and 500%. In one particular embodiment, a significant increase in risk is at least 20%. In other embodiments, a significant increase in risk is at least 30%, at least 40%, at least 50%, at least 60%, at least 70%, at least 80%, at least 90% and at least 100%. Other cutoffs or ranges as deemed suitable by the person skilled in the art to characterize the invention are however also contemplated, and those are also within scope of the present invention.

An at-risk polymorphic marker or haplotype of the present invention is one where at least one allele of at least one marker or haplotype is more frequently present in an individual at risk for the disease or trait (e.g., cardiac arrhythmia or stroke) (affected), compared to the frequency of its presence in a comparison group (control), and wherein the presence of the marker or haplotype is indicative of susceptibility to the disease or trait. The control group may in one embodiment be a population sample, i.e. a random sample from the general population. In another embodiment, the control group is represented by a group of individuals who are disease-free. Such disease-free control may in one embodiment be characterized by the absence of one or more specific disease-associated symptoms. In another embodiment, the disease-free control group is characterized by the absence of one or more disease-specific risk factors. Such risk factors are in one embodiment at least one environmental risk factor. Representative environmental factors are natural products, minerals or other chemicals which are known to affect, or contemplated to affect, the risk of developing the specific disease or trait. Other environmental risk factors are risk factors related to lifestyle, including but not limited to food and drink habits, geographical location of main habitat, and occupational risk factors. In another embodiment, the risk factors are at least one genetic risk factor.

As an example of a simple test for correlation would be a Fisher-exact test on a two by two table. Given a cohort of chromosomes, the two by two table is constructed out of the number of chromosomes that include both of the markers or haplotypes, one of the markers or haplotypes but not the other and neither of the markers or haplotypes.

In other embodiments of the invention, an individual who is at a decreased susceptibility (i.e., at a decreased risk) for the disease or trait is an individual in whom at least one specific allele at one or more polymorphic marker or haplotype conferring decreased susceptibility for the disease or trait is identified. The marker alleles and/or haplotypes conferring decreased risk are also said to be protective. In one aspect, the protective marker or haplotype is one that confers a significant decreased risk (or susceptibility) of the disease or trait. In one embodiment, significant decreased risk is measured as a relative risk of less than 0.9, including but not limited to less than 0.9, less than 0.8, less than 0.7, less than 0.6, less than 0.5, less than 0.4, less than 0.3, less than 0.2 and less than 0.1. In one particular embodiment, significant decreased risk is less than 0.7. In another embodiment, significant decreased risk is less than 0.5. In yet another embodiment, significant decreased risk is less than 0.3. In another embodiment, the decrease in risk (or susceptibility) is at least 20%, including but not limited to at least 25%, at least 30%, at least 35%, at least 40%, at least 45%, at least 50%, at least 55%, at least 60%, at least 65%, at least 70%, at least 75%, at least 80%, at least 85%, at least 90%, at least 95% and at least 98%. In one particular embodiment, a significant decrease in risk is at least about 30%. In another embodiment, a significant decrease in risk at least about 50%. In another embodiment, the decrease in risk is at least about 70%. Other cutoffs or ranges as deemed suitable by the person skilled in the art to characterize the invention are however also contemplated, and those are also within scope of the present invention.

The person skilled in the art will appreciate that for markers with two alleles present in the population being studied, and wherein one allele is found in increased frequency in a group of individuals with a trait or disease in the population, compared with controls, the other allele of the marker will be found in decreased frequency in the group of individuals with the trait or disease, compared with controls. In such a case, one allele of the marker (the one found in increased frequency in individuals with the trait or disease) will be the at-risk allele, while the other allele will be a protective allele.

Linkage Disequilibrium

The natural phenomenon of recombination, which occurs on average once for each chromosomal pair during each meiotic event, represents one way in which nature provides variations in sequence (and biological function by consequence). It has been discovered that recombination does not occur randombly in the genome; rather, there are large variations in the frequency of recombination rates, resulting in small regions of high recombination frequency (also called recombination hotspots) and larger regions of low recombination frequency, which are commonly referred to as Linkage Disequilibrium (LD) blocks (Myers, S. et al., *Biochem Soc Trans* 34:526-530 (2006); Jeffreys, A. J., et al., *Nature Genet.* 29:217-222 (2001); May, C. A., et al., *Nature Genet.* 31:272-275 (2002)).

Linkage Disequilibrium (LD) refers to a non-random assortment of two genetic elements. For example, if a particular genetic element (e.g., an allele of a polymorphic marker, or a haplotype) occurs in a population at a frequency of 0.25 (25%) and another element occurs at a frequency of 0.25 (25%), then the predicted occurrence of a person's having both elements is 0.125 (12.5%), assuming a random distribution of the elements. However, if it is discovered that the two elements occur together at a frequency higher than 0.125, then the elements are said to be in linkage disequilibrium, since they tend to be inherited together at a higher rate than what their independent frequencies of occurrence (e.g., allele or haplotype frequencies) would predict. Roughly speaking, LD is generally correlated with the frequency of recombination events between the two elements. Allele or haplotype frequencies can be determined in a population by genotyping individuals in a population and determining the frequency of the occurence of each allele or haplotype in the population. For populations of diploids, e.g., human populations, individuals will typically have two alleles for each genetic element (e.g., a marker, haplotype or gene).

Many different measures have been proposed for assessing the strength of linkage disequilibrium (LD). Most capture the strength of association between pairs of biallelic sites. Two important pairwise measures of LD are $r^2$ (sometimes denoted $\Delta^2$) and $|D'|$. Both measures range from 0 (no disequilibrium) to 1 ('complete' disequilibrium), but their interpretation is slightly different. $|D'|$ is defined in such a way that it is equal to 1 if just two or three of the possible haplotypes are present, and it is <1 if all four possible haplotypes are present. Therefore, a value of $|D'|$ that is <1 indicates that historical recombination may have occurred between two sites (recurrent mutation can also cause $|D'|$ to be <1, but for single nucleotide polymorphisms (SNPs) this is usually regarded as being less likely than recombination). The measure $r^2$ represents the statistical correlation between two sites, and takes the value of 1 if only two haplotypes are present.

The $r^2$ measure is arguably the most relevant measure for association mapping, because there is a simple inverse relationship between $r^2$ and the sample size required to detect association between susceptibility loci and SNPs. These measures are defined for pairs of sites, but for some applications a determination of how strong LD is across an entire region that contains many polymorphic sites might be desirable (e.g., testing whether the strength of LD differs significantly among loci or across populations, or whether there is more or less LD in a region than predicted under a particular model). Measuring LD across a region is not straightforward, but one approach is to use the measure r, which was developed in population genetics. Roughly speaking, r measures how much recombination would be required under a particular population model to generate the LD that is seen in the data. This type of method can potentially also provide a statistically rigorous approach to the problem of determining whether LD data provide evidence for the presence of recombination hotspots. For the methods and procedures described herein, a significant $r^2$ value can be at least 0.1 such as at least 0.1, 0.15, 0.2, 0.25, 0.3, 0.35, 0.4, 0.45, 0.5, 0.55, 0.6, 0.65, 0.7, 0.75, 0.8, 0.85, 0.9, 0.91, 0.92, 0.93, 0.94, 0.95, 0.96, 0.97, 0.98, 0.99 or 1.0. In one preferred embodiment, the significant $r^2$ value can be at least 0.2. Alternatively, linkage disequilibrium as described herein, refers to linkage disequilibrium characterized by values of |D'| of at least 0.2, such as 0.3, 0.4, 0.5, 0.6, 0.7, 0.8, 0.85, 0.9, 0.95, 0.96, 0.97, 0.98, 0.99. Thus, linkage disequilibrium represents a correlation between alleles of distinct markers. It is measured by correlation coefficient or |D'| ($r^2$ up to 1.0 and |D'| up to 1.0). Linkage disequilibrium can be determined in a single human population, as defined herein, or it can be determined in a collection of samples comprising individuals from more than one human population. In one embodiment of the invention, LD is determined in a sample from one or more of the HapMap populations (caucasian, african, japanese, chinese), as defined (http colon-slash-slash www.hapmap.org). In one such embodiment, LD is determined in the CEU population of the HapMap samples. In another embodiment, LD is determined in the YRI population. In yet another embodiment, LD is determined in samples from the Icelandic population.

If all polymorphisms in the genome were identical at the population level, then every single one of them would need to be investigated in association studies. However, due to linkage disequilibrium between polymorphisms, tightly linked polymorphisms are strongly correlated, which reduces the number of polymorphisms that need to be investigated in an association study to observe a significant association. Another consequence of LD is that many polymorphisms may give an association signal due to the fact that these polymorphisms are strongly correlated.

Genomic LD maps have been generated across the genome, and such LD maps have been proposed to serve as framework for mapping disease-genes (Risch, N. & Merkiangas, K, *Science* 273:1516-1517 (1996); Maniatis, N., et al., *Proc Nat Acad Sci USA* 99:2228-2233 (2002); Reich, D E et al, *Nature* 411:199-204 (2001)).

It is now established that many portions of the human genome can be broken into series of discrete haplotype blocks containing a few common haplotypes; for these blocks, linkage disequilibrium data provides little evidence indicating recombination (see, e.g., Wall., J. D. and Pritchard, J. K., *Nature Reviews Genetics* 4:587-597 (2003); Daly, M. et al., *Nature Genet.* 29:229-232 (2001); Gabriel, S. B. et al., *Science* 296:2225-2229 (2002); Patil, N. et al., *Science* 294:1719-1723 (2001); Dawson, E. et al., *Nature* 418:544-548 (2002); Phillips, M. S. et al., *Nature Genet.* 33:382-387 (2003)).

There are two main methods for defining these haplotype blocks: Blocks can be defined as regions of DNA that have limited haplotype diversity (see, e.g., Daly, M. et al., *Nature Genet.* 29:229-232 (2001); Patil, N. et al., *Science* 294:1719-1723 (2001); Dawson, E. et al., *Nature* 418:544-548 (2002); Zhang, K. et al., *Proc. Natl. Acad. Sci. USA* 99:7335-7339 (2002)), or as regions between transition zones having extensive historical recombination, identified using linkage disequilibrium (see, e.g., Gabriel, S. B. et al., *Science* 296:2225-2229 (2002); Phillips, M. S. et al., *Nature Genet.* 33:382-387 (2003); Wang, N. et al., *Am. J. Hum. Genet.* 71:1227-1234 (2002); Stumpf, M. P., and Goldstein, D. B., *Curr. Biol.* 13:1-8 (2003)). More recently, a fine-scale map of recombination rates and corresponding hotspots across the human genome has been generated (Myers, S., et al., *Science* 310:321-32324 (2005); Myers, S. et al., *Biochem Soc Trans* 34:526530 (2006)). The map reveals the enormous variation in recombination across the genome, with recombination rates as high as 10-60 cM/Mb in hotspots, while closer to 0 in intervening regions, which thus represent regions of limited haplotype diversity and high LD. The map can therefore be used to define haplotype blocks/LD blocks as regions flanked by recombination hotspots. As used herein, the terms "haplotype block" or "LD block" includes blocks defined by any of the above described characteristics, or other alternative methods used by the person skilled in the art to define such regions.

Haplotype blocks can be used to map associations between phenotype and haplotype status, using single markers or haplotypes comprising a plurality of markers. The main haplotypes can be identified in each haplotype block, and then a set of "tagging" SNPs or markers (the smallest set of SNPs or markers needed to distinguish among the haplotypes) can then be identified. These tagging SNPs or markers can then be used in assessment of samples from groups of individuals, in order to identify association between phenotype and haplotype. If desired, neighboring haplotype blocks can be assessed concurrently, as there may also exist linkage disequilibrium among the haplotype blocks.

It has thus become apparent that for any given observed association to a polymorphic marker in the genome, it is likely that additional markers in the genome also show association. This is a natural consequence of the uneven distribution of LD across the genome, as observed by the large variation in recombination rates. The markers used to detect association thus in a sense represent "tags" for a genomic region (i.e., a haplotype block or LD block) that is associating with a given disease or trait, and as such are useful for use in the methods and kits of the present invention. One or more causative (functional) variants or mutations may reside within the region found to be associating to the disease or trait. Such variants may confer a higher relative risk (RR) or odds ratio (OR) than observed for the tagging markers used to detect the association. The present invention thus refers to the markers used for detecting association to the disease, as described herein, as well as markers in linkage disequilibrium with the markers. Thus, in certain embodiments of the invention, markers that are in LD with the markers and/or haplotypes of the invention, as described herein, may be used as surrogate markers. The surrogate markers have in one embodiment relative risk (RR) and/or odds ratio (OR) values smaller than for the markers or haplotypes initially found to be associating with the disease, as described herein. In other embodiments, the surrogate markers have RR or OR values greater than those initially determined for the markers initially found to be associating with the disease, as described herein. An example of such an embodiment would be a rare, or relatively rare (<10% allelic population frequency) variant in LD with a more common variant (>10% population frequency) initially found to be associating with the disease, such as the variants described herein. Identifying and using such markers for detecting the association discovered by the inventors as described herein can be performed by routine methods well known to the person skilled in the art, and are therefore within the scope of the present invention.

It is possible that certain polymorphic markers in linkage disequilibrium with the markers shown herein to be associated with cardiac arrhythmia (e.g., atrial fibrillation and atrial flutter) and stroke are located outside the physical boundaries of the LD block C04 as defined herein by the sequence set forth in SEQ ID NO:50. This is a consequence of the historical recombination rates in the region in question, which may have led to a region of strong LD (the LD block), with residual markers outside the block in LD with markers within the block. Such markers are also within scope of the present invention, as they are also useful for practicing the invention by virtue of their genetic relationship with the markers shown herein to be associated with cardiac arrhythmia and stroke. Examples of such markers are shown in Table 18 (rs7668322 (SEQ ID NO:46), rs2197815 (SEQ ID NO:47), rs6831623 (SEQ ID NO:48), rs2595110 (SEQ ID NO:49))

Determination of Haplotype Frequency

The frequencies of haplotypes in patient and control groups can be estimated using an expectation-maximization algorithm (Dempster A. et al., *J. R. Stat. Soc. B,* 39:1-38 (1977)). An implementation of this algorithm that can handle missing genotypes and uncertainty with the phase can be used. Under the null hypothesis, the patients and the controls are assumed to have identical frequencies. Using a likelihood approach, an alternative hypothesis is tested, where a candidate at-risk-haplotype, which can include the markers described herein, is allowed to have a higher frequency in patients than controls, while the ratios of the frequencies of other haplotypes are assumed to be the same in both groups. Likelihoods are maximized separately under both hypotheses and a corresponding 1-df likelihood ratio statistic is used to evaluate the statistical significance.

To look for at-risk and protective markers and haplotypes within a linkage region, for example, association of all possible combinations of genotyped markers is studied, provided those markers span a practical region. The combined patient and control groups can be randomly divided into two sets, equal in size to the original group of patients and controls. The marker and haplotype analysis is then repeated and the most significant p-value registered is determined. This randomization scheme can be repeated, for example, over 100 times to construct an empirical distribution of p-values. In a preferred embodiment, a p-value of <0.05 is indicative of an significant marker and/or haplotype association.

Haplotype Analysis

One general approach to haplotype analysis involves using likelihood-based inference applied to NEsted MOdels (Gretarsdottir S., et al., *Nat. Genet.* 35:131-38 (2003)). The method is implemented in the program NEMO, which allows for many polymorphic markers, SNPs and microsatellites. The method and software are specifically designed for case-control studies where the purpose is to identify haplotype groups that confer different risks. It is also a tool for studying LD structures. In NEMO, maximum likelihood estimates, likelihood ratios and p-values are calculated directly, with the aid of the EM algorithm, for the observed data treating it as a missing-data problem.

Even though likelihood ratio tests based on likelihoods computed directly for the observed data, which have captured the information loss due to uncertainty in phase and missing genotypes, can be relied on to give valid p-values, it would still be of interest to know how much information had been lost due to the information being incomplete. The information measure for haplotype analysis is described in Nicolae and Kong (Technical Report 537, Department of Statistics, University of Statistics, University of Chicago; *Biometrics,* 60(2):368-75 (2004)) as a natural extension of information measures defined for linkage analysis, and is implemented in NEMO.

For single marker association to a disease, the Fisher exact test can be used to calculate two-sided p-values for each individual allele. Usually, all p-values are presented unadjusted for multiple comparisons unless specifically indicated. The presented frequencies (for microsatellites, SNPs and haplotypes) are allelic frequencies as opposed to carrier frequencies. To minimize any bias due the relatedness of the patients who were recruited as families for the linkage analysis, first and second-degree relatives can be eliminated from the patient list. Furthermore, the test can be repeated for association correcting for any remaining relatedness among the patients, by extending a variance adjustment procedure described in Risch, N. & Teng, J. (*Genome Res.,* 8:1273-1288 (1998)), DNA pooling (ibid) for sibships so that it can be applied to general familial relationships, and present both adjusted and unadjusted p-values for comparison. The differences are in general very small as expected. To assess the significance of single-marker association corrected for multiple testing we can carry out a randomization test using the same genotype data. Cohorts of patients and controls can be randomized and the association analysis redone multiple times (e.g., up to 500,000 times) and the p-value is the fraction of replications that produced a p-value for some marker allele that is lower than or equal to the p-value we observed using the original patient and control cohorts.

For both single-marker and haplotype analyses, relative risk (RR) and the population attributable risk (PAR) can be calculated assuming a multiplicative model (haplotype relative risk model) (Terwilliger, J. D. & Ott, J., *Hum. Hered.* 42:337-46 (1992) and Falk, C. T. & Rubinstein, P, *Ann. Hum. Genet.* 51 (Pt 3):227-33 (1987)), i.e., that the risks of the two alleles/haplotypes a person carries multiply. For example, if RR is the risk of A relative to a, then the risk of a person homozygote AA will be RR times that of a heterozygote Aa and $RR^2$ times that of a homozygote aa. The multiplicative model has a nice property that simplifies analysis and computations—haplotypes are independent, i.e., in Hardy-Weinberg equilibrium, within the affected population as well as within the control population. As a consequence, haplotype counts of the affecteds and controls each have multinomial distributions, but with different haplotype frequencies under the alternative hypothesis. Specifically, for two haplotypes, $h_i$ and $h_j$, $risk(h_i)/risk(h_j)=(f_i/p_i)/(f_j/p_j)$, where f and p denote, respectively, frequencies in the affected population and in the control population. While there is some power loss if the true model is not multiplicative, the loss tends to be mild except for extreme cases. Most importantly, p-values are always valid since they are computed with respect to null hypothesis.

Linkage Disequilibrium Using NEMO

LD between pairs of markers can be calculated using the standard definition of D' and $r^2$ (Lewontin, R., *Genetics* 49:49-67 (1964); Hill, W. G. & Robertson, A. *Theor. Appl.*

*Genet.* 22:226-231 (1968)). Using NEMO, frequencies of the two marker allele combinations are estimated by maximum likelihood and deviation from linkage equilibrium is evaluated by a likelihood ratio test. The definitions of D' and $r^2$ are extended to include microsatellites by averaging over the values for all possible allele combination of the two markers weighted by the marginal allele probabilities. When plotting all marker combination to elucidate the LD structure in a particular region, we plot D' in the upper left corner and the p-value in the lower right corner. In the LD plots the markers can be plotted equidistant rather than according to their physical location, if desired.

Risk Assessment and Diagnostics

As described herein, certain polymorphic markers and haplotypes comprising such markers are found to be useful for risk assessment of cardiac arrhythmia (e.g., atrial fibrillation or atrial flutter) or stroke. Risk assessment can involve the use of the markers for diagnosing a susceptibility to cardiac arrhythmia (e.g., atrial fibrillation or atrial flutter) or stroke. Particular alleles of polymorphic markers are found more frequently in individuals with cardiac arrhythmia (e.g., atrial fibrillation or atrial flutter) or stroke, than in individuals without diagnosis of cardiac arrhythmia (e.g., atrial fibrillation or atrial flutter) or stroke. Therefore, these marker alleles have predictive value for detecting cardiac arrhythmia (e.g., atrial fibrillation or atrial flutter) and/or stroke, or a susceptibility to cardiac arrhythmia (e.g., atrial fibrillation or atrial flutter) or stroke, in an individual. Tagging markers within haplotype blocks or LD blocks comprising at-risk markers, such as the markers of the present invention, can be used as surrogates for other markers and/or haplotypes within the haplotype block or LD block. Markers with values of $r^2$ equal to 1 are perfect surrogates for the at-risk variants, i.e. genotypes for one marker perfectly predicts genotypes for the other. Markers with smaller values of $r^2$ than 1 can also be surrogates for the at-risk variant, or alternatively represent variants with relative risk values as high or possibly even higher than the at-risk variant. The at-risk variant identified may not be the functional variant itself, but is in this instance in linkage disequilibrium with the true functional variant. The present invention encompasses the assessment of such surrogate markers for the markers as disclosed herein. Such markers are annotated, mapped and listed in public databases, as well known to the skilled person, or can alternatively be readily identified by sequencing the region or a part of the region identified by the markers of the present invention in a group of individuals, and identify polymorphisms in the resulting group of sequences As a consequence, the person skilled in the art can readily and without undue experimentation genotype surrogate markers in linkage disequilibrium with the markers and/or haplotypes as described herein. The tagging or surrogate markers in LD with the at-risk variants detected, also have predictive value for detecting association to cardiac arrhythmia (e.g., atrial fibrillation or atrial flutter) and/or stroke or a susceptibility to cardiac arrhythmia (e.g., atrial fibrillation or atrial flutter) or stroke, in an individual. These tagging or surrogate markers that are in LD with the markers of the present invention can also include other markers that distinguish among haplotypes, as these similarly have predictive value for detecting susceptibility to cardiac arrhythmia (e.g., atrial fibrillation or atrial flutter) and/or stroke.

The markers and haplotypes of the invention, e.g., the markers presented in Tables 5 and 9, as well as markers in linkage disequilibrium therewith, may be useful for risk assessment and diagnostic purposes for, either alone or in combination. Thus, even in cases where the increase in risk by individual markers is relatively modest, i.e. on the order of 10-30%, the association may have significant implications. Thus, relatively common variants may have significant contribution to the overall risk (Population Attributable Risk is high), or combination of markers can be used to define groups of individual who, based on the combined risk of the markers, is at significant combined risk of developing the disease.

Thus, in one embodiment of the invention, a plurality of variants (markers and/or haplotypes) is used for overall risk assessment. These variants are in one embodiment selected from the variants as disclosed herein. Other embodiments include the use of the variants of the present invention in combination with other variants known to be useful for diagnosing a susceptibility to cardiac arrhythmia (e.g., atrial fibrillation or atrial flutter) and/or stroke. In such embodiments, the genotype status of a plurality of markers and/or haplotypes is determined in an individual, and the status of the individual compared with the population frequency of the associated variants, or the frequency of the variants in clinically healthy subjects, such as age-matched and sex-matched subjects. Methods known in the art, such as multivariate analyses or joint risk analyses, may subsequently be used to determine the overall risk conferred based on the genotype status at the multiple loci. Assessment of risk based on such analysis may subsequently be used in the methods and kits of the invention, as described herein.

As described in the above, the haplotype block structure of the human genome has the effect that a large number of variants (markers and/or haplotypes) in linkage disequilibrium with the variant originally associated with a disease or trait may be used as surrogate markers for assessing association to the disease or trait. The number of such surrogate markers will depend on factors such as the historical recombination rate in the region, the mutational frequency in the region (i.e., the number of polymorphic sites or markers in the region), and the extent of LD (size of the LD block) in the region. These markers are usually located within the physical boundaries of the LD block or haplotype block in question as defined using the methods described herein, or by other methods known to the person skilled in the art. However, sometimes marker and haplotype association is found to extend beyond the physical boundaries of the haplotype block as defined. Such markers and/or haplotypes may in those cases be also used as surrogate markers and/or haplotypes for the markers and/or haplotypes physically residing within the haplotype block as defined. As a consequence, markers and haplotypes in LD (typically characterized by $r^2$ greater than 0.1, such as $r^2$ greater than 0.2, including $r^2$ greater than 0.3, also including $r^2$ greater than 0.4) with the markers and haplotypes of the present invention are also within the scope of the invention, even if they are physically located beyond the boundaries of the haplotype block as defined. This includes markers that are described herein (e.g., Tables 5 and 9), but may also include other markers that are in strong LD (characterized by $r^2$ greater than 0.1 or 0.2 and/or $|D'|>0.8$) with one or more of the markers listed in Tables 5 and 9.

For the SNP markers described herein, the opposite allele to the allele found to be in excess in patients (at-risk allele) is found in decreased frequency in cardiac arrhythmia (e.g., atrial fibrillation or atrial flutter) and/or stroke patients. These markers and haplotypes in LD and/or comprising such markers, are thus protective for cardiac arrhythmia (e.g., atrial fibrillation or atrial flutter) and/or stroke. i.e. they confer a decreased risk or susceptibility of individuals carrying these markers and/or haplotypes developing cardiac arrhythmia (e.g., atrial fibrillation or atrial flutter) and/or stroke.

Certain variants of the present invention, including certain haplotypes comprise, in some cases, a combination of various genetic markers, e.g., SNPs and microsatellites. Detecting haplotypes can be accomplished by methods known in the art and/or described herein for detecting sequences at polymorphic sites. Furthermore, correlation between certain haplotypes or sets of markers and disease phenotype can be verified using standard techniques. A representative example of a simple test for correlation would be a Fisher-exact test on a two by two table.

In specific embodiments, a marker or haplotype found to be associated with cardiac arrhythmia (e.g., atrial fibrillation or atrial flutter) and/or stroke., (e.g., markers as listed in Table 5 (Tables 5A and 5B), Table 9 and/or Table 19, and markers in linkage disequilibrium therewith) is one in which the marker allele or haplotype is more frequently present in an individual at risk for cardiac arrhythmia (e.g., atrial fibrillation or atrial flutter) and/or stroke (affected), compared to the frequency of its presence in a healthy individual (control), wherein the presence of the marker allele or haplotype is indicative of cardiac arrhythmia (e.g., atrial fibrillation or atrial flutter) and/or stroke. or a susceptibility to cardiac arrhythmia (e.g., atrial fibrillation or atrial flutter) and/or stroke. In other embodiments, at-risk markers in linkage disequilibrium with one or more markers found to be associated with cardiac arrhythmia (e.g., atrial fibrillation or atrial flutter) and/or stroke. (e.g., marker alleles as listed in Tables 5A and 5B, and markers in linkage disequilibrium therewith) are tagging markers that are more frequently present in an individual at risk for cardiac arrhythmia (e.g., atrial fibrillation or atrial flutter) and/or stroke (affected), compared to the frequency of their presence in a healthy individual (control), wherein the presence of the tagging markers is indicative of increased susceptibility to cardiac arrhythmia (e.g., atrial fibrillation or atrial flutter) and/or stroke. In a further embodiment, at-risk markers alleles (i.e. conferring increased susceptibility) in linkage disequilibrium with one or more markers found to be associated with cardiac arrhythmia (e.g., atrial fibrillation or atrial flutter) and/or stroke. (e.g., marker alleles as listed in Tables 5A and 5B and markers in linkage disequilibrium therewith), are markers comprising one or more allele that is more frequently present in an individual at risk for cardiac arrhythmia (e.g., atrial fibrillation or atrial flutter) and/or stroke compared to the frequency of their presence in a healthy individual (control), wherein the presence of the markers is indicative of increased susceptibility to cardiac arrhythmia (e.g., atrial fibrillation or atrial flutter) and/or stroke.

Study Population

In a general sense, the methods and kits of the invention can be utilized from samples containing genomic DNA from any source, i.e. any individual. In preferred embodiments, the individual is a human individual. The individual can be an adult, child, or fetus. The present invention also provides for assessing markers and/or haplotypes in individuals who are members of a target population. Such a target population is in one embodiment a population or group of individuals at risk of developing the disease, based on other genetic factors, biomarkers, biophysical parameters (e.g., weight, BMD, blood pressure), or general health and/or lifestyle parameters (e.g., history of disease or related diseases, previous diagnosis of disease, family history of disease).

The invention provides for embodiments that include individuals from specific age subgroups, such as those over the age of 40, over age of 45, or over age of 50, 55, 60, 65, 70, 75, 80, or 85. Other embodiments of the invention pertain to other age groups, such as individuals aged less than 85, such as less than age 80, less than age 75, or less than age 70, 65, 60, 55, 50, 45, 40, 35, or age 30. Other embodiments relate to individuals with age at onset of the disease in any of the age ranges described in the above. It is also contemplated that a range of ages may be relevant in certain embodiments, such as age at onset at more than age 45 but less than age 60. Other age ranges are however also contemplated, including all age ranges bracketed by the age values listed in the above.

Other embodiments related to individuals with age at onset of the disease at particular age or age range. Thus, it is known that predisposing factors, genetic and non-genetic, can affect at what age an individual develops a disease. For cardiovascular disorders, including cardiac arrhythmias and stroke, common risk factors can influence if, and at what age, an individual develops the disease. Some embodiments of the invention therefore relate to age at onset or age at diagnosis of cardiac arrhythmia (e.g., atrial fibrillation and/or atrial flutter) or stroke in a certain age range. In one embodiment, the individuals at risk for developing cardiac arrhythmia (e.g., atrial fibrillation and/or atrial flutter) or stroke have age at onset or age at diagnosis over the age of 40. In other embodiments, the individuals have age at onset or age at diagnosis over age of 45, or over age of 50, 55, 60, 65, 70, 75, 80, or 85. Other embodiments of the invention pertain to individuals who have an age at onset or age at diagnosis at age less than 85, such as less than age 80, less than age 75, or less than age 70, 65, 60, 55, 50, 45, 40, 35, or age 30. One preferred embodiment includes individuals diagnosed with atrial fibrillation or atrial flutter or stroke below age 80. Another preferred embodiment relates to individuals diagnosed with atrial fibrillation or atrial flutter or stroke below age 70. Another preferred embodiment, relates to individuals diagnosed with atrial fibrillation or atrial flutter or stroke below age 60. Yet another preferred embodiment relates to individuals diagnosed with atrial fibrillation or atrial flutter or stroke below age 50. Other embodiments relate to individuals with age at onset of the disease in specific age ranges, described in the above. It is also contemplated that a range of ages may be relevant in certain embodiments, such as age at onset at more than age 45 but less than age 60, age at onset at age more than 60 and less than age 70, age at onset at age more than 70 and less than 80, or age at onset at age more than 60 and less than 80. Other age ranges are however also contemplated, including all age ranges bracketed by the age values listed in the above.

The invention furthermore relates to individuals of either sex, males or females. It also provides for embodiments that relate to human subjects that are from one or more human population including, but not limited to, Bantu, Mandenk, Yoruba, San, Mbuti Pygmy, Orcadian, Adygel, Russian, Sardinian, Tuscan, Mozabite, Bedouin, Druze, Palestinian, Balochi, Brahui, Makrani, Sindhi, Pathan, Burusho, Hazara, Uygur, Kalash, Han, Dai, Daur, Hezhen, Lahu, Miao, Oroqen, She, Tujia, Tu, Xibo, Yi, Mongolan, Naxi, Cambodian, Japanese, Yakut, Melanesian, Papuan, Karitianan, Surui, Colmbian, Maya and Pima. The invention also relates to European populations, American populations, Eurasian populations, Asian populations, Central/South Asian populations, East Asian populations, Middle Eastern populations, African populations, Hispanic populations, and Oceanian populations. European populations include, but are not limited to, Swedish, Norwegian, Finnish, Russian, Danish, Icelandic, Irish, Kelt, English, Scottish, Dutch, Belgian, French, German, Spanish, Portuguese, Italian, Polish, Bulgarian, Slavic, Serbian, Bosnian, Chech, Greek and Turkish populations.

In one preferred embodiment, the invention relates to populations that include black African ancestry such as populations comprising persons of African descent or lineage.

Black African ancestry may be determined by self reporting as African-Americans, Afro-Americans, Black Americans, being a member of the black race or being a member of the negro race. For example, African Americans or Black Americans are those persons living in North America and having origins in any of the black racial groups of Africa. In another example, self-reported persons of black African ancestry may have at least one parent of black African ancestry or at least one grandparent of black African ancestry.

The racial contribution in individual subjects may also be determined by genetic analysis. Genetic analysis of ancestry may be carried out using unlinked microsatellite markers such as those set out in Smith et al. (*Am J Hum Genet.* 74, 1001-13 (2004)).

In certain embodiments, the invention relates to markers and/or haplotypes identified in specific populations, as described in the above. The person skilled in the art will appreciate that measures of linkage disequilibrium (LD) may give different results when applied to different populations. This is due to different population history of different human populations as well as differential selective pressures that may have led to differences in LD in specific genomic regions. It is also well known to the person skilled in the art that certain markers, e.g. SNP markers, are polymorphic in one population but not in another. The person skilled in the art will however apply the methods available and as taught ??herein to practice the present invention in any given human population. This may include assessment of polymorphic markers in the LD region of the present invention, so as to identify those markers that give strongest association within the specific population. Thus, the at-risk variants of the present invention may reside on different haplotype background and in different frequencies in various human populations. However, utilizing methods known in the art and the markers of the present invention, the invention can be practiced in any given human population.

Utility of Genetic Testing

The person skilled in the art will appreciate and understand that the variants described herein in general do not, by themselves, provide an absolute identification of individuals who will develop cardiac arrhythmia (e.g., atrial fibrillation or atrial flutter) and/or stroke. The variants described herein do however indicate increased and/or decreased likelihood that individuals carrying the at-risk or protective variants of the invention will develop symptoms associated with cardiac arrhythmia (e.g., atrial fibrillation or atrial flutter) and/or stroke This information is however extremely valuable in itself, as outlined in more detail in the below, as it can be used to, for example, initiate preventive measures at an early stage, perform regular physical and/or mental exams to monitor the progress and/or appearance of symptoms, or to schedule exams at a regular interval to identify the condition in question, so as to be able to apply treatment at an early stage.

The knowledge about a genetic variant that confers a risk of developing cardiac arrhythmia (e.g., atrial fibrillation or atrial flutter) and/or stroke offers the opportunity to apply a genetic test to distinguish between individuals with increased risk of developing the disease (i.e. carriers of the at-risk variant) and those with decreased risk of developing the disease (i.e. carriers of the protective variant). The core values of genetic testing, for individuals belonging to both of the above mentioned groups, are the possibilities of being able to diagnose cardiac arrhythmia (e.g., atrial fibrillation or atrial flutter) and/or stroke, or a predisposition to cardiac arrhythmia (e.g., atrial fibrillation or atrial flutter) and/or stroke at an early stage and provide information to the clinician about prognosis of cardiac arrhythmia (e.g., atrial fibrillation or atrial flutter) and/or stroke in order to be able to apply the most appropriate treatment.

Individuals with a family history of cardiac arrhythmia (e.g., atrial fibrillation or atrial flutter) and/or stroke and carriers of at-risk variants may benefit from genetic testing since the knowledge of the presence of a genetic risk factor, or evidence for increased risk of being a carrier of one or more risk factors, may provide increased incentive for implementing a healthier lifestyle, by avoiding or minimizing known environmental risk factors for cardiovascular diseases related to cardiac arrhythmia (e.g., atrial fibrillation or atrial flutter) and/or stroke. Genetic testing of cardiac arrhythmia (e.g., atrial fibrillation or atrial flutter) and/or stroke patients may furthermore give valuable information about the primary cause of the disease and can aid the clinician in selecting the best treatment options and medication for each individual.

The present invention furthermore relates to risk assessment for cardiac arrhythmia (e.g., atrial fibrillation or atrial flutter) and/or stroke, including determining whether an individual is at risk for developing cardiac arrhythmia (e.g., atrial fibrillation or atrial flutter) and/or stroke. The polymorphic markers of the present invention can be used alone or in combination, as well as in combination with other factors, including other genetic risk factors or biomarkers, for risk assessment of an individual for cardiac arrhythmia (e.g., atrial fibrillation or atrial flutter) and/or stroke. Many factors known to affect the predisposition of an individual towards developing risk of cardiovascular disease are susceptibility factors for cardiac arrhythmias (e.g., atrial fibrillation or atrial flutter) and/or stroke, and are known to the person skilled in the art and can be utilized in such assessment. These include, but are not limited to, age, gender, smoking status, physical activity, waist-to-hip circumference ratio, family history of cardiac arrhythmia (in particular atrial fibrillation and/or atrial flutter) and/or stroke, previously diagnosed cardiac arrhythmia (e.g., atrial fibrillation or atrial flutter) and/or stroke, obesity, hypertriglyceridemia, low HDL cholesterol, hypertension, elevated blood pressure, cholesterol levels, HDL cholesterol, LDL cholesterol, triglycerides, apolipoprotein AI and B levels, fibrinogen, ferritin, C-reactive protein and leukotriene levels. Particular biomarkers that have been associated with Atrial fibrillation/Atrial flutter and stroke are discussed in Allard et al. (*Clin Chem* 51:2043-2051 (2005) and Becker (*J Thromb Thrombolys* 19:71-75 (2005)). These include, but are not limited to, fibrin D-dimer, prothrombin activation fragment 1.2 (F1.2), thrombin-antithrombin III complexes (TAT), fibrinopeptide A (FPA), lipoprotein-associated phospholipase A2 (lp-PLA2), beta-thromboglobulin, platelet factor 4, P-selectin, von Willebrand Factor, pro-natriuretic peptide (BNP), matrix metalloproteinase-9 (MMP-9), PARK7, nucleoside diphosphate kinase (NDKA), tau, neuron-specific enolase, B-type neurotrophic growth factor, astroglial protein S-100b, glial fibrillary acidic protein, C-reactive protein, serum amyloid A, matrix metalloproteinase-9, vascular and intracellular cell adhesion molecules, tumor necrosis factor alpha, and interleukins, including interleukin-1, -6, and -8). Circulating progenitor cells have also been implicated as being useful biomarkers for AF. In particular embodiments, more than one biomarker is determined for an individual, and combined with results of a determination of at least one polymorphic marker as described herein. Preferably, biomarker is measured in plasma or serum from the individual. Alternatively, the biomarker is determined in other suitable tissues containing measurable amounts of the biomarker, and such embodiments are also within scope of the invention.

Methods known in the art can be used for overall risk assessment, including multivariate analyses or logistic regression.

Atrial fibrillation is a disease of great significance both to the individual patient and to the health care system as a whole. It can be a permanent condition but may also be paroxysmal and recurrent in which case it can be very challenging to diagnose. The most devastating complication of atrial fibrillation and atrial flutter is the occurrence of debilitating stroke. Importantly the risk of stroke is equal in permanent and paroxysmal atrial fibrillation. It has repeatedly been shown that therapy with warfarin anticoagulation can significantly reduce the risk of first or further episodes of stroke in the setting of atrial fibrillation. Therefor, anticoagulation with warfarin is standard therapy for almost all patients with atrial fibrillation for stroke-prevention, whether they have the permanent or paroxysmal type. The only patients for whom warfarin is not strongly recommended are those younger than 65 years old who are considered low-risk, i.e., they have no organic heart disease, including, neither hypertension no coronary artery disease, no previous history of stroke or transient ischemic attacks and no diabetes. This group has a lower risk of stroke and stroke-prevention with aspirin is recommended.

Due to the nature of paroxysmal atrial fibrillation it can be very difficult to diagnose. When the patient seeks medical attention due to disease-related symptoms, such as palpitations, chest pain, shortness of breath, dizziness, heart failure, transient ischemic attacks or even stroke, normal heart rhythm may already be restored precluding diagnosis of the arrhythmia. In these cases cardiac rhythm monitoring is frequently applied in the attempt to diagnose the condition. The cardiac rhythm is commonly monitored continuously for 24 to 48 hours. Unfortunately atrial fibrillation episodes are unpredictable and frequently missed by this approach. The opportunity to diagnose the arrhythmia, institute recommended therapy, and possibly prevent a debilitating first or recurrent stroke may be missed with devastating results to the patient. Prolonged and more complex cardiac rhythm monitoring measures are available and applied occasionally when the suspicion of atrial fibrillation is very strong. These tests are expensive, the diagnostic yield with current approach is often low, and they are used sparingly for this indication. In these circumstances additional risk stratification with genetic testing may be extremely helpful. Understanding that the individual in question carries either an at-risk or a protective genetic variant can be an invaluable contribution to diagnostic and/or treatment decision making. This way, in some cases, unnecessary testing and therapy may be avoided, and in other cases, with the help of more aggressive diagnostic approach, the arrhythmia may be diagnosed and/or proper therapy initiated and later complications of disease diminished.

Methods of the Invention

Methods for risk assessment of cardiac arrhythmia (e.g., atrial fibrillation or atrial flutter) and/or stroke are described herein and are encompassed by the invention. The invention also encompasses methods of assessing an individual for probability of response to a therapeutic agent for cardiac arrhythmia (e.g., atrial fibrillation or atrial flutter) and/or stroke, as well as methods for predicting the effectiveness of a therapeutic agent to treat patients with cardiac arrhythmia (e.g., atrial fibrillation or atrial flutter) and/or stroke. Kits for assaying a sample from a subject to detect susceptibility to cardiac arrhythmia (e.g., atrial fibrillation or atrial flutter) and/or stroke are also encompassed by the invention.

Diagnostic and Screening Assays of the Invention

In certain embodiments, the present invention pertains to methods of diagnosing, or aiding in the diagnosis of, cardiac arrhythmia (e.g., atrial fibrillation or atrial flutter) and/or stroke or a susceptibility to cardiac arrhythmia (e.g., atrial fibrillation or atrial flutter) and/or stroke, by detecting particular alleles at genetic markers that appear more frequently in cardiac arrhythmia (e.g., atrial fibrillation or atrial flutter) and/or stroke subjects or subjects who are susceptible to cardiac arrhythmia (e.g., atrial fibrillation or atrial flutter) and/or stroke. In a particular embodiment, the invention is a method of diagnosing a susceptibility to cardiac arrhythmia (e.g., atrial fibrillation or atrial flutter) and/or stroke by detecting at least one allele of at least one polymorphic marker (e.g., the markers described herein). The present invention describes methods whereby detection of particular alleles of particular markers or haplotypes is indicative of a susceptibility to cardiac arrhythmia (e.g., atrial fibrillation or atrial flutter) and/or stroke. Such prognostic or predictive assays can also be used to determine prophylactic treatment of a subject prior to the onset of symptoms of cardiac arrhythmia (e.g., atrial fibrillation or atrial flutter) and/or stroke.

The present invention pertains in some embodiments to methods of clinical applications of diagnosis, e.g., diagnosis performed by a medical professional, which may include an assessment or determination of genetic risk variants, and their interpretation. In other embodiments, the invention pertains to methods of risk assessment (or diagnosis) performed by a layman or a non-medical professional. Recent technological advances in genotyping technologies, including high-throughput genotyping of SNP markers, such as Molecular Inversion Probe array technology (e.g., Affymetrix GeneChip), and BeadArray Technologies (e.g., Illumina GoldenGate and Infinium assays) have made it possible for individuals to have their own genome assessed for large number of variations simultaneously, or up to one million SNPs. The resulting genotype information, made available to the individual, can be compared to information from the public scientific literature about disease or trait risk associated with various SNPs. The diagnostic application of disease-associated alleles as described herein, can thus be performed either by a health professional based on results of a clinical test or by a layman, or non-medical professional, including an individual providing service for performing an assessment of SNPs through SNP genotyping, either on an individual SNP basis or by large-scale high-throughput methods such as array technologies. In other words, the diagnosis or assessment of a susceptibility based on genetic risk can be made by health professionals, genetic counselors, genotype services providers or by the layman, based on information about his/her genotype and publications on various risk factors. In the present context, the term "diagnosing", and "diagnose a susceptibility", is meant to refer to any available diagnostic method, including those mentioned above.

In addition, in certain other embodiments, the present invention pertains to methods of diagnosing, or aiding in the diagnosis of, a decreased susceptibility to cardiac arrhythmia (e.g., atrial fibrillation or atrial flutter) and/or stroke by detecting particular genetic marker alleles or haplotypes that appear less frequently in cardiac arrhythmia (e.g., atrial fibrillation or atrial flutter) and/or stroke patients than in individual not diagnosed with cardiac arrhythmia (e.g., atrial fibrillation or atrial flutter) and/or stroke or in the general population.

As described and exemplified herein, particular marker alleles or haplotypes (e.g. the markers and haplotypes as listed in Table 5 (Tables 5A and 5B) and markers in linkage disequilibrium therewith, e.g., the markers listed in Tables 4 and/or 9 markers in linkage disequilibrium therewith, e.g., the markers as set forth in Table 19) are associated with cardiac arrhythmia (e.g., atrial fibrillation or atrial flutter) and/or stroke. In one embodiment, the marker allele or haplotype is one that confers a significant risk or susceptibility to cardiac arrhythmia (e.g., atrial fibrillation or atrial flutter) and/or stroke. In another embodiment, the invention relates to a method of diagnosing a susceptibility to cardiac arrhythmia (e.g., atrial fibrillation or atrial flutter) and/or stroke in a human individual, the method comprising determining the presence or absence of at least one allele of at least one polymorphic marker in a nucleic acid sample obtained from the individual, wherein the at least one polymorphic marker is selected from the group consisting of the polymorphic markers listed in Tables 5A and 5B, and markers in linkage disequilibrium therewith. In another embodiment, the invention pertains to methods of diagnosing a susceptibility to cardiac arrhythmia (e.g., atrial fibrillation or atrial flutter) and/or stroke in a human individual, by screening for at least one marker allele or haplotype as listed in Tables 5A and 5B or markers in linkage disequilibrium therewith. In another embodiment, the marker allele or haplotype is more frequently present in a subject having, or who is susceptible to, cardiac arrhythmia (e.g., atrial fibrillation or atrial flutter) and/or stroke (affected), as compared to the frequency of its presence in a healthy subject (control, such as population controls). In certain embodiments, the significance of association of the at least one marker allele or haplotype is characterized by a p value<0.05. In other embodiments, the significance of association is characterized by smaller p-values, such as <0.01, <0.001, <0.0001, <0.00001, <0.000001, <0.0000001, <0.00000001 or <0.000000001.

In these embodiments, the presence of the at least one marker allele or haplotype is indicative of a susceptibility to cardiac arrhythmia (e.g., atrial fibrillation or atrial flutter) and/or stroke. These diagnostic methods involve detecting the presence or absence of at least one marker allele or haplotype that is associated with cardiac arrhythmia (e.g., atrial fibrillation or atrial flutter) and/or stroke. The haplotypes described herein include combinations of alleles at various genetic markers (e.g., SNPs, microsatellites). The detection of the particular genetic marker alleles that make up the particular haplotypes can be performed by a variety of methods described herein and/or known in the art. For example, genetic markers can be detected at the nucleic acid level (e.g., by direct nucleotide sequencing or by other means known to the skilled in the art) or at the amino acid level if the genetic marker affects the coding sequence of a protein encoded by a cardiac arrhythmia (e.g., atrial fibrillation or atrial flutter) and/or stroke-associated nucleic acid (e.g., by protein sequencing or by immunoassays using antibodies that recognize such a protein). The marker alleles or haplotypes of the present invention correspond to fragments of a genomic DNA sequence associated with cardiac arrhythmia (e.g., atrial fibrillation or atrial flutter) and/or stroke. Such fragments encompass the DNA sequence of the polymorphic marker or haplotype in question, but may also include DNA segments in strong LD (linkage disequilibrium) with the marker or haplotype. In one embodiment, such segments comprises segments in LD with the marker or haplotype as determined by a value of $r^2$ greater than 0.2 and/or $|D'|>0.8$.

In one embodiment, diagnosis of a susceptibility to cardiac arrhythmia (e.g., atrial fibrillation or atrial flutter) and/or stroke can be accomplished using hybridization methods, such as Southern analysis, Northern analysis, and/or in situ hybridizations (see Current Protocols in Molecular Biology, Ausubel, F. et al., eds., John Wiley & Sons, including all supplements). A biological sample from a test subject or individual (a "test sample") of genomic DNA, RNA, or cDNA is obtained from a subject suspected of having, being susceptible to, or predisposed for cardiac arrhythmia (e.g., atrial fibrillation or atrial flutter) and/or stroke (the "test subject"). The subject can be an adult, child, or fetus. The test sample can be from any source that contains genomic DNA, such as a blood sample, sample of amniotic fluid, sample of cerebrospinal fluid, or tissue sample from skin, muscle, buccal or conjunctival mucosa, placenta, gastrointestinal tract or other organs. A test sample of DNA from fetal cells or tissue can be obtained by appropriate methods, such as by amniocentesis or chorionic villus sampling. The DNA, RNA, or cDNA sample is then examined. The presence of a specific marker allele can be indicated by sequence-specific hybridization of a nucleic acid probe specific for the particular allele. The presence of more than specific marker allele or a specific haplotype can be indicated by using several sequence-specific nucleic acid probes, each being specific for a particular allele. In one embodiment, a haplotype can be indicated by a single nucleic acid probe that is specific for the specific haplotype (i.e., hybridizes specifically to a DNA strand comprising the specific marker alleles characteristic of the haplotype). A sequence-specific probe can be directed to hybridize to genomic DNA, RNA, or cDNA. A "nucleic acid probe", as used herein, can be a DNA probe or an RNA probe that hybridizes to a complementary sequence. One of skill in the art would know how to design such a probe so that sequence specific hybridization will occur only if a particular allele is present in a genomic sequence from a test sample.

To diagnose a susceptibility to cardiac arrhythmia (e.g., atrial fibrillation or atrial flutter) and/or stroke, a hybridization sample is formed by contacting the test sample containing an atrial fibrillation and/or stroke-associated nucleic acid, such as a genomic DNA sample, with at least one nucleic acid probe. A non-limiting example of a probe for detecting mRNA or genomic DNA is a labeled nucleic acid probe that is capable of hybridizing to mRNA or genomic DNA sequences described herein. The nucleic acid probe can be, for example, a full-length nucleic acid molecule, or a portion thereof, such as an oligonucleotide of at least 15, 30, 50, 100, 250 or 500 nucleotides in length that is sufficient to specifically hybridize under stringent conditions to appropriate mRNA or genomic DNA. The nucleotide acid probe may be up to 1000 or more nucleotides in length, including up to 500 nucleotides, 400 nucleotide, 300 nucleotides, 200 nucleotides or 100 nucleotides. Certain embodiments include nucleotide probes that are from 15 to 1000 nucleotides in length. Other embodiments pertain to use of nucleotide probes that are from 15 to 500 nucleotides in length, or from 15 to 400 nucleotides in length, or from 20 to 400 nucleotides in length. Other size ranges of the nucleotide probes of the invention are contemplated, as well known to the skilled person. In one embodiment, the nucleic acid probe can comprise all or a portion of the nucleotide sequence of LD Block C04, as described herein, optionally comprising at least one allele of a marker described herein, or at least one haplotype described herein, or the probe can be the complementary sequence of such a sequence. In a particular embodiment, the nucleic acid probe is a portion of the nucleotide sequence of LD Block C04 as set forth in SEQ ID NO:50 or, as described herein, optionally comprising at least one allele of a marker described herein, or at least one allele of one polymorphic marker or haplotype comprising at least one polymorphic marker described herein, or the probe can be the complementary sequence of such a sequence. Other suitable probes for use in the diagnostic assays of the invention are described herein. Hybridization can be performed by methods well known to the person skilled in the art (see, e.g., Current Protocols in Molecular Biology, Ausubel, F. et al., eds., John Wiley & Sons, including all supplements). In one embodiment, hybridization refers to specific hybridization, i.e., hybridization with no mismatches (exact hybridization). In one embodiment, the hybridization conditions for specific hybridization are high stringency.

Specific hybridization, if present, is detected using standard methods. If specific hybridization occurs between the nucleic acid probe and the nucleic acid in the test sample, then the sample contains the allele that is complementary to the nucleotide that is present in the nucleic acid probe. The process can be repeated for any markers of the present invention, or markers that make up a haplotype of the present invention, or multiple probes can be used concurrently to detect more than one marker alleles at a time. It is also possible to design a single probe containing more than one marker alleles of a particular haplotype (e.g., a probe containing alleles complementary to 2, 3, 4, 5 or all of the markers that make up a particular haplotype). Detection of the particular markers of the haplotype in the sample is indicative that the source of the sample has the particular haplotype (e.g., a haplotype) and therefore is susceptible to cardiac arrhythmia (e.g., atrial fibrillation or atrial flutter) and/or stroke.

In another hybridization method, Northern analysis (see Current Protocols in Molecular Biology, Ausubel, F. et al., eds., John Wiley & Sons, supra) is used to identify the presence of a polymorphism associated with cardiac arrhythmia (e.g., atrial fibrillation or atrial flutter) and/or stroke. For Northern analysis, a test sample of RNA is obtained from the subject by appropriate means. As described herein, specific hybridization of a nucleic acid probe to RNA from the subject is indicative of a particular allele complementary to the probe. For representative examples of use of nucleic acid probes, see, for example, U.S. Pat. Nos. 5,288,611 and 4,851,330.

Additionally, or alternatively, a peptide nucleic acid (PNA) probe can be used in addition to, or instead of, a nucleic acid probe in the hybridization methods described herein. A PNA is a DNA mimic having a peptide-like, inorganic backbone, such as N-(2-aminoethyl)glycine units, with an organic base (A, G, C, T or U) attached to the glycine nitrogen via a methylene carbonyl linker (see, for example, Nielsen, P., et al., *Bioconjug. Chem.* 5:3-7 (1994)). The PNA probe can be designed to specifically hybridize to a molecule in a sample suspected of containing one or more of the marker alleles or haplotypes that are associated with cardiac arrhythmia (e.g., atrial fibrillation or atrial flutter) and/or stroke. Hybridization of the PNA probe is thus diagnostic for cardiac arrhythmia (e.g., atrial fibrillation or atrial flutter) and/or stroke or a susceptibility to cardiac arrhythmia (e.g., atrial fibrillation or atrial flutter) and/or stroke.

In one embodiment of the invention, a test sample containing genomic DNA obtained from the subject is collected and the polymerase chain reaction (PCR) is used to amplify a fragment comprising one or more markers or haplotypes of the present invention. As described herein, identification of a particular marker allele or haplotype associated with cardiac arrhythmia (e.g., atrial fibrillation or atrial flutter) and/or stroke, can be accomplished using a variety of methods (e.g., sequence analysis, analysis by restriction digestion, specific hybridization, single stranded conformation polymorphism assays (SSCP), electrophoretic analysis, etc.). In another embodiment, diagnosis is accomplished by expression analysis using quantitative PCR (kinetic thermal cycling). This technique can, for example, utilize commercially available technologies, such as TaqMan® (Applied Biosystems, Foster City, Calif.). The technique can assess the presence of an alteration in the expression or composition of a polypeptide or splicing variant(s) that is encoded by a nucleic acid associated with cardiac arrhythmia (e.g., atrial fibrillation or atrial flutter) and/or stroke. Further, the expression of the variant(s) can be quantified as physically or functionally different.

In another method of the invention, analysis by restriction digestion can be used to detect a particular allele if the allele results in the creation or elimination of a restriction site relative to a reference sequence. Restriction fragment length polymorphism (RFLP) analysis can be conducted, e.g., as described in Current Protocols in Molecular Biology, supra. The digestion pattern of the relevant DNA fragment indicates the presence or absence of the particular allele in the sample.

Sequence analysis can also be used to detect specific alleles or haplotypes associated with cardiac arrhythmia (e.g., atrial fibrillation or atrial flutter) and/or stroke (e.g. the polymorphic markers of Table 5 (Tables 5A and 5B), Table 9 and/or Table 19). Therefore, in one embodiment, determination of the presence or absence of a particular marker alleles or haplotypes comprises sequence analysis of a test sample of DNA or RNA obtained from a subject or individual. PCR or other appropriate methods can be used to amplify a portion of a nucleic acid associated with cardiac arrhythmia (e.g., atrial fibrillation or atrial flutter) and/or stroke, and the presence of a specific allele can then be detected directly by sequencing the polymorphic site (or multiple polymorphic sites in a haplotype) of the genomic DNA in the sample.

Allele-specific oligonucleotides can also be used to detect the presence of a particular allele in a nucleic acid associated with cardiac arrhythmia (e.g., atrial fibrillation or atrial flutter) and/or stroke, (e.g. the polymorphic markers of Table 5 (Tables 5A and 5B), Table 9 and/or Table 19), through the use of dot-blot hybridization of amplified oligonucleotides with allele-specific oligonucleotide (ASO) probes (see, for example, Saiki, R. et al., *Nature,* 324:163-166 (1986)). An "allele-specific oligonucleotide" (also referred to herein as an "allele-specific oligonucleotide probe") is an oligonucleotide of approximately 10-500 base pairs, approximately 15-400 base pairs, approximately 15-200 base pairs, approximately 15-100 base pairs, approximately 15-50 base pairs, or approximately 15-30 base pairs, that specifically hybridizes to a nucleic acid associated with cardiac arrhythmia (e.g., atrial fibrillation or atrial flutter) and/or stroke, and which contains a specific allele at a polymorphic site (e.g., a marker or haplotype as described herein). An allele-specific oligonucleotide probe that is specific for one or more particular a nucleic acid associated with cardiac arrhythmia (e.g., atrial fibrillation or atrial flutter) and/or stroke can be prepared using standard methods (see, e.g., Current Protocols in Molecular Biology, supra). PCR can be used to amplify the desired region. The DNA containing the amplified region can be dot-blotted using standard methods (see, e.g., Current Protocols in Molecular Biology, supra), and the blot can be contacted with the oligonucleotide probe. The presence of specific hybridization of the probe to the amplified region can then be detected. Specific hybridization of an allele-specific oligonucleotide probe to DNA from the subject is indicative of a specific allele at a polymorphic site associated with cardiac arrhythmia (e.g., atrial fibrillation or atrial flutter) and/or stroke (see, e.g., Gibbs, R. et al., *Nucleic Acids Res.,* 17:2437-2448 (1989) and WO 93/22456).

With the addition of such analogs as locked nucleic acids (LNAs), the size of primers and probes can be reduced to as few as 8 bases. LNAs are a novel class of bicyclic DNA analogs in which the 2' and 4' positions in the furanose ring are joined via an O-methylene (oxy-LNA), S-methylene (thio-LNA), or amino methylene (amino-LNA) moiety. Common to all of these LNA variants is an affinity toward complementary nucleic acids, which is by far the highest reported for a DNA analog. For example, particular all oxy-LNA nonamers have been shown to have melting temperatures ($T_m$) of 64° C. and 74° C. when in complex with complementary DNA or RNA, respectively, as opposed to 28° C. for both DNA and RNA for the corresponding DNA nonamer. Substantial increases in $T_m$ are also obtained when LNA monomers are used in combination with standard DNA or RNA monomers. For primers and probes, depending on where the LNA monomers are included (e.g., the 3' end, the 5' end, or in the middle), the $T_m$ could be increased considerably.

In another embodiment, arrays of oligonucleotide probes that are complementary to target nucleic acid sequence segments from a subject, can be used to identify polymorphisms in a nucleic acid associated with cardiac arrhythmia (e.g., atrial fibrillation or atrial flutter) and/or stroke (e.g. the polymorphic markers of Tables 5A and 5B and markers in linkage disequilibrium therewith). For example, an oligonucleotide array can be used. Oligonucleotide arrays typically comprise a plurality of different oligonucleotide probes that are coupled to a surface of a substrate in different known locations. These oligonucleotide arrays, also described as "Genechips™," have been generally described in the art (see, e.g., U.S. Pat. No. 5,143,854, PCT Patent Publication Nos. WO 90/15070 and 92/10092). These arrays can generally be produced using mechanical synthesis methods or light directed synthesis methods that incorporate a combination of photolithographic methods and solid phase oligonucleotide synthesis methods, or by other methods known to the person skilled in the art (see, e.g., Fodor, S. et al., *Science,* 251:767-773 (1991); Pirrung et al., U.S. Pat. No. 5,143,854 (see also published PCT Application No. WO 90/15070); and Fodor. S. et al., published PCT Application No. WO 92/10092 and U.S. Pat. No. 5,424,186, the entire teachings of each of which are incorporated by reference herein). Techniques for the synthesis of these arrays using mechanical synthesis methods are described in, e.g., U.S. Pat. No. 5,384,261; the entire teachings of which are incorporated by reference herein. In another example, linear arrays can be utilized. Additional descriptions of use of oligonucleotide arrays for detection of polymorphisms can be found, for example, in U.S. Pat. Nos. 5,858,659 and 5,837,832, the entire teachings of both of which are incorporated by reference herein.

Other methods of nucleic acid analysis that are available to those skilled in the art can be used to detect a particular allele at a polymorphic site associated with atrial fibrillation and/or stroke (e.g. the polymorphic markers of Table 5 (Tables 5A and 5B), Table 9 and/or Table 19). Representative methods include, for example, direct manual sequencing (Church and Gilbert, *Proc. Natl. Acad. Sci. USA,* 81: 1991-1995 (1988); Sanger, F., et al., *Proc. Natl. Acad. Sci. USA,* 74:5463-5467 (1977); Beavis, et al., U.S. Pat. No. 5,288,644); automated fluorescent sequencing; single-stranded conformation polymorphism assays (SSCP); clamped denaturing gel electrophoresis (CDGE); denaturing gradient gel electrophoresis (DGGE) (Sheffield, V., et al., *Proc. Natl. Acad. Sci. USA,* 86:232-236 (1989)), mobility shift analysis (Orita, M., et al., *Proc. Natl. Acad. Sci. USA,* 86:2766-2770 (1989)), restriction enzyme analysis (Flavell, R., et al., *Cell,* 15:25-41 (1978); Geever, R., et al., *Proc. Natl. Acad. Sci. USA,* 78:5081-5085 (1981)); heteroduplex analysis; chemical mismatch cleavage (CMC) (Cotton, R., et al., *Proc. Natl. Acad. Sci. USA,* 85:4397-4401 (1985)); RNase protection assays (Myers, R., et al., *Science,* 230:1242-1246 (1985); use of polypeptides that recognize nucleotide mismatches, such as *E. coli* mutS protein; and allele-specific PCR.

In another embodiment of the invention, diagnosis of cardiac arrhythmia (e.g., atrial fibrillation or atrial flutter) and/or stroke or a susceptibility to cardiac arrhythmia (e.g., atrial fibrillation or atrial flutter) and/or stroke can be made by examining expression and/or composition of a polypeptide encoded by a nucleic acid associated with cardiac arrhythmia (e.g., atrial fibrillation or atrial flutter) and/or stroke in those instances where the genetic marker(s) or haplotype(s) of the present invention result in a change in the composition or expression of the polypeptide. Thus, diagnosis of a susceptibility to cardiac arrhythmia (e.g., atrial fibrillation or atrial flutter) and/or stroke can be made by examining expression and/or composition of one of these polypeptides, or another polypeptide encoded by a nucleic acid associated with cardiac arrhythmia (e.g., atrial fibrillation or atrial flutter) and/or stroke, in those instances where the genetic marker or haplotype of the present invention results in a change in the composition or expression of the polypeptide. The haplotypes and markers of the present invention that show association to cardiac arrhythmia (e.g., atrial fibrillation or atrial flutter) and/or stroke may play a role through their effect on one or more of these nearby genes (e.g., the PITX2 gene). Possible mechanisms affecting these genes include, e.g., effects on transcription, effects on RNA splicing, alterations in relative amounts of alternative splice forms of mRNA, effects on RNA stability, effects on transport from the nucleus to cytoplasm, and effects on the efficiency and accuracy of translation.

Thus, in another embodiment, the variants (markers or haplotypes) of the invention showing association to cardiac arrhythmia (e.g., atrial fibrillation or atrial flutter) and/or stroke affect the expression of a nearby gene. It is well known that regulatory element affecting gene expression may be located tenths or even hundreds of kilobases away from the promoter region of a gene. By assaying for the presence or absence of at least one allele of at least one polymorphic marker of the present invention, it is thus possible to assess the expression level of such nearby genes. It is thus contemplated that the detection of the markers or haplotypes of the present invention can be used for assessing expression for one or more genes that are linked to cardiac arrhythmia (e.g., atrial fibrillation or atrial flutter) and/or stroke.

A variety of methods can be used for detecting protein expression levels, including enzyme linked immunosorbent assays (ELISA), Western blots, immunoprecipitations and immunofluorescence. A test sample from a subject is assessed for the presence of an alteration in the expression and/or an alteration in composition of the polypeptide encoded by a nucleic acid associated with cardiac arrhythmia (e.g., atrial fibrillation or atrial flutter) and/or stroke. An alteration in expression of a polypeptide encoded by a nucleic acid associated with cardiac arrhythmia (e.g., atrial fibrillation or atrial flutter) and/or stroke can be, for example, an alteration in the quantitative polypeptide expression (i.e., the amount of polypeptide produced). An alteration in the composition of a polypeptide encoded by a nucleic acid associated with cardiac arrhythmia (e.g., atrial fibrillation or atrial flutter) and/or stroke is an alteration in the qualitative polypeptide expression (e.g., expression of a mutant polypeptide or of a different splicing variant). In one embodiment, diagnosis of a susceptibility to cardiac arrhythmia (e.g., atrial fibrillation or atrial flutter) and/or stroke is made by detecting a particular splicing variant encoded by a nucleic acid associated with cardiac arrhythmia (e.g., atrial fibrillation or atrial flutter) and/or stroke, or a particular pattern of splicing variants.

Both such alterations (quantitative and qualitative) can also be present. An "alteration" in the polypeptide expression or composition, as used herein, refers to an alteration in expression or composition in a test sample, as compared to the expression or composition of the polypeptide in a control sample. A control sample is a sample that corresponds to the test sample (e.g., is from the same type of cells), and is from a subject who is not affected by, and/or who does not have a susceptibility to, cardiac arrhythmia (e.g., atrial fibrillation or atrial flutter) and/or stroke. In one embodiment, the control sample is from a subject that does not possess a marker allele or haplotype as described herein. Similarly, the presence of one or more different splicing variants in the test sample, or the presence of significantly different amounts of different splicing variants in the test sample, as compared with the control sample, can be indicative of a susceptibility to cardiac arrhythmia (e.g., atrial fibrillation or atrial flutter) and/or stroke. An alteration in the expression or composition of the polypeptide in the test sample, as compared with the control sample, can be indicative of a specific allele in the instance where the allele alters a splice site relative to the reference in the control sample. Various means of examining expression or composition of a polypeptide encoded by a nucleic acid are known to the person skilled in the art and can be used, including spectroscopy, colorimetry, electrophoresis, isoelectric focusing, and immunoassays (e.g., David et al., U.S. Pat. No. 4,376,110) such as immunoblotting (see, e.g., Current Protocols in Molecular Biology, particularly chapter 10, supra).

For example, in one embodiment, an antibody (e.g., an antibody with a detectable label) that is capable of binding to a polypeptide encoded by a nucleic acid associated with cardiac arrhythmia (e.g., atrial fibrillation or atrial flutter) and/or stroke can be used. Antibodies can be polyclonal or monoclonal. An intact antibody, or a fragment thereof (e.g., Fv, Fab, Fab', $F(ab')_2$) can be used. The term "labeled", with regard to the probe or antibody, is intended to encompass direct labeling of the probe or antibody by coupling (i.e., physically linking) a detectable substance to the probe or antibody, as well as indirect labeling of the probe or antibody by reactivity with another reagent that is directly labeled. Examples of indirect labeling include detection of a primary antibody using a labeled secondary antibody (e.g., a fluorescently-labeled secondary antibody) and end-labeling of a DNA probe with biotin such that it can be detected with fluorescently-labeled streptavidin.

In one embodiment of this method, the level or amount of polypeptide encoded by a nucleic acid associated with cardiac arrhythmia (e.g., atrial fibrillation or atrial flutter) and/or stroke in a test sample is compared with the level or amount of the polypeptide in a control sample. A level or amount of the polypeptide in the test sample that is higher or lower than the level or amount of the polypeptide in the control sample, such that the difference is statistically significant, is indicative of an alteration in the expression of the polypeptide encoded by the nucleic acid, and is diagnostic for a particular allele or haplotype responsible for causing the difference in expression. Alternatively, the composition of the polypeptide in a test sample is compared with the composition of the polypeptide in a control sample. In another embodiment, both the level or amount and the composition of the polypeptide can be assessed in the test sample and in the control sample.

In another embodiment, the diagnosis of a susceptibility to cardiac arrhythmia (e.g., atrial fibrillation or atrial flutter) and/or stroke is made by detecting at least one marker or haplotypes of the present invention (e.g., associated alleles of the markers listed in Tables 5A and 5B, and markers in linkage disequilibrium therewith), in combination with an additional protein-based, RNA-based or DNA-based assay. The methods of the invention can also be used in combination with an analysis of a subject's family history and risk factors (e.g., environmental risk factors, lifestyle risk factors).

Kits

Kits useful in the methods and procedures of the invention comprise components useful in any of the methods described herein, including for example, hybridization probes, restriction enzymes (e.g., for RFLP analysis), allele-specific oligonucleotides, antibodies that bind to an altered polypeptide encoded by a nucleic acid of the invention as described herein (e.g., a genomic segment comprising at least one polymorphic marker and/or haplotype of the present invention) or to a non-altered (native) polypeptide encoded by a nucleic acid of the invention as described herein, means for amplification of a nucleic acid associated with cardiac arrhythmia (e.g., atrial fibrillation or atrial flutter) and/or stroke, means for analyzing the nucleic acid sequence of a nucleic acid associated with cardiac arrhythmia (e.g., atrial fibrillation or atrial flutter) and/or stroke, means for analyzing the amino acid sequence of a polypeptide encoded by a nucleic acid associated with cardiac arrhythmia (e.g., atrial fibrillation or atrial flutter) and/or stroke, etc. The kits can for example include necessary buffers, nucleic acid primers for amplifying nucleic acids of the invention (e.g., one or more of the polymorphic markers as described herein), and reagents for allele-specific detection of the fragments amplified using such primers and necessary enzymes (e.g., DNA polymerase). Additionally, kits can provide reagents for assays to be used in combination with the methods of the present invention, e.g., reagents for use with cardiac arrhythmia (e.g., atrial fibrillation or atrial flutter) and/or stroke diagnostic assays.

In one embodiment, the invention is a kit for assaying a sample from a subject to detect the presence of cardiac arrhythmia (e.g., atrial fibrillation or atrial flutter) and/or stroke or a susceptibility to cardiac arrhythmia (e.g., atrial fibrillation or atrial flutter) and/or stroke in a subject, wherein the kit comprises reagents necessary for selectively detecting at least one allele of at least one polymorphism of the present invention in the genome of the individual. In a particular embodiment, the reagents comprise at least one contiguous oligonucleotide that hybridizes to a fragment of the genome of the individual comprising at least one polymorphism of the present invention. In another embodiment, the reagents comprise at least one pair of oligonucleotides that hybridize to opposite strands of a genomic segment obtained from a subject, wherein each oligonucleotide primer pair is designed to selectively amplify a fragment of the genome of the individual that includes at least one polymorphism, wherein the polymorphism is selected from the group consisting of the polymorphisms as listed in Tables 5A and 5B and polymorphic markers in linkage disequilibrium therewith. In yet another embodiment the fragment is at least 20 base pairs in size. Such oligonucleotides or nucleic acids (e.g., oligonucleotide primers) can be designed using portions of the nucleic acid sequence flanking polymorphisms (e.g., SNPs or microsatellites) that are indicative of cardiac arrhythmia (e.g., atrial fibrillation or atrial flutter) and/or stroke. In another embodiment, the kit comprises one or more labeled nucleic acids capable of allele-specific detection of one or more specific polymorphic markers or haplotypes associated with cardiac arrhythmia (e.g., atrial fibrillation or atrial flutter) and/or stroke, and reagents for detection of the label. Suitable labels include, e.g., a radioisotope, a fluorescent label, an enzyme label, an enzyme co-factor label, a magnetic label, a spin label, an epitope label.

In particular embodiments, the polymorphic marker or haplotype to be detected by the reagents of the kit comprises one or more markers, two or more markers, three or more markers, four or more markers or five or more markers selected from the group consisting of the markers in Tables 5A and 5B. In another embodiment, the marker or haplotype to be detected comprises the markers listed in Tables 5A and 5B. In another embodiment, the marker or haplotype to be detected comprises the markers listed in Tables 4 and 9. In another embodiment, the marker or haplotype to be detected comprises at least one marker from the group of markers in strong linkage disequilibrium, as defined by values of $r^2$ greater than 0.2, to at least one of the group of markers consisting of the markers listed in Tables 5A and 5B. In another embodiment, the marker or haplotype to be detected comprises at least one marker from the markers in strong linkage disequilibrium, as defined by values of $r^2$ greater than 0.2, to at least one of the group of markers consisting of the markers listed in Tables 4 and 9. In another embodiment, the marker or haplotype to be detected comprises marker rs2220427 (SEQ ID NO:1) or marker rs1033464 (SEQ ID NO:41), or markers in linkage disequilibrium therewith. In another embodiment, the marker or haplotype to be detected comprises at least one of the markers set forth in Table 19. In another embodiment, the marker or haplotype to be detected comprises markers D4S406 (SEQ ID NO:45), rs2634073 (SEQ ID NO:33), rs2200733 (SEQ ID NO:28), rs2220427 (SEQ ID NO:1), rs10033464 (SEQ ID NO:41), and rs13143308 (SEQ ID NO:51) and markers in linkage disequilibrium therewith. In yet another embodiment, the marker or haplotype comprises the at-risk alleles −2, −4 and/or −8 in marker D4S406, allele A of marker rs2634073, allele T of marker rs2200733, allele T of marker rs2220427, allele T of marker rs10033464, and/or allele G of marker rs13143308. In one such embodiment, linkage disequilibrium is defined by values of $r^2$ greater than 0.1. In another such embodiment, linkage disequilibrium is defined by values of $r^2$ greater than 0.2.

In one preferred embodiment, the kit for detecting the markers of the invention comprises a detection oligonucleotide probe, that hybridizes to a segment of template DNA containing a SNP polymorphisms to be detected, an enhancer oligonucleotide probe and an endonuclease. As explained in the above, the detection oligonucleotide probe comprises a fluorescent moiety or group at its 3' terminus and a quencher at its 5' terminus, and an enhancer oligonucleotide, is employed, as described by Kutyavin et al. (*Nucleic Acid Res.* 34:e128 (2006)). The fluorescent moiety can be Gig Harbor Green or Yakima Yellow, or other suitable fluorescent moieties. The detection probe is designed to hybridize to a short nucleotide sequence that includes the SNP polymorphism to be detected. Preferably, the SNP is anywhere from the terminal residue to −6 residues from the 3' end of the detection probe. The enhancer is a short oligonucleotide probe which hybridizes to the DNA template 3' relative to the detection probe. The probes are designed such that a single nucleotide gap exists between the detection probe and the enhancer nucleotide probe when both are bound to the template. The gap creates a synthetic abasic site that is recognized by an endonuclease, such as Endonuclease IV. The enzyme cleaves the dye off the fully complementary detection probe, but cannot cleave a detection probe containing a mismatch. Thus, by measuring the fluorescence of the released fluorescent moiety, assessment of the presence of a particular allele defined by nucleotide sequence of the detection probe can be performed.

The detection probe can be of any suitable size, although preferably the probe is relatively short. In one embodiment, the probe is from 5-100 nucleotides in length. In another embodiment, the probe is from 10-50 nucleotides in length, and in another embodiment, the probe is from 12-30 nucleotides in length. Other lengths of the probe are possible and within scope of the skill of the average person skilled in the art.

In a preferred embodiment, the DNA template containing the SNP polymorphism is amplified by Polymerase Chain Reaction (PCR) prior to detection, and primers for such amplification are included in the reagent kit. In such an embodiment, the amplified DNA serves as the template for the detection probe and the enhancer probe.

Certain embodiments of the detection probe, the enhancer probe, and/or the primers used for amplification of the template by PCR include the use of modified bases, including modified A and modified G. The use of modified bases can be useful for adjusting the melting temperature of the nucleotide molecule (probe and/or primer) to the template DNA, for example for increasing the melting temperature in regions containing a low percentage of G or C bases, in which modified A with the capability of forming three hydrogen bonds to its complementary T can be used, or for decreasing the melting temperature in regions containing a high percentage of G or C bases, for example by using modified G bases that form only two hydrogen bonds to their complementary C base in a double stranded DNA molecule. In a preferred embodiment, modified bases are used in the design of the detection nucleotide probe. Any modified base known to the skilled person can be selected in these methods, and the selection of suitable bases is well within the scope of the skilled person based on the teachings herein and known bases available from commercial sources as known to the skilled person.

In one of such embodiments, the presence of the marker or haplotype is indicative of a susceptibility (increased susceptibility or decreased susceptibility) to atrial fibrillation and/or stroke. In another embodiment, the presence of the marker or haplotype is indicative of response to atrial fibrillation and/or stroke therapeutic agent. In another embodiment, the presence of the marker or haplotype is indicative of atrial fibrillation and/or stroke prognosis. In yet another embodiment, the presence of the marker or haplotype is indicative of progress of atrial fibrillation and/or stroke treatment. Such treatment may include intervention by surgery, medication or by other means (e.g., lifestyle changes).

Therapeutic Agents

Variants of the present invention (e.g., the markers and/or haplotypes of the invention, e.g., the markers listed in Tables 5A and 5B and/or Table 19) can be used to identify novel therapeutic targets for cardiac arrhythmia (e.g., atrial fibrillation or atrial flutter) and/or stroke. For example, genes containing, or in linkage disequilibrium with, variants (markers and/or haplotypes) associated with cardiac arrhythmia (e.g., atrial fibrillation or atrial flutter) and/or stroke, or their products, as well as genes or their products that are directly or indirectly regulated by or interact with these variant genes or their products, can be targeted for the development of therapeutic agents to treat cardiac arrhythmia (e.g., atrial fibrillation or atrial flutter) and/or stroke, or prevent or delay onset of symptoms associated with cardiac arrhythmia (e.g., atrial fibrillation or atrial flutter) and/or stroke. Therapeutic agents may comprise one or more of, for example, small non-protein and non-nucleic acid molecules, proteins, peptides, protein fragments, nucleic acids (DNA, RNA), PNA (peptide nucleic acids), or their derivatives or mimetics which can modulate the function and/or levels of the target genes or their gene products.

The nucleic acids and/or variants of the invention, or nucleic acids comprising their complementary sequence, may be used as antisense constructs to control gene expression in cells, tissues or organs. The methodology associated with antisense techniques is well known to the skilled artisan, and is described and reviewed in *Antisense Drug Technology: Principles, Strategies, and Applications*, Crooke, ed., Marcel Dekker Inc., New York (2001). In general, antisense nucleic acid molecules are designed to be complementary to a region of mRNA expressed by a gene, so that the antisense molecule hybridizes to the mRNA, thus blocking translation of the mRNA into protein. Several classes of antisense oligonucleotide are known to those skilled in the art, including cleavers and blockers. The former bind to target RNA sites, activate intracellular nucleases (e.g., RnaseH or Rnase L), that cleave the target RNA. Blockers bind to target RNA, inhibit protein translation by steric hindrance of the ribosomes. Examples of blockers include nucleic acids, morpholino compounds, locked nucleic acids and methylphosphonates (Thompson, *Drug Discovery Today,* 7:912-917 (2002)). Antisense oligonucleotides are useful directly as therapeutic agents, and are also useful for determining and validating gene function, for example by gene knock-out or gene knock-down experiments. Antisense technology is further described in Lavery et al., *Curr. Opin. Drug Discov. Devel.* 6:561-569 (2003), Stephens et al., *Curr. Opin. Mol. Ther.* 5:118-122 (2003), Kurreck, *Eur. J. Biochem.* 270:1628-44 (2003), Dias et al., *Mol. Cancer. Ter.* 1:347-55 (2002), Chen, *Methods Mol. Med.* 75:621-636 (2003), Wang et al., *Curr. Cancer Drug Targets* 1:177-96 (2001), and Bennett, *Antisense Nucleic Acid Drug. Dev.* 12:215-24 (2002)

The variants described herein can be used for the selection and design of antisense reagents that are specific for particular variants. Using information about the variants described herein, antisense oligonucleotides or other antisense molecules that specifically target mRNA molecules that contain one or more variants of the invention can be designed. In this manner, expression of mRNA molecules that contain one or more variant of the present invention (markers and/or haplotypes) can be inhibited or blocked. In one embodiment, the antisense molecules are designed to specifically bind a particular allelic form (i.e., one or several variants (alleles and/or haplotypes)) of the target nucleic acid, thereby inhibiting translation of a product originating from this specific allele or haplotype, but which do not bind other or alternate variants at the specific polymorphic sites of the target nucleic acid molecule.

As antisense molecules can be used to inactivate mRNA so as to inhibit gene expression, and thus protein expression, the molecules can be used to treat a disease or disorder, such as cardiac arrhythmia (e.g., atrial fibrillation or atrial flutter) and/or stroke. The methodology can involve cleavage by means of ribozymes containing nucleotide sequences complementary to one or more regions in the mRNA that attenuate the ability of the mRNA to be translated. Such mRNA regions include, for example, protein-coding regions, in particular protein-coding regions corresponding to catalytic activity, substrate and/or ligand binding sites, or other functional domains of a protein.

The phenomenon of RNA interference (RNAi) has been actively studied for the last decade, since its original discovery in *C. elegans* (Fire et al., *Nature* 391:806-11 (1998)), and in recent years its potential use in treatment of human disease has been actively pursued (reviewed in Kim & Rossi, *Nature Rev. Genet.* 8:173-204 (2007)). RNA interference (RNAi), also called gene silencing, is based on using double-stranded RNA molecules (dsRNA) to turn off specific genes. In the cell, cytoplasmic double-stranded RNA molecules (dsRNA) are processed by cellular complexes into small interfering RNA (siRNA). The siRNA guide the targeting of a protein-RNA complex to specific sites on a target mRNA, leading to cleavage of the mRNA (Thompson, *Drug Discovery Today,* 7:912-917 (2002)). The siRNA molecules are typically about 20, 21, 22 or 23 nucleotides in length. Thus, one aspect of the invention relates to isolated nucleic acid molecules, and the use of those molecules for RNA interference, i.e. as small interfering RNA molecules (siRNA). In one embodiment, the isolated nucleic acid molecules are 18-26 nucleotides in length, preferably 19-25 nucleotides in length, more preferably 20-24 nucleotides in length, and more preferably 21, 22 or 23 nucleotides in length.

Another pathway for RNAi-mediated gene silencing originates in endogenously encoded primary microRNA (pri-miRNA) transcripts, which are processed in the cell to generate precursor miRNA (pre-miRNA). These miRNA molecules are exported from the nucleus to the cytoplasm, where they undergo processing to generate mature miRNA molecules (miRNA), which direct translational inhibition by recognizing target sites in the 3' untranslated regions of mRNAs, and subsequent mRNA degradation by processing P-bodies (reviewed in Kim & Rossi, *Nature Rev. Genet.* 8:173-204 (2007)).

Clinical applications of RNAi include the incorporation of synthetic siRNA duplexes, which preferably are approximately 20-23 nucleotides in size, and preferably have 3' overlaps of 2 nucleotides. Knockdown of gene expression is established by sequence-specific design for the target mRNA. Several commercial sites for optimal design and synthesis of such molecules are known to those skilled in the art.

Other applications provide longer siRNA molecules (typically 25-30 nucleotides in length, preferably about 27 nucleotides), as well as small hairpin RNAs (shRNAs; typically about 29 nucleotides in length). The latter are naturally expressed, as described in Amarzguloui et al. (*FEBS Lett.* 579:5974-81 (2005)). Chemically synthetic siRNAs and shRNAs are substrates for in vivo processing, and in some cases provide more potent gene-silencing than shorter designs (Kim et al., *Nature Biotechnol.* 23:222-226 (2005); Siolas et al., *Nature Biotechnol.* 23:227-231 (2005)). In general siRNAs provide for transient silencing of gene expression, because their intracellular concentration is diluted by subsequent cell divisions. By contrast, expressed shRNAs mediate long-term, stable knockdown of target transcripts, for as long as transcription of the shRNA takes place (Marques et al., *Nature Biotechnol.* 23:559-565 (2006); Brummelkamp et al., *Science* 296: 550-553 (2002)).

Since RNAi molecules, including siRNA, miRNA and shRNA, act in a sequence-dependent manner, the variants of the present invention (e.g., the markers and haplotypes associated with LD block C04, e.g., the markers listed in Tables 5A and 5B) can be used to design RNAi reagents that recognize specific nucleic acid molecules comprising specific alleles and/or haplotypes (e.g., the alleles and/or haplotypes of the present invention), while not recognizing nucleic acid molecules comprising other alleles or haplotypes. These RNAi reagents can thus recognize and destroy the target nucleic acid molecules. As with antisense reagents, RNAi reagents can be useful as therapeutic agents (i.e., for turning off disease-associated genes or disease-associated gene variants), but may also be useful for characterizing and validating gene function (e.g., by gene knock-out or gene knock-down experiments).

Delivery of RNAi may be performed by a range of methodologies known to those skilled in the art. Methods utilizing non-viral delivery include cholesterol, stable nucleic acid-lipid particle (SNALP), heavy-chain antibody fragment (Fab), aptamers and nanoparticles. Viral delivery methods include use of lentivirus, adenovirus and adeno-associated virus. The siRNA molecules are in some embodiments chemically modified to increase their stability. This can include modifications at the 2' position of the ribose, including 2'-O-methylpurines and 2'-fluoropyrimidines, which provide resistance to Rnase activity. Other chemical modifications are possible and known to those skilled in the art.

The following references provide a further summary of RNAi, and possibilities for targeting specific genes using RNAi: Kim & Rossi, *Nat. Rev. Genet.* 8:173-184 (2007), Chen & Rajewsky, *Nat. Rev. Genet.* 8: 93-103 (2007), Reynolds, et al., *Nat. Biotechnol.* 22:326-330 (2004), Chi et al., *Proc. Natl. Acad. Sci. USA* 100:6343-6346 (2003), Vickers et al., *J. Biol. Chem.* 278:7108-7118 (2003), Agami, *Curr. Opin. Chem. Biol.* 6:829-834 (2002), Lavery, et al., *Curr. Opin. Drug Discov. Devel.* 6:561-569 (2003), Shi, *Trends Genet.* 19:9-12 (2003), Shuey et al., *Drug Discov. Today* 7:1040-46 (2002), McManus et al., *Nat. Rev. Genet.* 3:737-747 (2002), Xia et al., *Nat. Biotechnol.* 20:1006-10 (2002), Plasterk et al., *curr. Opin. Genet. Dev.* 10:562-7 (2000), Bosher et al., *Nat. Cell Biol.* 2:E31-6 (2000), and Hunter, *Curr. Biol.* 9:R440-442 (1999).

A genetic defect leading to increased predisposition or risk for development of a disease, including cardiac arrhythmia (e.g., atrial fibrillation or atrial flutter) and/or stroke, or a defect causing the disease, may be corrected permanently by administering to a subject carrying the defect a nucleic acid fragment that incorporates a repair sequence that supplies the normal/wild-type nucleotide(s) at the site of the genetic defect. Such site-specific repair sequence may concompass an RNA/DNA oligonucleotide that operates to promote endogenous repair of a subject's genomic DNA. The administration of the repair sequence may be performed by an appropriate vehicle, such as a complex with polyethelenimine, encapsulated in anionic liposomes, a viral vector such as an adenovirus vector, or other pharmaceutical compositions suitable for promoting intracellular uptake of the administered nucleic acid. The genetic defect may then be overcome, since the chimeric oligonucleotides induce the incorporation of the normal sequence into the genome of the subject, leading to expression of the normal/wild-type gene product. The replacement is propagated, thus rendering a permanent repair and alleviation of the symptoms associated with the disease or condition.

The present invention provides methods for identifying compounds or agents that can be used to treat cardiac arrhythmia, e.g. atrial fibrillation and atrial flutter, and stroke. Thus, the variants of the invention are useful as targets for the identification and/or development of therapeutic agents. Such methods may include assaying the ability of an agent or compound to modulate the activity and/or expression of a nucleic acid that includes at least one of the variants (markers and/or haplotypes) of the present invention, or the encoded product of the nucleic acid. This in turn can be used to identify agents or compounds that inhibit or alter the undesired activity or expression of the encoded nucleic acid product. Assays for performing such experiments can be performed in cell-based systems or in cell-free systems, as known to the skilled person. Cell-based systems include cells naturally expressing the nucleic acid molecules of interest, or recombinant cells that have been genetically modified so as to express a certain desired nucleic acid molecule.

Variant gene expression in a patient can be assessed by expression of a variant-containing nucleic acid sequence (for example, a gene containing at least one variant of the present invention, which can be transcribed into RNA containing the at least one variant, and in turn translated into protein), or by altered expression of a normal/wild-type nucleic acid sequence due to variants affecting the level or pattern of expression of the normal transcripts, for example variants in the regulatory or control region of the gene. Assays for gene expression include direct nucleic acid assays (mRNA), assays for expressed protein levels, or assays of collateral compounds involved in a pathway, for example a signal pathway. Furthermore, the expression of genes that are up- or down-regulated in response to the signal pathway can also be assayed. One embodiment includes operably linking a reporter gene, such as luciferase, to the regulatory region of the gene(s) of interest.

Modulators of gene expression can in one embodiment be identified when a cell is contacted with a candidate compound or agent, and the expression of mRNA is determined. The expression level of mRNA in the presence of the candidate compound or agent is compared to the expression level in the absence of the compound or agent. Based on this comparison, candidate compounds or agents for treating disorders such as atrial fibrillation, atrial flutter and stroke can be identified as those modulating the gene expression of the variant gene. When expression of mRNA or the encoded protein is statistically significantly greater in the presence of the candidate compound or agent than in its absence, then the candidate compound or agent is identified as a stimulator or upregulator of expression of the nucleic acid. When nucleic acid expression or protein level is statistically significantly less in the presence of the candidate compound or agent than in its absence, then the candidate compound is identified as an inhibitor or down-regulator of the nucleic acid expression.

The invention further provides methods of treatment using a compound identified through drug (compound and/or agent) screening as a gene modulator (i.e. stimulator and/or inhibitor of gene expression).

In a further aspect of the present invention, a pharmaceutical pack (kit) is provided, the pack comprising a therapeutic agent and a set of instructions for administration of the therapeutic agent to humans diagnostically tested for one or more variants of the present invention, as disclosed herein. The therapeutic agent can be a small molecule drug, an antibody, a peptide, an antisense or RNAi molecule, or other therapeutic molecules. In one embodiment, an individual identified as a carrier of at least one variant of the present invention is instructed to take a prescribed dose of the therapeutic agent. In one such embodiment, an individual identified as a homozygous carrier of at least one variant of the present invention is instructed to take a prescribed dose of the therapeutic agent. In another embodiment, an individual identified as a non-carrier of at least one variant of the present invention is instructed to take a prescribed dose of the therapeutic agent.

Methods of Assessing Probability of Response to Therapeutic Agents, Methods of Monitoring Progress of Treatment and Methods of Treatment As is known in the art, individuals can have differential responses to a particular therapy (e.g., a therapeutic agent or therapeutic method). Pharmacogenomics addresses the issue of how genetic variations (e.g., the variants (markers and/or haplotypes) of the present invention) affect drug response, due to altered drug disposition and/or abnormal or altered action of the drug. Thus, the basis of the differential response may be genetically determined in part. Clinical outcomes due to genetic variations affecting drug response may result in toxicity of the drug in certain individuals (e.g., carriers or non-carriers of the genetic variants of the present invention), or therapeutic failure of the drug. Therefore, the variants of the present invention may determine the manner in which a therapeutic agent and/or method acts on the body, or the way in which the body metabolizes the therapeutic agent.

Accordingly, in one embodiment, the presence of a particular allele at a polymorphic site or haplotype is indicative of a different, e.g. a different response rate, to a particular treatment modality. This means that a patient diagnosed with cardiac arrhythmia (e.g., atrial fibrillation or atrial flutter) and/or stroke, and carrying a certain allele at a polymorphic or haplotype of the present invention (e.g., the at-risk and protective alleles and/or haplotypes of the invention) would respond better to, or worse to, a specific therapeutic, drug and/or other therapy used to treat the disease. Therefore, the presence or absence of the marker allele or haplotype could aid in deciding what treatment should be used for a the patient. For example, for a newly diagnosed patient, the presence of a marker or haplotype of the present invention may be assessed (e.g., through testing DNA derived from a blood sample, as described herein). If the patient is positive for a marker allele or haplotype at (that is, at least one specific allele of the marker, or haplotype, is present), then the physician recommends one particular therapy, while if the patient is negative for the at least one allele of a marker, or a haplotype, then a different course of therapy may be recommended (which may include recommending that no immediate therapy, other than serial monitoring for progression of the disease, be performed). Thus, the patient's carrier status could be used to help determine whether a particular treatment modality should be administered. The value lies within the possibilities of being able to diagnose the disease at an early stage, to select the most appropriate treatment, and provide information to the clinician about prognosis/aggressiveness of the disease in order to be able to apply the most appropriate treatment.

Treatment of Atrial Fibrillation and Atrial Flutter is Generally Directed by Two Main Objectives: (i) to Prevent Stroke and (ii) to Treat Symptoms.

(i) Stroke Prevention

Anticoagulation is the therapy of choice for stroke prevention in atrial fibrillation and is indicated for the majority of patients with this arrhythmia. The only patients for whom anticoagulation is not strongly recommended are those younger than 65 years old who are considered low-risk, i.e., they have no organic heart disease, no hypertension, no previous history of stroke or transient ischemic attacks and no diabetes. This group as a whole has a lower risk of stroke and stroke prevention with aspirin is generally recommended. For all other patients, anticoagulation is indicated whether the atrial fibrillation is permanent, recurrent paroxysmal or recurrent persistent. It cannot be generalized how patients who present with their first episode of paroxysmal atrial fibrillation should be treated and the decision needs to be individualized for each patient. Anticoagulation is also indicated even when the patient with atrial fibrillation is felt to be maintained in sinus rhythm with antiarrhythmic therapy (rhythm controlled) since this type of therapy does not affect stroke risk.

Anticoagulants. Anticoagulation is recommended in atrial fibrillation, as detailed above, for prevention of cardioembolism and stroke. The most widely studied oral anticoagulant is warfarin and this medication is universally recommended for chronic oral anticoagulation in atrial fibrillation. Warfarin has few side effects aside from the risk of bleeding but requires regular and careful monitoring of blood values during therapy (to measure the effect of the anticoagulation). The oral anticoagulant ximelagatran showed promise in stroke prevention in patients with atrial fibrillation and had the advantage of not requiring regular monitoring like warfarin. Ximelagatran was found however to cause unexplained liver injury and was withdrawn from the market in 2006. Several agents are available for intravenous and/or subcutaneous therapy, including heparin and the low molecular weight heparins (e.g. enoxaparin, dalteparin, tinzaparin, ardeparin, nadroparin and reviparin). These medications are recommended when rapid initiation of anticoagulation is necessary or if oral anticoagulation therapy has to be interrupted in high risk patients or for longer than one week in other patients for example due to a series of procedures. Other parenteral anticoagulants are available but not specifically recommended as therapy in atrial fibrillation; e.g., the factor Xa inhibitors fondaparinux and idraparinux, the thrombin-inhibitors lepirudin, bivalirudin and argatroban as well as danaparoid.

(ii) Symptom Control. Medical and surgical therapy applied to control symptoms of atrial fibrillation is tailored to the individual patient and consists of heart rate and/or rhythm control with medications, radiofrequency ablation and/or surgery.

Antiarrhythmic medications. In general terms, antiarrhythmic agents are used to suppress abnormal rhythms of the heart that are characteristic of cardiac arrhythmias, including atrial fibrillation and atrial flutter. One classification of antiarrhythmic agents is the Vaughan Williams classification, in which five main categories of antiarrhythmic agents are defined. Class I agents are fast sodium channel blockers and are subclassified based on kinetics and strength of blockade as well as their effect on repolarization. Class Ia includes disopyramide, moricizine, procainamide and quinidine. Class Ib agents are lidocaine, mexiletine, tocainide, and phenyloin. Class Ic agents are encainide, flecainide, propafenone, ajmaline, cibenzoline and detajmium. Class II agents are beta blockers, they block the effects of catecholamines at beta-adrenergic receptors. Examples of beta blockers are esmolol, propranolol, metoprolol, alprenolol, atenolol, carvedilol, bisoprolol, acebutolol, nadolol, pindolol, labetalol, oxprenotol, penbutolol, timolol, betaxolol, cartelol, sotalol and levobunolol. Class III agents have mixed properties but are collectively potassium channel blockers and prolong repolarization. Medications in this category are amiodarone, azimilide, bretylium, dofetilide, tedisamil, ibutilide, sematilide, sotalol, N-acetyl procainamide, nifekalant hydrochloride, vernakalant and ambasilide. Class IV agents are calcium channel blockers and include verapamil, mibefradil and diltiazem. Finally, class V consists of miscellaneous antiarrhythmics and includes digoxin and adenosine.

Heart rate control, Pharmacologic measures for maintenance of heart rate control include beta blockers, calcium channel blockers and digoxin. All these medications slow the electrical conduction through the atrioventricular node and slow the ventricular rate response to the rapid atrial fibrillation. Some antiarrhythmics used primarily for rhythm control (see below) also slow the atrioventricular node conduction rate and thus the ventricular heart rate response. These include some class III and Ic medications such as amiodarone, sotalol and flecainide.

Cardioversion. Cardioversion of the heart rhythm from atrial fibrillation or atrial flutter to sinus rhythm can be achieved electrically, with synchronized direct-current cardioversion, or with medications such as ibutilide, amiodarone, procainamide, propafenone and flecainide.

Heart Rhythm Control

Medications used for maintenance of sinus rhythm, i.e. rhythm control, include mainly antiarrhythmic medications from classes III, Ia and Ic. Examples are sotalol, amiodarone and dofetilide from class III, disopyramide, procainamide and quinidine from class Ia and flecinide and propafenone from class Ic. Treatment with these antiarrhythmic medications is complicated, can be hazardous, and should be directed by physicians specifically trained to use these medications. Many of the antiarrhythmics have serious side effects and should only be used in specific populations. For example, class Ic medications should not be used in patients with coronary artery disease and even if they can suppress atrial fibrillation, they can actually promote rapid ventricular response in atrial flutter. Class Ia medications can be used as last resort in patients without structural heart diseases. Sotalol (as most class III antiarrhythmics) can cause significant prolongation of the QT interval, specifically in patients with renal failure, and promote serious ventricular arrhythmias. Both sotalol and dofetilide as well as the Ia medications need to be initiated on an inpatient basis to monitor the QT interval. Although amiodarone is usually well tolerated and is widely used, amiodarone has many serious side effects with long-term therapy.

How Genetic Testing May Directly Affect Choice of Treatment

When individuals present with their first (diagnosed) episode of paroxysmal atrial fibrillation and either spontaneously convert to sinus rhythm or undergo electrical or chemical cardioversion less than 48 hours into the episode, the decision to initiate, or not to initiate, anticoagulation therapy, is individualized based on the risk profile of the patient in question and the managing physicians preference. This can be a difficult choice to make since committing the patient to anticoagulation therapy has a major impact on the patients life. Often the choice is made to withhold anticoagulation in such a situation and this may be of no significant consequence to the patient. On the other hand the patient may later develop a stroke and the opportunity of prevention may thus have been missed. In such circumstances, knowing that the patient is a carrier of the at-risk variant may be of great significance and support initiation of anticoagulation treatment.

Individuals who are diagnosed with atrial fibrillation under the age of 65 and are otherwise considered low risk for stroke, i.e. have no organic heart disease, no hypertension, no diabetes and no previous history of stroke, are generally treated with aspirin only for stroke-prevention and not anticoagulation. If such a patient is found to be carrier for the at-risk variants described herein, this could be considered support for initiating anticoagulation earlier than otherwise recommended. This would be a reasonable consideration since the results of stroke from atrial fibrillation can be devastating.

Ischemic stroke is generally classified into five subtypes based on suspected cause; large artery atherosclerosis, small artery occlusion, cardioembolism (majority due to atrial fibrillation), stroke of other determined cause and stroke of undetermined cause (either no cause found or more than 1 plausible cause). Importantly, strokes due to cardioembolism have the highest recurrence, are most disabling and are associated with the lowest survival. It is therefore imperative not to overlook atrial fibrillation as the major cause of stroke, particularly since treatment measures vary based on the subtype. Therefore, if an individual is diagnosed with stroke or a transient ischemic attack and a plausible cause is not identified despite standard work-up, knowing that the patient is a carrier of the at-risk variant may be of great value and support either initiation of anticoagulation treatment or more aggressive diagnostic testing in the attempt to diagnose atrial fibrillation.

Furthermore, the markers of the present invention can be used to increase power and effectiveness of clinical trials. Thus, individuals who are carriers of at least one at-risk variant of the present invention, i.e. individuals who are carriers of at least one allele of at least one polymorphic marker conferring increased risk of developing cardiac arrhythmia (e.g., atrial fibrillation or atrial flutter) and/or stroke may be more likely to respond to a particular treatment modality, e.g., as described in the above. In one embodiment, individuals who carry at-risk variants for gene(s) in a pathway and/or metabolic network for which a particular treatment (e.g., small molecule drug) is targeting, are more likely to be responders to the treatment. In another embodiment, individuals who carry at-risk variants for a gene, which expression and/or function is altered by the at-risk variant, are more likely to be responders to a treatment modality targeting that gene, its expression or its gene product. This application can improve the safety of clinical trials, but can also enhance the chance that a clinical trial will demonstrate statistically significant efficacy, which may be limited to a certain sub-group of the population. Thus, one possible outcome of such a trial is that carriers of certain genetic variants, e.g., the markers and haplotypes of the present invention, are statistically significantly likely to show positive response to the therapeutic agent, i.e. experience alleviation of symptoms associated with cardiac arrhythmia (e.g., atrial fibrillation or atrial flutter) and/or stroke when taking the therapeutic agent or drug as prescribed.

In a further aspect, the markers and haplotypes of the present invention can be used for targeting the selection of pharmaceutical agents for specific individuals. Personalized selection of treatment modalities, lifestyle changes or combination of the two, can be realized by the utilization of the at-risk variants of the present invention. Thus, the knowledge of an individual's status for particular markers of the present invention, can be useful for selection of treatment options that target genes or gene products affected by the at-risk variants of the invention. Certain combinations of variants may be suitable for one selection of treatment options, while other gene variant combinations may target other treatment options. Such combination of variant may include one variant, two variants, three variants, or four or more variants, as needed to determine with clinically reliable accuracy the selection of treatment module.

Computer-Implemented Applications

The present invention also relates to computer-implemented applications of the polymorphic markers and haplotypes described herein to be associated with cardiac arrhythmia (e.g., atrial fibrillation and atrial flutter) and stroke. Such applications can be useful for storing, manipulating or otherwise analyzing genotype data that is useful in the methods of the invention. One example pertains to storing genotype information derived from an individual on readable media, so as to be able to provide the genotype information to a third party (e.g., the individual), or for deriving information from the genotype data, e.g., by comparing the genotype data to information about genetic risk factors contributing to increased susceptibility to cardiac arrhythmia (e.g., atrial fibrillation and atrial flutter) and stroke, and reporting results based on such comparison.

One such aspect relates to computer-readable media. In general terms, such medium has capabilities of storing (i) identifier information for at least one polymorphic marker or a haplotype; (ii) an indicator of the frequency of at least one allele of said at least one marker, or the frequency of a haplotype, in individuals with cardiac arrhythmia (e.g., atrial fibrillation and atrial flutter) and/or stroke; and an indicator of the frequency of at least one allele of said at least one marker, or the frequency of a haplotype, in a reference population. The reference population can be a disease-free population of individuals. Alternatively, the reference population is a random sample from the general population, and is thus representative of the population at large. The frequency indicator may be a calculated frequency, a count of alleles and/or haplotype copies, or normalized or otherwise manipulated values of the actual frequencies that are suitable for the particular medium.

Additional information about the individual can be stored on the medium, such as ancestry information, information about sex, physical attributes or characteristics (including height and weight), biochemical measurements (such as blood pressure, blood lipid levels, fasting glucose levels, insulin response measurements), biomarker results, or other useful information that is desirable to store or manipulate in the context of the genotype status of a particular individual.

The invention furthermore relates to an apparatus that is suitable for determination or manipulation of genetic data useful for determining a susceptibility to cardiac arrhythmia (e.g., atrial fibrillation and atrial flutter) and stroke in a human individual. Such an apparatus can include a computer-readable memory, a routine for manipulating data stored on the computer-readable memory, and a routine for generating an output that includes a measure of the genetic data. Such measure can include values such as allelic or haplotype frequencies, genotype counts, sex, age, phenotype information, values for odds ratio (OR) or relative risk (RR), population attributable risk (PAR), or other useful information that is either a direct statistic of the original genotype data or based on calculations based on the genetic data.

The above-described applications can all be practiced with the markers and haplotypes of the invention that have in more detail been described with respect to methods of assessing susceptibility to cardiac arrhythmia (e.g., atrial fibrillation and atrial flutter) and stroke. Thus, these applications can in general be reduced to practice using markers listed in Tables 5, Table 4, Table 9, and Table 19, and markers in linkage disequilibrium therewith. In one embodiment, the markers or haplotypes are present within the genomic segment whose sequences is set forth in SEQ ID NO:50. In another embodiment, the markers or haplotypes comprise at least one marker selected from the markers set forth in Table 19. In another embodiment, the markers and haplotypes comprise at least one marker selected from D4S406 (SEQ ID NO:45), rs2634073 (SEQ ID NO:33), rs2200733 (SEQ ID NO:28), rs2220427 (SEQ ID NO:1), rs10033464 (SEQ ID NO:41), and rs13143308 (SEQ ID NO:51), optionally including markers in linkage disequilibrium therewith. In one such embodiment, linkage disequilibrium is defined by numerical values for $r^2$ of greater than 0.1. In another such embodiment, linkage disequilibrium is defined by numerical values for $r^2$ of greater than 0.2. In another embodiment, the marker or haplotype comprises at least one allele selected from alleles −2, −4 and/or −8 in marker D4S406, allele A of marker rs2634073, allele T of marker rs2200733, allele T of marker rs2220427, allele T of marker rs10033464, and/or allele G of marker rs13143308

Nucleic Acids and Polypeptides

The nucleic acids and polypeptides described herein can be used in methods an kits of the present invention, as described in the above.

An "isolated" nucleic acid molecule, as used herein, is one that is separated from nucleic acids that normally flank the gene or nucleotide sequence (as in genomic sequences) and/or has been completely or partially purified from other transcribed sequences (e.g., as in an RNA library). For example, an isolated nucleic acid of the invention can be substantially isolated with respect to the complex cellular milieu in which it naturally occurs, or culture medium when produced by recombinant techniques, or chemical precursors or other chemicals when chemically synthesized. In some instances, the isolated material will form part of a composition (for example, a crude extract containing other substances), buffer system or reagent mix. In other circumstances, the material can be purified to essential homogeneity, for example as determined by polyacrylamide gel electrophoresis (PAGE) or column chromatography (e.g., HPLC). An isolated nucleic acid molecule of the invention can comprise at least about 50%, at least about 80% or at least about 90% (on a molar basis) of all macromolecular species present. With regard to genomic DNA, the term "isolated" also can refer to nucleic acid molecules that are separated from the chromosome with which the genomic DNA is naturally associated. For example, the isolated nucleic acid molecule can contain less than about 250 kb, 200 kb, 150 kb, 100 kb, 75 kb, 50 kb, 25 kb, 10 kb, 5 kb, 4 kb, 3 kb, 2 kb, 1 kb, 0.5 kb or 0.1 kb of the nucleotides that flank the nucleic acid molecule in the genomic DNA of the cell from which the nucleic acid molecule is derived.

The nucleic acid molecule can be fused to other coding or regulatory sequences and still be considered isolated. Thus, recombinant DNA contained in a vector is included in the definition of "isolated" as used herein. Also, isolated nucleic acid molecules include recombinant DNA molecules in heterologous host cells or heterologous organisms, as well as partially or substantially purified DNA molecules in solution. "Isolated" nucleic acid molecules also encompass in vivo and in vitro RNA transcripts of the DNA molecules of the present invention. An isolated nucleic acid molecule or nucleotide sequence can include a nucleic acid molecule or nucleotide sequence that is synthesized chemically or by recombinant means. Such isolated nucleotide sequences are useful, for example, in the manufacture of the encoded polypeptide, as probes for isolating homologous sequences (e.g., from other mammalian species), for gene mapping (e.g., by in situ hybridization with chromosomes), or for detecting expression of the gene in tissue (e.g., human tissue), such as by Northern blot analysis or other hybridization techniques.

The invention also pertains to nucleic acid molecules that hybridize under high stringency hybridization conditions, such as for selective hybridization, to a nucleotide sequence described herein (e.g., nucleic acid molecules that specifically hybridize to a nucleotide sequence containing a polymorphic site associated with a marker or haplotype described herein). In one embodiment, the invention includes variants that hybridize under high stringency hybridization and wash conditions (e.g., for selective hybridization) to a nucleotide sequence that comprises the nucleotide sequence of LD Block C04 (SEQ ID NO:50). Such nucleic acid molecules can be detected and/or isolated by allele- or sequence-specific hybridization (e.g., under high stringency conditions). Stringency conditions and methods for nucleic acid hybridizations are well known to the skilled person (see, e.g., *Current Protocols in Molecular Biology*, Ausubel, F. et al, John Wiley & Sons, (1998), and Kraus, M. and Aaronson, S., *Methods Enzymol.,* 200:546-556 (1991), the entire teachings of which are incorporated by reference herein.

The percent identity of two nucleotide or amino acid sequences can be determined by aligning the sequences for optimal comparison purposes (e.g., gaps can be introduced in the sequence of a first sequence). The nucleotides or amino acids at corresponding positions are then compared, and the percent identity between the two sequences is a function of the number of identical positions shared by the sequences (i.e., % identity=# of identical positions/total # of positions×100). In certain embodiments, the length of a sequence aligned for comparison purposes is at least 30%, at least 40%, at least 50%, at least 60%, at least 70%, at least 80%, at least 90%, or at least 95%, of the length of the reference sequence. The actual comparison of the two sequences can be accomplished by well-known methods, for example, using a mathematical algorithm. A non-limiting example of such a mathematical algorithm is described in Karlin, S, and Altschul, S., *Proc. Natl. Acad. Sci. USA,* 90:5873-5877 (1993). Such an algorithm is incorporated into the NBLAST and XBLAST programs (version 2.0), as described in Altschul, S. et al., *Nucleic Acids Res.,* 25:3389-3402 (1997). When utilizing BLAST and Gapped BLAST programs, the default parameters of the respective programs (e.g., NBLAST) can be used. See the website on the world wide web at ncbi.nlm.nih.gov. In one embodiment, parameters for sequence comparison can be set at score=100, wordlength=12, or can be varied (e.g., W=5 or W=20).

Other examples include the algorithm of Myers and Miller, CABIOS (1989), ADVANCE and ADAM as described in Torellis, A. and Robotti, C., *Comput. Appl. Biosci.* 10:3-5 (1994); and FASTA described in Pearson, W. and Lipman, D., *Proc. Natl. Acad. Sci. USA,* 85:2444-48 (1988). In another embodiment, the percent identity between two amino acid sequences can be accomplished using the GAP program in the GCG software package (Accelrys, Cambridge, UK).

The present invention also provides isolated nucleic acid molecules that contain a fragment or portion that hybridizes under highly stringent conditions to a nucleic acid that comprises, or consists of, the nucleotide sequence of LD Block C04 (SEQ ID NO:50), or a nucleotide sequence comprising, or consisting of, the complement of the nucleotide sequence of LD Block C04 (SEQ ID NO:50), wherein the nucleotide sequence comprises at least one polymorphic allele contained in the markers and haplotypes described herein. The nucleic acid fragments of the invention are at least about 15, at least about 18, 20, 23 or 25 nucleotides, and can be 30, 40, 50, 100, 200, 500, 1000, 10,000 or more nucleotides in length.

The nucleic acid fragments of the invention are used as probes or primers in assays such as those described herein. "Probes" or "primers" are oligonucleotides that hybridize in a base-specific manner to a complementary strand of a nucleic acid molecule. In addition to DNA and RNA, such probes and primers include polypeptide nucleic acids (PNA), as described in Nielsen, P. et al., *Science* 254:1497-1500 (1991). A probe or primer comprises a region of nucleotide sequence that hybridizes to at least about 15, typically about 20-25, and in certain embodiments about 40, 50 or 75, consecutive nucleotides of a nucleic acid molecule. In one embodiment, the probe or primer comprises at least one allele of at least one polymorphic marker or at least one haplotype described herein, or the complement thereof. In particular embodiments, a probe or primer can comprise 100 or fewer nucleotides; for example, in certain embodiments from 6 to 50 nucleotides, or, for example, from 12 to 30 nucleotides. In other embodiments, the probe or primer is at least 70% identical, at least 80% identical, at least 85% identical, at least 90% identical, or at least 95% identical, to the contiguous nucleotide sequence or to the complement of the contiguous nucleotide sequence. In another embodiment, the probe or primer is capable of selectively hybridizing to the contiguous nucleotide sequence or to the complement of the contiguous nucleotide sequence. Often, the probe or primer further comprises a label, e.g., a radioisotope, a fluorescent label, an enzyme label, an enzyme co-factor label, a magnetic label, a spin label, an epitope label.

The nucleic acid molecules of the invention, such as those described above, can be identified and isolated using standard molecular biology techniques well known to the skilled person. The amplified DNA can be labeled (e.g., radiolabeled) and used as a probe for screening a cDNA library derived from human cells. The cDNA can be derived from mRNA and contained in a suitable vector. Corresponding clones can be isolated, DNA can obtained following in vivo excision, and the cloned insert can be sequenced in either or both orientations by art-recognized methods to identify the correct reading frame encoding a polypeptide of the appropriate molecular weight. Using these or similar methods, the polypeptide and the DNA encoding the polypeptide can be isolated, sequenced and further characterized.

In general, the isolated nucleic acid sequences of the invention can be used as molecular weight markers on Southern gels, and as chromosome markers that are labeled to map related gene positions. The nucleic acid sequences can also be used to compare with endogenous DNA sequences in patients to identify cardiac arrhythmia (e.g., atrial fibrillation or atrial flutter) and/or stroke or a susceptibility to cardiac arrhythmia (e.g., atrial fibrillation or atrial flutter) and/or stroke, and as probes, such as to hybridize and discover related DNA sequences or to subtract out known sequences from a sample (e.g., subtractive hybridization). The nucleic acid sequences can further be used to derive primers for genetic fingerprinting, to raise anti-polypeptide antibodies using immunization techniques, and/or as an antigen to raise anti-DNA antibodies or elicit immune responses.

Antibodies

Polyclonal antibodies and/or monoclonal antibodies that specifically bind one form of the gene product but not to the other form of the gene product are also provided. Antibodies are also provided which bind a portion of either the variant or the reference gene product that contains the polymorphic site or sites. The term "antibody" as used herein refers to immunoglobulin molecules and immunologically active portions of immunoglobulin molecules, i.e., molecules that contain antigen-binding sites that specifically bind an antigen. A molecule that specifically binds to a polypeptide of the invention is a molecule that binds to that polypeptide or a fragment thereof, but does not substantially bind other molecules in a sample, e.g., a biological sample, which naturally contains the polypeptide. Examples of immunologically active portions of immunoglobulin molecules include F(ab) and $F(ab')_2$ fragments which can be generated by treating the antibody with an enzyme such as pepsin. The invention provides polyclonal and monoclonal antibodies that bind to a polypeptide of the invention. The term "monoclonal antibody" or "monoclonal antibody composition", as used herein, refers to a population of antibody molecules that contain only one species of an antigen binding site capable of immunoreacting with a particular epitope of a polypeptide of the invention. A monoclonal antibody composition thus typically displays a single binding affinity for a particular polypeptide of the invention with which it immunoreacts.

Polyclonal antibodies can be prepared as described above by immunizing a suitable subject with a desired immunogen, e.g., polypeptide of the invention or a fragment thereof. The antibody titer in the immunized subject can be monitored over time by standard techniques, such as with an enzyme linked immunosorbent assay (ELISA) using immobilized polypeptide. If desired, the antibody molecules directed against the polypeptide can be isolated from the mammal (e.g., from the blood) and further purified by well-known techniques, such as protein A chromatography to obtain the IgG fraction. At an appropriate time after immunization, e.g., when the antibody titers are highest, antibody-producing cells can be obtained from the subject and used to prepare monoclonal antibodies by standard techniques, such as the hybridoma technique originally described by Kohler and Milstein, *Nature* 256:495-497 (1975), the human B cell hybridoma technique (Kozbor et al., *Immunol. Today* 4: 72 (1983)), the EBV-hybridoma technique (Cole et al., *Monoclonal Antibodies and Cancer Therapy*, Alan R. Liss, 1985, Inc., pp. 77-96) or trioma techniques. The technology for producing hybridomas is well known (see generally Current Protocols in Immunology (1994) Coligan et al., (eds.) John Wiley & Sons, Inc., New York, N.Y.). Briefly, an immortal cell line (typically a myeloma) is fused to lymphocytes (typically splenocytes) from a mammal immunized with an immunogen as described above, and the culture supernatants of the resulting hybridoma cells are screened to identify a hybridoma producing a monoclonal antibody that binds a polypeptide of the invention.

Any of the many well known protocols used for fusing lymphocytes and immortalized cell lines can be applied for the purpose of generating a monoclonal antibody to a polypeptide of the invention (see, e.g., Current Protocols in Immunology, supra; Galfre et al., *Nature* 266:55052 (1977); R. H. Kenneth, in *Monoclonal Antibodies: A New Dimension In Biological Analyses*, Plenum Publishing Corp., New York, N.Y. (1980); and Lerner, Yale *J. Biol. Med.* 54:387-402 (1981)). Moreover, the ordinarily skilled worker will appreciate that there are many variations of such methods that also would be useful.

Alternative to preparing monoclonal antibody-secreting hybridomas, a monoclonal antibody to a polypeptide of the invention can be identified and isolated by screening a recombinant combinatorial immunoglobulin library (e.g., an antibody phage display library) with the polypeptide to thereby isolate immunoglobulin library members that bind the polypeptide. Kits for generating and screening phage display libraries are commercially available (e.g., the Pharmacia Recombinant Phage Antibody System, Catalog No. 27-9400-01; and the Stratagene SurfZAP™ Phage Display Kit, Catalog No. 240612). Additionally, examples of methods and reagents particularly amenable for use in generating and screening antibody display library can be found in, for example, U.S. Pat. No. 5,223,409; PCT Publication No. WO 92/18619; PCT Publication No. WO 91/17271; PCT Publication No. WO 92/20791; PCT Publication No. WO 92/15679; PCT Publication No. WO 93/01288; PCT Publication No. WO 92/01047; PCT Publication No. WO 92/09690; PCT Publication No. WO 90/02809; Fuchs et al., *Bio/Technology* 9: 1370-1372 (1991); Hay et al., *Hum. Antibod. Hybridomas* 3:81-85 (1992); Huse et al., *Science* 246: 1275-1281 (1989); and Griffiths et al., *EMBO J.* 12:725-734 (1993).

Additionally, recombinant antibodies, such as chimeric and humanized monoclonal antibodies, comprising both human and non-human portions, which can be made using standard recombinant DNA techniques, are within the scope of the invention. Such chimeric and humanized monoclonal antibodies can be produced by recombinant DNA techniques known in the art.

In general, antibodies of the invention (e.g., a monoclonal antibody) can be used to isolate a polypeptide of the invention by standard techniques, such as affinity chromatography or immunoprecipitation. A polypeptide-specific antibody can facilitate the purification of natural polypeptide from cells and of recombinantly produced polypeptide expressed in host cells. Moreover, an antibody specific for a polypeptide of the invention can be used to detect the polypeptide (e.g., in a cellular lysate, cell supernatant, or tissue sample) in order to evaluate the abundance and pattern of expression of the polypeptide. Antibodies can be used diagnostically to monitor protein levels in tissue as part of a clinical testing procedure, e.g., to, for example, determine the efficacy of a given treatment regimen. The antibody can be coupled to a detectable substance to facilitate its detection. Examples of detectable substances include various enzymes, prosthetic groups, fluorescent materials, luminescent materials, bioluminescent materials, and radioactive materials. Examples of suitable enzymes include horseradish peroxidase, alkaline phosphatase, beta-galactosidase, or acetylcholinesterase; examples of suitable prosthetic group complexes include streptavidin/biotin and avidin/biotin; examples of suitable fluorescent materials include umbelliferone, fluorescein, fluorescein isothiocyanate, rhodamine, dichlorotriazinylamine fluorescein, dansyl chloride or phycoerythrin; an example of a luminescent material includes luminol; examples of bioluminescent materials include luciferase, luciferin, and aequorin, and examples of suitable radioactive material include $^{125}I$, $^{131}I$, $^{35}S$ or $^{3}H$.

Antibodies may also be useful in pharmacogenomic analysis. In such embodiments, antibodies against variant proteins encoded by nucleic acids according to the invention, such as variant proteins that are encoded by nucleic acids that contain at least one polymorphic marker of the invention, can be used to identify individuals that require modified treatment modalities.

Antibodies can furthermore be useful for assessing expression of variant proteins in disease states, such as in active stages of a disease, or in an individual with a predisposition to a disease related to the function of the protein, in particular cardiac arrhythmia (e.g., atrial fibrillation or atrial flutter) and/or stroke. Antibodies specific for a variant protein of the present invention that is encoded by a nucleic acid that comprises at least one polymorphic marker or haplotype as described herein can be used to screen for the presence of the variant protein, for example to screen for a predisposition to cardiac arrhythmia (e.g., atrial fibrillation or atrial flutter) and/or stroke as indicated by the presence of the variant protein.

Antibodies can be used in other methods. Thus, antibodies are useful as diagnostic tools for evaluating proteins, such as variant proteins of the invention, in conjunction with analysis by electrophoretic mobility, isoelectric point, tryptic or other protease digest, or for use in other physical assays known to those skilled in the art. Antibodies may also be used in tissue typing. In one such embodiment, a specific variant protein has been correlated with expression in a specific tissue type, and antibodies specific for the variant protein can then be used to identify the specific tissue type.

Subcellular localization of proteins, including variant proteins, can also be determined using antibodies, and can be applied to assess aberrant subcellular localization of the protein in cells in various tissues. Such use can be applied in genetic testing, but also in monitoring a particular treatment modality. In the case where treatment is aimed at correcting the expression level or presence of the variant protein or aberrant tissue distribution or developmental expression of the variant protein, antibodies specific for the variant protein or fragments thereof can be used to monitor therapeutic efficacy.

Antibodies are further useful for inhibiting variant protein function, for example by blocking the binding of a variant protein to a binding molecule or partner. Such uses can also be applied in a therapeutic context in which treatment involves inhibiting a variant protein's function. An antibody can be for example be used to block or competitively inhibit binding, thereby modulating (i.e., agonizing or antagonizing) the activity of the protein. Antibodies can be prepared against specific protein fragments containing sites required for specific function or against an intact protein that is associated with a cell or cell membrane. For administration in vivo, an antibody may be linked with an additional therapeutic payload, such as radionuclide, an enzyme, an immunogenic epitope, or a cytotoxic agent, including bacterial toxins (diphtheria or plant toxins, such as ricin). The in vivo half-life of an antibody or a fragment thereof may be increased by pegylation through conjugation to polyethylene glycol.

The present invention further relates to kits for using antibodies in the methods described herein. This includes, but is not limited to, kits for detecting the presence of a variant protein in a test sample. One preferred embodiment comprises antibodies such as a labelled or labelable antibody and a compound or agent for detecting variant proteins in a biological sample, means for determining the amount or the presence and/or absence of variant protein in the sample, and means for comparing the amount of variant protein in the sample with a standard, as well as instructions for use of the kit.

The present invention will now be exemplified by the following non-limiting example.

EXEMPLIFICATION

Example 1

Identification of At-Risk Variants for Atrial Fibrillation on Chromosome 4

The following contains description of the identification of susceptibility factors found to be associated with atrial fibrillation and stroke through single-point analysis of SNP markers.

Methods. The study was approved by the Data Protection Commission of Iceland and the National Bioethics Committee.

Icelandic AF cohort. The patients were all diagnosed with AF at the Landspitali University Hospital in Reykjavik, Iceland, from 1987 to 2003. Diagnoses were confirmed by a 12 lead electrocardiogram demonstrating no P waves and irregularly irregular R-R intervals. All ECGs were manually read by a cardiologist.

Icelandic Stroke cohort. The stroke cohort was derived from two major hospitals in Iceland and the Icelandic Heart Association. Patients with hemorrhagic stroke represented 6% of all patients (patients with the Icelandic type of hereditary cerebral hemorrhage with amyloidosis and patients with subarachnoid hemorrhage were excluded). Ischemic stroke accounted for 67% of the total patients and TIAs 27%. The distribution of stroke subtypes in this study is similar to that reported in other Caucasian populations (Mohr, J. P., et al., *Neurology,* 28:754-762 (1978); L. R. Caplan, *In Stroke, A Clinical Approach* (Butterworth-Heinemann, Stoneham, Mass., ed 3, (1993)).

Genotyping. A genome-wide scan of 437 Icelandic individuals diagnosed with Atrial Fibrillation (AF) and 7406 population controls was performed using Infinium HumanHap300 SNP chips from Illumina for assaying approximately 317,000 single nucleotide polymorphisms (SNPs) on a single chip (Illumina, San Diego, Calif., USA). SNP genotyping for replication in other case-control cohorts was carried using the Centaurus platform (Nanogen). A total of 347 individuals diagnosed with Stroke and 7497 controls was also performed for SNPs within the LD Block found to be associated with Atrial Fibrillation.

Statistical Methods for Association Analysis. For single marker association to atrial fibrillation or stroke, we used a likelihood ratio test to calculate a two-sided p-value for each allele. We calculated relative risk (RR) and population attributable risk (PAR) assuming a multiplicative model (C. T. Falk, P. Rubinstein, *Ann Hum Genet.* 51 (Pt 3), 227 (1987); J. D. Terwilliger, J. Ott, *Hum Hered* 42, 337 (1992)). For the CEPH Caucasian HapMap data, we calculated LD between pairs of SNPs using the standard definition of D' (R. C. Lewontin, *Genetics* 50, 757 (1964)) and $R^2$ W. G. Hill, A. Robertson, *Genetics* 60, 615 (November, 1968). When plotting all SNP combinations to elucidate the LD structure in a particular region, we plotted D' in the upper left corner and p-values in the lower right corner. In the LD plots we present, the markers are plotted equidistantly rather than according to their physical positions.

Results

Genome-Wide Association Study

We successfully genotyped 437 Icelandic Atrial Fibrialla-tion patients and 7406 population control individuals using the Illumina 330K chip. Association analysis was performed for single SNPs. The most significant association was found for markers rs2220427 and rs2220733, both of which give p-values close to $10^{-9}$. The value for rs2220427 is significant after correcting for the number of tests performed, i.e. the association is significant at the genome-wide level.

There is an apparent excess of homozygotes in affected individuals. We reject both the multiplicative model (P=0.002) and the recessive model (P=0.001). The best fitting model gives risk 1.46 to heterozygous carriers and 5.17 to homozygous carriers. The (uncorrected) P-value comparing this full model to the null model of no association is 5.43e-11. These data show that individuals with two copies of the at-risk allele are at greater risk than expected based on a simple multiplicative model.

Fitting an age at onset model for all genotypes gives a P-value of 4.84e-5. Heterozygotes are estimated to have onset 1.4090 years earlier than non-carriers and homozygote carriers are estimated to have onset 9.6126 years earlier than non-carriers. This shows a significant effect of age at onset—individuals carrying the at-risk variant are at significant risk of developing AF at a younger age than individuals who are non-carriers of the at-risk allele.

Investigating markers in the vicinity of rs2220427, we realized that the microsatellite marker D4S406 can be used as a surrogate marker for rs2220427. In particular, alleles −2, −4 and −8 (with respect to the CEPH reference) were found to be sufficient to tag the SNP based on haplotype frequencies:

TABLE 1

Relationship between rs2220427 and D4S406

| | Haplotype | | | |
|---|---|---|---|---|
| Frequency | MS allele | | SNP Allele | |
| 7.55E−05 | −2 | D4S406 | 2 | rs2220427 |
| 0.000109727 | 16 | D4S406 | 4 | rs2220427 |
| 0.000148065 | −6 | D4S406 | 4 | rs2220427 |
| 0.000149685 | 20 | D4S406 | 2 | rs2220427 |
| 0.000149756 | −4 | D4S406 | 2 | rs2220427 |
| 0.000210154 | 8 | D4S406 | 4 | rs2220427 |
| 0.000225802 | −8 | D4S406 | 2 | rs2220427 |
| 0.000227036 | 4 | D4S406 | 4 | rs2220427 |
| 0.000299371 | 18 | D4S406 | 2 | rs2220427 |
| 0.000899281 | 0 | D4S406 | 4 | rs2220427 |
| 0.00203518 | −4 | D4S406 | 4 | rs2220427 |
| 0.00673851 | −6 | D4S406 | 2 | rs2220427 |
| 0.0245484 | 2 | D4S406 | 2 | rs2220427 |

TABLE 1-continued

Relationship between rs2220427 and D4S406

| | Haplotype | | | |
|---|---|---|---|---|
| Frequency | MS allele | | SNP Allele | |
| 0.0394983 | −2 | D4S406 | 4 | rs2220427 |
| 0.0422112 | 14 | D4S406 | 2 | rs2220427 |
| 0.0594303 | 0 | D4S406 | 2 | rs2220427 |
| 0.0762831 | −8 | D4S406 | 4 | rs2220427 |
| 0.0855451 | 6 | D4S406 | 2 | rs2220427 |
| 0.0949753 | 12 | D4S406 | 2 | rs2220427 |
| 0.100105 | 16 | D4S406 | 2 | rs2220427 |
| 0.145942 | 4 | D4S406 | 2 | rs2220427 |
| 0.155838 | 8 | D4S406 | 2 | rs2220427 |
| 0.164354 | 10 | D4S406 | 2 | rs2220427 |

Thus, for individuals typed for the D4S406 marker but not rs222047, merging the −2, −4 and −8 alleles leads to a very good estimate of the frequency of the 4 allele of the SNP. We analyzed an Icelandic replication cohort for AF, comprised of 1269 cases and 69,070 controls, in this fashion. The results are quite dramatic in that the association is accompanied by a p-value of 2.94e-14 and a relative risk (multiplicative model) of 1.53. Thus, our initial finding has been replicated in an independent Icelandic cohort.

TABLE 2

Association of AF patients to Chromosome 4 (LD Block C04). Shown are values for RR under the multiplicative model.

| p-value | Relative Risk | Aff freq | Con freq | Allele | Marker |
|---|---|---|---|---|---|
| 0.16839039 | 0.8473 | 0.902746 | 0.916352 | 3 | rs10033464 |
| 0.16839039 | 1.1802 | 0.097254 | 0.083648 | 4 | rs10033464 |
| 0.24275346 | 0.8746 | 0.098398 | 0.110939 | 1 | rs13105878 |
| 0.24275346 | 1.1433 | 0.901602 | 0.889061 | 2 | rs13105878 |
| 4.89E−06 | 1.3816 | 0.441648 | 0.364078 | 1 | rs13141190 |
| 4.89E−06 | 0.7238 | 0.558352 | 0.635922 | 3 | rs13141190 |
| 1.25E−06 | 0.6905 | 0.677346 | 0.752498 | 1 | rs1448817 |
| 1.25E−06 | 1.4483 | 0.322654 | 0.247502 | 3 | rs1448817 |
| 0.00995996 | 0.7903 | 0.811213 | 0.844653 | 2 | rs16997168 |
| 0.00995996 | 1.2654 | 0.188787 | 0.155347 | 4 | rs16997168 |
| 1.07E−9 | 0.5601 | 0.811213 | 0.884688 | 2 | rs2200733 |
| 1.07E−9 | 1.7855 | 0.188787 | 0.115312 | 4 | rs2200733 |
| 7.78E−10 | 0.557 | 0.810345 | 0.884673 | 2 | rs2220427 |
| 7.78E−10 | 1.7953 | 0.189655 | 0.115327 | 4 | rs2220427 |
| 9.75E−08 | 1.5803 | 0.236239 | 0.163692 | 1 | rs2634073 |
| 9.75E−08 | 0.6328 | 0.763761 | 0.836308 | 3 | rs2634073 |

TABLE 2-continued

Association of AF patients to Chromosome 4 (LD Block C04). Shown are values for RR under the multiplicative model.

| p-value | Relative Risk | Aff freq | Con freq | Allele | Marker |
|---|---|---|---|---|---|
| 0.96927011 | 0.9968 | 0.768879 | 0.769444 | 1 | rs2723296 |
| 0.96927011 | 1.0032 | 0.231121 | 0.230556 | 3 | rs2723296 |
| 0.03281713 | 0.8529 | 0.665904 | 0.700311 | 2 | rs2723316 |
| 0.03281713 | 1.1724 | 0.334096 | 0.299689 | 4 | rs2723316 |
| 0.01803327 | 1.1855 | 0.635632 | 0.595393 | 1 | rs3853444 |
| 0.01803327 | 0.8435 | 0.364368 | 0.404607 | 3 | rs3853444 |
| 0.40105752 | 0.9214 | 0.146789 | 0.15734 | 2 | rs4576077 |
| 0.40105752 | 1.0853 | 0.853211 | 0.84266 | 4 | rs4576077 |
| 0.93269621 | 1.0084 | 0.145309 | 0.144275 | 1 | rs6419178 |
| 0.93269621 | 0.9917 | 0.854691 | 0.855725 | 3 | rs6419178 |

TABLE 3

Association of Stroke to markers within LD Block C04 (SEQ ID NO: 50)

| p-value | Relative Risk | Aff freq | Con freq | Allele | Marker |
|---|---|---|---|---|---|
| 0.37701852 | 0.8872 | 0.90634 | 0.916022 | 3 | rs10033464 |
| 0.37701852 | 1.1272 | 0.09366 | 0.083978 | 4 | rs10033464 |
| 0.2838194 | 0.8717 | 0.097983 | 0.110807 | 1 | rs13105878 |
| 0.2838194 | 1.1472 | 0.902017 | 0.889193 | 2 | rs13105878 |
| 0.01534596 | 1.2123 | 0.412104 | 0.366378 | 1 | rs13141190 |
| 0.01534596 | 0.8249 | 0.587896 | 0.633622 | 3 | rs13141190 |
| 0.04856224 | 0.8418 | 0.716138 | 0.7498 | 1 | rs1448817 |
| 0.04856224 | 1.1879 | 0.283862 | 0.2502 | 3 | rs1448817 |
| 0.14450185 | 0.8599 | 0.822767 | 0.843717 | 2 | rs16997168 |
| 0.14450185 | 1.1629 | 0.177233 | 0.156283 | 4 | rs16997168 |
| 0.00374992 | 0.724 | 0.84438 | 0.882271 | 2 | rs2200733 |
| 0.00374992 | 1.3812 | 0.15562 | 0.117729 | 4 | rs2200733 |
| 0.0025713 | 0.7141 | 0.842566 | 0.882274 | 2 | rs2220427 |
| 0.0025713 | 1.4003 | 0.157434 | 0.117726 | 4 | rs2220427 |
| 0.01664881 | 1.2682 | 0.201729 | 0.166154 | 1 | rs2634073 |
| 0.01664881 | 0.7885 | 0.798271 | 0.833846 | 3 | rs2634073 |
| 0.58350156 | 0.9511 | 0.760807 | 0.769811 | 1 | rs2723296 |
| 0.58350156 | 1.0514 | 0.239193 | 0.230189 | 3 | rs2723296 |
| 0.03150475 | 0.8367 | 0.661383 | 0.700107 | 2 | rs2723316 |
| 0.03150475 | 1.1952 | 0.338617 | 0.299893 | 4 | rs2723316 |
| 0.16517516 | 1.1172 | 0.622832 | 0.596462 | 1 | rs3853444 |
| 0.16517516 | 0.8951 | 0.377168 | 0.403538 | 3 | rs3853444 |
| 0.24301926 | 0.8797 | 0.14121 | 0.157473 | 2 | rs4576077 |
| 0.24301926 | 1.1367 | 0.85879 | 0.842527 | 4 | rs4576077 |
| 0.19773377 | 1.1482 | 0.161383 | 0.143543 | 1 | rs6419178 |
| 0.19773377 | 0.8709 | 0.838617 | 0.856457 | 3 | rs6419178 |

TABLE 4

Markers in perfect linkage disequilibrium ($r^2 = 1.0$) with rs2220427 in the CEU population in the International HapMap data set (Individuals of European descent). Also shown are correlation with samples from Yuroba (Nigeria), and Asia (China and Japan) - cohort description is further documented on (http colon-slash-slash www.hapmap.org).

| SNP | Allele | CEU_R2 | CEU_frq | YRI_R2 | YRI_frq | ASIA_R2 | ASIA_frq |
|---|---|---|---|---|---|---|---|
| rs17042059 | 1 | 1 | 0.117647 | 0.500382 | 0.117647 | 0.473183 | 0.30814 |
| rs4529121 | 1 | 1 | 0.116667 | 0.604601 | 0.1 | 0.539766 | 0.337079 |
| rs4543199 | 2 | 1 | 0.116667 | 0.502036 | 0.116667 | 0.539766 | 0.337079 |
| rs10019689 | 1 | 1 | 0.116667 | 0.128175 | 0.341667 | 0.664071 | 0.388889 |
| rs4626276 | 2 | 1 | 0.116667 | 0.603474 | 0.10084 | 0.537439 | 0.333333 |
| rs17042076 | 2 | 1 | 0.117647 | 0.128175 | 0.341667 | 0.664071 | 0.388889 |
| rs11098089 | 2 | 1 | 0.117647 | 0.549368 | 0.108333 | 0.539766 | 0.337079 |
| rs11930528 | 4 | 1 | 0.11017 | 0.120773 | 0.321429 | 0.662926 | 0.377907 |
| rs17042098 | 1 | 1 | 0.116667 | 0.669219 | 0.092437 | 0.64297 | 0.355556 |
| rs17042102 | 1 | 1 | 0.091743 | NA | NA | 0.580822 | 0.302632 |
| rs17042121 | 3 | 1 | 0.116667 | 0.736119 | 0.141667 | 0.639142 | 0.353933 |
| rs10516563 | 3 | 1 | 0.109244 | 0.846743 | 0.128205 | 0.636329 | 0.364706 |
| rs4605724 | 1 | 1 | 0.116667 | 0.748252 | 0.083333 | 0.645257 | 0.359551 |
| rs2350269 | 4 | 1 | 0.11017 | 0.495806 | 0.098214 | 0.628257 | 0.346154 |

TABLE 4-continued

Markers in perfect linkage disequilibrium ($r^2$ = 1.0) with rs2220427 in the CEU population in the International HapMap data set (Individuals of European descent). Also shown are correlation with samples from Yuroba (Nigeria), and Asia (China and Japan) - cohort description is further documented on (http colon-slash-slash www.hapmap.org).

| SNP | Allele | CEU_R2 | CEU_frq | YRI_R2 | YRI_frq | ASIA_R2 | ASIA_frq |
|---|---|---|---|---|---|---|---|
| rs6533527 | 1 | 1 | 0.116667 | 0.425151 | 0.133333 | 0.804123 | 0.421348 |
| rs17042144 | 2 | 1 | 0.119658 | 0.727891 | 0.077586 | NA | NA |
| rs1906618 | 2 | 1 | 0.115044 | NA | NA | NA | NA |
| rs1906617 | 2 | 1 | 0.116667 | 0.541206 | 0.183333 | 0.977348 | 0.454545 |
| rs12646447 | 2 | 1 | 0.119658 | 1 | 0.108333 | 1 | 0.444444 |
| rs12646754 | 4 | 1 | 0.119658 | 0.681842 | 0.11017 | 1 | 0.425 |
| rs2129981 | 1 | 1 | 0.116667 | 1 | 0.108333 | 1 | 0.444444 |
| rs12639654 | 4 | 1 | 0.116667 | 0.139505 | 0.016667 | 1 | 0.438202 |
| rs6817105 | 2 | 1 | 0.117647 | 0.27862 | 0.299145 | 1 | 0.440476 |
| rs17042171 | 1 | 1 | 0.109244 | 0.281063 | 0.302521 | 1 | 0.425287 |
| rs1906591 | 1 | 1 | 0.116667 | 1 | 0.108333 | 1 | 0.444444 |
| rs1906592 | 3 | 1 | 0.109244 | 0.283489 | 0.3 | 1 | 0.446429 |
| rs2200732 | 2 | 1 | 0.112069 | 0.272544 | 0.308334 | 1 | 0.449438 |
| rs2200733 | 4 | 1 | 0.116667 | 0.276161 | 0.301724 | 1 | 0.445783 |
| rs4611994 | 2 | 1 | 0.116667 | 0.272544 | 0.308334 | 1 | 0.449438 |
| rs4540107 | 1 | 1 | 0.116667 | 0.27862 | 0.305085 | 1 | 0.44382 |
| rs1906593 | 4 | 1 | 0.117647 | 0.285134 | 0.301724 | 1 | 0.438202 |
| rs1906596 | 2 | 1 | 0.121739 | 0.255864 | 0.330275 | 0.97478 | 0.448718 |

TABLE 5

A. SNP markers within LD Block C04 (Between 111,954,811 and 112,104,250 on C04; NCBI Build 35; SEQ ID NO: 50).

| Marker ID | Pos Build 35 | Pos in SEQ ID NO: 50 | Type | Strand |
|---|---|---|---|---|
| rs1448824 | 111954811 | 1 | A/G | – |
| rs1947189 | 111955221 | 411 | A/G | – |
| rs1947188 | 111955479 | 669 | C/G | – |
| rs1992927 | 111956353 | 1543 | C/T | – |
| rs1470619 | 111957122 | 2312 | A/G | – |
| rs1448823 | 111958486 | 3676 | A/G | – |
| rs4834327 | 111958676 | 3866 | A/T | + |
| rs1448822 | 111958702 | 3892 | C/T | – |
| rs2044674 | 111959075 | 4265 | A/G | – |
| rs28445748 | 111959470 | 4660 | A/T | + |
| rs2595116 | 111959591 | 4781 | C/T | – |
| rs2595115 | 111959725 | 4915 | A/C | – |
| rs13120244 | 111961948 | 7138 | A/G | + |
| rs2723296 | 111962087 | 7277 | A/G | + |
| rs2723297 | 111962201 | 7391 | A/T | + |
| rs10021211 | 111962246 | 7436 | C/T | + |
| rs17042011 | 111962331 | 7521 | C/T | + |
| rs2595114 | 111962791 | 7981 | C/G | – |
| rs2595113 | 111962792 | 7982 | C/G | – |
| rs2595112 | 111963368 | 8558 | C/G | – |
| rs6831623 | 111964677 | 9867 | C/T | + |
| rs6854883 | 111964919 | 10109 | C/T | + |
| rs2255793 | 111965457 | 10647 | A/G | + |
| rs2723298 | 111966089 | 11279 | C/T | + |
| rs12505886 | 111966218 | 11408 | A/T | + |
| rs28718263 | 111966220 | 11410 | A/T | + |
| rs12501913 | 111966355 | 11545 | A/C | + |
| rs13126974 | 111966385 | 11575 | A/T | + |
| rs36194761 | 111966385 | 11575 | A/T | + |
| rs28473341 | 111966486 | 11676 | C/T | + |
| rs36160675 | 111967780 | 12970 | G/T | + |
| rs13147139 | 111968764 | 13954 | A/G | + |
| rs13147489 | 111968795 | 13985 | C/T | + |
| rs13147299 | 111968812 | 14002 | A/C | + |
| rs13147726 | 111968923 | 14113 | C/T | + |
| rs13147730 | 111968926 | 14116 | C/T | + |
| rs13147552 | 111968949 | 14139 | A/G | + |
| rs13123918 | 111968996 | 14186 | A/T | + |
| rs35610510 | 111970561 | 15751 | C/T | + |
| rs36162200 | 111971480 | 16670 | G/T | + |
| rs11098086 | 111971997 | 17187 | C/T | + |
| rs4034950 | 111972120 | 17310 | A/G | – |
| rs11724067 | 111972144 | 17334 | A/G | + |

TABLE 5-continued

A. SNP markers within LD Block C04 (Between 111,954,811 and 112,104,250 on C04; NCBI Build 35; SEQ ID NO: 50).

| Marker ID | Pos Build 35 | Pos in SEQ ID NO: 50 | Type | Strand |
|---|---|---|---|---|
| rs2723299 | 111972436 | 17626 | A/G | + |
| rs2723300 | 111972512 | 17702 | A/G | + |
| rs13138211 | 111972606 | 17796 | A/G | + |
| rs2595075 | 111973312 | 18502 | C/T | – |
| rs2723301 | 111973731 | 18921 | C/G | + |
| rs2595074 | 111974709 | 19899 | A/T | – |
| rs2723302 | 111974736 | 19926 | C/G | + |
| rs2723303 | 111974741 | 19931 | A/G | + |
| rs2218698 | 111975356 | 20546 | G/T | – |
| rs2218697 | 111975357 | 20547 | C/T | – |
| rs2595073 | 111975436 | 20626 | A/G | – |
| rs2723307 | 111975800 | 20990 | A/T | + |
| rs1584430 | 111976043 | 21233 | C/G | – |
| rs1584429 | 111976151 | 21341 | C/G | – |
| rs1900828 | 111976526 | 21716 | C/T | – |
| rs7672226 | 111976785 | 21975 | C/T | + |
| rs1839189 | 111976971 | 22161 | C/T | – |
| rs1579946 | 111977724 | 22914 | A/G | – |
| rs12509115 | 111977892 | 23082 | A/G | + |
| rs1579945 | 111978096 | 23286 | A/T | – |
| rs7661383 | 111979181 | 24371 | A/C | + |
| rs2122078 | 111979201 | 24391 | A/G | – |
| rs2122077 | 111979254 | 24444 | C/T | – |
| rs2723311 | 111979626 | 24816 | A/G | + |
| rs7667461 | 111979738 | 24928 | A/G | + |
| rs1448799 | 111980386 | 25576 | C/T | – |
| rs1448798 | 111980789 | 25979 | C/T | – |
| rs12650829 | 111980880 | 26070 | A/G | + |
| rs2723312 | 111980956 | 26146 | A/G | + |
| rs1900827 | 111981343 | 26533 | A/G | – |
| rs6815628 | 111981980 | 27170 | C/T | + |
| rs6838131 | 111981993 | 27183 | A/G | + |
| rs6838139 | 111982000 | 27190 | A/C | + |
| rs6838295 | 111982012 | 27202 | C/T | + |
| rs4582211 | 111982043 | 27233 | A/G | + |
| rs4353966 | 111982088 | 27278 | A/T | + |
| rs6838536 | 111982144 | 27334 | C/T | + |
| rs1375302 | 111983068 | 28258 | C/T | + |
| rs1375303 | 111983069 | 28259 | A/G | + |
| rs7699114 | 111983094 | 28284 | C/T | + |
| rs2197814 | 111983098 | 28288 | A/C | + |
| rs2218700 | 111983340 | 28530 | A/G | + |
| rs969642 | 111983529 | 28719 | C/T | + |

TABLE 5-continued

A. SNP markers within LD Block C04 (Between 111,954,811 and 112,104,250 on C04; NCBI Build 35; SEQ ID NO: 50).

| Marker ID | Pos Build 35 | Pos in SEQ ID NO: 50 | Type | Strand |
|---|---|---|---|---|
| rs17042020 | 111984067 | 29257 | A/C | + |
| rs2595099 | 111984371 | 29561 | A/C | + |
| rs4371683 | 111984371 | 29561 | A/C | + |
| rs2595093 | 111984960 | 30150 | C/T | − |
| rs17625509 | 111984998 | 30188 | A/G | + |
| rs2723313 | 111985093 | 30283 | A/G | + |
| rs2723314 | 111985111 | 30301 | G/T | + |
| rs2595092 | 111985112 | 30302 | A/G | − |
| rs2595091 | 111985223 | 30413 | C/G | − |
| rs1375301 | 111985458 | 30648 | A/G | − |
| rs2245595 | 111985715 | 30905 | C/T | + |
| rs2595088 | 111985958 | 31148 | C/T | − |
| rs981150 | 111986232 | 31422 | C/T | − |
| rs16997168 | 111986643 | 31833 | C/T | + |
| rs6812840 | 111986654 | 31844 | A/T | + |
| rs16997169 | 111986685 | 31875 | C/T | + |
| rs4527540 | 111986742 | 31932 | C/T | + |
| rs2595078 | 111987397 | 32587 | A/G | + |
| rs11098087 | 111987538 | 32728 | C/T | + |
| rs6843456 | 111988165 | 33355 | C/T | + |
| rs998101 | 111988219 | 33409 | A/G | − |
| rs13120535 | 111989691 | 34881 | A/G | + |
| rs17042026 | 111989978 | 35168 | A/G | + |
| rs6840960 | 111991045 | 36235 | C/T | + |
| rs2122079 | 111991108 | 36298 | C/T | + |
| rs2166961 | 111991365 | 36555 | C/T | + |
| rs2723316 | 111991891 | 37081 | C/T | + |
| rs2595079 | 111992019 | 37209 | A/G | + |
| rs7665126 | 111992019 | 37209 | A/G | + |
| rs2595080 | 111992042 | 37232 | A/G | + |
| rs12646859 | 111992237 | 37427 | G/T | + |
| rs10222783 | 111992430 | 37620 | C/T | + |
| rs12498380 | 111992563 | 37753 | C/T | + |
| rs2595081 | 111992761 | 37951 | C/T | + |
| rs2595082 | 111992896 | 38086 | G/T | + |
| rs2723317 | 111993104 | 38294 | A/G | + |
| rs6419178 | 111993104 | 38294 | A/G | + |
| rs13110876 | 111993625 | 38815 | A/G | + |
| rs2595083 | 111993625 | 38815 | A/G | + |
| rs7690164 | 111994069 | 39259 | C/T | + |
| rs2595084 | 111994163 | 39353 | A/G | + |
| rs2595085 | 111994377 | 39567 | C/G | + |
| rs2595086 | 111994385 | 39575 | C/T | + |
| rs2723318 | 111994576 | 39766 | G/T | + |
| rs17042050 | 111994805 | 39995 | C/T | + |
| rs9998222 | 111995088 | 40278 | A/G | + |
| rs2723319 | 111995233 | 40423 | A/T | + |
| rs2595087 | 111995380 | 40570 | C/T | + |
| rs17042052 | 111995521 | 40711 | A/T | + |
| rs28558677 | 111995664 | 40854 | G/T | + |
| rs6812731 | 111995691 | 40881 | A/C | + |
| rs2723320 | 111997050 | 42240 | C/T | + |
| rs12644107 | 111997588 | 42778 | C/T | + |
| rs28482179 | 111998237 | 43427 | C/T | + |
| rs28759131 | 111998559 | 43749 | C/T | + |
| rs1448817 | 111998657 | 43847 | A/G | + |
| rs28526075 | 111998725 | 43915 | A/G | + |
| rs17042059 | 111998790 | 43980 | A/G | + |
| rs10014075 | 112000023 | 45213 | G/T | + |
| rs10026140 | 112000455 | 45645 | G/T | + |
| rs13351232 | 112000455 | 45645 | G/T | + |
| rs7666806 | 112000477 | 45667 | G/T | + |
| rs10028327 | 112000489 | 45679 | G/T | + |
| rs12650941 | 112002415 | 47605 | A/T | + |
| rs28650220 | 112002617 | 47807 | C/T | + |
| rs13113361 | 112002671 | 47861 | G/T | + |
| rs13113522 | 112002686 | 47876 | G/T | + |
| rs4529121 | 112003159 | 48349 | A/G | + |
| rs6831284 | 112003582 | 48772 | G/T | + |
| rs10009621 | 112003846 | 49036 | C/T | + |
| rs10021534 | 112003945 | 49135 | C/T | + |
| rs10032150 | 112004222 | 49412 | A/G | + |
| rs10024267 | 112004571 | 49761 | C/T | + |
| rs10012705 | 112004726 | 49916 | C/T | + |
| rs11943627 | 112005073 | 50263 | C/T | + |
| rs4543199 | 112005744 | 50934 | C/T | + |
| rs28410055 | 112006340 | 51530 | A/G | + |
| rs7693227 | 112006532 | 51722 | C/T | + |
| rs6852197 | 112006679 | 51869 | A/G | + |
| rs12647316 | 112006855 | 52045 | C/T | + |
| rs12647393 | 112006886 | 52076 | G/T | + |
| rs10019645 | 112007248 | 52438 | G/T | + |
| rs10019689 | 112007473 | 52663 | A/C | + |
| rs4626276 | 112007593 | 52783 | A/C | + |
| rs10022067 | 112007672 | 52862 | C/T | + |
| rs4469143 | 112007678 | 52868 | C/G | + |
| rs6836206 | 112007902 | 53092 | C/T | + |
| rs13150693 | 112008086 | 53276 | G/T | + |
| rs11737632 | 112008416 | 53606 | C/T | + |
| rs5011975 | 112008427 | 53617 | A/G | + |
| rs6811511 | 112008429 | 53619 | A/C | + |
| rs4383676 | 112008437 | 53627 | A/G | + |
| rs28392642 | 112009161 | 54351 | C/T | + |
| rs17631468 | 112009386 | 54576 | A/G | + |
| rs17042076 | 112009942 | 55132 | C/T | + |
| rs4434326 | 112010480 | 55670 | C/T | + |
| rs17042081 | 112010815 | 56005 | G/T | + |
| rs4833436 | 112011350 | 56540 | C/T | + |
| rs7679623 | 112011519 | 56709 | A/C | + |
| rs11098088 | 112011728 | 56918 | C/T | + |
| rs4530699 | 112011761 | 56951 | A/T | + |
| rs11098089 | 112011830 | 57020 | A/C | + |
| rs17042088 | 112012418 | 57608 | C/T | + |
| rs12648785 | 112013496 | 58686 | A/G | + |
| rs12639820 | 112013644 | 58834 | C/T | + |
| rs10001807 | 112013708 | 58898 | A/G | + |
| rs10024486 | 112013722 | 58912 | G/T | + |
| rs12648889 | 112013890 | 59080 | C/G | + |
| rs28376747 | 112013925 | 59115 | A/G | + |
| rs11098090 | 112014012 | 59202 | C/T | + |
| rs11944778 | 112014571 | 59761 | A/G | + |
| rs7436333 | 112014951 | 60141 | A/C | + |
| rs4307025 | 112015107 | 60297 | A/T | + |
| rs4447925 | 112015252 | 60442 | C/T | + |
| rs28523292 | 112015772 | 60962 | C/T | + |
| rs28635581 | 112015858 | 61048 | C/T | + |
| rs28508237 | 112016004 | 61194 | C/T | + |
| rs28521134 | 112016167 | 61357 | C/T | + |
| rs17042093 | 112017716 | 62906 | C/G | + |
| rs11930438 | 112017749 | 62939 | C/T | + |
| rs28542185 | 112017795 | 62985 | C/T | + |
| rs11930528 | 112017798 | 62988 | G/T | + |
| rs13121382 | 112020177 | 65367 | G/T | + |
| rs7439625 | 112021082 | 66272 | A/T | + |
| rs28501998 | 112021318 | 66508 | A/T | + |
| rs10016838 | 112021718 | 66908 | C/T | + |
| rs17042098 | 112021762 | 66952 | A/G | + |
| rs10005076 | 112021953 | 67143 | C/T | + |
| rs10027473 | 112022056 | 67246 | A/G | + |
| rs2634073 | 112023387 | 68577 | A/G | − |
| rs1906611 | 112023520 | 68710 | A/G | − |
| rs1906610 | 112023521 | 68711 | C/T | − |
| rs28446238 | 112024025 | 69215 | A/C | + |
| rs1906609 | 112024055 | 69245 | A/C | − |
| rs34916665 | 112025294 | 70484 | G/T | + |
| rs17042102 | 112026230 | 71420 | A/G | + |
| rs17042104 | 112026555 | 71745 | C/T | + |
| rs10015819 | 112026628 | 71818 | C/T | + |
| rs2634071 | 112026824 | 72014 | A/G | − |
| rs10007386 | 112028021 | 73211 | C/T | + |
| rs10007547 | 112028050 | 73240 | A/G | + |
| rs12647522 | 112028465 | 73655 | C/T | + |
| rs1906614 | 112028900 | 74090 | A/G | − |
| rs2723335 | 112029230 | 74420 | A/G | + |

TABLE 5-continued

| A. SNP markers within LD Block C04 (Between 111,954,811 and 112,104,250 on C04; NCBI Build 35; SEQ ID NO: 50). | | | | |
|---|---|---|---|---|
| Marker ID | Pos Build 35 | Pos in SEQ ID NO: 50 | Type | Strand |
| rs17042112 | 112029281 | 74471 | C/T | + |
| rs17042115 | 112029414 | 74604 | A/G | + |
| rs10013510 | 112029527 | 74717 | C/G | + |
| rs11939057 | 112029755 | 74945 | C/T | + |
| rs2634076 | 112029877 | 75067 | A/G | − |
| rs2723293 | 112031377 | 76567 | A/G | + |
| rs28494131 | 112032777 | 77967 | C/T | + |
| rs2634075 | 112033582 | 78772 | A/G | − |
| rs13121715 | 112034239 | 79429 | G/T | + |
| rs2634074 | 112034645 | 79835 | A/T | − |
| rs17042121 | 112034705 | 79895 | A/G | + |
| rs10516563 | 112035326 | 80516 | G/T | + |
| rs17042125 | 112035883 | 81073 | A/G | + |
| rs13136439 | 112036254 | 81444 | G/T | + |
| rs13114686 | 112036503 | 81693 | C/T | + |
| rs36166388 | 112037782 | 82972 | A/G | + |
| rs2450934 | 112038532 | 83722 | A/C | − |
| rs36138049 | 112040474 | 85664 | A/C | + |
| rs36168695 | 112040495 | 85685 | A/G | + |
| rs36129850 | 112040548 | 85738 | A/G | + |
| rs12513264 | 112041966 | 87156 | C/T | + |
| rs2882365 | 112041975 | 87165 | A/G | + |
| rs36139649 | 112042072 | 87262 | C/T | + |
| rs4033107 | 112042072 | 87262 | C/T | + |
| rs36176419 | 112042092 | 87282 | A/G | + |
| rs4033108 | 112042092 | 87282 | A/G | + |
| rs4450997 | 112042160 | 87350 | A/C | + |
| rs2350268 | 112042213 | 87403 | A/G | + |
| rs4613627 | 112042225 | 87415 | A/C | + |
| rs4033109 | 112042227 | 87417 | C/T | + |
| rs4833443 | 112042247 | 87437 | C/T | + |
| rs2723336 | 112042258 | 87448 | C/T | − |
| rs4033111 | 112042302 | 87492 | A/G | + |
| rs1807360 | 112042333 | 87523 | C/T | − |
| rs4605724 | 112042685 | 87875 | A/C | + |
| rs6856879 | 112043066 | 88256 | A/T | + |
| rs6834418 | 112043172 | 88362 | C/T | + |
| rs2466455 | 112043219 | 88409 | A/G | − |
| rs6857810 | 112043220 | 88410 | A/G | + |
| rs2634079 | 112043541 | 88731 | C/G | − |
| rs28366840 | 112043710 | 88900 | A/T | + |
| rs2350269 | 112044728 | 89918 | C/T | + |
| rs7665409 | 112045070 | 90260 | C/T | + |
| rs6533527 | 112045118 | 90308 | A/C | + |
| rs12649717 | 112045283 | 90473 | A/C | + |
| rs6822831 | 112045374 | 90564 | A/G | + |
| rs35916701 | 112046074 | 91264 | C/T | + |
| rs6829419 | 112046178 | 91368 | C/T | + |
| rs2723334 | 112046356 | 91546 | A/G | − |
| rs2634078 | 112046528 | 91718 | C/T | − |
| rs12512819 | 112046597 | 91787 | C/T | + |
| rs17042144 | 112047270 | 92460 | C/T | + |
| rs2171594 | 112047908 | 93098 | A/G | − |
| rs6842887 | 112048170 | 93360 | A/G | + |
| rs2171593 | 112048375 | 93565 | G/T | − |
| rs7690874 | 112048681 | 93871 | A/G | + |
| rs17042145 | 112049101 | 94291 | G/T | + |
| rs17042146 | 112049106 | 94296 | C/T | + |
| rs9998815 | 112049904 | 95094 | C/G | + |
| rs7683336 | 112051207 | 96397 | C/T | + |
| rs17042150 | 112051452 | 96642 | A/T | + |
| rs10016842 | 112051810 | 97000 | C/T | + |
| rs10005432 | 112052219 | 97409 | A/G | + |
| rs1906620 | 112052624 | 97814 | C/T | − |
| rs1906619 | 112052670 | 97860 | C/T | − |
| rs1906618 | 112053026 | 98216 | C/T | − |
| rs1906617 | 112053418 | 98608 | C/T | − |
| rs6847935 | 112054255 | 99445 | A/T | + |
| rs6831873 | 112055138 | 100328 | C/T | + |
| rs1906616 | 112055172 | 100362 | C/T | − |
| rs6837901 | 112055712 | 100902 | C/T | + |
| rs2723333 | 112056695 | 101885 | C/T | − |
| rs12646447 | 112056930 | 102120 | C/T | + |
| rs6820568 | 112057435 | 102625 | C/T | + |
| rs1906615 | 112059402 | 104592 | A/C | − |
| rs2634077 | 112061112 | 106302 | A/G | − |
| rs7689774 | 112061114 | 106304 | G/T | + |
| rs12646754 | 112061176 | 106366 | C/T | + |
| rs35807830 | 112061497 | 106687 | G/T | + |
| rs2129983 | 112061684 | 106874 | C/T | − |
| rs2129982 | 112061747 | 106937 | C/T | − |
| rs2129981 | 112061803 | 106993 | A/C | − |
| rs6854111 | 112062140 | 107330 | A/T | + |
| rs12639654 | 112062899 | 108089 | C/T | + |
| rs4515229 | 112062985 | 108175 | A/G | + |
| rs2129984 | 112063010 | 108200 | C/T | + |
| rs6817105 | 112063372 | 108562 | C/T | + |
| rs12503217 | 112063765 | 108955 | C/T | + |
| rs2634070 | 112064016 | 109206 | A/C | + |
| rs17042171 | 112065891 | 111081 | A/C | + |
| rs7434417 | 112066042 | 111232 | A/G | + |
| rs1906591 | 112066493 | 111683 | A/G | + |
| rs1906592 | 112066608 | 111798 | G/T | + |
| rs12510087 | 112066632 | 111822 | A/G | + |
| rs7661554 | 112067221 | 112411 | A/G | + |
| rs34796144 | 112067333 | 112523 | A/C | + |
| rs2200732 | 112067646 | 112836 | C/T | + |
| rs2200733 | 112067773 | 112963 | C/T | + |
| rs17042175 | 112068571 | 113761 | A/T | + |
| rs4611994 | 112068645 | 113835 | C/T | + |
| rs4540107 | 112068706 | 113896 | A/C | + |
| rs1906593 | 112069526 | 114716 | C/T | + |
| rs4371684 | 112069651 | 114841 | A/G | + |
| rs1906594 | 112069739 | 114929 | A/G | + |
| rs1906595 | 112069788 | 114978 | G/T | + |
| rs1906596 | 112069840 | 115030 | C/T | + |
| rs6838775 | 112069908 | 115098 | G/T | + |
| rs2129977 | 112070036 | 115226 | A/G | + |
| rs2129978 | 112070158 | 115348 | A/C | + |
| rs1906597 | 112070190 | 115380 | G/T | + |
| rs1906598 | 112070229 | 115419 | C/T | + |
| rs1906599 | 112070290 | 115480 | C/T | + |
| rs1906600 | 112070480 | 115670 | C/T | + |
| rs1906601 | 112070883 | 116073 | C/T | + |
| rs1906602 | 112070927 | 116117 | C/T | + |
| rs1906603 | 112071040 | 116230 | C/T | + |
| rs28645285 | 112071426 | 116616 | A/G | + |
| rs2171590 | 112071435 | 116625 | C/T | + |
| rs6852357 | 112071939 | 117129 | C/T | + |
| rs13143308 | 112072023 | 117213 | G/T | + |
| rs2220427 | 112072493 | 117683 | C/T | + |
| rs17632693 | 112072538 | 117728 | C/T | + |
| rs11935917 | 112072850 | 118040 | A/G | + |
| rs4833456 | 112073911 | 119101 | C/T | + |
| rs12644625 | 112074117 | 119307 | C/T | + |
| rs4400058 | 112074277 | 119467 | A/G | + |
| rs1906604 | 112074452 | 119642 | A/G | + |
| rs1906605 | 112074796 | 119986 | C/T | + |
| rs13126975 | 112075129 | 120319 | A/T | + |
| rs6837490 | 112075447 | 120637 | C/T | + |
| rs6843082 | 112075671 | 120861 | A/G | + |
| rs13105878 | 112075751 | 120941 | A/C | + |
| rs6533528 | 112076843 | 122033 | A/G | + |
| rs7692272 | 112076857 | 122047 | G/T | + |
| rs2171591 | 112077012 | 122202 | A/G | + |
| rs17042195 | 112077142 | 122332 | C/G | + |
| rs11931959 | 112077289 | 122479 | A/G | + |
| rs17042198 | 112077582 | 122772 | G/T | + |
| rs10033464 | 112078365 | 123555 | G/T | + |
| rs2171592 | 112078392 | 123582 | C/T | + |
| rs13121924 | 112078423 | 123613 | A/G | + |
| rs2129979 | 112078601 | 123791 | G/T | + |
| rs2350539 | 112078814 | 124004 | G/T | + |
| rs1906606 | 112080996 | 126186 | A/C | + |

TABLE 5-continued

A. SNP markers within LD Block C04 (Between 111,954,811 and 112,104,250 on C04; NCBI Build 35; SEQ ID NO: 50).

| Marker ID | Pos Build 35 | Pos in SEQ ID NO: 50 | Type | Strand |
|---|---|---|---|---|
| rs7672570 | 112081189 | 126379 | C/T | + |
| rs4834418 | 112081408 | 126598 | A/G | + |
| rs723364 | 112082075 | 127265 | C/G | − |
| rs723363 | 112082105 | 127295 | A/G | − |
| rs7697491 | 112083422 | 128612 | A/T | + |
| rs13125644 | 112083505 | 128695 | A/G | + |
| rs2350294 | 112084449 | 129639 | A/G | − |
| rs2350293 | 112084451 | 129641 | A/G | − |
| rs3855819 | 112084767 | 129957 | C/G | − |
| rs2220428 | 112085064 | 130254 | A/G | + |
| rs2220429 | 112085089 | 130279 | A/C | + |
| rs11727566 | 112085934 | 131124 | A/T | + |
| rs13141190 | 112086218 | 131408 | A/G | + |
| rs4032976 | 112086371 | 131561 | A/G | − |
| rs3866829 | 112086379 | 131569 | A/C | − |
| rs7671348 | 112086408 | 131598 | A/G | + |
| rs3866830 | 112086598 | 131788 | C/G | − |
| rs6811267 | 112086942 | 132132 | C/T | + |
| rs3853440 | 112087213 | 132403 | C/T | − |
| rs3853441 | 112087344 | 132534 | A/G | − |
| rs3853442 | 112087632 | 132822 | C/T | − |
| rs3853443 | 112087733 | 132923 | A/G | − |
| rs4124158 | 112087798 | 132988 | C/T | + |
| rs4124159 | 112087847 | 133037 | A/G | + |
| rs12506083 | 112088016 | 133206 | A/C | + |
| rs34809282 | 112088051 | 133241 | A/G | + |
| rs7683219 | 112088051 | 133241 | A/G | + |
| rs7683618 | 112088259 | 133449 | A/C | + |
| rs7683625 | 112088269 | 133459 | A/G | + |
| rs7662050 | 112088325 | 133515 | C/T | + |
| rs36183416 | 112088804 | 133994 | C/T | + |
| rs4447926 | 112088804 | 133994 | C/T | + |
| rs4594787 | 112088813 | 134003 | A/G | + |
| rs10390275 | 112089009 | 134199 | A/T | + |
| rs36179422 | 112089009 | 134199 | A/T | + |
| rs10006659 | 112089030 | 134220 | G/T | + |
| rs36181695 | 112089078 | 134268 | A/G | + |
| rs7440730 | 112089078 | 134268 | A/G | + |
| rs10006881 | 112089277 | 134467 | C/T | + |
| rs36149087 | 112089277 | 134467 | C/T | + |
| rs6533530 | 112089540 | 134730 | C/T | + |
| rs6533531 | 112089569 | 134759 | G/T | + |
| rs3866831 | 112089718 | 134908 | C/T | − |
| rs4269241 | 112089833 | 135023 | A/G | + |
| rs4032975 | 112089842 | 135032 | A/C | − |
| rs4032974 | 112090140 | 135330 | A/G | − |
| rs4124160 | 112090452 | 135642 | A/G | + |
| rs3866832 | 112091304 | 136494 | C/G | − |
| rs3853444 | 112091740 | 136930 | A/G | − |
| rs7662345 | 112091766 | 136956 | A/G | + |
| rs2350545 | 112092258 | 137448 | C/T | − |
| rs17042215 | 112092562 | 137752 | C/T | + |
| rs2003121 | 112093023 | 138213 | C/T | + |
| rs880309 | 112093143 | 138333 | A/G | + |
| rs9991046 | 112093346 | 138536 | G/T | + |
| rs17042216 | 112094463 | 139653 | C/T | + |
| rs17570669 | 112094486 | 139676 | A/T | + |
| rs17042218 | 112094520 | 139710 | A/G | + |
| rs17042223 | 112094922 | 140112 | C/T | + |
| rs3866833 | 112095138 | 140328 | C/T | − |
| rs17042224 | 112096509 | 141699 | G/T | + |
| rs13130446 | 112096760 | 141950 | C/T | + |
| rs10516564 | 112096896 | 142086 | A/G | + |
| rs7686320 | 112097215 | 142405 | A/T | + |
| rs7686499 | 112097282 | 142472 | C/T | + |
| rs17042230 | 112097319 | 142509 | C/T | + |
| rs4124161 | 112097459 | 142649 | C/T | + |
| rs4576077 | 112098061 | 143251 | C/T | + |
| rs4260600 | 112098098 | 143288 | C/T | + |
| rs12644093 | 112098445 | 143635 | A/G | + |
| rs4124162 | 112098593 | 143783 | A/G | + |
| rs7674295 | 112099042 | 144232 | A/G | + |
| rs11938968 | 112100356 | 145546 | A/G | + |
| rs28601812 | 112101457 | 146647 | A/C | + |
| rs4032983 | 112101551 | 146741 | G/T | + |
| rs3866834 | 112101617 | 146807 | A/G | + |
| rs6852021 | 112101716 | 146906 | A/G | + |
| rs28580491 | 112102583 | 147773 | C/T | + |
| rs13110989 | 112102671 | 147861 | G/T | + |
| rs3866835 | 112102983 | 148173 | C/T | − |
| rs4124163 | 112103203 | 148393 | A/G | + |
| rs3866836 | 112103244 | 148434 | A/G | + |
| rs17042238 | 112103458 | 148648 | A/G | + |
| rs4124164 | 112104250 | 149440 | C/T | + |

B. Microsatellite markers within LD Block C04 (Between 111, 954, 811 and 112, 104, 250 on C04; NCBI Build 35; SEQ ID NO: 50).

| Marker | Start position | End position | Forward primer | Reverse Primer |
|---|---|---|---|---|
| D4S193 | 112062811 | 112062911 | ACAACCCCATTTGTGAAGAC (SEQ ID NO: 52) | TTTATAGAAAATTTAGCATGGA (SEQ ID NO: 53) |
| D4S2940 | 112070055 | 112070267 | CTAAGTTGTGCAGCCATGAA (SEQ ID NO: 54) | TGGAACCACTTTTGCAGTAA (SEQ ID NO: 55) |
| D4S406 | 112076047 | 112076292 | CTGGTTTTAAGGCATGTTTG (SEQ ID NO: 56) | TCCTCAGGGAGGTCTAATCA (SEQ ID NO: 57) |

TABLE 6

Key to sequences presented in sequence listing.

| SEQ ID NO | Marker ID |
|---|---|
| 1 | rs2220427 |
| 2 | rs17042059 |
| 3 | rs4529121 |
| 4 | rs4543199 |
| 5 | rs10019689 |
| 6 | rs4626276 |
| 7 | rs17042076 |
| 8 | rs11098089 |
| 9 | rs11930528 |
| 10 | rs17042098 |
| 11 | rs17042102 |
| 12 | rs17042121 |
| 13 | rs10516563 |
| 14 | rs4605724 |
| 15 | rs2350269 |
| 16 | rs6533527 |
| 17 | rs17042144 |
| 18 | rs1906618 |
| 19 | rs1906617 |
| 20 | rs12646447 |
| 21 | rs12646754 |
| 22 | rs2129981 |
| 23 | rs12639654 |
| 24 | rs6817105 |
| 25 | rs17042171 |
| 26 | rs1906591 |
| 27 | rs2200732 |
| 28 | rs2200733 |
| 29 | rs4611994 |
| 30 | rs4540107 |
| 31 | rs1906593 |
| 32 | rs1906596 |
| 33 | rs2634073 |
| 34 | rs1906592 |
| 35 | rs2723296 |
| 36 | rs16997168 |
| 37 | rs2723316 |
| 38 | rs6419178 |
| 39 | rs1448817 |
| 40 | rs13105878 |
| 41 | rs10033464 |
| 42 | rs13141190 |
| 43 | rs3853444 |
| 44 | rs4576077 |
| 45 | D4S406 |
| 46 | rs7668322 |
| 47 | rs2197815 |
| 48 | rs6831623 |
| 49 | rs2595110 |
| 50 | LD Block C04 |
| 51 | rs13143308 |

Example 2

Characterization of AF Risk Variants

The following contains further description of the identification of variants conferring risk for atrial fibrillation on chromosome 4q25

Figure 2:
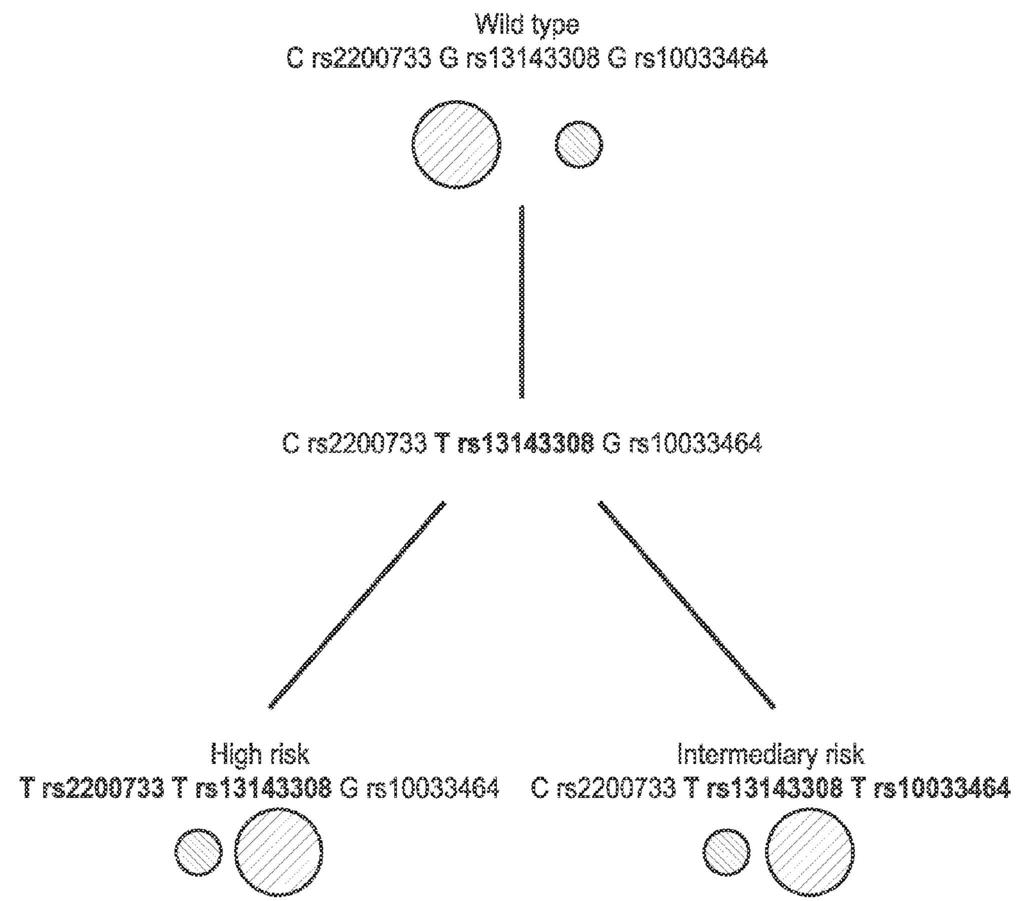
FIG. 2 Shows a schematic of the haplotype structure at the associated region within the LD block. The areas of the dark (left) circles are proportional to the haplotype frequencies of the haplotypes in Iceland and the areas of the light (right) circles are proportional to the haplotype frequencies in Hong Kong. The intermediary haplotype, shown in the middle of the graph, no longer exists with certainty in either of the two populations (its estimated frequency is less than 0.2% which is indistinguishable from genotyping errors).
Figure 4:
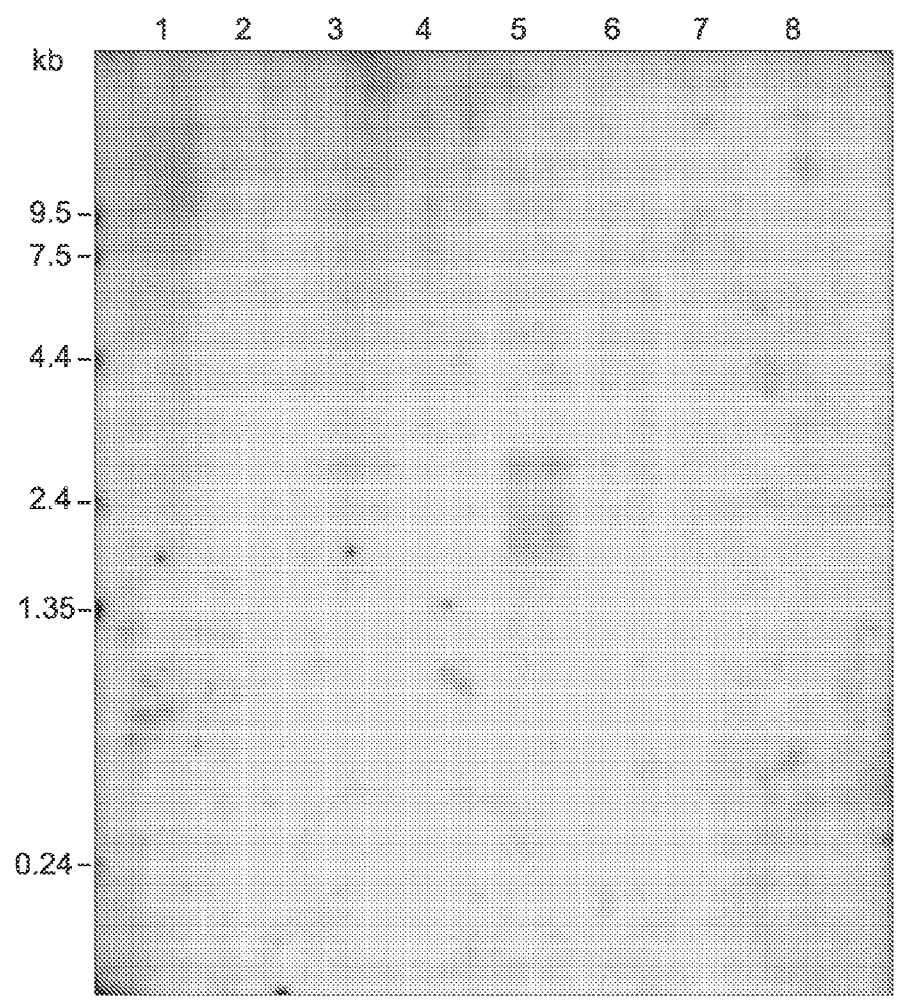
FIG. 4. Shows Northern Blot analysis of PITX2 expression in human heart and aorta.

Atrial fibrillation (AF) is the most common sustained cardiac arrhythmia in man and is characterized by chaotic electrical activity of the atria[1]. It affects one in ten individuals over eighty, causes significant morbidity, and is an independent predictor of mortality[2]. Recent studies have provided evidence of a genetic contribution to AF[3-5]. Mutations in potassium channel genes have been associated with familial AF[6-10] but account for only a small fraction of all AF cases[11,12]. We performed a genome-wide association scan, followed by replication studies in three populations of European descent and a Chinese population from Hong Kong and find a strong association between two sequence variants on chromosome 4q25 to AF. Approximately 35% of individuals of European descent have at least one of the variants and the risk of AF increases by 1.72 and 1.39 per copy. The association to the stronger variant was replicated in the Chinese population, where it is carried by 75% of individuals and risk of AF is increased by 1.42 per copy. A stronger association was observed in individuals with typical atrial flutter (AFl). Both variants are adjacent to PITX2, which is known to play a critical role in left-right asymmetry of the heart[13-15]. We conducted a genome-wide association study using the Illumina Hap300 BeadChip on an Icelandic population with AF and/or AFl. 316,515 SNPs satisfying our quality criteria were tested individually for association to AF/AFl in a sample of 550 patients and 4,476 controls from Iceland. Three strongly correlated SNPs, all located within a single linkage disequilibrium (LD) block on chromosome 4q25, were the only SNPs found to be genome-wide significant after accounting for the 316,515 SNPs tested ($P<0.05/316,515=1.58\times10^{-7}$): rs2200733 (OR=1.75; $P=1.6\times10^{-10}$), rs2220427 (OR=1.75; $P=1.9\times10^{-10}$) and rs2634073 (OR=1.60; $P=2.1\times10^{-9}$). These results and all other results based on the Icelandic population were adjusted for the relatedness of individuals. The two most significant SNPs, rs2200733 and rs2220427, are perfect proxies for one another in the CEPH CEU HapMap[16] dataset and are close to being perfect proxies for one another in the Icelandic dataset (D'=1, $r^2=0.999$), therefore, only rs2200733 will be referred to in the following discussion. The correlation of rs2634073 to rs2200733 is weaker in the Icelandic dataset (D'=0.95, $r^2=0.605$). Upon further study of the Illumina Hap300 SNPs in the vicinity of the first three SNPs and conditioning on the association to rs2200733, an association to a new SNP, rs10033464, was identified (OR=1.42; P=0.0024). After accounting for the association to rs2200733 and rs10033464, the association to rs2634073 was no longer significant (P=0.30). Henceforth, all association results for rs2200733 T and rs10033464 T, including those presented in Table 7, are based on comparison to the wild type haplotype which carries neither of the two at risk alleles, rather than comparison to the major alleles of each SNP separately. Specifically, odds-ratios for rs2200733 T and rs10033464 T are each computed conditionally and could be interpreted as the estimated relative risk of each variant compared to the wild-type. The at risk alleles T of rs2200733 and T of rs10033464 have estimated population allelic frequencies of 12.05% and 8.53% in Iceland, respectively, and are never observed together on the same chromosome, in the Icelandic dataset or in the CEU HapMap dataset. A third SNP, rs13143308, which has a minor allele that corresponds completely to chromosomes carrying either the T allele of rs2200733 or the T allele of rs10033464, was identified through the CEU HapMap dataset. FIG. 2 demonstrates the haplotype structure over the key SNPs of the associated region. Sets of SNPs, that are perfect proxies (i.e., perfect surrogates, r2=1.0 to the tagging SNP) of each of these three key SNPs in the CEU HapMap samples, are provided in Table 9 and relative locations displayed in FIG. 3. We emphasize that the SNPs named should be considered representatives of the haplotypes defined by the SNPs which they are equivalent to and are primarily chosen for the sake of convenience.

A microsatellite marker, D4S406, located in the same LD block as the two SNPs was identified. In Iceland, three of the four shortest alleles of D4S406 (−8, −4, and −2) combine to form a near perfect surrogate for the T allele of rs2200733 (D'=0.995, H=0.98) and the two shortest remaining alleles (−6 and 0) form a good surrogate of the T allele of rs10033464 (D'=0.98, $r^2=0.75$) (Table 10). None of the remaining (longer)

alleles of D4S406 are associated to AF/AFl after accounting for the effect of the short alleles. For the replication of the original observation in Iceland the D4S406 genotypes were used to provide information when SNP genotypes were not available.

In an attempt to replicate our original discovery we analyzed an additional Icelandic samples consisting of 2,251 AF/AFl patients and 13,238 controls (Table 7). The association of both SNPs to AF/AFl was replicated in these samples (OR=1.64, P=$2.7\times10^{-23}$ for rs2200733, OR=1.40, P=$8.2\times10^{-8}$ for rs10033464) and both achieve genome-wide significance in the combined Icelandic samples (OR=1.68, P=$1.9\times10^{-30}$ for rs2200733, OR=1.38, P=$9.4\times10^{-9}$ for rs10033464). We also typed all the 18 Hap300 Illumina SNPs in the region around our signal in 404 of the additional AF cases and 2,036 of the additional controls. None of these SNPs remained significant after accounting for the association to rs2200733 and rs10033464 (Table 11).

In further attempts to replicate our results, we tested these variants for an association to AF in two populations of European ancestry, one from Sweden, consisting of 143 cases and 738 controls, and the other from the United States (U.S.), consisting of 636 cases and 804 controls (Table 7). The association to rs2200733 was strongly replicated in both populations (OR=2.01, P=0.00027 in Sweden, OR=1.84, P=$9.8\times10^{-10}$ in the U.S.). The association to rs10033464 is weaker, but was nonetheless replicated in the Swedish population (OR=1.65, P=0.0087) and was nearly significant in the U.S. population (OR=1.30, P=0.052). When combined with the Icelandic samples, the association to rs2200733 was unequivocal (OR=1.72, P=$3.3\times10^{-41}$), and the significance of rs10033464 was well beyond the threshold of genome-wide significance (OR=1.39, P=$6.9\times10^{-11}$). Assuming the multiplicative model, the population attributable risk (PAR) of the two variants combined is approximately 20% in populations of European ancestry.

Finally, we attempted to replicate these signals in a Han Chinese population from Hong Kong consisting of 333 cases and 2,836 controls. The association to rs2200733 T was significantly replicated (OR=1.42, P=0.00064), but the association to rs10033464 T was not significant, although in the right direction (OR=1.08, P=0.55) (Table 7). Interestingly, the T allele of rs2200733 is much more frequent in the Chinese (allelic frequency in controls: 0.528) than in those of European descent (allelic frequency in controls: 0.098-0.139) (FIG. 2) which is reflected in a greater joint PAR of approximately 35%, even though the estimated risk is less. The LD block containing the two variants is more fragmented in the Chinese CHB and Japanese JPT HapMap samples than in the CEU HapMap samples (FIG. 3). We therefore analysed several markers in the Hong Kong population which were in perfect LD with rs2200733 in the CEU samples, but in imperfect LD in the CHB and JPT samples (Table 12). These markers had weaker apparent association to AF than rs2200733, suggesting that the functional variants driving the association is located in the approximately 20 kb region around the original rs2200733 variant and defined by the SNPs that remain equivalent to rs2200733 in the CHB and JPT samples (coloured red in FIG. 3).

For the initial Icelandic discovery samples, rs2200733 had a significantly higher OR than rs10033464 (P=0.041). This held true in the replication samples, and overall there is a significant difference in the risks associated with the two variants (P=0.00019 in the combined European samples and P=0.0099 in Hong Kong). When genotype-specific odds ratios were studied, some deviation away from the multiplicative model is detectable in the combined dataset (P=0.018 for European samples, see Table 13). Estimated risks of heterozygous carriers relative to non-carriers were similar, but homozygous carriers of rs2200733 T and rs10033464 T have estimated risks that were, respectively, higher and lower than that predicted by a multiplicative model. A similar trend was seen in the Hong Kong samples; although the sample size is too small to have power to detect such deviations with significance. In the combined populations of European descent the observed OR for individuals homozygous for rs2200733 T was 3.64 as compared to individuals homozygous for the wild type haplotype and 1.77 for the Chinese population demonstrating that these variants are important components in any predictive modeling of AF.

The age at diagnosis of AF/AFl for the Icelandic samples correlates with the two SNPs (diagnosis occurs 2.28 years earlier per T allele of rs2200733 and 1.10 years earlier per T allele of rs10033464, joint P=$1.29\times10^{-6}$). The effect of the age at diagnosis was also evaluated by measuring the strength of association while stratifying by age at diagnosis. The association of the two variants is strongest in those diagnosed at a younger age, although the risk remains significant even in those diagnosed after reaching 80 years of age (Table 8). Information on age at diagnosis of AF was not available for the Swedish samples. The U.S. samples were comprised of two main groups, younger patients with either lone AF or AF and hypertension (HTN), and older AF cases who are mostly hemorrhagic and ischemic stroke patients. In both populations there is a clear trend towards a stronger association in younger AF cases than in older cases. Our analysis of the data did not suggest any differential association by sex (Table 8).

AF1 often accompanies AF, but can occur in isolation[17]. Interestingly we observed a strong association between the variants and the small subset (N=116) of the AF1 Icelandic patients (OR=2.60, 95% confidence interval (CI)=1.83-3.68, P=$7.5\times10^{-8}$ for rs2200733, OR=1.94, 95% CI=1.26-3.00, P=0.0028 for rs10033464). Indeed, for rs2200733, the OR for these definite AFl cases is significantly higher than that for the cases with an AF phenotype (P=0.0026), and close to significantly higher for rs10033464 (P=0.084). Our results suggest that while these traits share genetic risk factors, AFl is less influenced by phenocopies than AF.

Neither variant showed a association to obesity, hypertension or myocardial infarction in the Icelandic samples, all known risk factors for AF (observed OR<1.1 in all instances, Table 14). Although these negative results do not exclude the possibility that the new variants associate with these phenotypes, they do suggest, along with the high risk in U.S. lone AF and earlier age at onset in carriers, that the new variants are not affecting risk of AF through these known risk factors.

There is no known gene present in the LD block containing rs2200733 and rs10033464 (FIG. 3). The LD block contains one spliced EST (DA725631) and two single-exon ESTs (DB324364 and AF017091). RT-PCR of cDNA libraries from various tissues did not detect the expression of these ESTs (Table 16). The PITX2 gene located in the adjacent upstream LD block is the gene closest to the risk variants. Several markers within the LD block containing the PITX2 gene are correlated to the markers showing association to AF and Afl, as shown in Table 18. The protein encoded by this gene, the paired-like homeodomain transcription factor 2, is an interesting candidate for AF/AFl as it is known to play an important role in cardiac development by directing asymmetric morphogenesis of the heart[13]. In a mouse knockout model Pitx2 was shown to suppress a default pathway for sinoatrial node formation in the left atrium[14,15]. There is very little mRNA expression of PITX2 in all easily accessible tissues, such as blood and adipose tissue, hampering the study of correlation between genotypes and expression levels. The next gene upstream of PITX2 is ENPEP, an aminopeptidase responsible for the breakdown of angiotensin II in the vascular endothelium[18]. This gene is expressed more widely, but the variants associated with AF showed no correlation to its expression in blood or adipose tissue. No other annotated genes are located within a 400 kb region upstream and 1.5 Mb regions downstream of the associated variants.

In summary, we have identified two variants on chromosome 4q25 that are strongly associated with AF in three distinct populations of European descent. The stronger variant also replicates well in a Chinese population where it is much more common and has higher PAR than in populations of European descent. This association is particularly compelling in younger patients and in those with lone AF, but is also present in older patients with more commonly encountered forms of AF. Although the mechanism for this association is unknown, our results provide a foundation for further studies on the molecular underpinnings of AF.

Methods

Subjects

The Icelandic cases consisted of all patients diagnosed with AF and/or AFl at the two largest hospitals in the country from 1987 to 2005. The Swedish cases were recruited from 1996 to 2002 as a part of an ongoing genetic epidemiology study, the South Stockholm Ischemic Stroke Study. The U.S. cases were a mixture of stroke patients with a AF diagnosis and younger consecutive patients with lone AF or AF with a coexisting diagnosis of hypertension. The Hong Kong cases were a collection of stroke and diabetes patients with an AF diagnosis. The AF diagnosis was confirmed by a twelve lead electrocardiogram in all study populations.

The Icelandic controls were chosen at random from individuals who have participated in other genetic studies at deCODE, excluding first-degree relatives of patients and controls (Table 15). The Swedish controls were recruited from the same region as patients from blood donors (in 2001) and healthy volunteers (1990-1994). The U.S. controls were recruited from a large primary care practice and from patients participating in a hemorrhagic stroke study. The Hong Kong controls were individuals without an AF diagnosis.

Icelandic Study Population

This study initially included the all patients consenting to participation, which were diagnosed with AF and/or AFl (ICD 10 diagnosis I48 and ICD 9 diagnosis 427.3) at Landspitali University Hospital in Reykjavik, the only tertiary referral centre in Iceland, and at Akureyri Regional Hospital, the second largest hospital in the country, from 1987 to 2005. All diagnoses were confirmed by a twelve lead electrocardiogram (EKG) which was manually read by a cardiologist. All cases were included, regardless of whether the patients had clinical symptoms or not, except those diagnosed only immediately after open cardiac surgery.

A set of 550 cases were successfully genotyped according to our quality control criteria in a genome-wide SNP genotyping effort, using the Infinium II assay method and the Sentrix HumanHap300 BeadChip (Illumina, San Diego, Calif., USA). The mean age at diagnosis for this initial group of 550 patients (370 males and 180 females) was 72.5 (SD=11.0) years and the range was from 34.7-96.2 years. The validation group of 2,273 patients (1,359 males and 913 females) had a mean age at diagnosis of 70.5 (SD=13.0) and the range was from 16.8-100.6. The AF/AFl free controls (2,201 males and 2,275 females at the initial genome-wide screening with mean age 61.5 (SD=15.8) and 5,654 males and 7,597 females at the validation stage with mean age 61.9 (SD=18.4)) used in this study consisted of controls randomly selected from the Icelandic genealogical database and individuals from other ongoing related genetic studies at deCODE. Controls having first-degree relatives (siblings, parents or offspring) with AF/AFl, or a first-degree control relative, were excluded from the analysis.

Icelandic MI, Obesity and Hypertension Populations

Individuals who suffered an MI were identified from a registry of over 10,000 individuals who: a) had an MI before the age of 75 in Iceland in the years 1981 to 2002 and satisfy the MONICA criteria 9 (REF II), or had MI discharge diagnosis from the major hospitals in Reykjavik in the years 2003 and 2005. MI diagnoses of all individuals in the registry follow strict diagnostic criteria based on signs, symptoms, electrocardiograms, cardiac enzymes and necropsy findings. Genotype information was available for 2,462 males and 1,114 females, mean age 72.6 (SD=11.7). Body mass index (BMI) was measured for individuals participating in the cardiovascular atrial fibrillation and/or stroke (CVD) genetics program at deCODE (either patients with CVD, their first degree relatives or spouses). For the purpose of this study subjects with BMI>35 were defined as obese. Genotype information was available for 555 males and 1,046 females, mean age 53.2 (SD=16.1). Hypertensive patients included those who had attended the ambulatory hypertension clinic at the Landspitali, University Hospital in Iceland and/or had been given the diagnosis on discharge from the hospital. The diagnosis was verified by confirming that they were taking antihypertensive medications as a treatment for hypertension. Genotype information was available for 1,293 males and 1,327 females, mean age 71.5 (SD=12.5). The study was approved by the Data Protection Commission of Iceland and the National Bioethics Committee of Iceland. Written informed consent was obtained from all patients, relatives and controls.

Swedish Study Population

Patients with ischemic stroke or TIA attending the stroke unit or the stroke outpatient clinic at Karolinska University Hospital, Huddinge unit in Stockholm, Sweden were recruited from 1996 to 2002 as part of an ongoing genetic epidemiology study, the South Stockholm Ischemic Stroke Study (SSISS). The study was approved by the Bioethics Committee of Karolinska Institutet (Dnr 286/96 and 08/02). AF diagnosis in the Swedish samples was based on a twelve lead EKG. The fraction of males in the Swedish AF cases was 46.2% and the mean age at stroke diagnosis for the Swedish AF cases was 74.4 (SD=8.7).

The Swedish controls used in this study are population-based controls recruited from the same region in central Sweden as the patients, representing the general population in this area. The individuals were either blood donors (recruited in 2001) or healthy volunteers (collected in 1990-1994) recruited by the clinical chemistry department at the Karolinska University Hospital to represent a normal reference population. The fraction of males in the Swedish controls was 59.7% and the mean age at recruitment for the Swedish controls was 43.1 (SD=12.3).

U.S. Study Population

U.S. subjects were enrolled in ongoing case-control and cohort studies at Massachusetts General Hospital (MGH) between January 1998 and July 2006. All aspects of these studies have been approved by the local Institutional Review Board. Subjects enrolled in the case-control study consisted of patients hospitalized with acute ischemic or hemorrhagic stroke confirmed by CT or MRI, admitted to a single acute care hospital. Of the 328 hemorrhagic stroke patients recruited 78 were diagnosed with AF and were used as cases for the current study, the remaining 250 were used as controls.

170 ischemic stroke patients had an AF diagnosis and were treated as cases but no ischemic stroke patients were treated as controls. Patients were excluded for primary subarachnoid hemorrhage and for intracerebral hemorrhage secondary to head trauma, tumor, vascular malformation, or vasculitis. 624 stroke-free controls were recruited from a large, primary care practice (>18 000 patients) serving the hospital catchment area as well as the hospital's Anticoagulation Management Service. 70 of the 624 individuals collected as controls were diagnosed with AF and treated cases for the purposes of the current study. 50.9% of all individuals used as controls were males and their mean age was 67.4 (SD=12.3). All subjects or an accompanying informant provided informed consent for participation in genetic studies and were interviewed prospectively regarding medical history, medications, social and family history. Presence or absence of atrial fibrillation was prospectively documented through interview and from review of medical records.

The second part of the U.S. subjects consisted of consecutive patients with lone AF or AF with coexisting diagnosis of hypertension referred to the arrhythmia service who provided written informed consent for participation in genetic. Inclusion criteria were AF documented by EKG, and an age less than or equal to 65 years. The exclusion criteria were structural heart atrial fibrillation and/or stroke as assessed by echocardiography, rheumatic heart atrial fibrillation and/or stroke, hyperthyroidism, myocardial infarction, or congestive heart failure. Each patient underwent a physical examination and a standardized interview to identify past medical conditions, medications, symptoms and possible triggers for initiation of AF. All patients were evaluated by twelve lead EKG, echocardiogram, and laboratory studies. EKGs and echocardiograms were interpreted using standard criteria.

Hong Kong Study Population

All subjects in the Hong Kong study population were of southern Han Chinese ancestry residing in Hong Kong. The cases consisted of 217 individuals (49.1% male, mean age 68.1 (SD=9.6)) selected from the Prince of Wales Hospital Diabetes Registry[23] and 116 subjects (300.2% male, mean age 76.1 (SD=10.9)) from the Stroke Registry[24]. All subjects were diagnosed to have atrial fibrillation by EKG. The controls consisted of 2,836 subjects without evidence of AF. Informed consent was obtained for each participating subject. This study was approved by the Clinical Research Ethics Committee of the Chinese University of Hong Kong.

Illumina Genome-Wide Genotyping

All Icelandic case- and control-samples were assayed with the Infinium HumanHap300 SNP chips (Illumina, San Diego, Calif., USA), containing 317 503 haplotype tagging SNPs derived from phase I of the International HapMap project. Of the SNPs assayed on the chip, 162 SNPs generated no genotypes, and an additional 178 SNPs had yield lower than 90%. Forty-eight SNPs were monomorphic and 107 others nearly monomorphic (i.e. the minor allele frequency in the combined cohort of patients and controls was less than 0.001). An additional 475 SNPs showed very significant distortion from Hardy-Weinberg equilibrium in the controls ($p<1\times10^{-10}$). Lastly, a few markers (n=18) were determined to have genotyping problems after investigation of particular regions and possible signals in several different on-going genome-wide association studies in house. Thus, the final analyses presented in the text utilizes 316,515 SNPs. Any samples with a call rate below 98% were excluded from the analysis.

Single SNP- and Microsatellite Genotyping.

SNP genotyping was carried out by the Centaurus (Nanogen) platform[25]. The quality of each Centaurus SNP assay was evaluated by genotyping each assay in the CEU and/or YRI HapMap samples and comparing the results with the HapMap data. Assays with >1.5% mismatch rate were not used and a linkage disequilibrium (LD) test was used for markers known to be in LD.

Association Analysis

An attempt was made to genotype all participating individuals for rs2200733, rs4611994 (a perfect proxy for rs2200733), rs13143308, and rs6843082 (a perfect proxy for rs13143308). For each of the SNPs, yield was higher than 90% in every group. In addition genotypes for the D4S406 microsatellite were available for all Icelandic and Swedish subjects. Because of the redundancy in genotyping, observed genotypes reduced the amount of information lost due to missing genotypes through a likelihood approach we have used before[26]. This ensured that results presented in the tables were always based on the same number of individuals, allowing meaningful comparisons of results. As data on rs10033464 was only directly available in the initial Icelandic discovery samples and in the HapMap project the rs2200733 C rs13143308 T haplotype was used to tag this SNP. This tagging was perfect in both the initial discovery samples and the CEPH CEU HapMap samples.

A likelihood procedure described in a previous, and implemented in the NEMO software, was used for the association analyses. We tested the association of an allele to each phenotype using a standard likelihood ratio statistic, which, if the subjects were unrelated, would have asymptotically a chi-square distribution, with one degree of freedom, under the null hypothesis. Allele-specific OR was calculated assuming a multiplicative model for the two chromosomes of an individual[4]. Results from multiple case-control groups were combined using a Mantel-Haenszel model[5] in which the groups were allowed to have different allelic population frequencies, haplotypes and genotypes but were assumed to have common relative risks. There was no significant deviation from Hardy-Weinberg equilibrium (HWE) in any control group.

In Tables 7 and 8, P values for both rs2200733 and rs10033464 were computed based on comparison to the wild type rs2200733 C, rs13143308 G, rs10033464 G haplotype carrying neither of the at risk alleles. The corresponding conditional odds ratio for rs2200733 T is defined as [f(rs2200733 T)/f(WT)]/[p(rs2200733 T)/p(WT)] where WT denotes the wild-type haplotype, and f(.) and p(.) denote frequencies in cases and controls respectively. Under the multiplicative model and when the controls could be considered as population controls, this conditional odds ratio is the appropriate estimate of the relative risk of rs2200733 T versus the wild-type. Conditional odd-ratio for rs13143308 T is similarly defined and has a similar interpretation.

Correction for Relatedness and Genomic Control.

Some of the individuals in the Icelandic case-control groups were related to each other, causing the aforementioned chi-square test statistic to have a mean>1 and median>0.675[26]. We estimated the inflation factor by using a previously described procedure where we simulated genotypes through the genealogy of 731,175 Icelanders[30]. For the initial discovery samples, where genotypes for the 316,515 genome-wide scan SNPs were available, we also estimated the inflation factor by using genomic controls and calculating the average of the 316,515 chi-square statistics, and by computing the median of the 316,515 chi-square statistics and dividing it by 0.675[26] as describe previously[31,32]. For these initial samples the inflation factors, estimated by our genealogy method and the two genomic control methods gave similar inflation factor estimates; 1.047, 1.058 and 1.054 respectively. The P values and confidence intervals presented are based on adjusting by the inflation factor estimated by the genealogy method.

PCR Screening of cDNA Libraries.

To confirm the expression of the spliced ESTs (DA725631, DB324364 and AF017091) within the LD block we screened commercially available cDNA libraries and libraries generated at deCODE. The commercial libraries screened were heart (Clontech-639304), aorta (Clontech-639325) bone marrow (Clontech 7416-1), testis (Clontech 7414-1) and whole brain (BD S0598) Marathon Ready cDNA libraries. In addition cDNA libraries were constructed for whole blood and EBV-transformed human lymphoblastoid cells. Total RNA was isolated from the lymphoblastoid cell lines and whole blood, using the RNeasy RNA isolation kit from Qiagen (Cat. 75144) and the RNeasy RNA isolation from whole blood kit (Cat. 52304), respectively. cDNA libraries were prepared at deCODE using High Capacity cDNA Archive Kit with random primers (Applied Biosystems PN 4322171).

PCR screening was carried out using the Advantage® 2 PCR Enzyme RT_PCR System (Clontech) according to manufacturers instructions and using PCR primers from Operon Biotechnologies. The PCR reactions were done in 10 μl volume at a final concentration of 3.5 μM of forward and reverse primers (Table 16), 2 mM dNTP, 1× Advantage 2 PCR buffer and 0.5 μl of cDNA library.

Northern Blot Analysis.

Commercial multiple tissue poly-A Northern blots were obtained from Clontech (Human Cardiovascular system, Cat. 636825).

Probes Used:

i) The PITX2 cDNA clone (HU3_p983E0327D), obtained from RZPD Deutsches Ressourcenzentrum für Genomforschung GmbH, Germany http colon-slash-slash www.rzpd.de/products/genomecube.shtml) (sequence verified, data not shown);

ii) cDNA clone that corresponded to exons 1-12 of the ENPEP transcripts obtained from RT-PCR experiments. The ENPEP clone was sequence verified:

(SEQ ID NO: 58)

```
TCCTGCTCCAGCTTGTGGATATTTTGCAAAAAAGCTCTCCATCTGCCACA
GTTGCAGTTCAGTGTTGAATGGCTCTGCTATTGTGACAATTCGGCCAAGG
TTTCTGTTATTGAGTGTATATCTGTTGACTAGATAGTCCCAGTTGAGTTG
TATCCAATTCCAGGCCATGTTCTTCCCATAGCTGTTATATGAGATATATC
GAATGACTGTAAACACATCCTGAGTTTTAATAAGGTTCGTGTCCTTGAGC
AAATCCAAATACCTTGACAAAAGAGTAACGTTCTTCACTGATGCTAATCC
ATACAGCAGTTTTTCTTTTTCTTGAGCTAATGAAGTTTCTGGTATTGCTC
AAGAGTGTAGTTCCATGAAATCTCATTGCCAGAGTTCTGCATCCCATACC
GATACACCAGAAGCCTGAGATTTACGGGAAGGCTTACAGTCCCATTTAGC
CACTGCTCAAATAACGAGGAAGCATTGTTCAAGGCTTCTCTGTCTCCCAT
CTTGCACGCAAACCCTAACACGGAGGAACGGAGTAACTTTGTGACATGGT
CTCCAGCATCATTCCATCCCAGAGAATCTGCAATAGGCTTCACTTGACCT
TGGAAGTATTCCTCAATCATAGGATATAGCTCTTTATCATCTTCAAACAT
GCTAATGATGTAGGTTACAGCTGAAATTACTCTCTGCCATGGTAAAAAAT
TCTCTTCCCTTTTGAGATACTTGGTCAAGTTCAAAGCCACCTTATAATCT
```

-continued

```
AGAAGTTGAGCTCTTGCCAAGGCAAAAGCATCATCAATAAGACTTGCACG
ATCTGCTGAAGAAAATGTCTTGTGGTTCAAGGAGAGCGCTGTAGCTATCG
AGTCCCAAGTTGCTACTTCATAATTTACACGATAAAACCCAATATGATCT
GGGTTTATTTTGAGAAAAGCATTTCCACTAGGATTAGAGGAGTTCAAAGT
GATTCCTTCTTTTTCTGACCTATTAAATAACACACTGCTTGTTATATTAT
CTTCAGTCCATTTAACTGGGATATTCCATGTATAACCAAGATCTGAAGGG
GGCTGAGAAGGGTTAGCTCTTGGGTCCAACAAAAAGCGTTTCTGTGTGAT
GTTCTTGACACCGTTCACGTTAAGCACAGGATAACCCATGTgGTCTGGTC
CAGGTGTCCATTACTTCTTTCACTGGTAGCCTACTTGCCTCTTCCAGTGC
TGCCCAAAAAT
```

cDNA fragments were radiolabelled with [$\alpha$-$^{32}$P]dCTP (specific activity 6000 Ci/mmol), using the Megaprime labeling kit (GE Healthcare Cat. RPN 1607) and unincorporated nucleotides removed from the reaction using ProbeQuant G-50 microcolumns (GE Healthcare Cat. 27-5335-01). Membranes were pre-hybridized in Rapid-hyb buffer (GE Healthcare Cat. RPN 1635) for at least 30 minutes and subsequently hybridized with 100-300 ng of the labelled cDNA probe. Hybridizations were performed in Rapid-hyb buffer at 65° C. overnight. The labelled probes were heated for 5 minutes at 95° C. before addition to the filters in the prehybridization solution. After hybridization, the membranes were washed at low stringency in 2×SSC, 0.05% SDS at room temperature for 30-40 minutes followed by two high stringency washes in 0.1×SSC, 0.1% SDS at 50° C. for 40 minutes. The blots were immediately sealed and exposed to Kodak BioMax MR X-ray film (Cat. 8715187).

Surveying for Candidate Regulatory Variants in the AF Region

The UCSC browser was used to extracted positions of SNPs and conserved transcription factor binding sites (TFBS) for a 172.5 kb region around the SNPs associated with AF (hg release 17, chromosome 4, 111,942,401-112,114,901). The two tables were cross referenced and SNPs that landed in binding sites were further interrogated for LD with rs2220427 or rs6843082 in the HapMap data. This was done for releases 16, 17 and 18 of the human genome, but the results are reported in hg 17 coordinates. This yielded 3 SNPs that land in conserved binding sites for known transcription factors (Table 17). Note, this analysis only detects a limited sample of functional candidates as i) the AF haplotypes have not been sequenced fully, ii) several candidate SNPs are not typed in Hapmap and it is unknown whether they sit on the AF haplotypes, iii) polymorphisms in less conserved regions could be functional.

Evolutionary Conservation of Three TFBS

Utilizing the Multiz alignment in the UCSC genome enabled an assessment of the evolutionary conservation of the regions affected by these SNPs. In all three cases is the core part of the TF binding sites intact, but the positions affected are preserved to a different degree. The SOX5 affected by rs12510087 is least conserved in mammals but the second one (affected by rs2220427) is strikingly preserved (with the exception of Opossum it is maintained in all species to the chicken). The rs17042171 mutation is in last position in the core GGAAAA motif of the NFAT binding site. The conservation indicates that a G is preferred at this location, resulting in a GGAAAG motif.

Correlation Between Genotype and Expression of ENPEP

Blood was collected in the morning, between 8 and 10 am, after overnight fasting (from 9 pm) and RNA extracted within 2 hours from phlebotomy from 1,002 individuals. RNA isolation was performed using the RNeasy Midi Kit (QIAGEN GmbH, Hilden, Germany). Subcutaneous fat samples (5-10 $cm^3$) were removed through a 3 cm incision at the bikini line (always from the same site to avoid site-specific variation) after local anesthesia using 10 ml of lidocaine-adrenalin (1%) from 673 individuals. Purification of the total RNA was performed with the RNeasy Mini Kit (QIAGEN GmbH, Hilden, Germany).

Integrity of the total RNA was assessed through analysis on the Agilent 2100 Bioanalyzer (Agilent Technologies, Palo Alto, U.S., Calif.). Each labelled RNA sample including reference pools, 1,765 samples in total, was hybridized to a Human 25K array manufactured by Agilent Technologies. Array images were processed as described previously to obtain background noise, single-channel intensity and associated measurement error estimates[11]. Expression changes between two samples were quantified as mean logarithm ($log_{10}$) expression ratio (MLR), i.e. expression ratios compared to background corrected intensity values for the two channels for each spot on the array[12]. The hybridizations went through standard QC process, i.e. signal to noise ratio, reproducibility and accuracy at spike-in compounds, comparing Cy3 to Cy5 intensities.

Neither associated SNP was correlated to the expression of ENPEP adjusted for age and sex in blood (P=0.90 and P=0.82 for rs2200733 and rs10033464, respectively) or adipose tissue (P=0.23 and P=0.37 for rs2200733 and rs10033464, respectively)

TABLE 7

Analysis of the association of rs2200733 and rs10033464 on chromosome 4q25 to AF/AFI.

| Sample | rs2200733 T[a] | | | rs10033464 T[a,b] | | | | |
|---|---|---|---|---|---|---|---|---|
| (N cases/ N controls) | Freq.[c] | OR (95% CI) | P | Freq.[c] | OR (95% CI) | P | Comparison P[d] | Joint PAR |
| Iceland[e] | | | | | | | | |
| Discovery (550/4,476) | 0.191 0.114 | 1.84 (1.54-2.21) | $2.0 \times 10^{-11}$ | 0.110 0.080 | 1.42 (1.13-1.77) | 0.0024 | 0.041 | 0.216 |
| Replication (2,251/13,238) | 0.166 0.108 | 1.64 (1.49-1.81) | $2.7 \times 10^{-23}$ | 0.108 0.080 | 1.40 (1.24-1.58) | $8.2 \times 10^{-8}$ | 0.028 | 0.176 |
| Combined (2,801/17,714) | 0.171 0.110 | 1.68 (1.53-1.83) | $1.9 \times 10^{-30}$ | 0.108 0.080 | 1.40 (1.25-1.55) | $9.4 \times 10^{-9}$ | 0.0025 | 0.180 |
| Other European ancestry | | | | | | | | |
| Sweden (143/738) | 0.179 0.098 | 2.01 (1.38-2.93) | 0.00027 | 0.172 0.111 | 1.65 (1.14-2.41) | 0.0087 | 0.41 | 0.272 |
| U.S. (636/804) | 0.229 0.139 | 1.84 (1.51-2.23) | $9.8 \times 10^{-10}$ | 0.105 0.083 | 1.30 (1.00-1.69) | 0.052 | 0.026 | 0.232 |
| Combined[f] | — — | 1.88 (1.58-2.23) | $1.2 \times 10^{-12}$ | — — | 1.41 (1.13-1.75) | 0.0019 | 0.027 | 0.237 |
| All European ancestry | | | | | | | | |
| Combined[f] | — — | 1.72 (1.59-1.86) | $3.3 \times 10^{-41}$ | — — | 1.39 (1.26-1.53) | $6.9 \times 10^{-11}$ | 0.00019 | 0.206 |
| Hong Kong | | | | | | | | |
| Hong Kong (333/2,836) | 0.605 0.528 | 1.42 (1.16-1.73) | 0.00064 | 0.190 0.218 | 1.08 (0.84-1.39) | 0.55 | 0.0099 | 0.346 |

Each row contains the results from a joint analysis of two variants, rs2200733 T and rs10033464 T[b]. The numbers of cases and controls (N) are shown for each case-control study and for each variant the allelic frequencies of the variant in cases and controls, the OR with a 95% CI and two-sided P values, are shown. In addition a P value for comparing the effect of the two variants and their joint population attributable risk (PAR) is reported. For example, the first row indicates that, for the initial Icelandic discovery samples, rs2200733 T has an estimated odds ratio (OR) of 1.84 (95% CI (1.54-2.21), P = $4.1 \times 10^{-11}$) vs the wild type (rs2200733 C, rs13143308 G, rs10033464 G haplotype), and rs10033464 T has an estimated OR of 1.42 (95% CI (1.13-1.77), P = 0.0024) vs the wild type.

[a]Results of comparing rs2200733 T and rs10033464 T to the wild type rs2200733 C, rs13143308 G, rs10033464 G haplotype.

[b]In the Swedish and the U.S. samples rs10033464 T was tagged by the rs2200733 C, rs13143308 T haplotype

[c]The frequency in cases (above) and controls (below)

[d]P value for comparing the ORs of rs2200733 T and rs10033464 T.

[e]The association analysis was adjusted for the relatedness of some of the individuals.

[f]For the combined study populations of European decent, the PAR was calculated by using the average, unweighted control frequency of the populations, while the OR and the P value were estimated using the Mantel-Haenszel model.

TABLE 8

Association by age at diagnosis in Iceland and by AF sub-phenotype in the U.S.

| Sample (N cases/ N controls) | Male % | Age ± SD | rs2200733[a] OR (95% CI) | rs10033464[a,b] OR (95% CI) | P | Sex P |
|---|---|---|---|---|---|---|
| Iceland[c] | | | | | | |
| Diagn. ≤ 60 (510/17,714) | 77.8 | 50.7 ± 8.4 | 2.12 (1.77-2.54) | 1.69 (1.34-2.12) | $6.3 \times 10^{-18}$ | 0.82 |

TABLE 8-continued

| Association by age at diagnosis in Iceland and by AF sub-phenotype in the U.S. | | | | | | |
|---|---|---|---|---|---|---|
| Sample (N cases/ N controls) | Male % | Age ± SD | rs2200733[a] OR (95% CI) | rs10033464[a,b] OR (95% CI) | P | Sex P |
| Diagn. 60-70 (654/17,714) | 66.2 | 65.6 ± 2.9 | 1.88 (1.60-2.21) | 1.44 (1.18-1.77) | $6.7 \times 10^{-15}$ | 0.58 |
| Diagn. 70-80 (958/17,714) | 58.9 | 75.0 ± 2.8 | 1.60 (1.39-1.84) | 1.23 (1.03-1.47) | $7.5 \times 10^{-11}$ | 0.96 |
| Diagn. > 80 (679/17,714) | 47.4 | 85.6 ± 4.2 | 1.20 (1.01-1.43) | 1.31 (1.08-1.60) | 0.0044 | 0.36 |
| U.S. | | | | | | |
| Lone AF (251/804) | 81.7 | 46.1 ± 11.5 | 2.32 (1.80-2.99) | 1.68 (1.19-2.37) | $1.2 \times 10^{-10}$ | 0.46 |
| AF/HTN (67/804) | 74.6 | 54.5 ± 10.2 | 2.23 (1.43-3.48) | 1.66 (0.90-3.04) | 0.0010 | 0.54 |
| Other AF (318/804) | 52.8 | 75.2 ± 11.3 | 1.44 (1.12-1.84) | 0.97 (0.69-1.37) | 0.015 | 0.85 |

Each row contains the results from a joint analysis of two variants, rs2200733 T and rs10033464 T[a]. The numbers of cases and controls (N), the percentage of male cases, and the mean age (±SD) for cases, are shown for each case-control study. The OR, with a 95% CI, and P values are shown for each variant. In addition a joint P value for the combined effect of the two variants, and a joint P value for testing if there is a difference of the allelic frequency of the variants between the sexes within each sub-group of patients.

[a]Results of comparing rs2200733 T and rs10033464 T to the wild type rs2200733 C, rs13143308 G, rs10033464 G haplotype.

[b]In the U.S. samples rs10033464 T was tagged by the rs2200733 C, rs13143308 T haplotype.

[c]The association analysis was adjusted for the relatedness of some of the individuals.

TABLE 9

SNPs equivalent to rs10033464, rs13143308 and rs2200733 in CEU HapMap data

| SNP | Tagging SNP | Build 35 location | SEQ ID NO: 50 location |
|---|---|---|---|
| rs12503217 | rs10033464 | 112063765 | 108955 |
| rs12510087 | rs10033464 | 112066632 | 111822 |
| rs6852357 | rs10033464 | 112071939 | 117129 |
| rs4400058 | rs10033464 | 112074277 | 119467 |
| rs10033464 | rs10033464 | 112078365 | 123555 |
| rs2171592 | rs10033464 | 112078392 | 123582 |
| rs2350539 | rs10033464 | 112078814 | 124004 |
| rs1906606 | rs10033464 | 112080996 | 126186 |
| rs723364 | rs10033464 | 112082075 | 127265 |
| rs2220429 | rs10033464 | 112085089 | 130279 |
| rs4032976 | rs10033464 | 112086371 | 131561 |
| rs3853440 | rs10033464 | 112087213 | 132403 |
| rs3853441 | rs10033464 | 112087344 | 132534 |
| rs3853442 | rs10033464 | 112087632 | 132822 |
| rs3853443 | rs10033464 | 112087733 | 132923 |
| rs4124158 | rs10033464 | 112087798 | 132988 |
| rs4124159 | rs10033464 | 112087847 | 133037 |
| rs12506083 | rs10033464 | 112088016 | 133206 |
| rs4032975 | rs10033464 | 112089842 | 135032 |
| rs4032974 | rs10033464 | 112090140 | 135330 |
| rs2634074 | rs13143308 | 112034645 | 79835 |
| rs2466455 | rs13143308 | 112043219 | 88409 |
| rs2723334 | rs13143308 | 112046356 | 91546 |
| rs1906616 | rs13143308 | 112055172 | 100362 |
| rs1906615 | rs13143308 | 112059402 | 104592 |
| rs2129983 | rs13143308 | 112061684 | 106874 |
| rs2129982 | rs13143308 | 112061747 | 106937 |
| rs1906599 | rs13143308 | 112070290 | 115480 |
| rs13143308 | rs13143308 | 112072023 | 117213 |
| rs6843082 | rs13143308 | 112075671 | 120861 |
| rs17042059 | rs2200733 | 111998790 | 43980 |
| rs4529121 | rs2200733 | 112003159 | 48349 |
| rs4543199 | rs2200733 | 112005744 | 50934 |
| rs12647316 | rs2200733 | 112006855 | 52045 |
| rs10019689 | rs2200733 | 112007473 | 52663 |
| rs4626276 | rs2200733 | 112007593 | 52783 |

TABLE 9-continued

SNPs equivalent to rs10033464, rs13143308 and rs2200733 in CEU HapMap data

| SNP | Tagging SNP | Build 35 location | SEQ ID NO: 50 location |
|---|---|---|---|
| rs17042076 | rs2200733 | 112009942 | 55132 |
| rs11098089 | rs2200733 | 112011830 | 57020 |
| rs17042088 | rs2200733 | 112012418 | 57608 |
| rs11930528 | rs2200733 | 112017798 | 62988 |
| rs17042098 | rs2200733 | 112021762 | 66952 |
| rs17042102 | rs2200733 | 112026230 | 71420 |
| rs17042121 | rs2200733 | 112034705 | 79895 |
| rs10516563 | rs2200733 | 112035326 | 80516 |
| rs4605724 | rs2200733 | 112042685 | 87875 |
| rs2350269 | rs2200733 | 112044728 | 89918 |
| rs6533527 | rs2200733 | 112045118 | 90308 |
| rs17042144 | rs2200733 | 112047270 | 92460 |
| rs1906618 | rs2200733 | 112053026 | 98216 |
| rs1906617 | rs2200733 | 112053418 | 98608 |
| rs12646447 | rs2200733 | 112056930 | 102120 |
| rs12646754 | rs2200733 | 112061176 | 106366 |
| rs2129981 | rs2200733 | 112061803 | 106993 |
| rs12639654 | rs2200733 | 112062899 | 108089 |
| rs6817105 | rs2200733 | 112063372 | 108562 |
| rs17042171 | rs2200733 | 112065891 | 111081 |
| rs1906591 | rs2200733 | 112066493 | 111683 |
| rs1906592 | rs2200733 | 112066608 | 111798 |
| rs2200732 | rs2200733 | 112067646 | 112836 |
| rs2200733 | rs2200733 | 112067773 | 112963 |
| rs4611994 | rs2200733 | 112068645 | 113835 |
| rs4540107 | rs2200733 | 112068706 | 113896 |
| rs1906593 | rs2200733 | 112069526 | 114716 |
| rs1906596 | rs2200733 | 112069840 | 115030 |
| rs2220427 | rs2200733 | 112072493 | 117683 |

TABLE 10

| Haplotype structure (haplotypes with estimated frequency > 0.1%) over key SNPs and the D4S406 microsatellite in Iceland | | | | |
|---|---|---|---|---|
| Frequency | D4S406 | rs2200733 | rs13143308 | rs10033464 |
| 0.0800 | −8 | T | T | G |
| 0.00647 | −6 | C | T | T |
| 0.00225 | −4 | T | T | G |
| 0.0415 | −2 | T | T | G |
| 0.00108 | 0 | T | T | G |
| 0.0592 | 0 | C | T | T |
| 0.00679 | 2 | C | T | T |
| 0.0169 | 2 | C | G | G |
| 0.00923 | 4 | C | T | T |
| 0.135 | 4 | C | G | G |
| 0.0853 | 6 | C | G | G |
| 0.1587 | 8 | C | G | G |
| 0.163 | 10 | C | G | G |
| 0.0928 | 12 | C | G | G |
| 0.0398 | 14 | C | G | G |
| 0.101 | 16 | C | G | G |

TABLE 13

Association to AF/AFI by genotype

| | Allelic RR | | Genotype RR | | | | | | |
|---|---|---|---|---|---|---|---|---|---|
| | 1 | 2 | 00 | 01 | 02 | 11 | 12 | 22 | P value |
| Iceland | 1.68 | 1.38 | 1 | 1.55 | 1.36 | 3.42 | 2.47 | 1.58 | 0.12 |
| Sweden | 2.01 | 1.65 | 1 | 1.66 | 1.72 | 5.86 | 3.10 | 2.04 | 0.68 |
| U.S. | 1.84 | 1.30 | 1 | 1.63 | 1.40 | 4.86 | 2.31 | 0.90 | 0.25 |
| Combined | 1.71 | 1.38 | 1 | 1.56 | 1.37 | 3.64 | 2.44 | 1.43 | 0.018 |
| Hong Kong | 1.42 | 1.07 | 1 | 1.15 | 0.95 | 1.77 | 1.34 | 0.97 | 0.87 |

The three possible haplotypes are coded as
0 = rs2200733 C, rs13143308 G, rs10033464 G
1 = rs2200733 T, rs13143308 T, rs10033464 G
2 = rs2200733 C, rs13143308 T, rs10033464 T

TABLE 11

Association to all Hap300 Illumina SNPs in a 200 kb region around rs2200733 and rs10033464 in an extended set of Icelandic AF/AFI cases and controls. Results have not been adjusted for relatedness of individuals.

| | | | | | | Adjusting for rs2220427 | | Also adjusting for rs10033464 | |
|---|---|---|---|---|---|---|---|---|---|
| SNP | Location | All. | Freq | OR | P value | OR | P value | OR | P value |
| rs4834295 | 111892810 | G | 0.817 | 1.0 | 0.27 | 1.0 | 0.39 | 1.03 | 0.63 |
| rs2278782 | 111899758 | C | 0.883 | 1.0 | 0.79 | 0.9 | 0.70 | 0.99 | 0.93 |
| rs2595110 | 111902927 | T | 0.637 | 1.0 | 0.13 | 1.0 | 1.0 | 1.01 | 0.89 |
| rs976568 | 111908325 | A | 0.743 | 1.0 | 0.83 | 0.9 | 0.62 | 0.97 | 0.58 |
| rs2197815 | 111924481 | T | 0.030 | 1.1 | 0.34 | 1.1 | 0.34 | 0.97 | 0.84 |
| rs2723286 | 111940938 | A | 0.231 | 1.0 | 0.26 | 1.0 | 0.50 | 1.03 | 0.59 |
| rs2723296 | 111962087 | G | 0.229 | 1.0 | 0.38 | 1.0 | 0.60 | 1.03 | 0.67 |
| rs1699716 | 111986643 | T | 0.153 | 1.3 | $4.7 \times 10^{-5}$ | 0.9 | 0.59 | 0.95 | 0.53 |
| rs2723316 | 111991891 | T | 0.297 | 1.2 | $1.9 \times 10^{-5}$ | 1.0 | 0.59 | 0.95 | 0.40 |
| rs6419178 | 111993104 | A | 0.143 | 1.1 | 0.17 | 1.0 | 0.25 | 0.98 | 0.77 |
| rs1448817 | 111998657 | G | 0.252 | 1.4 | $4.2 \times 10^{-}$ | 1.1 | 0.035 | 1.06 | 0.46 |
| rs2634073 | 112023387 | A | 0.167 | 1.6 | $2.4 \times 10^{-}$ | 1.2 | 0.039 | 0.90 | 0.48 |
| rs2200733 | 112067773 | T | 0.119 | 1.7 | $7.6 \times 10^{-}$ | — | — | — | — |
| rs2220427 | 112072493 | T | 0.120 | 1.7 | $5.6 \times 10^{-}$ | — | — | — | — |
| rs1310587 | 112075751 | C | 0.888 | 1.0 | 0.33 | 0.9 | 0.89 | 0.95 | 0.56 |
| rs1003346 | 112078365 | T | 0.082 | 1.2 | 0.013 | 1.3 | $5.1 \times 10^{-4}$ | — | — |
| rs1314119 | 112086218 | A | 0.368 | 1.3 | $2.0 \times 10^{-}$ | 1.1 | 0.0067 | 1.08 | 0.29 |
| rs3853444 | 112091740 | A | 0.604 | 1.1 | 0.053 | 1.0 | 0.45 | 1.06 | 0.24 |

TABLE 12

Association study of SNPs which are equivalent to rs2200733 in CEU HapMap samples in the Chinese samples from Hong Kong.

| SNP | Location | All. | Freq | OR | P value | HapMap D' | HapMap $R^2$ |
|---|---|---|---|---|---|---|---|
| rs11930528 | 112017798 | T | 0.472 | 1.27 | 0.011 | 0.91 | 0.66 |
| rs17042121 | 112034705 | G | 0.418 | 1.32 | 0.0029 | 0.97 | 0.64 |
| rs6533527 | 112045118 | A | 0.518 | 1.37 | 0.0014 | 0.95 | 0.79 |
| rs1906617 | 112053418 | C | 0.524 | 1.35 | 0.0026 | 1.00 | 0.98 |
| rs12639654 | 112062899 | T | 0.519 | 1.39 | 0.0012 | 1.00 | 1.00 |
| rs2200733 | 112067773 | T | 0.516 | 1.42 | $6.4 \times 10^{-4}$ | — | — |
| rs4611994 | 112068645 | C | 0.518 | 1.39 | 0.0012 | 1.00 | 1.00 |

The LD values reported are to rs2200733 in the combined CHB and JPT HapMap samples

TABLE 14

Association of various phenotypes, considered risk factors for AF to risk variants.

| Phenotype | T rs2200733 | | T rs10033464 | |
|---|---|---|---|---|
| (N cases/N controls) | OR | P value | OR | P value |
| Hypertension (2,620/19,862) | 1.08 | 0.11 | 1.05 | 0.37 |
| Myocardial infarction (3,576/19,542) | 1.05 | 0.26 | 1.04 | 0.49 |
| Obesity - BMI > 35 (1,601/21,593) | 0.96 | 0.51 | 1.00 | 1.00 |

TABLE 15

A summary of the source of the Icelandic controls. Note that individuals may come from multiple project and that some individuals may have been collected as relatives of probands.

| Source Project | Count | Frequency of T rs2200733 | Frequency of T rs10033464 |
|---|---|---|---|
| Discovery Controls | | | |
| Addiction | 376 | 0.096 | 0.082 |
| Anxiety | 337 | 0.110 | 0.088 |
| Breast Cancer | 876 | 0.116 | 0.085 |
| Colon Cancer | 370 | 0.119 | 0.070 |
| Infectious Disease | 297 | 0.109 | 0.096 |
| MI | 454 | 0.104 | 0.076 |
| Population Controls | 389 | 0.099 | 0.077 |
| Prostate Cancer | 713 | 0.123 | 0.081 |
| Schizophrenia | 291 | 0.110 | 0.091 |
| Type II Diabetes | 551 | 0.102 | 0.078 |
| Replication Controls | | | |
| Breast Cancer | 228 | 0.122 | 0.074 |
| Type II Diabetes | 340 | 0.097 | 0.082 |
| Alzheimer | 459 | 0.107 | 0.061 |
| Osteoarthritis | 1,175 | 0.107 | 0.081 |
| PAD | 479 | 0.096 | 0.083 |
| COPD | 326 | 0.125 | 0.082 |
| Stroke | 414 | 0.092 | 0.069 |
| Osteoporosis | 1,155 | 0.109 | 0.072 |
| MI | 390 | 0.112 | 0.075 |
| Hypertension | 210 | 0.118 | 0.101 |
| Depression | 152 | 0.128 | 0.061 |
| Asthma | 538 | 0.106 | 0.076 |
| Parkinson | 173 | 0.102 | 0.058 |
| Population Controls | 305 | 0.105 | 0.097 |
| Ankylosing Spondylitis | 155 | 0.095 | 0.077 |

TABLE 15-continued

A summary of the source of the Icelandic controls. Note that individuals may come from multiple project and that some individuals may have been collected as relatives of probands.

| Source Project | Count | Frequency of T rs2200733 | Frequency of T rs10033464 |
|---|---|---|---|
| Sleep Apnea | 422 | 0.118 | 0.074 |
| AMD | 442 | 0.101 | 0.067 |
| Rheumatoid Arthritis | 430 | 0.100 | 0.094 |
| Lung Cancer | 237 | 0.106 | 0.084 |
| FCH | 265 | 0.112 | 0.057 |
| Longevity | 392 | 0.09 | 0.077 |
| Benign Prostatic Hyperplasia | 245 | 0.101 | 0.058 |
| Pre-eclampsia | 262 | 0.129 | 0.083 |
| Enuresis | 249 | 0.104 | 0.087 |
| Migrane | 590 | 0.112 | 0.085 |
| Myopia | 353 | 0.123 | 0.085 |
| Thyroid Cancer | 104 | 0.121 | 0.097 |
| ADHD | 123 | 0.119 | 0.089 |
| Prostate Cancer | 580 | 0.117 | 0.073 |
| Anxiety | 546 | 0.121 | 0.096 |
| Obesity | 162 | 0.081 | 0.092 |
| Endometriosis | 258 | 0.106 | 0.084 |
| Kidney Cancer | 174 | 0.099 | 0.100 |
| Melanoma | 283 | 0.088 | 0.089 |
| Addiction | 201 | 0.138 | 0.098 |
| Psoriasis | 392 | 0.136 | 0.079 |
| IBD | 356 | 0.093 | 0.102 |

TABLE 16

Primers used for ESTs screening of cDNA libraries

| ESTs* | Forward primer | Reverse primer |
|---|---|---|
| DA725631 | AGTGGAGGCTGCCAGACTTC (SEQ ID NO: 59) | TGCACCACTCATCACC AACA (SEQ ID NO: 60) |
| DB324364 | CCGAGGATGTCTTTAGTCTG CAA (SEQ ID NO: 61) | ATCATACAGCAGGAATGC AAACA (SEQ ID NO: 62) |
| AF017091 | TGAGATTCCACATCCAACATC TTT (SEQ ID NO: 63) | TGGCAAACTTGATATTGT TCTTG (SEQ ID NO: 64) |

*EST names are from NCBI BUILD 35

TABLE 17

SNPs that land in conserved TFBS in the region associated with AF.

| SNP | Location | Strand | Ancestral | Polym. | TFBS | TF start | TF end |
|---|---|---|---|---|---|---|---|
| rs17042171 | 112065890 | + | C | A/C | NFAT | 112065889 | 112065900 |
| rs12510087 | 112066631 | + | A | A/G | SOX5 | 112066632 | 112066641 |
| rs2220427 | 112072492 | + | C | C/T | SOX5 | 112072483 | 112072493 |

Strand indicates the strand in genome alignment that the mutation lands in.

Polym. is the two alleles of the polymorphism at this site.

TABLE 18

Markers in or near the PITX2 gene in LD with markers in the LD block C04. Shown are markers in or near PITX2 (marker 1) and their correlation to markers in LD block C04 (marker 2).

| Marker 1 | Marker 2 | D' | r2 | p-value |
|---|---|---|---|---|
| rs7668322 | rs10033464 | 0.46291 | 0.133423 | 0.000953 |
| rs2197815 | rs10033464 | 0.660377 | 0.300172 | 2.55E−06 |
| rs6831623 | rs2200733 | 1 | 0.02834 | 0.025473 |
| rs2595110 | rs2200733 | 0.699643 | 0.02996 | 0.067245 |

TABLE 19

Markers in linkage disequilibrium with marker rs2220427 and markerrs10033464 by values for $r^2$ of greater than 0.1. LD was calculated based on the HapMap CEU population sample.

| Marker 1 | anchor | D' | r2 | P-value | Pos in B35 | Pos in SEQ ID NO: 50 |
|---|---|---|---|---|---|---|
| rs9994891 | rs2220427 | 1 | 0.128329 | 0.002914 | 111149057 | |
| rs11568995 | rs2220427 | 1 | 0.128329 | 0.002914 | 111255189 | |
| rs4698804 | rs2220427 | 1 | 0.128329 | 0.002914 | 111297649 | |
| rs721413 | rs2220427 | 1 | 0.128329 | 0.002914 | 111305212 | |
| rs10488883 | rs2220427 | 1 | 0.128329 | 0.002914 | 111305486 | |
| rs6854883 | rs2220427 | 0.788889 | 0.510189 | 4.17E−09 | 111964919 | 10109 |
| rs2255793 | rs2220427 | 1 | 0.245283 | 9.27E−09 | 111965457 | 10647 |
| rs2723298 | rs2220427 | 1 | 0.274924 | 8.39E−09 | 111966089 | 11279 |
| rs2723300 | rs2220427 | 1 | 0.236507 | 1.40E−08 | 111972512 | 17702 |
| rs2723307 | rs2220427 | 1 | 0.176558 | 2.98E−07 | 111975800 | 20990 |
| rs1584429 | rs2220427 | 1 | 0.245283 | 9.27E−09 | 111976151 | 21341 |
| rs1448799 | rs2220427 | 1 | 0.245283 | 9.27E−09 | 111980386 | 25576 |
| rs1448798 | rs2220427 | 1 | 0.245283 | 9.27E−09 | 111980789 | 25979 |
| rs1900827 | rs2220427 | 1 | 0.246741 | 8.60E−08 | 111981343 | 26533 |
| rs2197814 | rs2220427 | 1 | 0.240506 | 1.20E−08 | 111983098 | 28288 |
| rs969642 | rs2220427 | 1 | 0.245283 | 9.27E−09 | 111983529 | 28719 |
| rs2595093 | rs2220427 | 0.830131 | 0.513828 | 1.59E−10 | 111984960 | 30150 |
| rs2245595 | rs2220427 | 1 | 0.252078 | 6.90E−09 | 111985715 | 30905 |
| rs2595088 | rs2220427 | 1 | 0.254302 | 1.99E−08 | 111985958 | 31148 |
| rs981150 | rs2220427 | 1 | 0.245283 | 9.27E−09 | 111986232 | 31422 |
| rs16997168 | rs2220427 | 0.819277 | 0.507451 | 2.11E−10 | 111986643 | 31833 |
| rs16997169 | rs2220427 | 1 | 0.245283 | 9.27E−09 | 111986685 | 31875 |
| rs4527540 | rs2220427 | 1 | 0.245283 | 9.27E−09 | 111986742 | 31932 |
| rs17042026 | rs2220427 | 0.833488 | 0.554106 | 1.23E−11 | 111989978 | 35168 |
| rs2723316 | rs2220427 | 1 | 0.245283 | 9.27E−09 | 111991891 | 37081 |
| rs2595081 | rs2220427 | 0.832621 | 0.549261 | 3.07E−11 | 111992761 | 37951 |
| rs2595085 | rs2220427 | 1 | 0.242283 | 1.16E−08 | 111994377 | 39567 |
| rs2723318 | rs2220427 | 1 | 0.236507 | 1.40E−08 | 111994576 | 39766 |
| rs1448817 | rs2220427 | 1 | 0.296277 | 9.75E−10 | 111998657 | 43847 |
| rs17042059 | rs2220427 | 1 | 1 | 1.62E−20 | 111998790 | 43980 |
| rs4529121 | rs2220427 | 1 | 1 | 1.43E−20 | 112003159 | 48349 |
| rs10032150 | rs2220427 | 1 | 0.296277 | 9.75E−10 | 112004222 | 49412 |
| rs4543199 | rs2220427 | 1 | 1 | 1.43E−20 | 112005744 | 50934 |
| rs12647316 | rs2220427 | 1 | 1 | 1.43E−20 | 112006855 | 52045 |
| rs12647393 | rs2220427 | 1 | 0.917379 | 1.57E−15 | 112006886 | 52076 |
| rs10019689 | rs2220427 | 1 | 1 | 1.43E−20 | 112007473 | 52663 |
| rs4626276 | rs2220427 | 1 | 1 | 1.43E−20 | 112007593 | 52783 |
| rs17042076 | rs2220427 | 1 | 1 | 1.62E−20 | 112009942 | 55132 |
| rs11098089 | rs2220427 | 1 | 1 | 1.62E−20 | 112011830 | 57020 |
| rs17042088 | rs2220427 | 1 | 1 | 1.62E−20 | 112012418 | 57608 |
| rs11944778 | rs2220427 | 0.91509 | 0.811642 | 4.20E−12 | 112014571 | 59761 |
| rs4307025 | rs2220427 | 1 | 0.296277 | 9.75E−10 | 112015107 | 60297 |
| rs11930528 | rs2220427 | 1 | 1 | 1.42E−19 | 112017798 | 62988 |
| rs17042098 | rs2220427 | 1 | 1 | 1.43E−20 | 112021762 | 66952 |
| rs2634073 | rs2220427 | 1 | 0.523052 | 1.42E−12 | 112023387 | 68577 |
| rs17042102 | rs2220427 | 1 | 1 | 2.07E−16 | 112026230 | 71420 |
| rs2634071 | rs2220427 | 1 | 0.528302 | 2.16E−13 | 112026824 | 72014 |
| rs2634074 | rs2220427 | 1 | 0.433962 | 5.12E−12 | 112034645 | 79835 |
| rs17042121 | rs2220427 | 1 | 1 | 1.43E−20 | 112034705 | 79895 |
| rs10516563 | rs2220427 | 1 | 1 | 1.43E−20 | 112035326 | 80516 |
| rs4605724 | rs2220427 | 1 | 1 | 1.43E−20 | 112042685 | 87875 |
| rs2466455 | rs2220427 | 1 | 0.491956 | 5.72E−12 | 112043219 | 88409 |
| rs2350269 | rs2220427 | 1 | 1 | 1.42E−19 | 112044728 | 89918 |
| rs6533527 | rs2220427 | 1 | 1 | 1.43E−20 | 112045118 | 90308 |
| rs2723334 | rs2220427 | 1 | 0.433962 | 5.12E−12 | 112046356 | 91546 |
| rs17042144 | rs2220427 | 1 | 1 | 1.43E−20 | 112047270 | 92460 |
| rs1906618 | rs2220427 | 1 | 1 | 2.67E−19 | 112053026 | 98216 |
| rs1906617 | rs2220427 | 1 | 1 | 1.43E−20 | 112053418 | 98608 |
| rs6847935 | rs2220427 | 1 | 0.921053 | 1.10E−18 | 112054255 | 99445 |

TABLE 19-continued

Markers in linkage disequilibrium with marker rs2220427 and markerrs10033464 by values for $r^2$ of greater than 0.1. LD was calculated based on the HapMap CEU population sample.

| Marker 1 | anchor | D' | r2 | P-value | Pos in B35 | Pos in SEQ ID NO: 50 |
|---|---|---|---|---|---|---|
| rs1906616 | rs2220427 | 1 | 0.433962 | 5.12E−12 | 112055172 | 100362 |
| rs12646447 | rs2220427 | 1 | 1 | 1.84E−20 | 112056930 | 102120 |
| rs1906615 | rs2220427 | 1 | 0.433962 | 5.12E−12 | 112059402 | 104592 |
| rs12646754 | rs2220427 | 1 | 1 | 2.08E−20 | 112061176 | 106366 |
| rs2129983 | rs2220427 | 1 | 0.428571 | 6.61E−12 | 112061684 | 106874 |
| rs2129982 | rs2220427 | 1 | 0.433962 | 5.12E−12 | 112061747 | 106937 |
| rs2129981 | rs2220427 | 1 | 1 | 1.43E−20 | 112061803 | 106993 |
| rs12639654 | rs2220427 | 1 | 1 | 1.43E−20 | 112062899 | 108089 |
| rs6817105 | rs2220427 | 1 | 1 | 1.62E−20 | 112063372 | 108562 |
| rs17042171 | rs2220427 | 1 | 1 | 1.43E−20 | 112065891 | 111081 |
| rs1906591 | rs2220427 | 1 | 1 | 1.43E−20 | 112066493 | 111683 |
| rs1906592 | rs2220427 | 1 | 1 | 1.26E−19 | 112066608 | 111798 |
| rs2200732 | rs2220427 | 1 | 1 | 1.85E−19 | 112067646 | 112836 |
| rs2200733 | rs2220427 | 1 | 1 | 1.43E−20 | 112067773 | 112963 |
| rs4611994 | rs2220427 | 1 | 1 | 1.43E−20 | 112068645 | 113835 |
| rs4540107 | rs2220427 | 1 | 1 | 1.43E−20 | 112068706 | 113896 |
| rs1906593 | rs2220427 | 1 | 1 | 1.62E−20 | 112069526 | 114716 |
| rs1906596 | rs2220427 | 1 | 1 | 2.68E−20 | 112069840 | 115030 |
| rs1906599 | rs2220427 | 1 | 0.433962 | 5.12E−12 | 112070290 | 115480 |
| rs13143308 | rs2220427 | 1 | 0.438445 | 5.36E−12 | 112072023 | 117213 |
| rs6843082 | rs2220427 | 1 | 0.433962 | 5.12E−12 | 112075671 | 120861 |
| rs11931959 | rs2220427 | 1 | 0.249653 | 7.85E−09 | 112077289 | 122479 |
| rs13121924 | rs2220427 | 1 | 0.156089 | 9.36E−07 | 112078423 | 123613 |
| rs2129979 | rs2220427 | 1 | 0.256789 | 5.78E−09 | 112078601 | 123791 |
| rs723363 | rs2220427 | 1 | 0.156089 | 9.36E−07 | 112082105 | 127295 |
| rs7697491 | rs2220427 | 1 | 0.154058 | 1.07E−06 | 112083422 | 128612 |
| rs13141190 | rs2220427 | 1 | 0.156089 | 9.36E−07 | 112086218 | 131408 |
| rs6533530 | rs2220427 | 1 | 0.156089 | 9.36E−07 | 112089540 | 134730 |
| rs6533531 | rs2220427 | 1 | 0.156089 | 9.36E−07 | 112089569 | 134759 |
| rs3866831 | rs2220427 | 1 | 0.156089 | 9.36E−07 | 112089718 | 134908 |
| rs3866832 | rs2220427 | 0.857992 | 0.109603 | 0.000186 | 112091304 | 136494 |
| rs11098083 | rs10033464 | 0.407276 | 0.12964 | 0.00205 | 111855920 | |
| rs11721423 | rs10033464 | 0.365905 | 0.11129 | 0.003321 | 111858873 | |
| rs10005945 | rs10033464 | 0.433962 | 0.101848 | 0.004763 | 111860013 | |
| rs7668322 | rs10033464 | 0.46291 | 0.133423 | 0.000953 | 111906200 | |
| rs2197815 | rs10033464 | 0.660377 | 0.300172 | 2.55E−06 | 111924481 | |
| rs6831623 | rs10033464 | 1 | 0.511236 | 3.33E−10 | 111964677 | 9867 |
| rs7661383 | rs10033464 | 0.637611 | 0.21478 | 0.000011 | 111979181 | 24371 |
| rs7667461 | rs10033464 | 0.637611 | 0.21478 | 0.000011 | 111979738 | 24928 |
| rs1900827 | rs10033464 | 0.735008 | 0.134278 | 0.000368 | 111981343 | 26533 |
| rs998101 | rs10033464 | 0.635887 | 0.20914 | 0.000014 | 111988219 | 33409 |
| rs12646859 | rs10033464 | 0.719793 | 0.271646 | 0.000191 | 111992237 | 37427 |
| rs12498380 | rs10033464 | 0.60232 | 0.178165 | 0.000097 | 111992563 | 37753 |
| rs7690164 | rs10033464 | 0.496308 | 0.148782 | 0.005455 | 111994069 | 39259 |
| rs11098090 | rs10033464 | 0.551083 | 0.169161 | 0.000104 | 112014012 | 59202 |
| rs2634073 | rs10033464 | 0.640189 | 0.223694 | 8.35E−06 | 112023387 | 68577 |
| rs2634071 | rs10033464 | 0.637611 | 0.21478 | 0.000011 | 112026824 | 72014 |
| rs2634074 | rs10033464 | 1 | 0.433962 | 5.12E−12 | 112034645 | 79835 |
| rs2466455 | rs10033464 | 1 | 0.428256 | 1.77E−09 | 112043219 | 88409 |
| rs2723334 | rs10033464 | 1 | 0.433962 | 5.12E−12 | 112046356 | 91546 |
| rs1906616 | rs10033464 | 1 | 0.433962 | 5.12E−12 | 112055172 | 100362 |
| rs1906615 | rs10033464 | 1 | 0.433962 | 5.12E−12 | 112059402 | 104592 |
| rs2129983 | rs10033464 | 1 | 0.428571 | 6.61E−12 | 112061684 | 106874 |
| rs2129982 | rs10033464 | 1 | 0.433962 | 5.12E−12 | 112061747 | 106937 |
| rs12503217 | rs10033464 | 1 | 1 | 1.43E−20 | 112063765 | 108955 |
| rs12510087 | rs10033464 | 1 | 1 | 1.43E−20 | 112066632 | 111822 |
| rs1906599 | rs10033464 | 1 | 0.433962 | 5.12E−12 | 112070290 | 115480 |
| rs6852357 | rs10033464 | 1 | 1 | 1.43E−20 | 112071939 | 117129 |
| rs13143308 | rs10033464 | 1 | 0.421583 | 2.22E−11 | 112072023 | 117213 |
| rs4833456 | rs10033464 | 1 | 0.923858 | 6.67E−19 | 112073911 | 119101 |
| rs4400058 | rs10033464 | 1 | 1 | 1.43E−20 | 112074277 | 119467 |
| rs6843082 | rs10033464 | 1 | 0.433962 | 5.12E−12 | 112075671 | 120861 |
| rs2171592 | rs10033464 | 1 | 1 | 1.43E−20 | 112078392 | 123582 |
| rs13121924 | rs10033464 | 1 | 0.156089 | 9.36E−07 | 112078423 | 123613 |
| rs2350539 | rs10033464 | 1 | 1 | 1.43E−20 | 112078814 | 124004 |
| rs1906606 | rs10033464 | 1 | 1 | 1.43E−20 | 112080996 | 126186 |
| rs723364 | rs10033464 | 1 | 1 | 1.43E−20 | 112082075 | 127265 |
| rs723363 | rs10033464 | 1 | 0.156089 | 9.36E−07 | 112082105 | 127295 |
| rs7697491 | rs10033464 | 1 | 0.154058 | 1.07E−06 | 112083422 | 128612 |
| rs2220429 | rs10033464 | 1 | 1 | 1.43E−20 | 112085089 | 130279 |
| rs13141190 | rs10033464 | 1 | 0.156089 | 9.36E−07 | 112086218 | 131408 |
| rs4032976 | rs10033464 | 1 | 1 | 1.62E−20 | 112086371 | 131561 |
| rs3853440 | rs10033464 | 1 | 1 | 1.62E−20 | 112087213 | 132403 |

TABLE 19-continued

Markers in linkage disequilibrium with marker rs2220427 and markerrs10033464 by values for $r^2$ of greater than 0.1. LD was calculated based on the HapMap CEU population sample.

| Marker 1 | anchor | D' | r2 | P-value | Pos in B35 | Pos in SEQ ID NO: 50 |
|---|---|---|---|---|---|---|
| rs3853441 | rs10033464 | 1 | 1 | 1.43E−20 | 112087344 | 132534 |
| rs3853442 | rs10033464 | 1 | 1 | 1.43E−20 | 112087632 | 132822 |
| rs3853443 | rs10033464 | 1 | 1 | 1.43E−20 | 112087733 | 132923 |
| rs4124158 | rs10033464 | 1 | 1 | 1.10E−17 | 112087798 | 132988 |
| rs4124159 | rs10033464 | 1 | 1 | 1.43E−20 | 112087847 | 133037 |
| rs12506083 | rs10033464 | 1 | 1 | 1.43E−20 | 112088016 | 133206 |
| rs6533530 | rs10033464 | 1 | 0.156089 | 9.36E−07 | 112089540 | 134730 |
| rs6533531 | rs10033464 | 1 | 0.156089 | 9.36E−07 | 112089569 | 134759 |
| rs3866831 | rs10033464 | 1 | 0.156089 | 9.36E−07 | 112089718 | 134908 |
| rs4032975 | rs10033464 | 1 | 1 | 7.06E−20 | 112089842 | 135032 |
| rs4032974 | rs10033464 | 1 | 1 | 1.43E−20 | 112090140 | 135330 |
| rs3866832 | rs10033464 | 1 | 0.148936 | 1.44E−06 | 112091304 | 136494 |
| rs7654080 | rs10033464 | 1 | 0.151515 | 0.002495 | 112585323 | |

References

1. Go, A. S. et al. Prevalence of diagnosed atrial fibrillation in adults: national implications for rhythm management and stroke prevention: the AnTicoagulation and Risk Factors in Atrial Fibrillation (ATRIA) Study. Jama 285, 2370-5 (2001).
2. Miyasaka, Y. et al. Secular trends in incidence of atrial fibrillation in Olmsted County, Minnesota, 1980 to 2000, and implications on the projections for future prevalence. Circulation 114, 119-25 (2006).
3. Arnar, D. O. et al. Familial aggregation of atrial fibrillation in Iceland. Eur Heart J 27, 708-12 (2006).
4. Fox, C. S. et al. Parental atrial fibrillation as a risk factor for atrial fibrillation in offspring. Jama 291, 2851-5 (2004).
5. Ellinor, P. T., Yoerger, D. M., Ruskin, J. N. & MacRae, C. A. Familial aggregation in lone atrial fibrillation. Hum Genet. 118, 179-84 (2005).
6. Chen, Y. H. et al. KCNQ1 gain-of-function mutation in familial atrial fibrillation. Science 299, 251-4 (2003).
7. Yang, Y. et al. Identification of a KCNE2 gain-of-function mutation in patients with familial atrial fibrillation. Am J Hum Genet. 75, 899-905 (2004).
8. Xia, M. et al. A Kir2.1 gain-of-function mutation underlies familial atrial fibrillation. Biochem Biophys Res Commun 332, 1012-9 (2005).
9. Olson, T. M. et al. Kv1.5 channelopathy due to KCNA5 loss-of-function mutation causes human atrial fibrillation. Hum Mol Genet. 15, 2185-91 (2006).
10. Hong, K., Bjerregaard, P., Gussak, I. & Brugada, R. Short QT syndrome and atrial fibrillation caused by mutation in KCNH2. J Cardiovasc Electrophysiol 16, 394-6 (2005).
11. Ellinor, P. T. et al. Mutations in the long QT gene, KCNQ1, are an uncommon cause of atrial fibrillation. Heart 90, 1487-8 (2004).
12. Ellinor, P. T., Petrov-Kondratov, V. I., Zakharova, E., Nam, E. G. & MacRae, C. A. Potassium channel gene mutations rarely cause atrial fibrillation. BMC Med Genet. 7, 70 (2006).
13. Franco, D. & Campione, M. The role of Pitx2 during cardiac development. Linking left-right signaling and congenital heart atrial fibrillation and/or strokes. Trends Cardiovasc Med 13, 157-63 (2003).
14. Faucourt, M., Houliston, E., Besnardeau, L., Kimelman, D. & Lepage, T. The pitx2 homeobox protein is required early for endoderm formation and nodal signaling. Dev Biol 229, 287-306 (2001).
15. Mommersteeg, M. T. et al. Molecular Pathway for the Localized Formation of the Sinoatrial Node. Circ Res (2007).
16. A haplotype map of the human genome. Nature 437, 1299-320 (2005).
17. Waldo, A. L. The interrelationship between atrial fibrillation and atrial flutter. Prog Cardiovasc Dis 48, 41-56 (2005).
18. Zini, S. et al. Identification of metabolic pathways of brain angiotensin II and III using specific aminopeptidase inhibitors: predominant role of angiotensin III in the control of vasopressin release. Proc Natl Acad Sci USA 93, 11968-73 (1996).
19. Gretarsdottir, S. et al. The gene encoding phosphodiesterase 4D confers risk of ischemic stroke. Nat Genet. 35, 131-8 (2003).
20. Falk, C. T. & Rubinstein, P. Haplotype relative risks: an easy reliable way to construct a proper control sample for risk calculations. Ann Hum Genet. 51 (Pt 3), 227-33 (1987).
21. Mantel, N. & Haenszel, W. Statistical aspects of the analysis of data from retrospective studies of atrial fibrillation and/or stroke. J Natl Cancer Inst. 22, 719-48 (1959).
22. Grant, S. F. et al. Variant of transcription factor 7-like 2 (TCF7L2) gene confers risk of type 2 diabetes. Nat Genet. 38, 320-3 (2006).
23. Yang, X. et al. Development and validation of stroke risk equation for Hong Kong Chinese patients with type 2 diabetes: the Hong Kong Diabetes Registry. Diabetes Care 30, 65-70 (2007).
24. Baum, L. et al. *Methylenetetrahydrofolate reductase gene A*222V polymorphism and risk of ischemic stroke. Clin Chem Lab Med 42, 1370-6 (2004).
25. Kutyavin, I. V. et al. A novel endonuclease IV post-PCR genotyping system. Nucleic Acids Research 34, e128 (2006).
26. Amundadottir, L. T. et al. A common variant associated with prostate cancer in European and African populations. Nat Genet. 38, 652-8 (2006).
27. Gretarsdottir, S. et al. The gene encoding phosphodiesterase 4D confers risk of ischemic stroke. Nat Genet. 35, 131-8 (2003).
28. Falk, C. T. & Rubinstein, P. Haplotype relative risks: an easy reliable way to construct a proper control sample for risk calculations. Ann Hum Genet. 51 (Pt 3), 227-33 (1987).

29. Mantel, N. & Haenszel, W. Statistical aspects of the analysis of data from retrospective studies of atrial fibrillation and/or stroke. J Natl Cancer Inst. 22, 719-48 (1959).

30. Grant, S. F. et al. Variant of transcription factor 7-like 2 (TCF7L2) gene confers risk of type 2 diabetes. Nat Genet. 38, 320-3 (2006).

31. Devlin, B. & Roeder, K. Genomic Control for association studies. Biometrics 55, 997-1004 (1999).

32. Devlin, B., Bacanu, S.-A. & Roeder, K. Genomic control to the extreme. Nature Genetics 36, 1129-1130 (2004).

33. Nomenclature and criteria for diagnosis of ischemic heart atrial fibrillation and/or stroke. Report of the Joint International Society and Federation of Cardiology/World Health Organization task force on standardization of clinical nomenclature. Circulation 59, 607-9 (1979).

34. Alpert, J. S., Thygesen, K., Antman, E. & Bassand, J. P. Myocardial infarction redefined—a consensus document of The Joint European Society of Cardiology/American College of Cardiology Committee for the redefinition of myocardial infarction. J Am Coll Cardiol 36, 959-69 (2000).

35. Monks, S. A. et al. Genetic inheritance of gene expression in human cell lines. Am J Hum Genet. 75, 1094-105 (2004).

36. Schadt, E. E. et al. Genetics of gene expression surveyed in maize, mouse and man. Nature 422, 297-302 (2003).

Example 3

Association of Chromosome 4 Variants to Ischemic Stroke

Stroke is a common cause of death and the leading cause of adult disability in Western societies. It is now also becoming a major health problem in low-income and middle-income countries due to population ageing and changes in modifiable risk factors for cardiovascular diseases[1]. Stroke is not a single disease but a highly complex syndrome consisting of a group of heterogeneous disorders with many genetic and environmental risk factors[2,3]. Studies on twins, family history and animal models[4-8] provide evidence for genetic contribution to the common forms of stroke but no major risk variant has yet been identified showing consistent results across populations.

Ischemic strokes (IS), accounting for the majority of cerebral insults (>80%), result from thrombosis or embolism leading to obstruction of cerebral arteries. Various pathophysiological mechanisms can cause IS but the most common ones are large artery atherosclerosis (LAA), cardioembolic stroke (CES) and small vessel disease (SVD)[9].

Methods

Study Populations.

Iceland: Icelandic stroke patients were recruited from a registry of over 4,000 individuals diagnosed with ischemic stroke or TIA at the only university hospital in Reykjavik, the Landspitali University Hospital, during the years 1993 to 2006. Stroke patients have been enrolled over the last nine years through the cardiovascular disease (CVD) genetics program at deCODE. Stroke diagnosis was clinically confirmed by neurologists (see below). The discovery cohort included 1,661 patients and when analysing the SNPs on 4q25 we used an additional set of 282 patients (mean age±SD: 77.2±11.3 years, 45% females). We used 25,708 controls (mean age±SD: 59.2±21.1 years, 59% females) from various genetic programs under study at Decode, including: abdominal aneurysm (250), atrial fibrillation (1,150), addiction (750), Alzheimer (350), anxiety (200), asthma (1300), COPD (850), colon cancer (200), deep vein thrombosis (550), dyslexia (200), infection diseases (250), longevity (400), lung cancer (750), myocardial infarction (2,400), migraine (1,100), peripheral artery disease (1,200), polycystic ovary syndrome (1,200), pre-eclampsia (700), prostate cancer (400), psoriasis (750), rheumatic arthritis (550), restless leg syndrome (350), and type 2 diabetes (400).

The study was approved by the Data Protection Commission of Iceland (DPC) and the National Bioethics Committee of Iceland. All participants gave informed consent.

Sweden: Swedish patients with ischemic stroke attending the stroke unit or the stroke outpatient clinic at Karolinska University Hospital, Huddinge unit in Stockholm, Sweden, were recruited from 1996 to 2002 as part of an ongoing genetic epidemiology study, the South Stockholm Ischemic Stroke Study (SSISS) (mean age±SD: 67.3±11.8 years, 44% females). The Swedish controls used in this study are population-based controls recruited from the same region in central Sweden as the patients, representing the general population in this area. The individuals were either blood donors recruited at the Huddinge or Karolinska University Hospitals or healthy volunteers (recruited in 1990-1994) recruited by the Clinical Chemistry Department at the Karolinska University Hospital to represent a normal reference population (mean age±SD: 46.8±15.9 years for controls from Huddinge hospital, 41% females, age information not available for blood donors recruited at the Karolinska hospital). The study was approved by the Bioethics Committee of Karolinska Institutet.

South-Germany: The German population, herein referred to as Germany-S, consisted of IS patients consecutively recruited during the period 2001-2006 at the stroke unit of the Department of Neurology, Klinikum Grosshadern, University of Munich, Germany (mean age±SD: 65.3±13.7 years, 38% females). The control group consisted of age and gender matched individuals without a history of cardiovascular disease (mean age±SD: 62.7±10.9 years, 38% females). These were selected from the KORA S4 study, a community based epidemiological project near Munich[23]. The study was approved by the local ethics committee and informed consent was obtained from all individuals (or relatives or legal guardians).

Westphalia region, Germany: The second German population, referred to as Germany-W, recruited ischemic stroke patients through hospitals participating in the regional Westphalian Stroke Register, located in the west of the country, during the period 2000-2003 (mean age±SD: 70.4±12.6 years, 53% females). Population controls without a self-reported history of stroke were drawn from the cross-sectional, prospective, population based Dortmund Health Study[24], conducted in the same region, and subsequently frequency matched to the cases (mean age±SD: 52.3±13.7 years, 53% females). Both studies were approved by the ethics committee of the University of Munster. All participants gave their informed consent.

SE-England, United Kingdom. Ischemic stroke patients of European descent attending a cerebrovascular service were recruited 1995-2002. All cases were phenotyped by one experienced stroke neurologist with review of original imaging (mean age±SD: 64.6±12.7 years, 41% females). Community controls free of symptomatic cerebrovascular disease were also recruited by sampling family doctor lists from the same geographical region as the patients. Sampling was stratified to provide a similar distribution of age and gender as in the patient group (mean age±SD: 64.8±8.6 years, 41% females). The study was approved by local research ethics committees and informed consent was obtained from all participants.

Phenotyping. Only patients with ischemic but not with hemorrhagic strokes were included in the study. All patients had clinically relevant diagnostic work-up performed, including brain imaging with computed tomography (CT) or/and magnetic resonance imaging (MRI) as well as ancillary diagnostic investigations including duplex ultrasonography of the carotid and vertebral arteries, echocardiography, Holter monitoring, MR-angiography, CT-angiography and blood tests. Patients with clinically confirmed Transient Ischemic Attack (TIA) were included in the Ischemic stroke group from Iceland, Germany-S and Sweden. Patients were classified into etiologic subtypes according to the Trial of Org 10172 in Acute Stroke Treatment (TOAST)[25]. This classification includes six categories: (1) large-artery occlusive disease (large vessel disease), (2) cardioembolism (cardiogenic stroke), (3) small vessel disease (lacunar stroke), (4) other determined etiology, (5) etiology unknown despite diagnostic efforts, or (6) more than one etiology. Patients classified into the TOAST categories 4-6 were excluded from the stroke population from Germany-W. In Iceland, patients were classified as having large-artery occlusive disease if stenosis was ≥70% which is a stricter criterion than usually used i.e. ≥50%. Classification of stroke patients into subtypes according to the Trial of Org 10172 in Acute Stroke Treatment (TOAST) classification system[25] in the Icelandic discovery and the four replication sample sets is listed in Table 1.

Illumina genome-wide genotyping. All Icelandic cases and control samples were assayed with the Infinium HumanHap300 SNP chips (Illumina), containing 317,503 tagging SNPs derived from phase 1 of the International HapMap project. OF the SNPs assayed on the chip, 6,622 SNPs were excluded because they showed either (i) a call rate lower than 95% in cases or controls, (ii) minor allele frequency less than 1% in the population or (iii) significant distortion from Hardy-Weinberg equilibrium in the controls ($P<1\times10^{-10}$). Any sample with yield <98% were excluded from the analysis. In the final analysis 310,881 SNPs were used.

Single SNP Genotyping. Single-SNP genotyping for all 121 SNP was carried out at deCODE genetics in Reykjavik, Iceland using the Centaurus (Nanogen) platform[26]. The quality of each SNP assay was evaluated by comparing the genotyping of the CEU HapMap samples with the publicly available HapMap data. All SNPs passed mismatch tests, linkage disequilibrium (LD) tests and were in Hardy-Weinberg equilibrium.

Association analysis. For association analysis a standard likelihood ratio statistics was used, as implemented in the NEMO software created at deCODE[27], to calculate two-sided P values and odds ratio (OR) for each individual allele, assuming a multiplicative model for risk, i.e., that the risk of the two alleles a person carries multiply. Allelic frequencies, rather than carrier frequencies are presented for the markers.

At the locus on chromosome 4q25, we analysed 3 SNPs, rs2200733, rs10033464 and rs13143308. The third SNP, rs13143308, is in high LD with both rs2200733 and rs10033464 (D'=0.99 for both) and has a minor allele that corresponds completely to chromosomes carrying either rs2200733 allele T or rs10033464 allele T. It was genotyped in all populations using a Centaurus assay, and was used to infer genotypes for those individuals who had missing data for either rs2200733 or rs10033464 on the Illumina Infinium platform. In Table 21 and Supplementary Table 22, P values and OR for both risk alleles rs2200733-T and rs10033464-T were computed on the basis of comparison with the wild-type rs2200733 allele C, rs13143308 allele G, rs10033464 allele G haplotype, which contains neither of the at-risk alleles[11].

For the Icelandic study groups, P values are given after adjustment for the relatedness of the subjects and other possible population stratification using the method of genomic control[10]. The inflation factors for the chi-squared statistics are estimated to be 1.07, 1.04, 1.06 and 1.02 for the genome-wide association analysis of the IS, CES, LAA of SVD patient groups respectively. With the additional cases and controls typed for the 4q locus, we estimated the inflation factors using simulations as previously described[28]. The resulting inflation factors are 1.09, 1.03, 1.06, 1.05, 1.01, 1.00, 1.01 and 1.00, for the groups IS, CES, IS excl CES, LVD, SVD, other, unknown and more than one cause, respectively.

Due to the large number of controls used, the effective samples size after adjusting for the relatedness of the cases and controls corresponds to testing 2,690 IS patients and 2,690 controls. The corresponding effective sample sizes for the CES, LAA and SVD patients are 710, 417 and 467, respectively.

Results from multiple case-control groups were combined using a Mantel-Haenszel model in which the groups were allowed to have different population frequencies for alleles, haplotypes and genotypes but were assumed to have a common relative risk[29]

Results

The association of variants within the LD Block C04 region to Ischemic Stroke was investigated. In order to investigate further the contribution of the two AF risk variants on 4q25, rs2200733 and rs10033464, to the risk of developing Ischemic Stroke and its subtypes, large artery atherosclerosis (LAA), cardioembolic stroke (CES) and small vessel disease (SVD), we genotyped marker rs2200733 and marker rs10033464 in Icelandic samples, and for replication purposes we also analyzed replication data sets in cohorts from South-Germany (1,181 cases and 1,189 controls, Germany-S), Sweden (1,032 cases and 1,387 controls), Westphalia region in Germany (1,388 cases and 1,106 controls, Germany-W), and United Kingdom (654 cases/676 controls, UK). The phenotype classification of the study cohorts is shown in Table 20.

TABLE 20

TOAST subclassification of genotyped stroke cases, n (%)

| | Discovery group | Replication groups | | | |
|---|---|---|---|---|---|
| | Iceland | Germany-S | Sweden | Germany-W | United Kingdom |
| Ischemic stroke | 1943 | 1183 | 1066 | 1391 | 654 |
| TOAST subtyping: | 1443 | 1183 | 1061 | 1389 | 654 |
| Cardioembolism | 385 (45) | 297 (38) | 185 (37) | 554 (40) | 78 (18) |
| Large artery atherosclerosis | 229 (27) | 372 (47) | 230 (46) | 560 (40) | 232 (55) |
| Small vessel disease | 246 (29) | 118 (15) | 82 (16) | 275 (20) | 114 (27) |
| other cause | 42 | 67 | 56 | not recruited | 3 |

TABLE 20-continued

TOAST subclassification of genotyped stroke cases, n (%)

| | Discovery group | Replication groups | | | |
|---|---|---|---|---|---|
| | Iceland | Germany-S | Sweden | Germany-W | United Kingdom |
| more than one cause | 34 | | 42 | not recruited | 40 |
| unknown cause | 507 | 329 | 466 | not recruited | 187 |

TOAST = Trial of Org 10172 in Acute Stroke Treatment.

Additional patients (282) and controls (14,893) from Iceland were also genotyped for these particular SNPs. The association test was done by comparing each SNP with the wild-type haplotype (see Methods). As shown in Table 21, rs2200733 conferred an increased risk of Ischemic Stroke in all sample sets, and the association with Ischemic Stroke was highly significant with a combined OR=1.26 ($P=8.8\times10^{-11}$). For rs10033464, the association with Ischemic Stroke was not significant (OR=1.03, P=0.45). Both SNPs however, associated significantly with Cardiembolic Stroke and this risk was significantly greater than in the Ischemic Stroke group as a whole (rs2200733: OR=1.53, $P=1.5\times10^{-12}$; rs10033464: OR=1.27, $P=5.9\times10^{-4}$). This is as expected given the known contribution of Atrial Fibrillation to this subphenotype. By removing patients with Cardioembolic Stroke from the Ischemic Stroke group, the observed effect for both SNPs was weaker in the remaining Ischemic Stroke patients, but remained significant for the stronger variant (rs2200733: OR=1.18, $P=1.5\times10^{-5}$, rs10033464: OR=0.96, P=0.39). Apart from Cardioembolic Stroke, Large Artery Atherosclerosis and stroke of undetermined cause were the only subphenotypes showing significant association with rs2200733 (OR=1.22, $P=1.5\times10^{-3}$, Table 2 and OR=1.18, P=0.01). These results suggest that a significant portion of strokes classified as either cryptogenic stroke or large artery atherosclerosis may be due to undiagnosed, intermittent AF.

TABLE 21

Association between rs2200733 (allele T) and rs1033464 (allele T) and Ischemic stroke. Association results for rs2200733 allele T and rs10033464 allele T for ischemic stroke and the subphenotypes; cardioembolic stroke, large artery atherosclerosis and small vessel disease, in five study populations. Also presented are the results for ischemic stroke after excluding patients with cardioembolism. Results for each phenotype are also included after combining the study populations using a Mantel-Haenszel model (All groups). Number of controls (m) and cases (n) is shown in parenthesis, the allelic frequencies in each group, the OR with a 95% CI and two-sided P value for comparison to the wild type haplotype (see Supplementary Methods). The results for the Icelandic population are adjusted for relatedness of the individuals.

| | Phenotype | | | | | | | |
|---|---|---|---|---|---|---|---|---|
| | rs2200733-T frequency | | | | rs10033464-T frequency | | | |
| Study population (m/n) | Controls | Cases | OR (95% CI) | P | Controls | Cases | OR (95% CI) | P |
| Ischemic stroke | | | | | | | | |
| Iceland (25708/1943) | 0.119 | 0.142 | 1.23 (1.11-1.36) | $4.7\times10^{-5}$ | 0.082 | 0.085 | 1.07 (0.95-1.21) | 0.28 |
| Germany-S (1186/1183) | 0.118 | 0.138 | 1.19 (1.00-1.41) | 0.05 | 0.093 | 0.083 | 0.90 (0.73-1.10) | 0.31 |
| Germany-W (1107/1391) | 0.114 | 0.146 | 1.34 (1.13-1.58) | $7.0\times10^{-4}$ | 0.092 | 0.096 | 1.10 (0.91-1.33) | 0.34 |
| Sweden (740/1066) | 0.098 | 0.121 | 1.27 (1.02-1.58) | 0.03 | 0.113 | 0.111 | 1.01 (0.81-1.24) | 0.96 |
| UK (676/654) | 0.087 | 0.119 | 1.43 (1.11-1.74) | 0.0056 | 0.090 | 0.088 | 1.02 (0.78-1.33) | 0.90 |
| All groups (29417/6237) | 0.107 | 0.133 | 1.26 (1.17-1.35) | $8.8\times10^{-11}$ | 0.094 | 0.093 | 1.03 (0.95-1.12) | 0.45 |
| Cardioembolism | | | | | | | | |
| Iceland (25708/385) | 0.119 | 0.164 | 1.50 (1.22-1.85) | $1.1\times10^{-4}$ | 0.082 | 0.105 | 1.39 (1.09-1.79) | 0.009 |
| Germany-S (1186/297) | 0.118 | 0.175 | 1.61 (1.25-2.08) | $2.5\times10^{-4}$ | 0.093 | 0.096 | 1.11 (0.81-1.52) | 0.502 |
| Germany-W (1107/554) | 0.114 | 0.161 | 1.52 (1.23-1.88) | $1.0\times10^{-4}$ | 0.092 | 0.104 | 1.22 (0.95-1.56) | 0.113 |
| Sweden (740/185) | 0.098 | 0.149 | 1.67 (1.18-2.36) | $4.0\times10^{-3}$ | 0.113 | 0.133 | 1.28 (0.90-1.82) | 0.162 |
| UK (676/78) | 0.087 | 0.090 | 1.08 (0.60-1.95) | 0.79 | 0.090 | 0.122 | 1.42 (0.83-2.43) | 0.198 |
| All groups (29417/1499) | 0.107 | 0.148 | 1.53 (1.36-1.72) | $1.5\times10^{-12}$ | 0.094 | 0.112 | 1.27 (1.11-1.45) | $5.9\times10^{-4}$ |
| Ischemic stroke excl Cardioembolism | | | | | | | | |
| Iceland (25708/1558) | 0.119 | 0.136 | 1.17 (1.05-1.31) | 0.01 | 0.082 | 0.081 | 1.00 (0.87-1.14) | 0.95 |
| Germany-S (1186/886) | 0.118 | 0.125 | 1.06 (0.87-1.28) | 0.57 | 0.093 | 0.078 | 0.83 (0.67-1.04) | 0.11 |
| Germany-W (1107/837) | 0.114 | 0.136 | 1.22 (1.01-1.48) | 0.04 | 0.092 | 0.091 | 1.02 (0.82-1.28) | 0.84 |
| Sweden (740/881) | 0.098 | 0.115 | 1.19 (0.95-1.50) | 0.13 | 0.113 | 0.106 | 0.95 (0.76-1.19) | 0.66 |
| UK (676/576) | 0.087 | 0.123 | 1.48 (1.14-1.91) | 0.003 | 0.090 | 0.083 | 0.96 (0.73-1.28) | 0.80 |
| All groups (29417/4738) | 0.107 | 0.127 | 1.18 (1.10-1.28) | $1.5\times10^{-5}$ | 0.094 | 0.088 | 0.96 (0.88-1.05) | 0.39 |
| Large artery atherosclerosis | | | | | | | | |
| Iceland (25708/229) | 0.119 | 0.157 | 1.41 (1.08-1.86) | 0.012 | 0.082 | 0.096 | 1.25 (0.89-1.74) | 0.19 |
| Germany-S (1186/372) | 0.118 | 0.117 | 0.96 (0.75-1.25) | 0.78 | 0.093 | 0.071 | 0.74 (0.54-1.00) | 0.05 |
| Germany-W (1107/560) | 0.114 | 0.140 | 1.28 (1.03-1.59) | 0.03 | 0.092 | 0.100 | 1.14 (0.89-1.46) | 0.30 |
| Sweden (740/230) | 0.098 | 0.094 | 0.94 (0.65-1.34) | 0.72 | 0.113 | 0.096 | 0.82 (0.58-1.17) | 0.27 |

TABLE 21-continued

Association between rs2200733 (allele T) and rs1033464 (allele T) and Ischemic stroke. Association results for rs2200733 allele T and rs10033464 allele T for ischemic stroke and the subphenotypes; cardioembolic stroke, large artery atherosclerosis and small vessel disease, in five study populations. Also presented are the results for ischemic stroke after excluding patients with cardioembolism. Results for each phenotype are also included after combining the study populations using a Mantel-Haenszel model (All groups). Number of controls (m) and cases (n) is shown in parenthesis, the allelic frequencies in each group, the OR with a 95% CI and two-sided P value for comparison to the wild type haplotype (see Supplementary Methods). The results for the Icelandic population are adjusted for relatedness of the individuals.

| | Phenotype | | | | | | | |
|---|---|---|---|---|---|---|---|---|
| | rs2200733-T frequency | | | | rs10033464-T frequency | | | |
| Study population (m/n) | Controls | Cases | OR (95% CI) | P | Controls | Cases | OR (95% CI) | P |
| UK (676/232) | 0.087 | 0.138 | 1.66 (1.19-2.31) | $3.0 \times 10^{-3}$ | 0.090 | 0.071 | 0.82 (0.55-1.23) | 0.34 |
| All groups (29417/1623) | 0.107 | 0.129 | 1.22 (1.08-1.38) | $1.5 \times 10^{-3}$ | 0.094 | 0.087 | 0.96 (0.83-1.11) | 0.57 |
| Small vessel disease | | | | | | | | |
| Iceland (25708/246) | 0.119 | 0.112 | 0.94 (0.71-1.24) | 0.64 | 0.082 | 0.085 | 1.03 (0.75-1.42) | 0.86 |
| Germany-S (1186/118) | 0.118 | 0.145 | 1.23 (0.83-1.83) | 0.30 | 0.093 | 0.063 | 0.68 (0.40-1.14) | 0.14 |
| Germany-W (1107/275) | 0.114 | 0.126 | 1.10 (0.83-1.47) | 0.51 | 0.092 | 0.075 | 0.81 (0.57-1.14) | 0.22 |
| Sweden (740/82) | 0.098 | 0.110 | 1.11 (0.66-1.88) | 0.70 | 0.113 | 0.091 | 0.80 (0.46-1.37) | 0.42 |
| UK (676/114) | 0.087 | 0.101 | 1.18 (0.73-1.91) | 0.50 | 0.090 | 0.087 | 0.99 (0.60-1.63) | 0.97 |
| All groups (29417/835) | 0.107 | 0.119 | 1.07 (0.91-1.26) | 0.39 | 0.094 | 0.080 | 0.88 (0.73-1.05) | 0.16 |

TABLE 22

Association results for rs2200733 allele T and rs10033464 allele T for the TOAST subphenotypes; other cause, more than one cause and unknown cause in three or four study populations. Results for each phenotype are also included after combining the study populations using a Mantel-Haenszel model (All groups). Number of controls (m) and cases (n) is shown in parenthesis, the allelic frequencies in each group, the OR with a 95% CI and two-sided P value for comparison to the wild type haplotype (see Supplementary Methods). The results for the Icelandic population are adjusted for relatedness of the individuals.

| | Phenotype | | | | | | | |
|---|---|---|---|---|---|---|---|---|
| | rs2200733-T frequency | | | | rs10033464-T frequency | | | |
| Study population (m/n) | Controls | Cases | OR (95% CI) | P | Controls | Cases | OR (95% CI) | P |
| Other cause | | | | | | | | |
| Iceland (25708/42) | 0.119 | 0.155 | 1.32 (0.72-2.45) | 0.37 | 0.082 | 0.060 | 0.73 (0.31-1.75) | 0.48 |
| Germany-S (1186/67) | 0.118 | 0.119 | 1.03 (0.60-1.77) | 0.91 | 0.093 | 0.105 | 1.14 (0.64-2.04) | 0.66 |
| Sweden (740/56) | 0.098 | 0.125 | 1.36 (0.74-2.50) | 0.32 | 0.113 | 0.134 | 1.26 (0.70-2.26) | 0.44 |
| All groups (27634/168) | 0.111 | 0.133 | 1.19 (0.85-1.66) | 0.32 | 0.096 | 0.099 | 1.06 (0.74-1.54) | 0.74 |
| More than one cause | | | | | | | | |
| Iceland (25708/34) | 0.119 | 0.088 | 0.68 (0.31-1.52) | 0.35 | 0.082 | 0.044 | 0.49 (0.17-1.39) | 0.18 |
| Sweden (740/42) | 0.098 | 0.112 | 1.27 (0.61-2.66) | 0.52 | 0.113 | 0.187 | 1.84 (0.99-3.41) | 0.05 |
| UK (676/40) | 0.087 | 0.213 | 2.89 (1.54-5.39) | $8.9 \times 10^{-4}$ | 0.090 | 0.088 | 1.15 (0.51-2.61) | 0.74 |
| All groups (27124/116) | 0.101 | 0.138 | 1.48 (0.99-2.21) | 0.06 | 0.095 | 0.106 | 1.21 (0.78-1.88) | 0.41 |
| Unknown cause | | | | | | | | |
| Iceland (25708/507) | 0.119 | 0.135 | 1.15 (0.95-1.38) | 0.15 | 0.082 | 0.073 | 0.89 (0.70-1.13) | 0.35 |
| Germany-S (1186/329) | 0.118 | 0.129 | 1.10 (0.85-1.44) | 0.46 | 0.093 | 0.087 | 0.94 (0.69-1.28) | 0.70 |
| Sweden (740/466) | 0.098 | 0.126 | 1.32 (1.01-1.71) | 0.04 | 0.113 | 0.104 | 0.94 (0.72-1.23) | 0.65 |
| UK (760/187) | 0.087 | 0.102 | 1.20 (0.81-1.78) | 0.35 | 0.090 | 0.096 | 1.10 (0.74-1.64) | 0.63 |
| All groups (28310/1489) | 0.105 | 0.123 | 1.18 (1.04-1.34) | 0.01 | 0.095 | 0.090 | 0.94 (0.82-1.08) | 0.41 |

As discussed in the above (Example 2), the risk alleles of rs2200733 and rs10033464 correlate significantly with the age of diagnosis of Atrial Fibrillation. A non-significant trend in the same direction was observed in our study for the age at diagnosis of Cardioembolic Stroke (0.62 years per copy of T rs2200733, P=0.33, and 0.29 years per copy of T rs10033464, P=0.71, Table 23), suggesting that the observed age effect on AF may apply to Cardioembolic Stroke also, albeit being a weaker effect.

TABLE 23

Linear regression of age at diagnosis on the number of risk alleles of rs2200733 allele T and rs10033464 allele T. Shown are the regression coefficients and the corresponding two-sided P-values obtained using the age at diagnostics as a response (in years) and the number of at risk alleles as predictor variables. The sex was included as a covariate factor in all tests, and also the population in the test for all groups combined. Numbers of cases used in the analysis are shown in parenthesis (n).

| | rs2200733-T reg. coeff | rs2200733-T P | rs10033464-T reg. coeff | rs10033464-T P |
|---|---|---|---|---|
| Ischemic | | | | |
| Iceland (1830) | 0.11 | 0.85 | −0.35 | 0.62 |
| Germany-S (1174) | 0.29 | 0.73 | 0.85 | 0.43 |
| Sweden (780) | 0.56 | 0.56 | 1.11 | 0.23 |
| Germany-W (1352) | 0.17 | 0.80 | 1.21 | 0.14 |
| UK (654) | 0.24 | 0.83 | 0.47 | 0.71 |
| All Groups (5790) | 0.40 | 0.25 | 0.68 | 0.10 |
| Cardioembolic | | | | |
| Iceland (356) | −1.52 | 0.16 | −0.29 | 0.85 |
| Germany-S (296) | −1.72 | 0.21 | −2.53 | 0.18 |
| Sweden (173) | −2.09 | 0.20 | 0.81 | 0.62 |
| Germany-W (1352) | −0.04 | 1.00 | 0.82 | 0.53 |
| UK (78) | 7.11 | 0.084 | −5.29 | 0.16 |
| All Groups (1441) | −0.62 | 0.33 | −0.29 | 0.71 |

Discussion

Through this study on 1661 Icelandic IS patients and 10815 controls and the follow-up replication in large and well characterized European Ischemic Stroke case/control sample sets we identified and validated a risk variant on chromosome 4q25, tagged by rs2200733, that associates with Iscemic Stroke. In our study, as expected, these variants associated most strongly with the subphenotype Cardioembolic Stroke, which is a major complication of Atrial Fibrillation. The risk that is observed in Ischemic Stroke patients without Cardioembolic Stroke is possibly due to an underdiagnosis of Atrial Fibrillation and thereby Cardioembolic Stroke, since Atrial Fibrillation is often asymptomatic or intermittent and can consequently be difficult to detect in stroke patients.

Up to 30% of Ischemic Stroke are caused by cardioembolism (5, 6) of which a large proportion occurs in the presence of Atrial Fibrillation (7, 8). Atrial Fibrillation is the most common sustained cardiac arrhythmia of man and its prevalence increases with age, affecting approximately 10% of those over 80 years of age (3, 9). As such, AF is one of the most powerful independent risk factors for stroke and on a population level, AF is associated with a fourfold to fivefold increase in the risk of stroke (3, 7, 8, 10). Moreover, Carid-embolic Stroke is generally severe, reflected by greater disability, higher rates of stroke recurrence and higher mortality than in other subtypes of strokes (6, 11). Early detection of those at risk for AF is important in order to reduce the risk of suffering a future stroke. Clinical trials on stroke prevention in patients with AF have shown that anticoagulant medications (e.g. warfarin) reduce the risk of stroke substantially (7, 12) and is much more effective than anti-platelet agents such as aspirin and clopidogrel. Our results strongly suggest that a significant portion of stroke patients have undiagnosed atrial fibrillation and are classified either as cryptogenic stroke or as large vessel stroke. Such patients may have asymptomatic, intermittent AF that is not detected during routine workup of 24 to 48 hours of cardiac monitoring. This is supported by two studies of post-stroke patients who underwent another 4 to 7 days of ambulatory cardiac monitoring; the rates of intermittent AF previously undiagnosed were 5.6 and 14.3% (13, 14). Stroke patients with asymptomatic or intermittent AF would be inadequately treated if misdiagnosed instead as e.g. cryptogenic stroke or large vessel stroke since such patients are placed on an anti-platelet agent instead of warfarin. Therefore, these markers for AF may help determine which patient might benefit from prolonged cardiac monitoring as an outpatient to document the presence or absence of AF. Prospective studies are needed to determine whether these findings can be translated into better prevention or treatment for stroke.

References

1. Strong, K., Mathers, C. & Bonita, R. Preventing stroke: saving lives around the world. *Lancet Neurol* 6, 182-7 (2007).
2. Hassan, A. & Markus, H. S. Genetics and ischaemic stroke. *Brain* 123 (Pt 9), 1784-812 (2000).
3. Markus, H. Genes for stroke. *J Neurol Neurosurg Psychiatry* 75, 1229-31 (2004).
4. Flossmann, E., Schulz, U. G. & Rothwell, P. M. Systematic review of methods and results of studies of the genetic epidemiology of ischemic stroke. *Stroke* 35, 212-27 (2004).
5. Brass, L. M., Isaacsohn, J. L., Merikangas, K. R. & Robinette, C. D. A study of twins and stroke. *Stroke* 23, 221-3 (1992).
6. Jerrard-Dunne, P., Cloud, G., Hassan, A. & Markus, H. S. Evaluating the genetic component of ischemic stroke subtypes: a family history study. *Stroke* 34, 1364-9 (2003).
7. Jousilahti, P., Rastenyte, D., Tuomilehto, J., Sarti, C. & Vartialnen, E. Parental history of cardiovascular disease and risk of stroke. A prospective follow-up of 14371 middle-aged men and women in Finland. *Stroke* 28, 1361-6 (1997).
8. Rubattu, S. et al. Chromosomal mapping of quantitative trait loci contributing to stroke in a rat model of complex human disease. *Nat Genet.* 13, 429-34 (1996).
9. Dichgans, M. Genetics of ischaemic stroke. *Lancet Neurol* 6, 149-61 (2007).
10. Devlin, B. & Roeder, K. Genomic control for association studies. *Biometrics* 55, 997-1004 (1999).
11. Gudbjartsson, D. F. et al. Variants conferring risk of atrial fibrillation on chromosome 4q25. *Nature* 448, 353-7 (2007).

12. Ferro, J. M. Cardioembolic stroke: an update. *Lancet Neurol* 2, 177-88 (2003).
13. Murtagh, B. & Smalling, R. W. Cardioembolic stroke. *Curr Atheroscler Rep* 8, 310-6 (2006).
14. Lip, G. Y. & Lim, H. S. Atrial fibrillation and stroke prevention. *Lancet Neurol* 6, 981-93 (2007).
15. Wolf, P. A. & Singer, D. E. Preventing stroke in atrial fibrillation. *Am Fam Physician* 56, 2242-50 (1997).
16. Feinberg, W. M., Blackshear, J. L., Laupacis, A., Kronmal, R. & Hart, R. G. Prevalence, age distribution, and gender of patients with atrial fibrillation. Analysis and implications. *Arch Intern Med* 155, 469-73 (1995).
17. Go, A. S. et al. Prevalence of diagnosed atrial fibrillation in adults: national implications for rhythm management and stroke prevention: the AnTicoagulation and Risk Factors in Atrial Fibrillation (ATRIA) Study. *Jama* 285, 2370-5 (2001).
18. Wolf, P. A., Abbott, R. D. & Kannel, W. B. Atrial fibrillation as an independent risk factor for stroke: the Framingham Study. *Stroke* 22, 983-8 (1991).
19. Lip, G. Y. & Boos, C. J. Antithrombotic treatment in atrial fibrillation. *Heart* 92, 155-61 (2006).
20. Hart, R. G., Pearce, L. A. & Aguilar, M. I. Meta-analysis: antithrombotic therapy to prevent stroke in patients who have nonvalvular atrial fibrillation. *Ann Intern Med* 146, 857-67 (2007).
21. Barthelemy, J. C. et al. Automatic cardiac event recorders reveal paroxysmal atrial fibrillation after unexplained strokes or transient ischemic attacks. *Ann Noninvasive Electrocardiol* 8, 194-9 (2003).
22. Jabaudon, D., Sztajzel, J., Sievert, K., Landis, T. & Sztajzel, R. Usefulness of ambulatory 7-day ECG monitoring for the detection of atrial fibrillation and flutter after acute stroke and transient ischemic attack. *Stroke* 35, 1647-51 (2004).
23. Wichmann, H. E., Gieger, C. & Illig, T. KORA-gen—resource for population genetics, controls and a broad spectrum of disease phenotypes. *Gesundheitswesen* 67 Suppl 1, S26-30 (2005).
24. Berger, K. et al. The glu298asp polymorphism in the nitric oxide synthase 3 gene is associated with the risk of ischemic stroke in two large independent case-control studies. *Hum Genet.* 121, 169-78 (2007).
25. Adams, H. P., Jr. et al. Classification of subtype of acute ischemic stroke. Definitions for use in a multicenter clinical trial. TOAST. Trial of Org 10172 in Acute Stroke Treatment. *Stroke* 24, 35-41 (1993).
26. Kutyavin, I. V. et al. A novel endonuclease IV post-PCR genotyping system. *Nucleic Acids Res* 34, e128 (2006).
27. Gretarsdottir, S. et al. The gene encoding phosphodiesterase 4D confers risk of ischemic stroke. *Nat Genet.* 35, 131-8 (2003).
28. Stefansson, H. et al. A common inversion under selection in Europeans. *Nat. Genet.* 37, 129-37 (2005).
29. Mantel, N. & Haenszel, W. Statistical aspects of the analysis of data from retrospective studies of disease. *J Natl Cancer Inst* 22, 719-48 (1959).

The invention claimed is:

1. A method of determining a susceptibility to atrial fibrillation, atrial flutter, or stroke in a human individual, the method comprising:

- analyzing a nucleic acid sample from the individual to determine the presence or absence of at least one polymorphic marker allele selected from allele T of polymorphic marker rs2220427, allele T of polymorphic marker rs2200733, and allele T of polymorphic marker rs10033464, and detecting the presence of at least one of the polymorphic marker alleles in the nucleic acid sample, and
- determining susceptibility to atrial fibrillation, atrial flutter or stroke in the human individual by calculating a risk score for the human individual that includes a relative risk (RR) or an odds ratio (OR) of at least 1.3 attributed to the presence of the at least one polymorphic marker allele in the nucleic acid sample from the individual, wherein the determining is performed using an apparatus comprising:
- a computer readable memory;
- a processor; and
- a routine stored on the computer readable memory;
- wherein the routine is adapted to be executed on the processor to analyze genotype data with respect to the at least one polymorphic marker and generate an output based on the genotype data, wherein the output comprises a risk score for the human individual with respect to susceptibility to atrial fibrillation, atrial flutter, or stroke.

2. The method of claim 1, wherein the at least one polymorphic marker allele is allele T of polymorphic marker rs2220427.

3. The method of claim 1, wherein the at least one polymorphic marker allele is polymorphic marker rs2200733, allele T.

4. The method of claim 1, wherein the at least one polymorphic marker allele is allele T of polymorphic marker rs10033464.

5. The method of claim 1, wherein the method comprises determining a susceptibility to atrial fibrillation or atrial flutter.

6. The method of claim 5, wherein atrial fibrillation or atrial flutter is further characterized by an age of onset in the individual of less than 80 years.

7. The method of claim 5, wherein atrial fibrillation or atrial flutter is further characterized by an age of onset in the individual of less than 70 years.

8. The method of claim 5, wherein atrial fibrillation or atrial flutter is further characterized by an age of onset in the individual of less than 60 years.

9. The method of claim 1, wherein the method comprises determining a susceptibility to ischemic stroke.

10. The method of claim 1, further comprising measuring at least one additional biomarker for atrial fibrillation, atrial flutter and/or stroke in a sample from the individual, wherein the at least one additional biomarker is a polymorphic marker or a protein biomarker.

11. The method of claim 1, further comprising determining non-genetic information about the individual.

12. The method according to claim 1, wherein the human individual has a self-reported Caucasian ancestry.

13. The method of claim 1, wherein the analyzing of the nucleic acid sample is performed using a process selected from allele-specific probe hybridization, allele-specific primer extension, allele-specific amplification, nucleic acid sequencing, 5'-exonuclease digestion, molecular beacon assay, oligonucleotide ligation assay, size analysis, and single-stranded conformation analysis.

14. The method of claim 13, wherein the process is allele-specific probe hybridization or nucleic acid sequencing.

15. The method according to claim 1, wherein the analyzing of the nucleic acid sample comprises contacting nucleic acid from the sample with at least one oligonucleotide probe that is 15 to 500 nucleotides in length and that hybridizes to a segment of a nucleic acid whose sequence is shown in SEQ ID NO: 1, 28, 41, or 50, or the complements thereof, wherein the hybridization is sequence-specific and identifies the presence or absence of the at least one polymorphic marker allele.

16. The method according to claim 1, wherein the nucleic acid sample is from a human individual who has not been diagnosed with atrial fibrillation, atrial flutter, or stroke.

17. The method of claim 16, further comprising physical examination of the individual, for symptoms or evidence of atrial fibrillation, atrial flutter, or stroke.

18. The method of claim 10, wherein the at least one additional marker is a protein biomarker selected from the group consisting of fibrin D-dimer, prothrombin activation fragment 1.2 (F1.2), thrombin-antithrombin III complexes (TAT), fibrinopeptide A (FPA), lipoprotein-associated phospholipase A2 (1p-PLA2), beta-thromboglobulin, platelet factor 4, P-selectin, von Willebrand Factor, pro-natriuretic peptide (BNP), matrix metalloproteinase-9 (MMP-9), PARK7, nucleoside diphosphate kinase (NDKA), tau, neuron-specific enolase, B-type neurotrophic growth factor, astroglial protein S-100b, glial fibrillary acidic protein, C-reactive protein, serum amyloid A, matrix metalloproteinase-9, vascular and/or intracellular cell adhesion molecules, tumor necrosis factor alpha, and an interleukin, wherein the protein biomarker is measured in a plasma sample from the individual.

19. The method of claim 11, wherein the non-genetic information is selected from age, age at onset of disease, gender, ethnicity, socioeconomic status, previous disease diagnosis, medical history of subject, family history of atrial fibrillation, atrial flutter and/or stroke, biochemical measurements, and clinical measurements.

20. The method of claim 19, further comprising calculating overall susceptibility by logistic regression.

21. A method of using a nucleic acid sample isolated from a human individual to measure a susceptibility to atrial fibrillation, atrial flutter, or stroke, the method comprising:

analyzing the nucleic acid sample to determine the presence or absence of at least one polymorphic marker allele selected from allele T of marker rs2220427, allele T of marker rs2200733, or allele T of marker rs10033464, and determining that at least one of allele T of marker rs2220427, allele T of marker rs2200733, or allele T of marker rs10033464 is present in the sample, determining an increased susceptibility to atrial fibrillation, atrial flutter or stroke in the individual from the presence of the at least one allele in the nucleic acid sample, and performing a physical examination for symptoms or evidence of atrial fibrillation, atrial flutter, or stroke on the individual determined to have the increased susceptibility.

22. The method of claim 21, wherein the determining of an increased susceptibility includes calculating a risk score for the human individual that includes a relative risk (RR) or an odds ratio (OR) of at least 1.3 attributed to the at least one polymorphic marker allele being present in the nucleic acid sample from the individual.

23. The method of claim 21, wherein the analyzing of the nucleic acid sample is performed using a process selected from allele-specific probe hybridization, allele-specific primer extension, allele-specific amplification, nucleic acid sequencing, 5'-exonuclease digestion, molecular beacon assay, oligonucleotide ligation assay, size analysis, and single-stranded conformation analysis.

24. A method of using a nucleic acid sample isolated from a human individual to calculate a risk for atrial fibrillation, atrial flutter, or stroke, the method comprising:

analyzing at least one of polymorphic marker rs2220427, polymorphic marker rs2200733, or polymorphic marker rs10033464 in the nucleic acid sample and determining that a T allele of one or more of the polymorphic markers is present in the nucleic acid sample, and calculating a risk score for atrial fibrillation, atrial flutter or stroke in the individual that includes a relative risk (RR) or an odds ratio (OR) of at least 1.3 attributed to allele T of the marker(s) being present in the nucleic acid sample from the individual, using an apparatus comprising:

a computer readable memory;

a processor; and a routine stored on the computer readable memory;

wherein the routine is adapted to be executed on the processor to analyze genotype data with respect to the at least one polymorphic marker and generate an output based on the genotype data, wherein the output comprises a risk score for the human individual with respect to susceptibility to atrial fibrillation, atrial flutter, or stroke.

25. The method of claim 24, wherein the analyzing of the at least one polymorphic marker in the nucleic acid sample is performed using a process selected from allele-specific probe hybridization, allele-specific primer extension, allele-specific amplification, nucleic acid sequencing, 5'-exonuclease digestion, molecular beacon assay, oligonucleotide ligation assay, size analysis, and single-stranded conformation analysis.

26. The method of claim 21 wherein the physical examination includes cardiac rhythm monitoring for 24 to 48 hours.

* * * * *